(12) United States Patent
Pierson et al.

(10) Patent No.: US 11,465,141 B2
(45) Date of Patent: Oct. 11, 2022

(54) METHODS AND COMPOSITIONS FOR DETECTING ANALYTES

(71) Applicant: Alveo Technologies, Inc., Alameda, CA (US)

(72) Inventors: Shad Pierson, Sacramento, CA (US); Timothy D. Meehan, Alameda, CA (US); Kyle William Montgomery, Concord, CA (US); Daniel J. Wade, Bay Point, CA (US); Jess M. Sustarich, San Francisco, CA (US); Brenna Hearn Lord, San Francisco, CA (US); Ronald Phillip Chiarello, Orinda, CA (US)

(73) Assignee: ALVEO TECHNOLOGIES, INC., Alameda, CA (US)

( * ) Notice: Subject to any disclaimer, the term of this patent is extended or adjusted under 35 U.S.C. 154(b) by 488 days.

(21) Appl. No.: 16/334,647

(22) PCT Filed: Sep. 20, 2017

(86) PCT No.: PCT/US2017/052555
§ 371 (c)(1),
(2) Date: Mar. 19, 2019

(87) PCT Pub. No.: WO2018/057647
PCT Pub. Date: Mar. 29, 2018

(65) Prior Publication Data
US 2019/0232282 A1 Aug. 1, 2019

Related U.S. Application Data

(60) Provisional application No. 62/399,047, filed on Sep. 23, 2016, provisional application No. 62/398,959, filed on Sep. 23, 2016, provisional application No. 62/398,925, filed on Sep. 23, 2016, provisional application No. 62/398,965, filed on Sep. 23, 2016, provisional application No. 62/398,913, filed on Sep. 23, 2016, provisional application No. 62/398,955, filed on Sep. 23, 2016.

(51) Int. Cl.
*B01L 3/00* (2006.01)
*C12Q 1/6806* (2018.01)
*C12Q 1/6825* (2018.01)
*C12Q 1/6804* (2018.01)
*C12Q 1/68* (2018.01)
*B01L 7/00* (2006.01)

(52) U.S. Cl.
CPC ..... *B01L 3/502715* (2013.01); *B01L 3/50851* (2013.01); *B01L 7/52* (2013.01); *C12Q 1/68* (2013.01); *C12Q 1/6804* (2013.01); *C12Q 1/6806* (2013.01); *C12Q 1/6825* (2013.01); *C12Q 2531/119* (2013.01); *C12Q 2563/116* (2013.01); *C12Q 2565/629* (2013.01)

(58) Field of Classification Search
CPC .. C12Q 1/6804; C12Q 1/6806; C12Q 1/6825; C12Q 2531/119; C12Q 2563/116; C12Q 2565/629; B01L 3/502715; B01L 3/50851; B01L 7/52
See application file for complete search history.

(56) References Cited

U.S. PATENT DOCUMENTS

| | | | |
|---|---|---|---|
| 5,589,136 | A | 12/1996 | Northrup et al. |
| 6,403,367 | B1 | 6/2002 | Cheng et al. |
| 6,524,532 | B1 | 2/2003 | Northrup |
| 6,576,459 | B2 | 6/2003 | Miles et al. |
| 6,602,473 | B1 | 8/2003 | Northrup |
| 6,699,713 | B2 | 3/2004 | Benett et al. |
| 6,875,602 | B2 | 4/2005 | Gutierrez |
| 7,062,385 | B2 | 6/2006 | White et al. |
| 7,135,294 | B2 | 11/2006 | Lee |
| 7,157,050 | B2 | 1/2007 | Yazawa et al. |
| 7,172,896 | B2 | 2/2007 | Cheng et al. |
| 7,483,805 | B2 | 1/2009 | Sparks et al. |
| 7,708,944 | B1 | 5/2010 | Sadik et al. |
| 7,915,030 | B2 | 3/2011 | Inoue et al. |
| 8,078,408 | B2 | 12/2011 | Albert et al. |
| 8,106,428 | B2 | 1/2012 | Koh et al. |

(Continued)

FOREIGN PATENT DOCUMENTS

| | | |
|---|---|---|
| CN | 101981445 | 2/2011 |
| CN | 102004126 | 4/2011 |

(Continued)

OTHER PUBLICATIONS

Andersen et al, "Surface-dependent chemical equilibrium constants and capacitances for bare and 3-10 cyanopropyldimethylchlorosilane coated silica nanochannels" J. Colloid Interface Sci. 353:301-310 (2011).
Backer et al., "Planar and 3D interdigitated electrodes for biosensing applications: The impact of a dielectric barrier on the sensor properties" Phys. Status Solidi A, 1-7 (2014).
Bhat, "Salinity (conductivity) sensor based on parallel plate capacitors" Thesis, 2005, Univ. South Florida.
Brito-Neto et al., "Understanding Capacitively Coupled Contactless Conductivity Detection in Capillary and Microchip Electrophoresis. Part 1. Fundamentals" Electroanalysis 2005, 17, No. 13.

(Continued)

*Primary Examiner* — David C Thomas
(74) *Attorney, Agent, or Firm* — Knobbe Martens Olson & Bear LLP

(57) ABSTRACT

The present application is generally directed to systems, methods, and devices for diagnostics for sensing and/or identifying pathogens, genomic materials, proteins, and/or other small molecules or biomarkers. In some implementations, a small footprint low cost device provides rapid and robust sensing and identification. Such a device may utilize microfluidics, biochemistry, and electronics to detect one or more targets at once in the field and closer to or at the point of care.

20 Claims, 48 Drawing Sheets
Specification includes a Sequence Listing.

(56) References Cited

U.S. PATENT DOCUMENTS

| | | | |
|---|---|---|---|
| 8,133,671 B2 | 3/2012 | Williams et al. | |
| 8,173,077 B2 | 5/2012 | Korampally et al. | |
| 8,283,155 B2 | 10/2012 | Holmes et al. | |
| 8,329,453 B2 | 12/2012 | Battrell et al. | |
| 8,354,074 B2 | 1/2013 | Silverbrook et al. | |
| 8,370,070 B2 | 2/2013 | Fernandez | |
| 8,383,064 B2 | 2/2013 | Azimi et al. | |
| 8,414,844 B2 | 4/2013 | Sadik et al. | |
| 8,431,389 B2 | 4/2013 | Battrell et al. | |
| 8,431,390 B2 | 4/2013 | Jovanovich et al. | |
| 8,480,980 B2 | 7/2013 | Yoo | |
| 8,524,490 B2 | 9/2013 | Lipscomb et al. | |
| 8,614,059 B2 | 12/2013 | Young | |
| 8,716,007 B2 | 5/2014 | Battrell et al. | |
| 8,841,076 B2 | 9/2014 | Holmes et al. | |
| 8,865,075 B2 | 10/2014 | Guzman | |
| 8,865,401 B2 | 10/2014 | Young et al. | |
| 8,883,487 B2 | 11/2014 | Collier et al. | |
| 8,951,472 B2 | 2/2015 | Kellner et al. | |
| 8,956,858 B2 | 2/2015 | Dineen et al. | |
| 9,029,168 B2 | 5/2015 | McAlpine et al. | |
| 9,921,182 B2 | 3/2018 | Pennathur et al. | |
| 10,196,678 B2 | 2/2019 | Pennathur et al. | |
| 10,626,448 B2 | 4/2020 | Pennathur et al. | |
| 2002/0067174 A1 | 6/2002 | McAllister | |
| 2004/0132059 A1 | 7/2004 | Scurati et al. | |
| 2004/0166504 A1 | 8/2004 | Rossier et al. | |
| 2004/0170530 A1 | 9/2004 | Hefti | |
| 2005/0274612 A1 | 12/2005 | Segawa | |
| 2006/0176179 A1 | 8/2006 | Skorpik et al. | |
| 2006/0177842 A1 | 8/2006 | Wangh | |
| 2007/0141605 A1 | 6/2007 | Vann et al. | |
| 2007/0298487 A1 | 12/2007 | Bachur et al. | |
| 2008/0308846 A1 | 12/2008 | Shim et al. | |
| 2009/0061450 A1 | 3/2009 | Hunter | |
| 2010/0041056 A1 | 2/2010 | Kinnon et al. | |
| 2010/0075311 A1 | 3/2010 | Barrault et al. | |
| 2010/0075312 A1 | 3/2010 | Davies et al. | |
| 2010/0105035 A1 | 4/2010 | Hashsham et al. | |
| 2010/0193378 A1 | 8/2010 | Bratov et al. | |
| 2010/0200400 A1 | 8/2010 | Revol-Cavalier | |
| 2010/0216225 A1 | 8/2010 | Dyer et al. | |
| 2010/0240044 A1 | 9/2010 | Kumar et al. | |
| 2010/0243449 A1 | 9/2010 | Oliver | |
| 2010/0261286 A1* | 10/2010 | Kim | B82Y 30/00 436/149 |
| 2011/0039261 A1 | 2/2011 | Hillebrand et al. | |
| 2011/0068015 A1 | 3/2011 | Park | |
| 2011/0091879 A1 | 4/2011 | Hillebrand et al. | |
| 2011/0136104 A1 | 6/2011 | Pregibon et al. | |
| 2011/0165572 A1 | 7/2011 | O'Halloran | |
| 2011/0244467 A1 | 10/2011 | Haswell | |
| 2011/0275162 A1 | 11/2011 | Xie et al. | |
| 2011/0312073 A1 | 12/2011 | Silverbrook et al. | |
| 2011/0312074 A1 | 12/2011 | Azimi et al. | |
| 2011/0312610 A1 | 12/2011 | Azimi et al. | |
| 2011/0312657 A1 | 12/2011 | Azimi et al. | |
| 2011/0312683 A1 | 12/2011 | Silverbrook et al. | |
| 2011/0312791 A1 | 12/2011 | Silverbrook et al. | |
| 2011/0312826 A1 | 12/2011 | Silverbrook et al. | |
| 2011/0312841 A1 | 12/2011 | Silverbrook et al. | |
| 2011/0318728 A1 | 12/2011 | Phan et al. | |
| 2012/0052562 A1 | 3/2012 | Silverbrook et al. | |
| 2012/0053088 A1 | 3/2012 | Azimi et al. | |
| 2012/0058547 A1 | 3/2012 | Hsing et al. | |
| 2012/0064523 A1 | 3/2012 | Ecker et al. | |
| 2012/0129709 A1 | 5/2012 | Zhang | |
| 2012/0150004 A1 | 6/2012 | Currie et al. | |
| 2012/0183965 A1 | 6/2012 | Ward et al. | |
| 2012/0168306 A1 | 7/2012 | Hassibi et al. | |
| 2012/0329144 A1 | 12/2012 | Kwak | |
| 2013/0011912 A1 | 1/2013 | Battrell et al. | |
| 2013/0029333 A1 | 1/2013 | Son et al. | |
| 2013/0079254 A1 | 3/2013 | Azimi et al. | |
| 2013/0085680 A1 | 4/2013 | Arlen et al. | |
| 2013/0101990 A1 | 4/2013 | Handique et al. | |
| 2013/0109021 A1 | 5/2013 | Hwang | |
| 2013/0109022 A1 | 5/2013 | Hwang | |
| 2013/0115685 A1 | 5/2013 | Holmes et al. | |
| 2013/0130369 A1 | 5/2013 | Wilson et al. | |
| 2013/0143775 A1 | 6/2013 | Lee | |
| 2013/0154671 A1 | 6/2013 | Lee | |
| 2013/0183750 A1 | 7/2013 | Sadik et al. | |
| 2013/0244898 A1 | 9/2013 | Burd et al. | |
| 2013/0252320 A1 | 9/2013 | Burd et al. | |
| 2013/0267016 A1 | 10/2013 | Niemz et al. | |
| 2013/0273528 A1 | 10/2013 | Ehrenkranz | |
| 2013/0280725 A1 | 10/2013 | Ismagilov et al. | |
| 2013/0309676 A1 | 11/2013 | Layne | |
| 2013/0309679 A1 | 11/2013 | Ismagilov et al. | |
| 2014/0050620 A1 | 2/2014 | Johnson et al. | |
| 2014/0072962 A1 | 3/2014 | Kelley et al. | |
| 2014/0099636 A1 | 4/2014 | Lee | |
| 2014/0102915 A1 | 4/2014 | Hu | |
| 2014/0170646 A1 | 6/2014 | Kelley et al. | |
| 2014/0186935 A1 | 7/2014 | Yoo | |
| 2014/0194305 A1 | 7/2014 | Kayyem et al. | |
| 2014/0206562 A1 | 7/2014 | McCormack et al. | |
| 2014/0287414 A1 | 9/2014 | Chung et al. | |
| 2014/0329244 A1 | 11/2014 | Ding et al. | |
| 2014/0335527 A1 | 11/2014 | Goel | |
| 2014/0349298 A1 | 11/2014 | Stanchina et al. | |
| 2014/0349381 A1 | 11/2014 | Battrell et al. | |
| 2015/0041315 A1 | 2/2015 | Jack | |
| 2015/0041317 A1 | 2/2015 | Chan | |
| 2015/0041328 A1 | 2/2015 | Chan | |
| 2015/0041336 A1 | 2/2015 | Chan | |
| 2015/0044679 A1 | 2/2015 | Jack | |
| 2015/0045254 A1 | 2/2015 | Jack | |
| 2015/0064707 A1 | 3/2015 | Collier | |
| 2015/0093304 A1 | 4/2015 | Guzman | |
| 2015/0104792 A1 | 4/2015 | Mazumdar et al. | |
| 2015/0111287 A1 | 4/2015 | Rawle | |
| 2015/0141264 A1 | 5/2015 | Jung et al. | |
| 2015/0141268 A1 | 5/2015 | Rothberg et al. | |
| 2016/0097739 A1 | 4/2016 | Pennathur | |
| 2016/0097740 A1 | 4/2016 | Pennathur | |
| 2016/0097741 A1 | 4/2016 | Pennathur | |
| 2016/0097742 A1 | 4/2016 | Pennathur | |
| 2016/0129437 A1 | 5/2016 | Kayyem et al. | |
| 2016/0130639 A1 | 5/2016 | Pennathur | |
| 2016/0362748 A1 | 12/2016 | Mongan et al. | |
| 2017/0039339 A1 | 2/2017 | Bitran et al. | |
| 2017/0113221 A1 | 4/2017 | Hoffman et al. | |
| 2018/0135117 A1 | 5/2018 | Link | |
| 2018/0169658 A1 | 6/2018 | Lei et al. | |
| 2019/0228247 A1 | 7/2019 | Schueren et al. | |
| 2020/0277660 A1 | 9/2020 | Pennathur et al. | |
| 2022/0048031 A1 | 2/2022 | Chiang et al. | |
| 2022/0056511 A1 | 2/2022 | Gaiteri et al. | |
| 2022/0072539 A1 | 3/2022 | Montgomery et al. | |
| 2022/0073975 A1 | 3/2022 | Fang et al. | |

FOREIGN PATENT DOCUMENTS

| | | |
|---|---|---|
| CN | 205538786 U | 8/2016 |
| EP | 2003446 | 12/2008 |
| JP | S59-139624 | 8/1984 |
| JP | H11-241977 | 9/1999 |
| JP | 2001-527220 | 12/2001 |
| JP | 2008-532005 | 8/2008 |
| JP | 2011-517769 | 6/2011 |
| JP | 2012-501627 | 1/2012 |
| JP | 2012-177599 | 9/2012 |
| JP | 2016-527510 | 9/2016 |
| KR | 10-2009-0101764 | 9/2009 |
| TW | 2007-45551 | 12/2007 |
| TW | 2013-33188 | 8/2013 |
| WO | WO 1999/033559 | 7/1999 |
| WO | WO 2009/018642 | 2/2009 |
| WO | WO 2009/119971 | 10/2009 |
| WO | WO 2010/111605 | 9/2010 |
| WO | WO 2012/142192 | 10/2012 |
| WO | WO 2015/015175 | 2/2015 |

(56) References Cited

FOREIGN PATENT DOCUMENTS

| WO | WO 2016/064635 | 4/2016 |
|----|----------------|--------|
| WO | WO 2016/129894 | 8/2016 |
| WO | WO 2017/106790 | 6/2017 |
| WO | WO 2017/147486 | 8/2017 |
| WO | WO 2018/017884 | 1/2018 |
| WO | WO 2018/057647 | 3/2018 |
| WO | WO 2018/085151 | 5/2018 |
| WO | WO 2020/132008 | 6/2020 |

OTHER PUBLICATIONS

Coltro et al., "Capacitively coupled contactless conductivity detection on microfluidic systems—ten years of development" Anal. Methods, 2012, 4, 25.

Coltro et al., "Microfluidic devices with integrated dual-capacitively coupled contactless conductivity detection to monitor binding events in realtime" Sensors and Actuators B 192 (2014) 239-246.

"Conductivity Theory and Practice" Radiometer analytical SAS, 2004.

Ghaith, "Development of a reverse transcription loop-mediated isothermal amplification assay for rapid detection of foot-and-mouth disease virus", Master of Science Thesis, Aug. 2018.

Hilland, "Simple sensor system for measuring the dielectric properties of saline solutions" Meas. Sci. Technol. 8 (1997) 901-910.

Hsieh et al., "Rapid, Sensitive and Quantitative Detection of Pathogenic DNA at the Point of Care via Microfluidic Electrochemical Quantative Loop-Mediated Isothermal Amplification (MEQ-LAMP)" Angew Chem Intl Ed Engl 51(20):4896-4900 (2012).

International Search Report for PCT/US2019/067134 dated Apr. 1, 2020, in 4 pages.

International Search Report for PCT/US2019/067077 dated Apr. 21, 2020, in 4 pages.

International Search Report for PCT/US2019/067082 dated May 11, 2020, in 5 pages.

International Search Report and Written Opinion for PCT/US2019/067080 dated Feb. 28, 2020, in 13 pages.

Jensen et al., "Hydronium-domination ion transport in carbon-dioxide-saturated electrolytes at low salt concentrations in nanochannels" Phys. Review E. 83:5 (2011), 056307.

Kuban et al., "A review of the recent achievements in capacitively coupled contactless conductivity detection" Analytica Chimica Acta 607 (2008) 15-29.

Kuban et al., "Contactless conductivity detection for analytical techniques: Developments from 2010 to 2012" Electrophoresis 2013, 34, 55-69.

Kuban et al., "Effects of the cell geometry and operating parameters on the performance of an external contactless conductivity detector for microchip electrophoresis" Lab Chip, 2005, 5, 407-415.

Lasia, "Electrochemical Impedance Spectroscopy and Its Applications", Modern Aspects of Electrochemistry, B. E. Conway, J. Bockris, and R.E. White, Edts., Kluwer Academic/Plenum Publishers, New York, 1999, vol. 32, p. 143-248.

Lima et al., "Contactless conductivity biosensor in microchip containing folic acid as bioreceptor" Lab Chip, 2012, 12, 1963-1966.

Lima et al., "Highly sensitive contactless conductivity microchips based on concentric electrodes for flow analysis" Chem. Commun., 2013, 49, 11382.

Liu et al., "Fluorescence Turn on Chemosensors for Ag+ and Hg2+ based on tetraphenylethylene Motif Featuring Adenine and Thymine Moieties", Organic Letters 10(20):4581-4584 (2008).

Macdonald et al., "Fundamentals of impedance spectroscopy" Chapter1, Impedance Spectroscopy, Second Edition, edited by Evgenij Barsoukov and J. Ross Macdonald (2005).

Mahabadi et al., "Capacitively coupled contactless conductivity detection with dual top-bottom cell configuration for microchip electrophoresis". Electrophoresis 2010, 31, 1063-1070.

Mori et al, "Detection of Loop-Mediated Isothermal Amplification Reaction by Turbidity Derived from Magnesium Pyrophosphate Formation" Biochemical and Biophysical Research Communications 289:150-154 (2001).

Mori et al, "Real-time turbidimetry of LAMP reaction for quantifying template DNA" J. Biochem Biphys Methods 59:145-157 (2004).

Nagamine et al, "Accelerated reaction by loop-mediated isothermal amplification using loop primers" Molecular and Cellular Probes 16:223-229 (2002).

Nakamura et al, "Detection of Six Single-Nucleotide Polymorphisms Associated with Rheumatoid Arthritis by a Loop-Mediated Isothermal Amplification Method and an Electrochemical DNA Chip" Anal Chem 79:9484-9493 (2007).

Notomi et al, "Loop-mediated isothermal amplification of DNA" Nucleic Acids Res 25(12): i-vii (2000).

Opekar et al., "Contactless Impedance Sensors and Their Application to Flow Measurements" Sensors 2013, 13, 2786-2801.

Pennathur et al, "Low Temperature Fabrication and Surface Modification Methods for Fused Silica Micro- and Nanochannels," MRS Proceedings, 1659:15-26 (2014). doi:10.1557/opl.2014.32.

Pumera et al., "Contactless Conductivity Detector for Microchip Capillary Electrophoresis" Anal. Chem. 2002, 74, 1968-1971.

Pumera, "Contactless conductivity detection for microfluidics: Designs and applications" Talanta 74 (2007) 358-364.

Raistrick et al., "Theory" Chapter2, Impedance Spectroscopy, Second Edition, edited by Evgenij Barsoukov and J. Ross Macdonald (2005).

Ramos et al., "A Four-Terminal Water-Quality-Monitoring Conductivity Sensor". IEEE Transactions on Instrumentation and Measurement, vol. 57, No. 3, Mar. 2008.

Rana et al., "Comparison of Planar and 3-D Interdigitated Electrodes as Electrochemical Impedance Biosensors" Electroanalysis 2011, 23, No. 10, 2485-2490.

Rana et al., "Impedance spectra analysis to characterize interdigitated electrodes as electrochemical sensors" Electrochimica Acta 56 (2011) 8559-8563.

Rosenfeld et al, Lab on a Chip: 100-fold sample on paper-based microfluidic devices, Lab Chip http:pubs.rsc.org/en/content/articlelanding/2014/lc/c41c00734d (2014).

Schwartz et at, "Microfluidic Assay for Continuous Bacteria Detection Using Antimicrobial Peptides and Isotachophoresis" Anal Chem 86:10106-10113 (2014).

Simon et al., "Label-Free Detection Of Dna Amplification In Droplets Using Electrical Impedance" 15th International Conference on Miniaturized Systems for Chemistry and Life Sciences Oct. 2-6, 2011, Seattle, Washington, USA, pp. 1683-1685.

Tanyanyiwa et al., "High-Voltage Capacitively Coupled Contactless Conductivity Detection for Microchip Capillary Electrophoresis" Anal. Chem. 2002, 74, 6378-6382.

Tomita et al, "Loop-mediated isothermal amplification (LAMP) of gene sequences and simple visual detection of products" Nature Protocols 3(5):877-822 (2008).

Tomsic et al., "Conductivity of Magnesium Sulfate in Water from 5 to 35° C. and from Infinite Dilution to Saturation" Journal of Solution Chemistry, vol. 31, No. 1, Jan. 2002.

Wang et al., "Microchip enzymatic assay of organophosphate nerve agents" Analytica Chimica Acta 505 (2004) 183-187.

Wang et al., "Recombinase Polymerase Amplification Assay—A Simple, Fast and Cost-Effective Alternative to Real Time PCR for Specific Detection of Feline Herpesvirus-1" PLoS One, Jan. 2017, pp. 1-8, vol. 12, No. 1.

Xie et al, "Development of an electrochemical method for Ochratoxin A detection based on aptamer and loop-mediated isothermal amplification" Biosensors and Bioeletronics 55:324-329 (2014).

Abdelhalim, Mak., et al., Dielectric constant, electrical conductivity and relaxation time measurements of different gold nanoparticle sizes, International Journal of the Physical Sciences, 6 :5487-5491 (2011).

Angayarkanni Sa., et al., Effect of nanoparticles aggregation on thermal and electrical conductivities of nanofluids, Journal of Nanofluids, 3: 17-25 (2014).

(56) References Cited

OTHER PUBLICATIONS

Arruebo M. et al., Antibody-Conjugated Nanoparticles for Biomedical Applications, Journal of Nanomaterials 2009:Article ID 439389.
Credo G.M. et al., Label-free electrical detection of pyrophosphate generated from DNA polymerase reactions on field-effect devices, Analyst 137:1351-1362 (2011).
Damen, M. et al., Characterization of the quantitative HCV NASBA assay, J. Virol. Methods, 82, 45-54 (1999).
Fang, X, et al., Integrated biochip for label-free and real-time detection of NDA amplification by contactless impedance measurements based on interdigitated electrodes, 2013, 44, 241-247.
Felhofer, et al, Recent developments in intstrumentation for capillary electrophoresis and microchip-capillary electrophoresis, Eletrophoresis, 31(15): 2469-2486 (2010).
Fox, J. D et al., Development and evaluation of nucleic acid sequence based amplification (NASBA) for diagnosis of enterovirus infections using the NucliSens Basic Kit, J. Clin. Virol., 24:117-130 (2002).
Haldar B.C. "Pyrophosphato-Complexes of Nickel and Cobalt in Solution" Nature 4226:744-745 (1950).
Hong, T. C. T et al, Development and evaluation of a novel loop-mediated isothermal amplification method for rapid detection of severe acute respiratory syndrome coronavirus, J. Clin. Microbiol., 42:1956-1961 (2004).
Imai, M. et al., Rapid diagnosis of H5N1 avian influenza virus infection by newly developed influenza H5 hemagglutinin gene-specific loop mediated isothermal amplification method, J. Virol. Methods 141:173-180 (2007).
Kim S.K. et al., Chemosensors for pyrophosphate, Accounts of Chemical Research 42: 23-31 (2009).
Lee D-H, et al., A fluorescent confirmation method for DNA amplification in PCR through a fluorescent pyrophosphate sensor, Bull. Korean Chem. Soc. 29: 497-498 (2007).
Lu J., et al., Plasmonic-based electrochemical impedance spectroscopy: application to molecular binding, Anal Chem. 84: 327-333 (2012).
Maier, et al, An impedimetric sensor for real-time detection of antiobiotic resistance genes employing rolling circle amplification, Int. J. Electrochem. Sci International Journal, 2015, 2026-2034.
Morre, S. A et al., Monitoring of chlamydia trachomatis infections after antibiotic treatment using rnA detection by nucleic acid sequence based amplification, J. Clin. Pathol.: Clin. Mol. Pathol. 51:149-154 (1998).
Murphy, D. G. et al., Multicenter comparison of Roche COBAS Amplicor Monitor Version 1.5, Organon Teknika NucliSens QT with Extractor, and Bayer Quantiplex Version 3.0 for Quantification of Human Immunodeficiency Virus Type 1 RNA in Plasma, J. Clin. Microbiol., 38: 4034-4041 (2000).
Parida, M. et al., et al., Development and evaluation of reverse transcriotion-loop-mediated isothermal amplification assay for rapid and real-time detection of Japanese encephalitis virus, J. Clin. Microbiol., 44:4172-4178 (2006).
Parida, M. et al., et al., Rapid and real-time detection of chikungunya virus by reverse transcription loop-mediated isothermal amplification assay, J. Clin. Microbiol., 45: 351-357 (2007).
Parida, M. et al., Real-time reverse transcription loop-mediated isothermal amplification for rapid detection of West Nile Virus, J. Clin. Microbiol., 42: 257-263 (2004).
Parida, M. et al.,, et al., Rapid detection and differentiation of dengue virus serotypes by a real-time reverse transcription-loop-mediated isothermal amplification assay, J. Clin. Microbiol., 43: 2895-2903 (2005).
Pourhassan-Moghaddam et al., Protein detection through different platforms of immune-loop-mediated isothermal amplification, Nanoscale Research Letters, 8:485-496 (2013).
Vincent, et al., Helicase-dependent isothermal DNA amplification, EMBO Rep., 5: 795-800 (2004).
Yan L., et al., Isothermal amplified detection of DNA and RNA, Mol. BioSyst., 10: 970-1003 (2014).
Zawrah MF., et al., Stability and electrical conductivity of water-base $Al_2O_3$ nanofluids for different amplifications, HBRC Journal 12:227-234 (2016).
Zhang F., et al., Detection of human cytomegalovirus pp67 late gene transcripts in cerebrospinal fluid of human immunodeficiency virus type 1-infected patients by nucleic acid sequence-based amplification, J. Clin. Microbiol., 38: 1920-1925 (2000).
Zhang, X, et al, Quantitative determination of target gene with electrical sensor, Scientific Reports, 5(1):12539 (2015).
International Search Report and Written Opinion for PCT/US2021/45610 dated Feb. 4, 2022, in 19 pages.
International Search Report and Written Opinion for PCT/US2021/45608 dated Feb. 4, 2022, in 19 pages.
International Search Report and Written Opinion for PCT/US2021/45596, dated Nov. 15, 2021, in 14 pages.
International Search Report and Written Opinion for PCT/US2021/45600, dated Feb. 17, 2022, in 16 pages.
Phillips et al., "Strand displacement probes combined with idothermal nucleic acid amplification for instrument-free detection from complex samples", Anal. Chem. vol. 90(11):6580-6586 (Apr. 18, 2018).
Wang et al., "Towards disposable lab-on-a-chip: Poly(methylmethacrylate) microchip electrophoresis device with electrochemical detection", Electrophoresis vol. 23:596-601 (2002).
Zhang et al., "Monitoring the progression of loop-mediated isothermal amplification using conductivity", Analytical Biochemistry, vol. 466:16-18 (2014).

\* cited by examiner

HEIGHT
WIDTH

SEQUENCE LISTING

<160> NUMBER OF SEQ ID NOS: 13

<210> SEQ ID NO 1
<211> LENGTH: 206
<212> TYPE: DNA
<213> ORGANISM: Artificial Sequence
<220> FEATURE:
<223> OTHER INFORMATION: hepatitis B virus target

<400> SEQUENCE: 1
gacaagaatc ctcacaatac cgcagagtct agactcgtgg tggacttctc tcaattttct    60
agggggatca cccgtgtgtc ttggccaaaa ttcgcagtcc ccaacctcca atcactcacc   120
aacctcctgt cctccaattt gtcctggtta tcgctggatg tgtctgcggc gttttatcat   180
attcctcttc atcctgctgc tatgcc                                        206

<210> SEQ ID NO 2
<211> LENGTH: 20
<212> TYPE: DNA
<213> ORGANISM: Artificial Sequence
<220> FEATURE:
<223> OTHER INFORMATION: hepatitis B virus F3 primer

<400> SEQUENCE: 2
tcctcacaat accgcagagt                                                20

<210> SEQ ID NO 3
<211> LENGTH: 20
<212> TYPE: DNA
<213> ORGANISM: Artificial Sequence
<220> FEATURE:
<223> OTHER INFORMATION: hepatitis B virus B3 primer

<400> SEQUENCE: 3
gcatagcagc aggatgaaga                                                20

<210> SEQ ID NO 4
<211> LENGTH: 42
<212> TYPE: DNA
<213> ORGANISM: Artificial Sequence
<220> FEATURE:
<223> OTHER INFORMATION: hepatitis B virus FIP primer

<400> SEQUENCE: 4
gttggggact gcgaattttg gcctcgtggt ggacttctct ca                       42

<210> SEQ ID NO 5
<211> LENGTH: 42
<212> TYPE: DNA
<213> ORGANISM: Artificial Sequence
<220> FEATURE:
<223> OTHER INFORMATION: hepatitis B virus BIP primer

<400> SEQUENCE: 5
tcaccaacct cctgtcctcc aaataaaacg ccgcagacac at                       42

<210> SEQ ID NO 6
<211> LENGTH: 21
<212> TYPE: DNA
<213> ORGANISM: Artificial Sequence
<220> FEATURE:
<223> OTHER INFORMATION: hepatitis B virus LF primer

<400> SEQUENCE: 6
acgggtgatc ccccctagaaa a                                             21

<210> SEQ ID NO 7
<211> LENGTH: 20
<212> TYPE: DNA
<213> ORGANISM: Artificial Sequence
<220> FEATURE:
<223> OTHER INFORMATION: hepatitis B virus LB primer

<400> SEQUENCE: 7
tttgtcctgg ttatcgctgg            20

<210> SEQ ID NO 8
<211> LENGTH: 300
<212> TYPE: DNA
<213> ORGANISM: Artificial Sequence
<220> FEATURE:
<223> OTHER INFORMATION: Haemophilus influenza target

<400> SEQUENCE: 8
tggtacgcca atacattcaa caagaaatta atccaaaaga aaaatttgcg tttgttgaat      60
tctgggggcg aggctataca caagatacct tggtcgtct gctaaatgat gcctttggta     120
aagaagtaaa aaacccattc tattatgtca gaagttttac tgatgatatg ggtacatctg    180
ttcgccataa cttcatctta gcaccacaaa acttctcatt cttcgagcct atttttgcac    240 aaacccccata cgacagtatt cctgattact acgaagaaaa aggcagaatt gaaccaatta   300

<210> SEQ ID NO 9
<211> LENGTH: 22
<212> TYPE: DNA
<213> ORGANISM: Artificial Sequence
<220> FEATURE:
<223> OTHER INFORMATION: Haemophilus influenza LF primer

<400> SEQUENCE: 9
gcagacgacc aaaggtatct tg            22

<210> SEQ ID NO 10
<211> LENGTH: 17
<212> TYPE: DNA
<213> ORGANISM: Artificial Sequence
<220> FEATURE:
<223> OTHER INFORMATION: Haemophilus influenza B3 primer

<400> SEQUENCE: 10
cgtatggggt ttgtgca            17

<210> SEQ ID NO 11
<211> LENGTH: 20
<212> TYPE: DNA
<213> ORGANISM: Artificial Sequence
<220> FEATURE:
<223> OTHER INFORMATION: Haemophilus influenza F3 primer

<400> SEQUENCE: 11
cgccaataca ttcaacaaga            20

<210> SEQ ID NO 12
<211> LENGTH: 47
<212> TYPE: DNA
<213> ORGANISM: Artificial Sequence
<220> FEATURE:
<223> OTHER INFORMATION: Haemophilus influenza BIP primer

<400> SEQUENCE: 12

-continued

```
ctgatgatat gggtacatct gttcgcgaag aatgagaagt tttgtgg                47

<210> SEQ ID NO 13
<211> LENGTH: 49
<212> TYPE: DNA
<213> ORGANISM: Artificial Sequence
<220> FEATURE:
<223> OTHER INFORMATION: Haemophilus influenza FIP primer sequence

<400> SEQUENCE: 13
acttctttac caaaggcatc attttgcgtt tgttgacgcc aaattctgg              49
```

METHODS AND COMPOSITIONS FOR DETECTING ANALYTES

CROSS REFERENCE TO RELATED APPLICATIONS

This application is a U.S. National Phase Application of PCT International Application Number PCT/US2017/052555, filed on Sep. 20, 2017, designating the United States of America and published in the English language, which is an International Application of and claims the benefit of priority to U.S. Provisional Application No. 62/399,047, filed on Sep. 23, 2016, U.S. Provisional Application No. 62/398,959, filed on Sep. 23, 2016, U.S. Provisional Application No. 62/398,925, filed on Sep. 23, 2016, U.S. Provisional Application No. 62/398,965, filed on Sep. 23, 2016, U.S. Provisional Application No. 62/398,913, filed on Sep. 23, 2016, and U.S. Provisional Application No. 62/398,955, filed on Sep. 23, 2016. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-ALVEO-010APC.txt, the date of creation of the ASCII text file is Mar. 15, 2019, and the size of the ASCII text file is 4 KB.

FIELD

The present application is generally directed to systems, methods, and devices for diagnostics for sensing and/or identifying pathogens, genomic materials, proteins, and/or other small molecules or biomarkers. In some implementations, a small footprint low cost device provides rapid and robust sensing and identification. Such a device may utilize microfluidics, biochemistry, and electronics to detect one or more targets at once in the field and closer to or at the point of care.

BACKGROUND

Pathogens in a sample may be identified by detecting specific genomic material (DNA or RNA). Beyond pathogen detection, many other biomarkers are available for testing, including molecules that provide early detection of cancer, vital prenatal information, or a greater understanding of a patient's microbiome. In conventional nucleic acid testing ("NAT"), genomic material in a sample may first be exponentially copied using a molecular amplification process known as the polymerase chain reaction ("PCR") until the quantity of DNA present is great enough to be measurable. In the case of RNA, the genomic material of many viruses, an additional step can be included to first transcribe the RNA into DNA before amplifying by PCR.

SUMMARY

Some embodiments include a system for detecting a target agent, the system comprising: an assay cartridge including a test well containing an excitation electrode and a sensing electrode, wherein the test well is configured to contain a sample comprising the target agent undergoing an amplification process; and a reader device including: a region configured to receive the assay cartridge, a heater positioned to heat the assay cartridge in use within the cavity, a memory storing at least computer-readable storing instructions, and a processor configured by the instructions to at least: cause the heater to heat the assay cartridge to a predetermined temperature for performing the amplification process within the test well; provide an excitation current to the excitation electrode for at least a portion of a duration of the amplification process, receive a signal from the sensing electrode, the signal representing the excitation current after attenuation by at least the sample within the test well, decompose the signal into a resistance component and a reactance component, analyze the reactance component to determine whether a signal cliff indicative of a positive sample including the target agent occurred during at least the portion of the duration of the amplification process, and in response to determining that the signal cliff occurred, output a positive test result or, in response to determining that the signal cliff did not occur, output a negative test result.

In some embodiments, the assay cartridge further comprises: a sample introduction area configured to receive the sample; and a fluid path fluidically coupling the sample introduction area to the test well.

In some embodiments, the assay cartridge also includes a sealed chamber containing liquid constituents of the amplification process, the sealed chamber positioned in a region of the assay cartridge having an aperture leading into the fluid path, wherein the sample introduction area is positioned between the aperture and the test well along the fluid path; and a pneumatic fluid path fluidically coupling a pneumatic interface to the region of the assay cartridge, wherein the test well is provided with dried constituents of the amplification process.

In some embodiments, the reader device includes a pneumatic system configured to apply pressure through the pneumatic interface, the processor further configured by the instructions to at least: actuate a motor coupled to an actuator positioned to rupture the sealed chamber and cause the liquid constituents to flow into the region of the assay cartridge; activate the pneumatic system to cause the liquid constituents to flow into the fluid path and carry the sample received at the sample introduction area to the test well.

In some embodiments, the assay cartridge further comprises a mixing chamber positioned between the sample introduction area and the test well along the fluid path, the mixing chamber configured to mix the liquid constituents and the sample into a substantially evenly mixed test fluid.

In some embodiments, the assay cartridge comprises a first electrode interface including a first contact pad leading to the excitation electrode and a second contact pad leading to the sensing electrode.

In some embodiments, the reader device comprises a second electrode interface configured to couple to the first electrode interface with the assay cartridge received in the region of the reader device.

In some embodiments, the reader device further comprises a voltage source configured to generate the excitation current, and wherein the second electrode interface includes: a third contact pad positioned to couple to the first contact pad, the third contact pad coupled to the voltage source; and a fourth contact pad positioned to couple to the second contact pad, the fourth contact pad coupled to the memory.

In some embodiments, to decompose the signal into the resistance component and the reactance component, the processor is further configured by the instructions to at least: sample the signal faster than its Nyquist frequency, the signal representing an impedance of the sample; decompose the signal into an in-phase component and an out-of-phase component; and calculate the resistance component based on the in-phase component and calculate the reactance component based on the out-of-phase component.

In some embodiments, to analyze the reactance component, the processor is further configured by the instructions to at least access predetermined expected characteristics of the signal cliff from the memory.

In some embodiments, the predetermined expected characteristics of the signal cliff stored in the memory include a window of time during the duration of the amplification process at which the signal cliff is predicted to occur.

In some embodiments, the predetermined expected characteristics of the signal cliff stored in the memory include a threshold change in a value of the reactance component.

In some embodiments, the predetermined expected characteristics of the signal cliff stored in the memory include a threshold slope of a curve of the reactance component, the curve of the reactance component representing values of the reactance component sampled throughout at least a portion of the duration of the amplification process.

In some embodiments, the amplification process comprises contacting the processed sample with a capture probe. In some embodiments, the capture probe is selected from the group consisting of an antibody or an antigen-binding fragment thereof, a protein receptor, and a nucleic acid. In some embodiments, the capture probe comprises a detectable nucleic acid. In some embodiments, the detectable nucleic acid is amplified.

In some embodiments, the amplification process comprises isothermal amplification. In some embodiments, the amplification process comprises an isothermal amplification reaction selected from the group consisting of self-sustaining sequence replication reaction (3SR); 90-I; BAD Amp; cross priming amplification (CPA); isothermal exponential amplification reaction (EXPAR); isothermal chimeric primer initiated amplification of nucleic acids (ICAN); isothermal multi displacement amplification (IMDA); ligation-mediated SDA; multi displacement amplification; polymerase spiral reaction (PSR); restriction cascade exponential amplification (RCEA); smart amplification process (SMAP2); single primer isothermal amplification (SPIA); transcription-based amplification system (TAS); transcription meditated amplification (TMA); ligase chain reaction (LCR); and multiple cross displacement amplification (MCDA). In some embodiments, the amplification process comprises loop-mediated isothermal amplification (LAMP).

In some embodiments, the predetermined temperature for performing the amplification process within the test well is greater than 30° C. In some embodiments, the predetermined temperature for performing the amplification process within the test well is greater than 37° C. In some embodiments, the predetermined temperature for performing the amplification process within the test well is greater than 60° C. In some embodiments, the predetermined temperature for performing the amplification process within the test well is in a range from 60° C. to 70° C.

In some embodiments, the liquid constituents of the amplification process comprise a component selected from the group consisting of an antibody or an antigen-binding fragment thereof, a protein receptor, a nucleic acid such as a primer, a buffer, and an enzyme such as a polymerase.

In some embodiments, the dried constituents of the amplification process comprise a component selected from the group consisting of an antibody or an antigen-binding fragment thereof, a protein receptor, a nucleic acid such as a primer, a buffer, and an enzyme such as a polymerase.

Some embodiments include a device for testing a sample for a target agent, the device comprising: a sample introduction area configured to receive a sample comprising the target agent; a test well containing an excitation electrode and a sensing electrode, wherein the test well is configured to: contain the sample during an amplification process, apply a current to the sample during the amplification process using the excitation electrode, and sense a signal using the sensing electrode, the signal representing the current after attenuation by at least the sample within the test well; and a fluid path fluidically coupling the sample introduction area to the test well.

Some embodiments also include a sealed chamber containing liquid constituents of the amplification process, the sealed chamber positioned in a region of the device having an aperture leading into the fluid path, wherein the sample introduction area is positioned between the aperture and the test well along the fluid path; and dried constituents of the amplification process provided within the test well.

Some embodiments also include a sharp configured to rupture the sealed chamber and cause the liquid constituents to flow into the region; and a pneumatic fluid path fluidically coupling a pneumatic interface to the region of the device, the pneumatic fluid path configured to apply pressure to the region to cause the liquid constituents to flow into the fluid path and carry the sample received at the sample introduction area to the test well.

Some embodiments also include a mixing chamber positioned between the sample introduction area and the test well along the fluid path, the mixing chamber configured to mix the liquid constituents and the sample into a substantially evenly mixed test fluid.

In some embodiments, the assay cartridge comprises a first electrode interface including a first contact pad leading to the excitation electrode and a second contact pad leading to the sensing electrode.

Some embodiments also include a circuit board including the excitation electrode and the sensing electrode, wherein the sample introduction area and at least a portion of the fluid path are formed in a unitary piece of a liquid impermeable material, and wherein the circuit board is adhered to a portion of the liquid impermeable material.

Some embodiments also include a cover positioned over the liquid impermeable material and the circuit board, the cover comprising an aperture positioned over the sample introduction area and a cap configured to releasably seal the aperture.

In some embodiments, sides of the test well are formed as a circular aperture through the liquid impermeable material, and wherein a bottom of the test well is formed by the circuit board.

In some embodiments, the excitation electrode and the sensing electrode are positioned on the bottom of the test well and away from the sides of the test well.

In some embodiments, the excitation electrode and the sensing electrode are configured to be substantially flush with an underlying layer of the circuit board.

Some embodiments also include a vent configured to release gas from the test well, wherein the vent is covered by a liquid impermeable, gas permeable filter.

In some embodiments, the excitation electrode comprises a circular electrode disposed within the center of the well and wherein the sensing electrode comprises an annular electrode positioned concentrically around the excitation electrode.

In some embodiments, the annular electrode is separated from the circular electrode by a gap approximately equal to a radius of the annular electrode.

In some embodiments, the annular electrode is separated from the circular electrode by a gap at least twice as large as a radius of the annular electrode.

In some embodiments, the excitation electrode comprises a first semicircular electrode and wherein the sensing electrode comprises a second semicircular electrode separated by a gap from the first semicircular electrode, wherein straight portions of the first and second semicircular electrodes face each other across the gap.

In some embodiments, the excitation electrode comprises a first linear electrode and wherein the sensing electrode comprises a second linear electrode separated by a gap from the first linear electrode.

In some embodiments, the excitation electrode comprises a first square electrode and wherein the sensing electrode comprises a second square electrode separated by a gap from the first linear electrode.

In some embodiments, the amplification process comprises contacting the processed sample with a capture probe. In some embodiments, the capture probe is selected from the group consisting of an antibody or an antigen-binding fragment thereof, a protein receptor, and a nucleic acid. In some embodiments, the capture probe comprises a detectable nucleic acid. In some embodiments, the detectable nucleic acid is amplified.

In some embodiments, the amplification process comprises isothermal amplification. In some embodiments, the amplification process comprises an isothermal amplification reaction selected from the group consisting of self-sustaining sequence replication reaction (3SR); 90-I; BAD Amp; cross priming amplification (CPA); isothermal exponential amplification reaction (EXPAR); isothermal chimeric primer initiated amplification of nucleic acids (ICAN); isothermal multi displacement amplification (IMDA); ligation-mediated SDA; multi displacement amplification; polymerase spiral reaction (PSR); restriction cascade exponential amplification (RCEA); smart amplification process (SMAP2); single primer isothermal amplification (SPIA); transcription-based amplification system (TAS); transcription meditated amplification (TMA); ligase chain reaction (LCR); and multiple cross displacement amplification (MCDA). In some embodiments, the amplification process comprises loop-mediated isothermal amplification (LAMP).

In some embodiments, the test well is configured to heat the sample to a temperature greater than 30° C. In some embodiments, the test well is configured to heat the sample to a temperature greater than 37° C. In some embodiments, the test well is configured to heat the sample to a temperature greater than 60° C. In some embodiments, the test well is configured to heat the sample to a temperature in a range from 60° C. to 70° C.

In some embodiments, the liquid constituents of the amplification process comprise a component selected from the group consisting of an antibody or an antigen-binding fragment thereof, a protein receptor, a nucleic acid such as a primer, a buffer, and an enzyme such as a polymerase.

In some embodiments, the dried constituents of the amplification process comprise a component selected from the group consisting of an antibody or an antigen-binding fragment thereof, a protein receptor, a nucleic acid such as a primer, a buffer, and an enzyme such as a polymerase.

Some embodiments include a non-transitory computer-readable medium storing instructions that, when executed by a reader device configured to receive an assay cartridge containing a sample comprising a target agent, and a test well, cause the reader device to perform operations comprising: providing an excitation current to an excitation electrode positioned within the test well for at least a portion of a duration of an amplification process occurring within the test well; receiving a signal from a sensing electrode positioned within the test well, the signal representing the excitation current after attenuation by at least the sample undergoing amplification within the test well; decomposing the signal into a resistance component and a reactance component; analyzing the reactance component to determine whether a signal cliff indicative of a positive sample including the target agent occurred during the least the portion of a duration of the amplification process; and in response to determining that the signal cliff occurred, outputting a positive test result or, in response to determining that the signal cliff did not occur, outputting a negative test result.

In some embodiments, the operations further comprising causing a heater to heat the assay cartridge to a predetermined temperature for performing the amplification process.

In some embodiments, the operations further comprising transmitting the positive test result or the negative test result over a network.

In some embodiments, the operations for the decomposing further comprising: sampling the signal faster than its Nyquist frequency, the signal representing an impedance of the sample; decomposing the signal into an in-phase component and an out-of-phase component; and calculating the resistance component based on the in-phase component and calculate the reactance component based on the out-of-phase component.

In some embodiments, the operations for the analyzing the reactance component further comprising accessing predetermined expected characteristics of the signal cliff from a memory.

In some embodiments, the predetermined expected characteristics of the signal cliff stored in the memory include a window of time during the duration of the amplification process at which the signal cliff is predicted to occur.

In some embodiments, the predetermined expected characteristics of the signal cliff stored in the memory include a threshold change in a value of the reactance component.

In some embodiments, the predetermined expected characteristics of the signal cliff stored in the memory include a threshold slope of a curve of the reactance component, the curve of the reactance component representing values of the reactance component sampled throughout the least a portion of the duration of the amplification process.

In some embodiments, the operations further comprising activating a pneumatic system to apply pressure to a fluid path of the assay cartridge to cause the sample to mix with constituents of the amplification process provided in the assay cartridge and to flow into the test well.

In some embodiments, the operations further comprising activating a motor to push an actuator into a blister pack of the assay cartridge to cause liquid constituents of the amplification process to be released into the fluid path.

In some embodiments, the amplification process comprises contacting the processed sample with a capture probe. In some embodiments, the capture probe is selected from the group consisting of an antibody or an antigen-binding fragment thereof, a protein receptor, and a nucleic acid. In some embodiments, the capture probe comprises a detectable nucleic acid. In some embodiments, the detectable nucleic acid is amplified.

In some embodiments, the amplification process comprises isothermal amplification. In some embodiments, the amplification process comprises an isothermal amplification reaction selected from the group consisting of self-sustaining sequence replication reaction (3SR); 90-I; BAD Amp; cross priming amplification (CPA); isothermal exponential amplification reaction (EXPAR); isothermal chimeric primer initiated amplification of nucleic acids (ICAN); isothermal multi displacement amplification (IMDA); ligation-mediated SDA; multi displacement amplification; polymerase spiral reaction (PSR); restriction cascade exponential amplification (RCEA); smart amplification process (SMAP2); single primer isothermal amplification (SPIA); transcription-based amplification system (TAS); transcription meditated amplification (TMA); ligase chain reaction (LCR); and multiple cross displacement amplification (MCDA). In some embodiments, the amplification process comprises loop-mediated isothermal amplification (LAMP).

In some embodiments, the predetermined temperature for performing the amplification process is greater than 30° C. In some embodiments, the predetermined temperature for performing the amplification process is greater than 37° C. In some embodiments, the predetermined temperature for performing the amplification process is greater than 60° C. In some embodiments, the predetermined temperature for performing the amplification process is in a range from 60° C. to 70° C.

In some embodiments, the liquid constituents of the amplification process comprise a component selected from the group consisting of an antibody or an antigen-binding fragment thereof, a protein receptor, a nucleic acid such as a primer, a buffer, and an enzyme such as a polymerase.

In some embodiments, the amplification process further comprises dried constituents selected from the group consisting of an antibody or an antigen-binding fragment thereof, a protein receptor, a nucleic acid such as a primer, a buffer, and an enzyme such as a polymerase.

Some embodiments include a method of detecting a target agent, the method comprising: providing a cartridge comprising a test well including an excitation electrode and a sensor electrode; introducing a sample comprising the target agent into the cartridge; inserting the cartridge into a reader device; performing an amplification of the target agent comprised in the sample within the test well; applying an excitation signal from the reader device to the excitation electrode; sensing a signal from the test well using the excitation electrode, the signal representing an impedance of the sample undergoing the amplification; transmitting the signal to the reader device; and detecting the target agent based on the reader device analyzing a reactance portion of the impedance.

Some embodiments also include applying the sample at a sample introduction area of the cartridge; rupturing a sealed chamber within the cartridge to release liquid constituents of the amplification process into a fluid path of the cartridge; and causing the liquid constituents and the sample to flow along the fluid path to the test well, thereby mixing the liquid constituents and the sample into a test fluid.

Some embodiments also include hydrating dried components of the amplification process provided within the test well with test fluid.

Some embodiments also include pushing gas trapped in the test fluid out through a vent in fluid communication with the test well.

Some embodiments also include analyzing the reactance portion of the signal to identify a signal cliff indicative of a positive test result.

Some embodiments also include identifying the signal cliff based on a portion of a curve generated based on the reactance portion that has one or both of greater than a threshold change in value and a temporal location within predetermined window of time of the amplification process.

In some embodiments, the amplification process comprises contacting the processed sample with a capture probe. In some embodiments, the capture probe is selected from the group consisting of an antibody or an antigen-binding fragment thereof, a protein receptor, and a nucleic acid. In some embodiments, the capture probe comprises a detectable nucleic acid. In some embodiments, the detectable nucleic acid is amplified.

In some embodiments, the amplification comprises isothermal amplification. In some embodiments, the amplification comprises an isothermal amplification reaction selected from the group consisting of self-sustaining sequence replication reaction (3SR); 90-I; BAD Amp; cross priming amplification (CPA); isothermal exponential amplification reaction (EXPAR); isothermal chimeric primer initiated amplification of nucleic acids (ICAN); isothermal multi displacement amplification (IMDA); ligation-mediated SDA; multi displacement amplification; polymerase spiral reaction (PSR); restriction cascade exponential amplification (RCEA); smart amplification process (SMAP2); single primer isothermal amplification (SPIA); transcription-based amplification system (TAS); transcription meditated amplification (TMA); ligase chain reaction (LCR); and multiple cross displacement amplification (MCDA). In some embodiments, the amplification comprises loop-mediated isothermal amplification (LAMP).

In some embodiments, performing an amplification of the target agent comprises heating the sample to a temperature great than 30° C. In some embodiments, performing an amplification of the target agent comprises heating the sample to a temperature great than 37° C. In some embodiments, performing an amplification of the target agent comprises heating the sample to a temperature great than 60° C. In some embodiments, performing an amplification of the target agent comprises heating the sample to a temperature in a range from 60° C. to 70° C.

In some embodiments, the liquid constituents of the amplification process comprise a component selected from the group consisting of an antibody or an antigen-binding fragment thereof, a protein receptor, a nucleic acid such as a primer, a buffer, and an enzyme such as a polymerase.

In some embodiments, the dried constituents of the amplification process comprise a component selected from the group consisting of an antibody or an antigen-binding fragment thereof, a protein receptor, a nucleic acid such as a primer, a buffer, and an enzyme such as a polymerase.

Some embodiments include a method of detecting a target agent, the method comprising: providing a device comprising an excitation electrode and a sensor electrode; introducing a sample comprising the target agent into the device; processing the sample within the device; and detecting the target by measuring an electrical property of the processed sample.

In some embodiments, the electrical property of selected from the group consisting of complex admittance, impedance, conductivity, resistivity, resistance, and a dialectric constant.

In some embodiments, the electrical property is complex admittance.

In some embodiments, detecting comprises applying an excitation signal to the excitation electrode.

In some embodiments, the excitation signal comprises an alternating current.

In some embodiments, the excitation signal comprises a direct current.

In some embodiments, the excitation signal comprises a sweeping voltage and frequency.

In some embodiments, detecting comprises measuring an induced current at the sensor electrode.

In some embodiments, the electrical property is measured over a period of time.

In some embodiments, at least one electrode is passivated.

In some embodiments, the electrode is passivated with a dielectric material.

In some embodiments, the electrode is passivated with titanium oxide.

In some embodiments, detecting comprises contacting the processed sample with a capture probe. In some embodiments, the capture probe comprises a magnetic bead.

In some embodiments, the capture probe is selected from the group consisting of an antibody or an antigen-binding fragment thereof, a protein receptor, and a nucleic acid. In some embodiments, the capture probe comprises a detectable nucleic acid. In some embodiments, detecting comprises amplifying the detectable nucleic acid.

In some embodiments, the amplification comprises isothermal amplification. In some embodiments, the amplification comprises loop-mediated isothermal amplification (LAMP). In some embodiments, the processed sample comprises a low ionic solution.

In some embodiments, the processed sample lacks ammonium sulfate.

In some embodiments, detecting comprises contacting the sample with an agent to enhance changes in the conductivity of a solution comprising the sample. In some embodiments, the agent binds to inorganic pyrophosphate. In some embodiments, the agent is selected from the group consisting of Cd2+-cyclen-coumarin; Zn2+ complex with a bis(2-pyridylmethyl)amine (DPA) unit; DPA-2Zn2+-phenoxide; acridine-DPA-Zn2+; DPA-Zn2+-pyrene; and an azacrown-Cu2+ complex. In some embodiments, the agent comprises 2-amino-6-mercapto-7-methylpurine ribonucleoside.

Some embodiments include a method of detecting a target agent using a frequency dependent capacitively coupled contactless conductivity detection device, the method comprising: introducing a sample comprising the target agent into the device; processing the sample within the device; and detecting the target by analyzing the frequency dependent capacitively coupled contactless conductivity of the sample.

In some embodiments, processing comprises a step selected from the group consisting of enriching the sample for the target agent, removing non-target agent material from the sample, lysing cells, precipitating proteins, and adding a preservative agent.

In some embodiments, detecting comprises contacting the processed sample with a capture probe. In some embodiments, the capture probe is selected from the group consisting of an antibody or an antigen-binding fragment thereof, a protein receptor, and a nucleic acid. In some embodiments, the capture probe comprises a detectable nucleic acid. In some embodiments, detecting comprises amplifying the detectable nucleic acid.

In some embodiments, the amplification comprises isothermal amplification. In some embodiments, the amplification comprises an isothermal amplification reaction selected from the group consisting of self-sustaining sequence replication reaction (3SR); 90-I; BAD Amp; cross priming amplification (CPA); isothermal exponential amplification reaction (EXPAR); isothermal chimeric primer initiated amplification of nucleic acids (ICAN); isothermal multi displacement amplification (IMDA); ligation-mediated SDA; multi displacement amplification; polymerase spiral reaction (PSR); restriction cascade exponential amplification (RCEA); smart amplification process (SMAP2); single primer isothermal amplification (SPIA); transcription-based amplification system (TAS); transcription meditated amplification (TMA); ligase chain reaction (LCR); and multiple cross displacement amplification (MCDA). In some embodiments, the amplification comprises loop-mediated isothermal amplification (LAMP).

In some embodiments, detecting comprises contacting the sample with an agent to enhance changes in the conductivity of a solution comprising the sample. In some embodiments, the agent binds to inorganic pyrophosphate. In some embodiments, the agent is selected from the group consisting of Cd2+-cyclen-coumarin; Zn2+ complex with a bis(2-pyridylmethyl)amine (DPA) unit; DPA-2Zn2+-phenoxide; acridine-DPA-Zn2+; DPA-Zn2+-pyrene; and an azacrown-Cu2+ complex. In some embodiments, the agent comprises 2-amino-6-mercapto-7-methylpurine ribonucleoside.

In some embodiments, the detecting utilizes an alternating current.

In some embodiments, the detecting utilizes a high-frequency alternating current.

In some embodiments, the detecting utilizes a direct current.

Some embodiments include a device for detecting a target agent in a sample comprising: a chamber capable of containing a liquid sample; a channel having at least one side wall, the channel in fluid communication with the chamber and including one or more reagents for nucleic acid amplification; a heater capable of heating the channel; a first electrode in contact with the side wall; a second electrode in contact with the side wall and spaced apart from the first electrode along the channel; and circuitry electrically connected to the first and second electrodes, the circuitry capable of applying a current to the first electrode and detecting a current signal received by the second electrode that is indicative of the target agent.

In some embodiments, the current is a direct current.

In some embodiments, the current is an alternating current.

In some embodiments, the heater is capable of heating a liquid sample to at least 30° C. In some embodiments, the heater is capable of heating a liquid sample to at least 37° C. In some embodiments, the heater is capable of heating a liquid sample to at least 60° C. In some embodiments, the heater is capable of heating a liquid sample in a range from 60° C. to 70° C.

In some embodiments, the channel is formed in a dielectric substrate and the heater is disposed adjacent to the channel.

In some embodiments, the device is configured to be electronically and mechanically coupled to a companion device.

In some embodiments, the companion device is a consumer product comprising a processor, memory, a graphical user display.

In some embodiments, the companion device is selected from the group consisting of a smart phone, a tablet, a laptop, and a smart watch.

In some embodiments, the one or more reagents for nucleic acid amplification comprise a primer, and a polymerase.

In some embodiments, the one or more reagents for nucleic acid amplification comprise an agent to enhance changes in the conductivity of a solution comprising the sample. In some embodiments, the agent binds to inorganic pyrophosphate. In some embodiments, the agent is selected from the group consisting of Cd2+-cyclen-coumarin; Zn2+ complex with a bis(2-pyridylmethyl)amine (DPA) unit; DPA-2Zn2+-phenoxide; acridine-DPA-Zn2+; DPA-Zn2+-pyrene; and an azacrown-Cu2+ complex. In some embodiments, the agent comprises 2-amino-6-mercapto-7-methylpurine ribonucleoside.

Some of the foregoing embodiments include a device, a non-transitory computer-readable medium, or a method in which the target agent is selected from the group consisting of a viral nucleic acid, a viral capsid protein, a viral structural protein, a viral glycoprotein, a viral membrane fusion protein, a viral protease, and a viral polymerase In some embodiments, a virus comprises the target agent.

In some embodiments, the virus is selected from the group consisting of a double-stranded DNA virus, a single-stranded DNA virus, a double-stranded RNA virus, a single-stranded (+) RNA virus, a single-stranded (−) RNA virus, a single-stranded retro-transcribing RNA virus, and a double-stranded retro-transcribing DNA virus.

In some embodiments, the virus is selected from the group consisting of Adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus 68, 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16,18, Human parainfluenza, Human parvovirus B 19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, Semliki forest virus, Seoul virus, Simian foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, and Zika virus.

Some of the foregoing embodiments include a device, a non-transitory computer-readable medium, or a method in which the target agent is selected from the group consisting of a bacterial nucleic acid, a bacterial protein, and bacterial toxin.

In some embodiments, a bacterium comprises the target agent.

In some embodiments, the bacterium is selected from the group consisting of a gram-positive bacterium or a gram-negative bacterium.

In some embodiments, the bacterium is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* and *Staphylococcus saccharolyticus.*

Some of the foregoing embodiments include a device, a non-transitory computer-readable medium, or a method in which the target agent is selected from the group consisting of a protein, a polypeptide, a nucleic acid, a small molecule, and a pharmaceutical compound.

Some of the foregoing embodiments include a device, a non-transitory computer-readable medium, or a method in which a parasite comprises the target agent.

In some embodiments, the parasite is selected from the group consisting of an endoparasite and an ectoparasite.

In some embodiments, the parasite is selected from the group consisting of protozoan, helminth, fluke and roundworm.

In some embodiments, the endoparasite is selected from the group consisting of *Acanthamoeba* spp. *Babesia* spp., *B. divergens, B. bigemina, B. equi, B. microfti, B. duncani, Balamuthia mandrillaris, Balantidium coli, Blastocystis* spp., *Cryptosporidium* spp., *Cyclospora cayetanensis, Dientamoeba fragilis, Entamoeba histolytica, Giardia lamblia, Isospora belli, Leishmania* spp., *Naegleria fowleri, Plasmodium falciparum, Plasmodium vivax, Plasmodium ovale curtisi, Plasmodium ovale wallikeri, Plasmodium malariae, Plasmodium knowlesi, Rhinosporidium seeberi, Sarcocystis bovihominis, Sarcocystis suihominis, Toxoplasma gondii, Trichomonas vaginalis, Trypanosoma brucei, Trypanosoma cruzi, Bertiella mucronata, Bertiella studeri, Cestoda, Taenia multiceps, Diphyllobothrium latum, Echinococcus granulosus, Echinococcus multilocularis, E. vogeli, E. oligarthrus, Hymenolepis nana, Hymenolepis diminuta, Spirometra erinaceieuropaei, Taenia saginata, Taenia solium, Clonorchis sinensis; Clonorchis viverrini, Dicrocoelium dendriticum, Echinostoma echinatum, Fasciola hepatica, Fasciola gigantica, Fasciolopsis buski, Gnathostoma spinigerum, Gnathostoma hispidum, Metagonimus yokogawai, Metorchis conjunctus, Opisthorchis viverrini, Opisthorchis felineus, Clonorchis sinensis, Paragonimus westermani, Paragonimus africanus, Paragonimus caliensis, Paragonimus kellicotti, Paragonimus skrjabini; Paragonimus uterobilateralis, Schistosoma haematobium, Schistosoma japonicum, Schistosoma mansoni* and *Schistosoma intercalatum, Schistosoma mekongi, Schistosoma* sp, *Trichobilharzia regenti, Schistosomatidae, Ancylostoma duodenale, Necator americanus, Angiostrongylus costaricensis, Anisakis, Ascaris* sp. *Ascaris lumbricoides, Baylisascaris procyonis, Brugia malayi, Brugia timori, Dioctophyme renale, Dracunculus medinensis, Enterobius vermicularis, Enterobius gregorii, Halicephalobus gingivalis, Loa loa filaria, Mansonella streptocerca, Onchocerca volvulus, Strongyloides stercoralis, Thelazia californiensis, Thelazia callipaeda, Toxocara canis, Toxocara cati, Trichinella spiralis, Trichinella britovi, Trichinella nelsoni, Trichinella nativa, Trichuris trichiura, Trichuris vulpis, Wuchereria bancrofti, Archiacanthocephala, Moniliformis moniliformis, Linguatula serrata, Oestroidea,* Calliphoridae, Sarcophagidae, *Cochliomyia hominivorax* (family Calliphoridae), *Tunga penetrans,* Cimicidae: *Cimex lectularius,* and *Dermatobia hominis.*

In some embodiments, the parasite is an ectoparasite selected from the group consisting of *Pediculus humanus, Pediculus humanus corporis, Pthirus pubis, Demodex folliculorum, Demodex brevis, Demodex canis, Sarcoptes scabiei,* Trombiculidae, *Pulex irritans,* Ixodidae and Argasidae.

Some of the foregoing embodiments include a device, a non-transitory computer-readable medium, or a method in which a microRNA comprises the target agent.

In some embodiments, the microRNA is mammalian. In some embodiments, the microRNA is human.

In some embodiments, the microRNA is selected from the group consisting of hsa-miR-1, hsa-miR-1-2, hsa-miR-100, hsa-miR-100-1, hsa-miR-100-2, hsa-miR-101, hsa-miR-101-1, hsa-miR-101a, hsa-miR-101b-2, hsa-miR-102, hsa-miR-103, hsa-miR-103-1, hsa-miR-103-2, hsa-miR-104, hsa-miR-105, hsa-miR-106a, hsa-miR-106a-1, hsa-miR-106b, hsa-miR-106b-1, hsa-miR-107, hsa-miR-10a, hsa-miR-10b, hsa-miR-122, hsa-miR-122a, hsa-miR-123, hsa-miR-124a, hsa-miR-124a-1, hsa-miR-124a-2, hsa-miR-124a-3, hsa-miR-125a, hsa-miR-125a-5p, hsa-miR-125b, hsa-miR-125b-1, hsa-miR-125b-2, hsa-miR-126, hsa-miR-126-5p, hsa-miR-127, hsa-miR-128a, hsa-miR-128b, hsa-miR-129, hsa-miR-129-1, hsa-miR-129-2, hsa-miR-130, hsa-miR-130a, hsa-miR-130a-1, hsa-miR-130b, hsa-miR-130b-1, hsa-miR-132, hsa-miR-133a, hsa-miR-133b, hsa-miR-134, hsa-miR-135a, hsa-miR-135b, hsa-miR-136, hsa-miR-137, hsa-miR-138, hsa-miR-138-1, hsa-miR-138-2, hsa-miR-139, hsa-miR-139-5p, hsa-miR-140, hsa-miR-140-3p, hsa-miR-141, hsa-miR-142-3p, hsa-miR-142-5p, hsa-miR-143, hsa-miR-144, hsa-miR-145, hsa-miR-146a, hsa-miR-146b, hsa-miR-147, hsa-miR-148a, hsa-miR-148b, hsa-miR-149, hsa-miR-15, hsa-miR-150, hsa-miR-151, hsa-miR-151-5p, hsa-miR-152, hsa-miR-153, hsa-miR-154, hsa-miR-155, hsa-miR-15a, hsa-miR-15a-2, hsa-miR-15b, hsa-miR-16, hsa-miR-16-1, hsa-miR-16-2, hsa-miR-16a, hsa-miR-164, hsa-miR-170, hsa-miR-172a-2, hsa-miR-17, hsa-miR-17-3p, hsa-miR-17-5p, hsa-miR-17-92, hsa-miR-18, hsa-miR-18a, hsa-miR-18b, hsa-miR-181a, hsa-miR-181a-1, hsa-miR-181a-2, hsa-miR-181b, hsa-miR-181b-1, hsa-miR-181b-2, hsa-miR-181c, hsa-miR-181d, hsa-miR-182, hsa-miR-183, hsa-miR-184, hsa-miR-185, hsa-miR-186, hsa-miR-187, hsa-miR-188, hsa-miR-189, hsa-miR-190, hsa-miR-191, hsa-miR-192, hsa-miR-192-1, hsa-miR-192-2, hsa-miR-192-3, hsa-miR-193a, hsa-miR-193b, hsa-miR-194, hsa-miR-195, hsa-miR-196a, hsa-miR-196a-2, hsa-miR-196b, hsa-miR-197, hsa-miR-198, hsa-miR-199a, hsa-miR-199a-1, hsa-miR-199a-1-5p, hsa-miR-199a-2, hsa-miR-199a-2-5p, hsa-miR-199a-3p, hsa-miR-199b, hsa-miR-199b-5p, hsa-miR-19a, hsa-miR-19b, hsa-miR-19b-1, hsa-miR-19b-2, hsa-miR-200a, hsa-miR-200b, hsa-miR-200c, hsa-miR-202, hsa-miR-203, hsa-miR-204, hsa-miR-205, hsa-miR-206, hsa-miR-207, hsa-miR-208, hsa-miR-208a, hsa-miR-20a, hsa-miR-20b, hsa-miR-21, hsa-miR-22, hsa-miR-210, hsa-miR-211, hsa-miR-212, hsa-miR-213, hsa-miR-214, hsa-miR-215, hsa-miR-216, hsa-miR-217, hsa-miR-218, hsa-miR-218-2, hsa-miR-219, hsa-miR-219-1, hsa-miR-22, hsa-miR-220, hsa-miR-221, hsa-miR-222, hsa-miR-223, hsa-miR-224, hsa-miR-23a, hsa-miR-23b, hsa-miR-24, hsa-miR-24-1, hsa-miR-24-2, hsa-miR-25, hsa-miR-26a, hsa-miR-26a-1, hsa-miR-26a-2, hsa-miR-26b, hsa-miR-27a, hsa-miR-27b, hsa-miR-28, hsa-miR-296, hsa-miR-298, hsa-miR-299-3p, hsa-miR-299-5p, hsa-miR-29a, hsa-miR-29a-2, hsa-miR-29b, hsa-miR-29b-1, hsa-miR-29b-2, hsa-miR-29c, hsa-miR-301, hsa-miR-302, hsa-miR-302a, hsa-miR-302b, hsa-miR-302c, hsa-miR-302c, hsa-miR-302d, hsa-miR-30a, hsa-miR-30a-3p, hsa-miR-30a-5p, hsa-miR-30b, hsa-miR-30c, hsa-miR-30c-1, hsa-miR-30d, hsa-miR-30e, hsa-miR-30e, hsa-miR-30e-5p, hsa-miR-31, hsa-miR-31a, hsa-miR-32, hsa-miR-32, hsa-miR-320, hsa-miR-320-2, hsa-miR-320a, hsa-miR-322, hsa-miR-323, hsa-miR-324-3p, hsa-miR-324-5p, hsa-miR-325, hsa-miR-326, hsa-miR-328, hsa-miR-328-1, hsa-miR-33, hsa-miR-330, hsa-miR-331, hsa-miR-335, hsa-miR-337, hsa-miR-337-3p, hsa-miR-338, hsa-miR-338-5p, hsa-miR-339, hsa-miR-339-5p, hsa-miR-34a, hsa-miR-340, hsa-miR-340, hsa-miR-341, hsa-miR-342, hsa-miR-342-3p, hsa-miR-345, hsa-miR-346, hsa-miR-347, hsa-miR-34a, hsa-miR-34b, hsa-miR-34c, hsa-miR-351, hsa-miR-352, hsa-miR-361, hsa-miR-362, hsa-miR-363, hsa-miR-355, hsa-miR-365, hsa-miR-367, hsa-miR-368, hsa-miR-369-5p, hsa-miR-370, hsa-miR-371, hsa-miR-372, hsa-miR-373, hsa-miR-374, hsa-miR-375, hsa-miR-376a, hsa-miR-376b, hsa-miR-377, hsa-miR-378, hsa-miR-378, hsa-miR-379, hsa-miR-381, hsa-miR-382, hsa-miR-383, hsa-miR-409-3p, hsa-miR-419, hsa-miR-422a, hsa-miR-422b, hsa-miR-423, hsa-miR-424, hsa-miR-429, hsa-miR-431, hsa-miR-432, hsa-miR-433, hsa-miR-449a, hsa-miR-451, hsa-miR-452, hsa-miR-451, hsa-miR- 452, hsa-miR-452, hsa-miR-483, hsa-miR-483-3p, hsa-miR-484, hsa-miR-485-5p, hsa-miR-485-3p, hsa-miR-486, hsa-miR-487b, hsa-miR-489, hsa-miR-491, hsa-miR-491-5p, hsa-miR-492, hsa-miR-493-3p, hsa-miR-493-5p, hsa-miR-494, hsa-miR-495, hsa-miR-497, hsa-miR-498, hsa-miR-499, hsa-miR-5, hsa-miR-500, hsa-miR-501, hsa-miR-503, hsa-miR-508, hsa-miR-509, hsa-miR-510, hsa-miR-511, hsa-miR-512-5p, hsa-miR-513, hsa-miR-513-1, hsa-miR-513-2, hsa-miR-515-3p, hsa-miR-516-5p, hsa-miR-516-3p, hsa-miR-518b, hsa-miR-519a, hsa-miR-519d, hsa-miR-520a, hsa-miR-520c, hsa-miR-521, hsa-miR-532-5p, hsa-miR-539, hsa-miR-542-3p, hsa-miR-542-5p, hsa-miR-550, hsa-miR-551a, hsa-miR-561, hsa-miR-563, hsa-miR-565, hsa-miR-572, hsa-miR-582, hsa-miR-584, hsa-miR-594, hsa-miR-595, hsa-miR-598, hsa-miR-599, hsa-miR-600, hsa-miR-601, hsa-miR-602, hsa-miR-605, hsa-miR-608, hsa-miR-611, hsa-miR-612, hsa-miR-614, hsa-miR-615, hsa-miR-615-3p, hsa-miR-622, hsa-miR-627, hsa-miR-628, hsa-miR-635, hsa-miR-637, hsa-miR-638, hsa-miR-642, hsa-miR-648, hsa-miR-652, hsa-miR-654, hsa-miR-657, hsa-miR-658, hsa-miR-659, hsa-miR-661, hsa-miR-662, hsa-miR-663, hsa-miR-664, hsa-miR-7, hsa-miR-7-1, hsa-miR-7-2, hsa-miR-7-3, hsa-miR-708, hsa-miR-765, hsa-miR-769-3p, hsa-miR-802, hsa-miR-885-3p, hsa-miR-9, hsa-miR-9-1, hsa-miR-9-3, hsa-miR-9-3p, hsa-miR-92, hsa-miR-92-1, hsa-miR-92-2, hsa-miR-9-2, hsa-miR-92, hsa-miR-92a, hsa-miR-93, hsa-miR-95, hsa-miR-96, hsa-miR-98, hsa-miR-99a, and/or hsa-miR-99b.

Some of the foregoing embodiments include a device, a non-transitory computer-readable medium, or a method in which an agricultural analyte comprises the target agent.

In some embodiments, the agricultural analyte is indicative of the source of a food product. In some embodiments, the agricultural analyte is indicative of the animal source of a food product. In some embodiments, the agricultural analyte is indicative of the genus of the animal source. In some embodiments, the agricultural analyte is indicative of the plant source of a food product. In some embodiments, the agricultural analyte is indicative of the genus of the plant source.

In some embodiments, the agricultural analyte is a pesticide. In some embodiments, the agricultural analyte is a pesticide selected from the group consisting of a herbicide, an insecticide, and a fungicide. In some embodiments, the agricultural analyte is a herbicide selected from the group consisting of 2,4-dichlorophenoxyacetic acid (2,4-D), atrazine, glyphosate, mecoprop, dicamba, paraquat, glufosinate, metam-sodium, dazomet, dithopyr, pendimethalin, EPTC, trifluralin, flazasulfuron, metsulfuron-methyl, diuron, nitrofen, nitrofluorfen, acifluorfen, mesotrione, sulcotrione, and nitisinone. In some embodiments, the agricultural analyte is an insecticide selected from the group consisting of an organochloride, an organophosphates, a carbamate, a pyrethroid, a neonicotinoid, and a ryanoid. In some embodiments, the agricultural analyte is a fungicide selected from the group consisting of carbendazim, diethofencarb, azoxystrobin, metalaxyl, metalaxyl-m, streptomycin, oxytetracycline, chlorothalonil, tebuconazole, zineb, mancozeb, tebuconazole, myclobutanil, triadimefon, fenbuconazole, deoxynivalenol, and mancozeb.

Some of the foregoing embodiments include a device, a non-transitory computer-readable medium, or a method in which a biomarker for a disorder comprises the target agent. In some embodiments, the disorder is a cancer. In some embodiments, the cancer is selected from breast cancers, colorectal cancers, gastric cancers, gastrointestinal stromal tumors, leukemias and lymphomas, lung cancers, melanomas, brain cancers, and pancreatic cancers. In some embodiments, the biomarker is selected from include estrogen receptor, progesterone receptor, HER-2/neu, EGFR, KRAS, UGT1A1, c-KIT, CD20, CD30, FIP1L1-PDGFRalpha, PDGFR, Philadelphia chromosome (BCR/ABL), PML/RAR-alpha, TPMT, UGT1A1, EML4/ALK, BRAF, and elevated levels of certain amino acids such as leucine, isoleucine, and valine.

Some of the foregoing embodiments include a device, a non-transitory computer-readable medium, or a method in which the sample is avian.

Some of the foregoing embodiments include a device, a non-transitory computer-readable medium, or a method in which the sample is mammalian.

Some of the foregoing embodiments include a device, a non-transitory computer-readable medium, or a method in which the sample is human.

Some of the foregoing embodiments include a device, a non-transitory computer-readable medium, or a method in which the sample is selected from the group consisting of blood, serum, plasma, urine, saliva, ascites fluid, spinal fluid, semen, lung lavage, sputum, phlegm, mucous, a liquid medium comprising cells or nucleic acids, a solid medium comprising cells or nucleic acids and tissue.

Some of the foregoing embodiments include a device, a non-transitory computer-readable medium, or a method in which the sample is obtained by performing a step selected from a finger stick, a heel stick, a venipuncture, an adult nasal aspirate, a child nasal aspirate, a nasopharyngeal wash, a nasopharyngeal aspirate, a swab, a bulk collection in cup, a tissue biopsy, and a lavage.

Some of the foregoing embodiments include a device, a non-transitory computer-readable medium, or a method in which the sample is vegetable.

Some of the foregoing embodiments include a device, a non-transitory computer-readable medium, or a method in which the sample is an environmental sample.

Some of the foregoing embodiments include a device, a non-transitory computer-readable medium, or a method in which the sample is a soil sample or a water sample.

BRIEF DESCRIPTION OF THE DRAWINGS

FIG. 17A is a top view of the system, while FIG. 17B is a cross-sectional side view of the system.

DETAILED DESCRIPTION

Figure 1A:
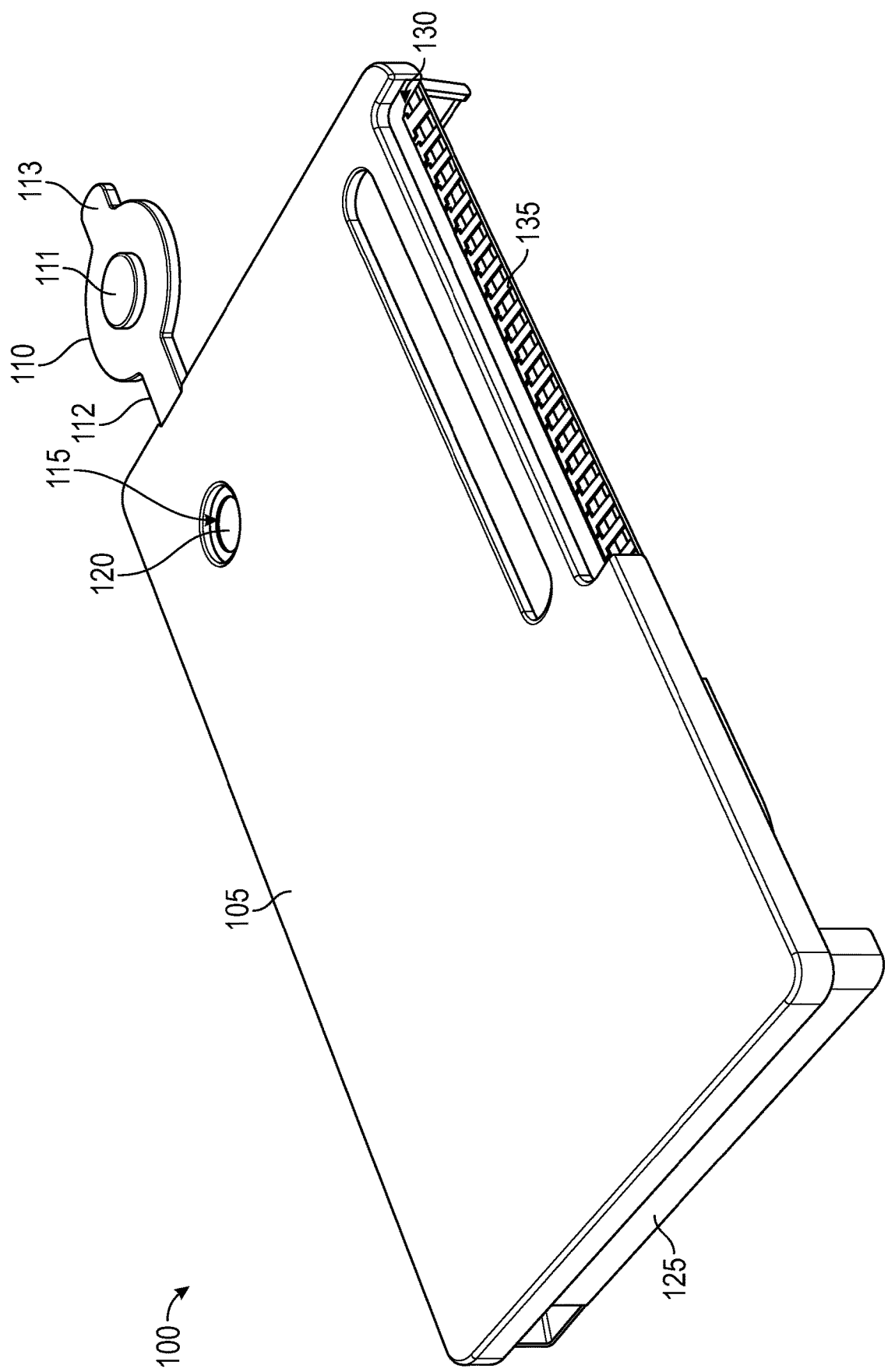
FIGS. 1A-1D depict an example cartridge for detection of a target.

Aspects of the disclosure herein concern the use of amplification and contactless electrical sensing to detect the presence of a target in a sample. Such a diagnostic platform may replace the complex optical systems and expensive fluorescent labels used for optical detection and the electrodes and electroactive agents used in existing electrochemical and FET techniques with common electronic components. In some aspects, the amplification can be isothermal. The platform described herein is inexpensive, robust, portable, and consumes less power than traditional diagnostic systems. In some aspects, the diagnostic platform is small enough to fit in the palm of a consumer's hand and capable of performing in the field, for example, a diagnosis in a doctor's office, in the home, in a location remote from a medical facility.

Many commercially available nucleic acid detection platforms utilize traditional PCR, thereby requiring temperature cycling, fluorescent labels and optical detection instrumentation. These factors result in expensive, lab-based instrumentation which employ delicate, vibration sensitive detectors, costly fluorescent markers, and have a large footprint. The equipment requires operation, and frequent calibration, by highly trained personnel.

These large, unwieldy platforms make routine use of conventional NAT challenging to use in the clinic, much less in the home. NAT remains a costly and slow strategy closely tied to centralized laboratory facilities. The presently disclosed technology, in contrast, avoids these challenges.

A hurdle to point of care ("POC") testing is the potential inhibition of amplification by interferents often encountered in crude, unprocessed clinical samples such as whole blood or mucus. The mitigation of amplification inhibitors may challenge the direct detection of target nucleic acids from clinically relevant biologic samples.

Traditional detection strategies commonly rely on fluorescence detection techniques. Such techniques may be complex, more expensive, and require precision optical systems. The present disclosure however, generally relies on electrical detection systems. Such electrical detection systems may leverage microelectronics that consume relatively low power and can be manufactured at a reduced cost due to high volume manufacturing. Thus, electrical detection of genomic material may transfer the advances of the computer industry to bioassay sensing.

Existing electronic methods for monitoring amplification may require the binding of an electrochemically active label or the selective binding of the amplified material to a surface. However, when used in real world clinical applications, these techniques often suffer from slow response times, biofouling of the electrode or binding surfaces resulting in poor signal to noise ratios, and limitations on the lifetime and reliability of the device. While potentially enabling great sensitivity, the use of electrochemical or field effect transistor "FET" detection adds a layer of complexity to the detection. This can result in more expensive and less robust strategies than POC and other consumer applications typically dictate. Accordingly, the need for additional diagnostic devices is manifest.

The platform disclosed herein relies on measurement of the change in electrical conductivity that occurs during nucleic acid amplification. In sum, during biochemical synthesis of DNA from nucleotide triphosphates, the number and the mobility of electrically charged molecules are altered. This, in turn, results in a change in the solution conductivity as amplification progresses. This change in solution electrical conductivity may be sensed using frequency-dependent capacitively coupled contactless conductivity detection ("fC$^4$D").

In some implementations, fC$^4$D uses a pair of electrodes in close proximity to, but not in contact with, a fluid disposed in an amplification chamber to measure the solution's electrical properties. The ability to measure the properties of the solution in this way, without direct contact, avoids the challenges of surface fouling common to other electrical measurement methods.

In some implementations, utilizing fC$^4$D, a high-frequency alternating current ("AC") signal is applied to the excitation electrode. This signal is capacitively coupled through the solution where it is detected at the signal electrode. By comparing the excitation signal with the signal at the signal electrode, the solution's conductivity can be determined.

Informed by high-resolution finite element models and empirical studies, specific tolerances of fC$^4$D based technology may achieve the optimal detection sensitivity and dynamic sensing range for particular implementations of the platform. Such calculated and empirically determined parameters of microfluidic dimensions, capacitive coupling characteristics, and the applied frequency can enable the determination of the effective parameters for detecting solution conductivity changes. In some embodiments, the parameters corresponding to optimal detection can be interdependent variables. According to the following equation, the measured impedance is a function of the solution resistance, capacitance and the applied frequency:

$$Z=R-(1/pi*f*C)*j$$

As the thickness of the electrode passivation layer increases, a parasitic capacitance due to this layer consequently increases. The optimal AC frequency with which to measure solution conductivity by fC$^4$D therefore can be chosen with respect to the capacitance of the passivation layer.

Overview of Example Cartridges, Readers, and Signal Processing

In some aspects, a system for detecting a target in a sample includes a removable fluidics cartridge that is couplable to a companion reader device. A user can apply a sample to the cartridge and then insert it into the reader device. The reader device is configured for performing the testing procedures using the cartridge and analyzing the test data to determine the presence, absence, or quantity of a target in the sample. For example, the cartridge can be provided with the desired agents, proteins, or other chemical matter for an amplification process by which a target initially present in the sample is amplified. Specifically, some cartridges can be provided with the desired chemical matter for nucleic acid testing, wherein genomic material in the sample is exponentially copied using a molecular amplification process, as described herein. The cartridge can also include a test well for containing the amplification process, where a test well refers to a well, chamber, channel, or other geometry configured for containing (or substantially containing) test fluid and constituents of the amplification process. The reader device may maintain a desired temperature or other test environment parameters for the cartridge to facilitate the amplification process, and can electronically monitor a test well of the cartridge throughout some or all of the amplification process. The reader device can thus gather signal data representing the impedance of the test well over time during the amplification process, and can analyze the impedance as described herein to ascertain the presence, absence, or quantity of the target in the sample. As an example, the amplification process can range from five minutes to sixty minutes, with some examples ranging from ten minutes to thirty minutes. Preferably, in some embodiments, the amplification products are detected while being suspended in the fluid within the wells such that the amplification products are not attached or sequestered to the wells or fixed or bound to probes, which are bound to the wells. In other embodiments, the amplification products are detected as they are attached or sequestered to the wells e.g., fixed or bound to probes, which are bound to the wells.

Such systems can beneficially provide target detection performable in a clinical setting or even the home of a user, rather than requiring the sample to be sent to a laboratory for amplification and analysis. In the clinical setting, this can avoid the delays of conventional nucleic acid testing thereby enabling clinicians to determine diagnoses within the typical timeframe of a patient's office visit. As such, the disclosed systems enable clinicians to develop treatment plans for patients during their initial office visit, rather than requiring the clinician to wait for hours or even days to receive test results back from a laboratory. For example, when a patient visits a clinic a nurse or other healthcare practitioner can collect a sample from the patient and begin testing using the described system. The system can provide the test result by the time the patient consults with their doctor or clinician to determine a treatment plan. Particularly when used to diagnose pathologies that progress quickly, the disclosed systems can avoid the delays associated with laboratory testing that can negatively impact the treatment and outcome of the patient.

As another benefit, the disclosed systems can be used outside of the clinical setting (e.g., in the field, in rural settings without easy access to an established healthcare clinic) to detect health conditions such as contagious diseases (e.g., ebola), thus enabling the appropriate personnel to take immediate action to prevent or mitigate the spread of a contagious disease. Similarly, the disclosed systems can be used in the field or at the site of a suspected hazardous contaminant (e.g., anthrax) to quickly determine whether a sample contains the hazardous contaminant, thus enabling the appropriate personnel to take immediate action to prevent or mitigate human exposure to the contaminant. Additionally, the disclosed systems can be used to detect contaminants in the blood or plasma supply or in the food industry. It will be appreciated that the disclosed systems can provide similar benefits in other scenarios in which real-time detection of a target enables more effective action than delayed detection through sending a sample to an off-site laboratory.

Another benefit of such systems is their use of low-cost, disposable single use cartridges together with a reusable reader device that can be used many times with different cartridges and/or for tests with different targets.

FIGS. 1A-ID depict an example cartridge 100 configured for detection of a target. As described herein, the target may be a viral target, bacterial target, antigen target, parasite target, microRNA target, or agricultural analyte. Some embodiments of the cartridge 100 can be configured for testing for a single target, while some embodiments of the cartridge 100 can be configured for testing for multiple targets.

FIG. 1A depicts the cartridge 100 with cover 105 provided over its base 125. In use, the cover 105 can operate to seal a provided sample within the cartridge 100, thereby preventing exposure of test operators to the sample and preventing any liquid from escaping into the electronics of an associated reader device. The cover 105 may be permanently affixed to the base 125 or may be removable in certain embodiments. The cover 105 can be formed from suitable materials such as plastic, and may be opaque as depicted or in other examples may be translucent or transparent.

The cover 105 includes an aperture 115 positioned over a sample introduction area 120 of the base 125. Over, as used here, refers to the aperture 115 being above the sample introduction area 120 when the cartridge 100 is viewed from a top-down perspective orthogonally to the planar surface of the cover 105 including the aperture 115. The cover 105 also includes a cap 110 configured to fluidically seal the aperture 115 before and after provision of a sample through the aperture 115. The cap 110 includes a cylindrical protrusion 111 that plugs the aperture 115 when the cap 110 is sealed with the aperture 115, a release tab 113 configured to assist a user in pulling the cap 110 out of the aperture 115 when the cap 110 is sealed with the aperture 115, and a hinge 112 configured to enable the cap 110 to be moved away from the aperture 115 and out of a sample provision path while keeping the cap 110 secured to the cover 105. It will be appreciated that other variations of the shape of the cap 110 can similarly be used to achieve the sealing of aperture 115, and in some embodiments the hinge 112 and/or release tab 113 can be modified or omitted. In the illustrated embodiment, the cover 105 and cap 110 are formed integrally as a single piece of material, however in other embodiments the cap 110 can be a separate structure from the cover 105.

In use, a user opens the cap 110 and applies a sample potentially containing the target(s) to the sample introduction area 120 of the base 125 through the aperture 115 in the cover. For example, a user can prick a finger and apply a whole blood sample to the sample introduction area 120, for example through a capillary. The cartridge 100 can be configured to accept one or more of liquid, semi-solid, and solid samples. After applying the sample, the user can close the cap 110 to seal the aperture 115. Beneficially, sealing the entrance to the fluid path of the base 125 allows the sample (and other liquids) to be moved through the fluid path of the base 125 to a test well. For example, the user can insert the sealed cartridge 100 containing the sample into a reader device as described herein, and the reader device can activate an optional pneumatic interface for moving the sample to the test well. The fluid path and test well are described in more detail with respect to FIGS. 1B and 1C, and an example reader device is described with respect to FIG. 6.

The cover 105 also includes a recess 130 for exposing an electrode interface 135 of the base 125, described in more detail below. In some embodiments, the cover 105 can include a movable flap or removable sheath for protecting the electrode interface 135 prior to use.

Figure 1B:
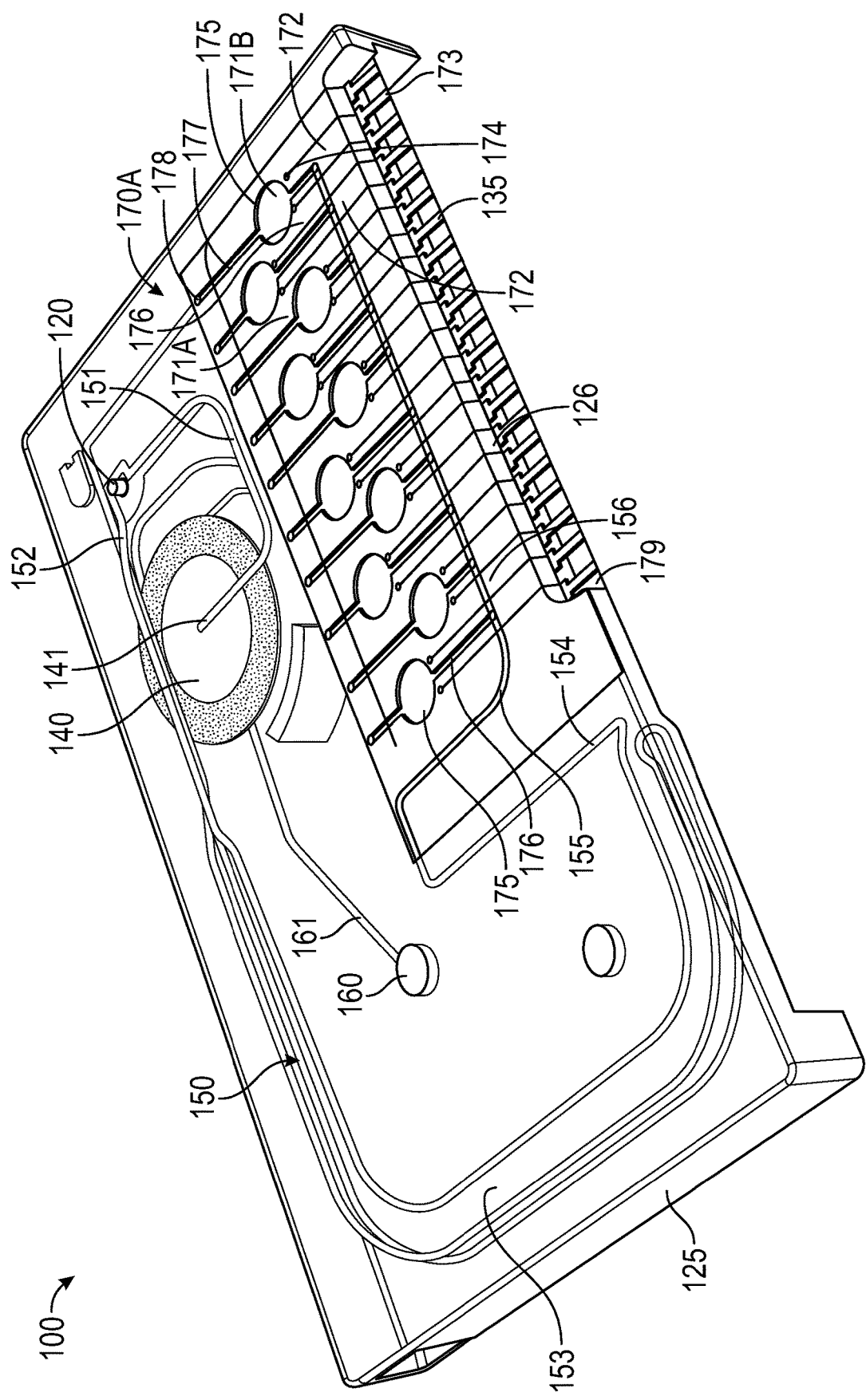

FIG. 1B depicts the cartridge 100 of FIG. 1A with the cover removed to expose the features of the base 125. The base 125 can be formed from a fluid impermeable material, for example injection molded or milled acrylic or plastic. The base 125 includes sample introduction area 120, a blister pack 140, pneumatic interface 160, test region 170A including test wells 175, and a fluid path 150 configured for mixing the applied sample with the liquids contained in the blister pack 140 and for carrying this mixed liquid to the test wells 175. It will be appreciated that the particular geometric configurations or relative arrangements of these features may be varied in other embodiments.

Blister pack 140 includes a film, for example a thermoformed plastic, forming a sealed chamber containing liquids for mixing with the applied sample. These liquids can include amplification reagents, buffer solutions, water, or other desired liquid constituents for the testing process. The particular selection and chemistry of these liquids can be tailored to a particular target or targets for which the cartridge 100 is designed to test. Some embodiments of the blister pack 140 can additionally include non-liquid compounds dissolved or suspended in the enclosed liquid. The blister pack 140 can be secured to the base 125, for example within a fluid-tight chamber having a pneumatic fluid path 161 leading into the chamber and aperture 141 leading out of the chamber into the fluid path 150. For example, a ring of pressure-sensitive adhesive disposed along the outer edge of one or both surfaces of the blister pack 140 can be used to secure the blister pack 140 in place.

In use, a user or reader device can mechanically actuate a sharp (e.g., a needle or other body having a sharp point) to puncture the blister pack 140 and release its liquid contents through aperture 141 and into the first segment 151 of the fluid path 150. The sharp may be incorporated into the cartridge 100, for example located in a chamber containing the blister pack 140 with the chamber in fluidic communication with the first segment 151 of the fluid path. As used herein, fluidic communication refers to the capability to transfer fluids (e.g., liquid gas gas). In another embodiment, the user or reader device can press on a lower surface of the blister pack 140 (though not illustrated, the lower surface opposes the surface visible in FIG. 1B) to push it upward into the sharp and puncture the blister pack 140. In other embodiments, the sharp can be omitted, and the blister pack 140 can be compressed by the user or reader device until the pressure of its liquid contents causes the blister pack 140 to rupture. Though described as a rupturable blister pack, other embodiments can implement mechanically openable chambers configured to similarly release the enclosed liquids into the first segment 151 of the fluid path 150.

As described above, after application of the sample the user seals the aperture 115 of the cover, thereby sealing the fluid path 150 within the cartridge 100. The pneumatic interface 160 is configured to provide a fluid such as air into the sealed fluid path 150 through the blister pack chamber in order to promote flow of fluid in the desired direction along the fluid path 150 to the test wells 175. Pneumatic interface 160 can be an aperture leading into and in fluidic communication with a pneumatic fluid path 161 that in turn leads into and is in fluidic communication with the blister pack 140 or the chamber containing the blister pack 140. In some embodiments, the pneumatic interface 160 can be a compressible one-way valve that forces ambient air into the pneumatic fluid path 161 when compressed and takes in ambient air from its environment as it decompresses. In such embodiments, repeated compression of the pneumatic interface 160 can force the fluid in the cartridge along the fluid path.

The fluid path 150 includes segments 151, 152, 153, 154, 155, and 156 as well as sample introduction area 120, test well 175, test well inlet path 176, and test well outlet path 177. The first segment 151 of the fluid path 150 leads from the blister pack 140 to the sample introduction area 120. The second segment 152 of the fluid path 150 leads from the sample introduction area 120 to the mixing chamber 153. The mixing chamber 153 is the third segment of the fluid path 150 and is widened relative to the second segment 152 and fourth segment 154. The fourth segment 154 of the fluid path 150 leads from the mixing chamber 153 to the fifth segment 155 of the fluid path. The fifth segment 155 of the fluid path 150 is formed in the test region 170A. The fifth segment 155 of the fluid path 150 leads into both the first test well inlet path 176 and into the sixth segments 156 of the fluid path 150. The sixth segments 156 of the fluid path 150 each form a continuation of the fluid path 150 between adjacent test well inlets until the last test well inlet 176. A test well inlet path 176 fluidically connects a test well 175 to the fluid path 150, and may closed off by a valve 174, for example to prevent cross-amplification between the test wells. A test well outlet path 177 leads from a test well 175 to an outlet aperture 178 that allows gas to escape from the test well 175 and out of the cartridge 100.

Even or homogenous mixing of the liquid from the blister pack 140 with the applied sample can yield more accurate test results in some embodiments. As such, the mixing chamber 153 is configured to promote even mixing of the liquid from the blister pack 140 with the applied sample, for example by including curved regions and/or a cross-sectional shape that promote turbulent flow rather than laminar flow of the liquids within the mixing chamber 153. Turbulent flow is a flow regime in fluid dynamics characterized by chaotic changes in pressure and flow velocity of a fluid. Turbulent flow is in contrast to laminar flow, which occurs when fluid flows in parallel layers, with no disruption between those layers.

The segments 151, 152, 153, 154 of the fluid path 150 can be entirely encased within the material of the base 125, or can have three surfaces formed from the material of the base 125 with the cover 105 forming an upper surface that seals these channels. The segments 155, 156 of the fluid path 150 and the test well inlet path 176 and test well outlet path 177 can be entirely encased within the material of the base 125, can have three surfaces formed from the material of the base 125 with the cover 105 forming an upper surface that seals these features, or can have two surfaces formed from the material of the base 125 with the circuit board 179 forming a lower surface of these features and the cover 105 forming an upper surface of these features.

Figure 1C:
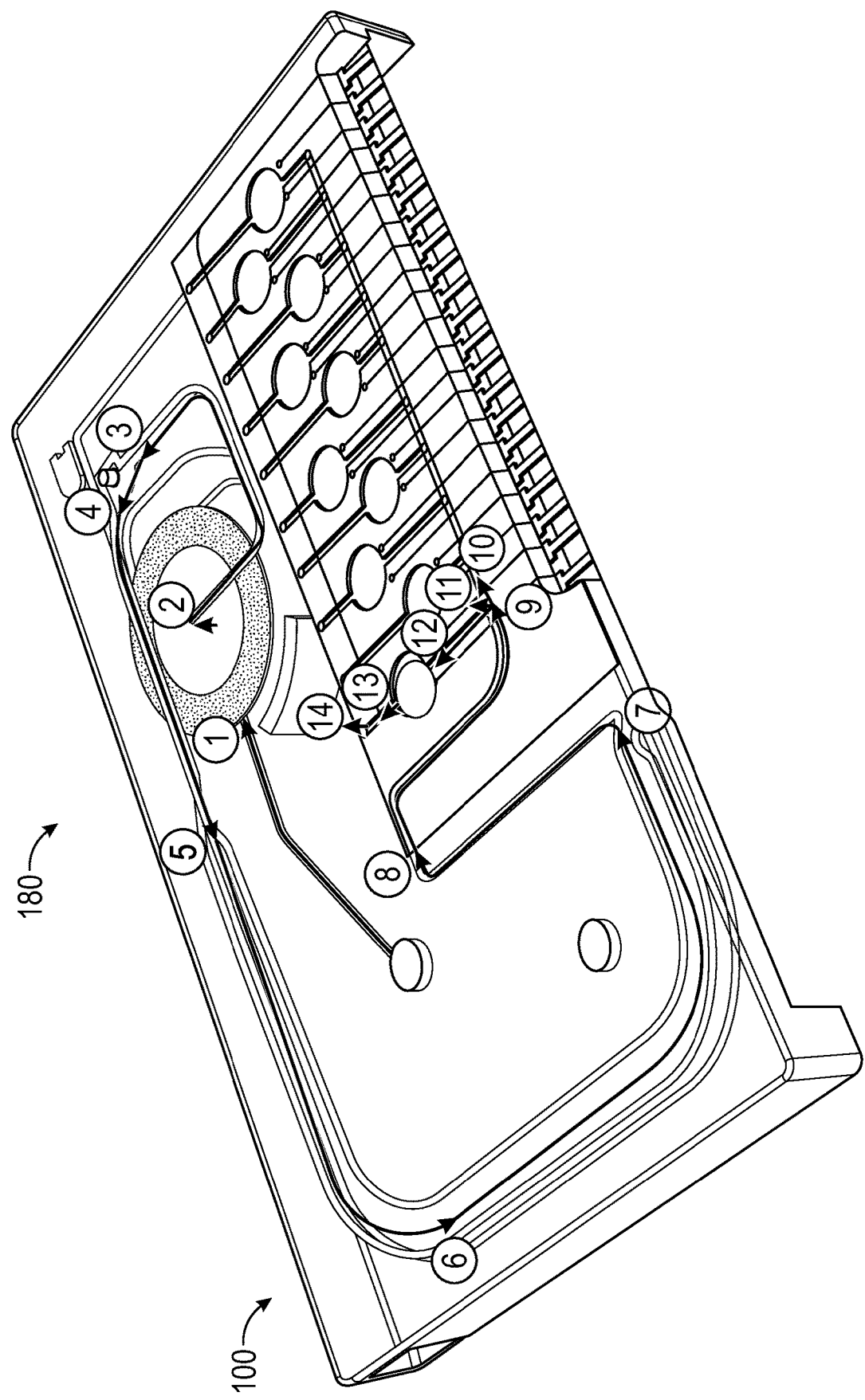

FIG. 1C illustrates the direction of flow along the fluid path 150 with encircled numbers shown as labels for certain points along the fluid path. The encircled numbers are discussed below as example steps of a progression of fluid 180 as it travels through the fluid path 150 within the cartridge 100, with each step including a directional arrow showing the direction of fluid travel at that step.

Prior to step (1), a user applies a sample at the sample introduction area 120. For clarity and simplicity of FIG. 1C, the components labeled with reference numbers in FIG. 1B are not labeled in FIG. 1C. Also prior to step (1), the blister pack 140 is ruptured so that its liquid contents are released from its previously sealed chamber.

At step (1), air or other fluid flowing from the pneumatic interface 160 travels in the illustrated direction along pneumatic fluid path 161 towards the ruptured blister pack 140.

At step (2), the liquid released from the ruptured blister pack 140 (referred to herein as a "master mix") travels through the aperture 141 in the illustrated direction and into the first segment 151 of the fluid path 150. The master mix continues flowing along the first segment 151 until step (3), when it enters the sample introduction area 120 and begins to carry the sample with itself further along the fluid path.

At step (4), the master mix and sample leave the sample introduction area 120 and flow along the second segment 152 of the fluid path 150 in the illustrated direction. The volume of the master mix can be pre-selected to completely or substantially completely flush the applied sample from the sample introduction area 120 and/or to at least fill the test wells 175 and their respective inlet paths 176.

At step (5), the master mix and sample flow in the illustrated direction into the entrance to the wider third segment 153 of the fluid path 150, and at step (6) the master mix and sample are mixed into a homogenous solution in which the sample is evenly distributed throughout the master mix. As described above, the third segment 153 includes curved segments and a planar mixing chamber configured to promote mixing of the master mix and the sample. The rate of fluid provided by the pneumatic interface 160 can be selected to further facilitate this mixing in some embodiments.

At step (7), the mixed master mix and sample (referred to as the "test fluid") leave the mixing chamber 153 and enter the fourth segment 154 of the fluid path 150 that leads into the test region 170A.

At step (8), the test fluid travels along the fifth segment 155 of the fluid path 150 in the illustrated direction through the test region 170A towards the test wells 175.

At step (9), the test fluid reaches the first test well inlet path 176 and its flow is directed along the three possible paths shown trifurcating from the arrow of the fluid path of step (9).

The path of step (10) shows the flow of the test fluid further along the segment 156 of the fluid path 150 to subsequent test well inlet paths 176. Optionally, the valve 174 at the test well inlet path 176 may be closed, preventing the flow of the test fluid to step (10).

The path of step (11) shows the optional flow of a gas portion of the test fluid through the valve 174. In some embodiments, the valve 174 can include a liquid impermeable, gas permeable filter to allow any gas present in the test fluid to vent through the valve 174 prior to entering the test well 175. In some embodiments the valve 174 may not be configured to vent gas.

The path of step (12) shows the direction of the flow of the test fluid into the test well 175. In some embodiments, the valve 174 can be closed to seal off the test well 175 upon occurrence of a predetermined trigger. The trigger can occur after a predetermined volume of liquid corresponding to the volume of at least the test well 175 (and additionally the inlet and outlet paths 176, 177) has flowed along the path of step (12). Another example of the valve closing trigger can occur after a predetermined amount of time has elapsed corresponding to the time expected for this volume of liquid to flow along the path of step (12). In another embodiment, the trigger can be the deactivation of the pneumatic interface 160, at which point fluid may begin to flow backward along the illustrated paths, causing cross-contamination of the amplification processes occurring in different test wells. In some embodiments, the depicted location of the valve 174 may instead be a gas outlet aperture optionally covered with a liquid impermeable, gas permeable filter, and the described valve can be located along the test well inlet path 176 or along the fluid path segment 156.

The path of step (13) shows the direction of the flow of the test fluid or a gas component thereof out of the test well 175 through the outlet path 177. The outlet path 177 can be a channel leading out of the test well 175, and the test fluid can be pushed into the outlet path 177 by the pressure provided by the pneumatic interface 160. In some embodiments, a liquid impermeable, gas permeable filter can be provided at the interface of the test well 175 and the outlet path 177 so that only a gas component of the test fluid flows through the outlet path 177.

At step (14), gas from the test fluid is vented from the cartridge 100 through the outlet aperture 178. Outlet aperture 178 can be covered by a liquid impermeable, gas permeable filter to allow gas to escape and prevent liquid from escaping the cartridge 100. Beneficially, allowing and facilitating the venting of gas from the test fluid can minimize the amount of gas that remains in the test well, maximizing the amount of liquid in the test well. As described below, minimizing the potential for gas bubbles to form in the path between electrodes can beneficially lead to more reliable signals and more accurate test results.

Returning to FIG. 1B, the test region 170A includes the segments 155, 156 of the fluid path 150, the test wells 175, the test well inlet paths 176, the test well outlet paths 177, the apertures/valves 176, 178, and a circuit board 179. The circuit board 179 includes the electrodes 171A, 171B of the test wells, the conductors 172 for carrying current or other electric signals, and the electrode interface 135. The electrode interface 135 includes contact pads 173; half of the contact pads 173 are configured for coupling an excitation electrode of a test well with a voltage or current source of a reader device and the other half of the contact pads 173 are configured for electrically coupling a signal electrode of the test well with a signal reading conductor of the test device. For clarity of FIG. 1B, only certain ones of the repeated features of the test region 170A are labeled with reference numbers.

The circuit board 179 can be a printed circuit board, for example a screen-printed or silkscreen printed circuit board having multiple layers. The circuit board 179 can be a printed onto a flexible plastic substrate or semiconductor substrate. The circuit board 179 can be formed at least partly from a separate material from the base 125 and secured to the underside of the base 125, with an overlying region 126 of the base 125 including the segments 155, 156 of the fluid path 150, the test wells 175, the test well inlets 176, the test well outlets 178, and the apertures/valves 176, 178. For example, the circuit board 179 can be a multilayered printed circuit board adhered, affixed, or laminated to the acrylic of the overlying region 126. The electrode interface 135 can extend beyond the edge of the overlying region 126. The test wells 175 can be formed as openings in the material of the overlying region 126 such that the electrodes 171A, 171B of the circuit board 179 are exposed within a well 175. As such, the electrodes 171A, 171B can be in direct contact with fluid that flows into the well 175. The circuit board 179 can be butter coated by having a resin on its upper surface in order to create a smooth, flat surface for the bottoms of the test wells.

The test wells 175 can be provided with solid dried constituents for the testing process, for example primers and proteins. The particular selection and chemistry of these dried constituents can be tailored to a particular target or targets for which the cartridge 100 is designed to test. The test wells 175 can be provided with the same or different dried constituents. These dried constituents can be hydrated with the liquid that flows into the test well (e.g., the liquid from the blister pack 140 mixed with the applied sample) and thus activated for the test procedure. Beneficially, providing the liquid constituents in the blister pack 140 separately from the dried solid constituents in the test wells 175 enables the cartridge 100 to be stored before use containing the components needed for the amplification process, while also delaying initiation of amplification until after the sample has been applied.

The test wells 175 are depicted as circular wells arranged in two rows at staggered distances from the electrode interface 135. The test wells 175 can be generally cylindrical, for example formed as circular openings in the material of the overlying region 126 and bounded by planar surfaces at their upper (e.g., cover 105 or a portion of the overlying region 126) and lower (e.g., circuit board 179) sides. Each test well 175 contains two electrodes 171A, 171B, with one electrode being an excitation electrode configured to apply current to the sample in the test well 175 and the other electrode being a signal electrode configured to detect current flowing from the excitation electrode through the liquid sample. In some embodiments, one or more test wells can be provided with a thermistor in place of the electrodes in order to provide for monitoring of the temperature of the fluid within the cartridge 100.

Each test well can be monitored independently of the other test wells, and thus each test well can constitute a different test. The depicted electrodes 171A, 171B within each test well are linear electrodes positioned parallel to one another. The depicted arrangement of the test wells 175 provides a compact test region 170A with access from the fluid path 150 to each test well 175. Some embodiments can include only a single test well, and various embodiments can include two or more test wells arranged in other configurations. Further, the shape of the test wells can be varied in other embodiments, and the electrode shapes can be any of the electrodes shown in FIGS. 4A-4G.

In some embodiments, gas bubbles within a test well 175, particularly if positioned along the current path between the electrodes 171A, 171B, can create noise in the signal picked up by the signal electrode. This noise can reduce the accuracy of test results determined based on the signal from the signal electrode. A desired high-quality signal may be obtained when only liquid is present along the current path or when minimal gas bubbles are present along the current path. As described above, any air initially present in the fluid flowing along the fluid path 150 can be pushed out through the outlet aperture 178. In addition, the electrodes 171A, 171B and/or test well 175 can be shaped to mitigate or prevent nucleation of the liquid sample in which air or gas bubbles form in the liquid sample and collect along the electrodes.

For example, the electrodes 171A, 171B are positioned at the bottom of the test well 175. This can allow any air or gas to rise to the top of the fluid in the test well and away from the path between the electrodes. As used herein, the bottom of the test well refers to the portion of the test well in which heavier liquid settles due to gravity, and the top of the test well refers to the portion of the test well in which lighter gas rises above the heavier liquids. Further, the electrodes 171A, 171B are positioned away from the perimeter or edges of the test well 175 which is a location at which bubble nucleation typically occurs.

Further, the electrodes 171A, 171B can be formed from a thin, flat layer of material that has minimal height relative to the underlying circuit board layer that forms the bottom of the test well. In some embodiments, the electrodes 171A, 171B can be formed using electrodeposition and patterning to form a thin layer of metal film, for example around 300 nm in height. This minimal height can help prevent or mitigate air bubbles from becoming trapped along the interface between the electrode and the underlying layer. In some embodiments, a layer of conductive material can be deposited on top of each electrodes to create a smoother transition between the edge of the electrode and the bottom of the test well. For example, a thin polymid layer (e.g., around 5 microns in height) can be deposited on top of the electrode or the circuit board can be butter coated. Additionally or alternatively, the electrodes can be positioned in grooves in the underlying layer with the grooves having a depth approximately equal to the height of the electrode. These and other suitable methods can achieve an electrode that is approximately flat or flush with the bottom surface of the well.

Beneficially, the above-described features can help to keep the electrodes 171A, 171B surrounded by liquid and prevent or reduce gas bubbles from becoming positioned along the current path between the electrodes 171A, 171B.

Figure 1D:
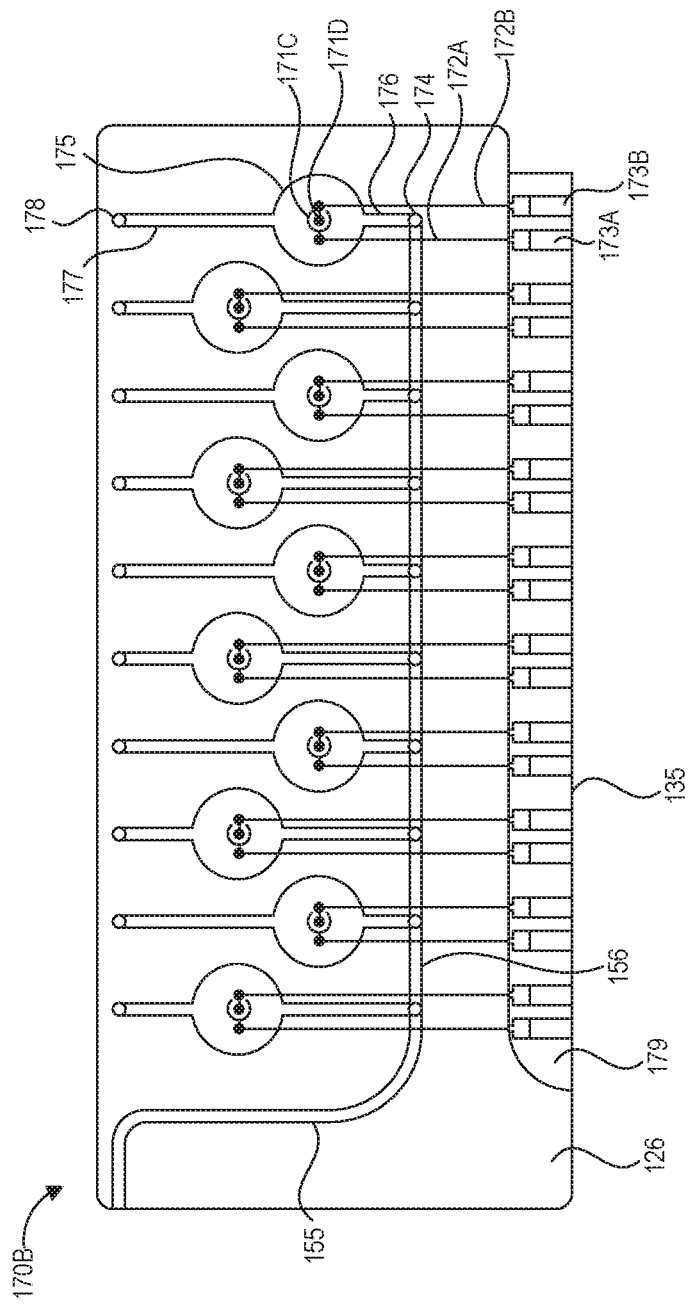

FIG. 1D is a line drawing depicting a top plan view of test region 170B of the cartridge 100. As with FIG. 1B, certain repeated features are labeled with reference numbers in only one location for simplicity and clarity of the drawing of FIG. 1D.

The test region 170B is an alternate embodiment of the test region 170A, with the difference between the two embodiments being a different electrode configuration within the test wells 175. In the embodiment of the test region 170B, the test wells are provided with annular electrodes 171C and 171D. With the linear electrodes 171A, 171B of the test region 170A, either electrode can be the excitation electrode or the signal electrode. In the embodiment of the test region 170B, the inner electrode 171D is the excitation electrode and the outer electrode 171C is the signal electrode.

The inner electrode 171D can be a disc or circular-shaped electrode coupled to the current providing conductor 172B, which is in turn coupled to a current providing pad 173 of the electrode interface 135 that transmits current (e.g., AC current at a specified frequency) to the inner electrode 171D from a reader device. The inner electrode 171D can be positioned in the center of the test well 175. The outer electrode 171C is a semicircular electrode formed concentrically around the inner electrode 171D and separated from the inner electrode 171D by a gap. A break in the semicircle of the outer electrode 171C occurs where a conductive lead connects the inner electrode 171D to the current providing conductor 172B. The outer electrode 171C is coupled to the current sensing conductor 172B, which is in turn coupled to a current sensing pad 173 of the electrode interface 135 that transmits the sensed current to the reader device.

The cartridge 100 of FIGS. 1A-1D provides a self-contained, easy to use device for performing an amplification-based test for a target, for example nucleic acid testing wherein genomic material in the sample is exponentially copied using a molecular amplification process. Beneficially, the user only needs to apply the sample and insert the cartridge 100 into a reader device in order to ascertain the result of the test in some embodiments, as the liquid and solid constituents of the amplification process are pre-provided within the cartridge and automatically mixed with the sample. In some embodiments, one or both of the cartridge or reader may include a heater and a controller configured to operate the heater to maintain the cartridge at the desired temperature for amplification. In some embodiments, one or both of the cartridge or reader may include a motor to impart vibrations to or otherwise agitate the cartridge to cause any trapped gas to rise to the top of the liquid and vent from the test wells.

Figure 2:
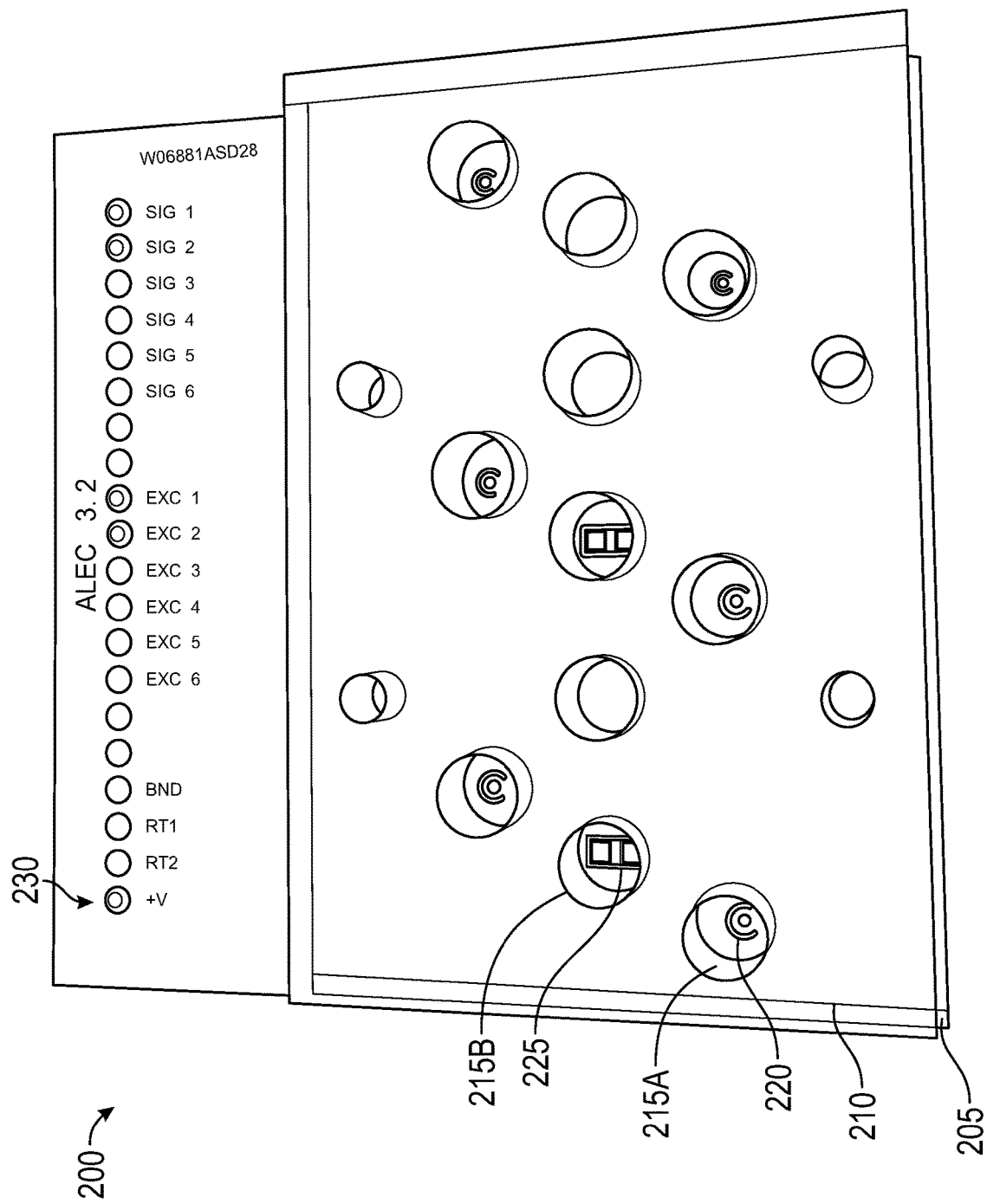
FIG. 2 depicts another example cartridge for detection of a target.

FIG. 2 depicts a photograph of another example cartridge 200 configured for detection of a target. The cartridge 200 was used to generate some of the test data described herein, and represents an alternate configuration of some of the components described with respect to the cartridge 100.

Cartridge 200 includes a printed circuit board layer 205 and an acrylic layer 210 overlying and adhered to a portion of the printed circuit board layer 205 using a pressure-sensitive adhesive. The acrylic layer 210 includes a number of test wells 215A and a number of temperature monitoring wells 215B formed as circular apertures extending through the height of the acrylic layer 210. The printed circuit board layer 205 can be formed similarly to the circuit board 179 described above, and includes a pair of electrodes 220 positioned within each test well 215A and a thermistor 225 positioned within each temperature monitoring well 215B. The electrodes 220 and thermistors 225 are each coupled to conductors terminating at a number of leads 230 of the printed circuit board. As illustrated, six of the leads are labeled "SIG" followed by a number 1-6 for the signal electrodes, six of the leads are labeled "EXC" followed by a number 1-6 for the excitation electrodes, and two leads are labeled RT1 and RT2 for the thermistors.

During some of the tests described herein, the following example protocol was followed. First, the user filled the wells 215A with a test fluid and capped the fluid with mineral oil. The test fluid can have no primer control, allowing for a definitive negative control as there is no primer to cause amplification.

Next, the user heated the cartridge 200 to 65 degrees Celsius for ten minutes to expand any trapped air in the test fluid and cause it to rise as bubbles to the top of the liquid. During this initial heating, bubbles formed in the wells 215A.

At the next step, the user scraped the bubbles from the surface of the liquid in the wells 215A using a pipette or other tool. As described above, elimination of air bubbles can promote more accurate test results.

After eliminating the bubbles, the user allowed the cartridge 200 to cool to room temperature. Next, the user injected loop mediated isothermal amplification (LAMP) positive control (PC) into the bottom of each of the test wells 215A, placed the cartridge 200 on a heat block, and began performing the LAMP tests. The signals detected from the signal electrodes were analyzed as described herein to identify a positive signal cliff.

Figure 3A:
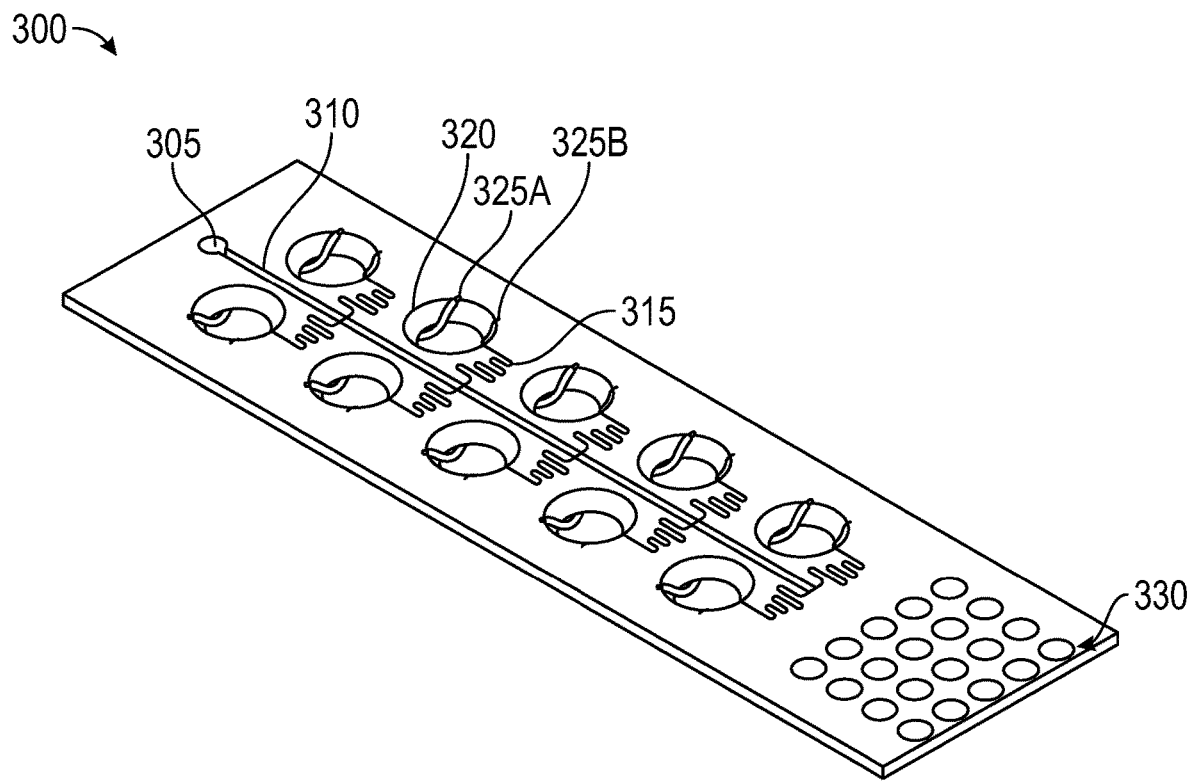
FIGS. 3A and 3B depict another example cartridge for detection of a target.
Figure 3B:
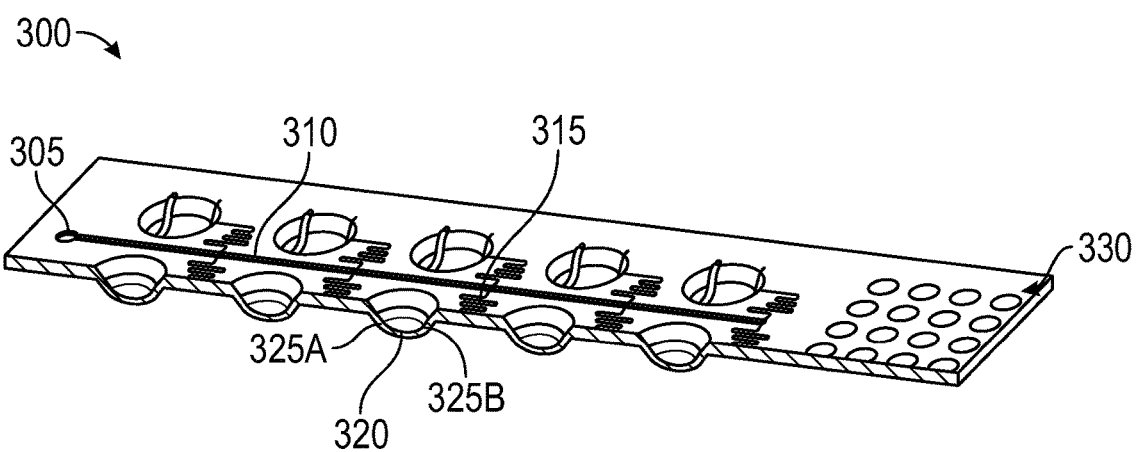

FIGS. 3A and 3B depict another example cartridge 300 configured for detection of a target. FIG. 3A depicts a top, front, and left perspective view of the cartridge 300 and FIG. 3B depicts a perspective cutaway view showing the contour of the wells 320 of the cartridge 300. The cartridge 300 represents an alternate configuration of some of the components described with respect to the cartridge 100.

The cartridge 300 includes sample introduction area 305, central channel 310, test wells 320, branches 315 fluidically connecting the test wells 320 to the central channel 310, electrodes 325A, 325B positioned within each test well 320, and an electrode interface 320 including contact pads coupled to conductors that are in turn coupled to respective ones of the electrodes 325A, 325B and configured to receive or send signals from or to a reader device. As shown in FIG. 3B, the wells 320 can have a curved bottom surface such that each well is generally hemispherical. The cartridge 300 is depicted as having an open top for purposes of revealing its interior components, however in use a cover or other upper layer can be provided to seal the fluid pathways of the cartridge 300. The cover can include vents to allow gas to escape from the cartridge 300, for example provided with liquid impermeable gas permeable filters, as described above with respect to FIGS. 1A-1D.

The fluid sample applied at the sample introduction area 305 flows down the central channel 310, for example in response to pressure from a reader device injecting the sample into the cartridge 300 through a port coupled above the sample introduction area 305. Such a reader device can be provided with a set of cartridges in some embodiments, for example positioned in a stack, and can provide the same or different sample to each cartridge. The fluid sample can be predominantly liquid with dissolved or trapped gas (e.g., air bubbles). The fluid can flow from the central channel 310 through the branched channels 315 into the test wells 320. The branched channels 315 can inlet into the top of the well and can be tortuous (e.g., including a number of turns having small radii) in order to prevent or mitigate backflow of fluid that could lead to cross-contamination of the amplification processes between the various wells.

FIGS. 4A-4G depict various examples of electrode configurations that can be used in a test well of the cartridges of FIGS. 1A-3B or in the test well or channel of another suitable target detection cartridge as described herein. The test wells shown in FIGS. 4A-4G are depicted as circular, however the electrodes can be used in test wells of other geometries in other examples. Unless otherwise noted, the solid circles in FIGS. 4A-4G represent contacts between the disclosed electrodes and conductors leading to or from the electrode. "Width" as used below refers to a dimension along the horizontal direction of the page of FIGS. 4A-4G, and "height" as used below refers to a dimension along the vertical direction of the page of FIGS. 4A-4G. Though depicted in a particular orientation, the illustrated electrodes of FIGS. 4A-4G can be rotated in other implementations. Further, the disclosed example dimensions represent certain potential implementations of the electrode configurations 400A-400G, and variations can have different dimensions that follow the same ratios between the provided example dimensions. The electrodes shown in FIGS. 4A-4G can be made from suitable materials including platinum, gold, steel, or tin. In experimental testing, tin and platinum performed similarly and suitable for certain test setups and test targets.

Figure 4A:
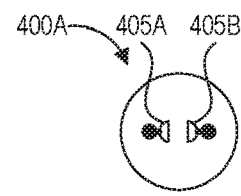
FIGS. 4A-4G depict various examples of electrodes that can be used in a test well of the cartridges of FIGS. 1A-3B or in the test well or channel of another suitable target detection cartridge as described herein.

FIG. 4A depicts a first electrode configuration 400A wherein the first and second electrodes 405A, 405B are each formed as a semicircular perimeter. The straight edge of the first electrode 405A is positioned adjacent to the straight edge of the second electrode 405B and separated by a gap along the width of the configuration 400A. The gap is larger than the radius of the semicircle of the electrodes. Thus, the first and second electrodes 405A, 405B are positioned as mirrored semicircular perimeters. In one example of the first electrode configuration 400A, the gap between the closest portions of the first and second electrodes 405A, 405B spans approximately 26.369 mm, the height (along the straight edge) of each of the electrodes 405A, 405B is approximately 25.399 mm, and the radius of the semicircle of each of the electrodes 405A, 405B is approximately 12.703 mm.

Figure 4B:
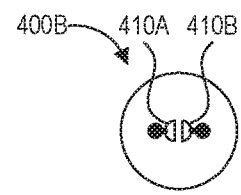

FIG. 4B depicts a second electrode configuration 400B. Similar to the first electrode configuration 400A, the first and second electrodes 410A, 410B of the second electrode configuration 400B are each formed as a semicircular perimeter and are positioned as mirrored semicircles with their straight edges facing one another. The first and second electrodes 410A, 410B of the second electrode configuration 400B can be the same size as the first and second electrodes 405A, 405B of the first configuration 400A. In the second electrode configuration 400B, the gap along the width of the configuration 400B between the first and second electrodes 410A, 410B is smaller than in the first configuration 400A, and the gap is smaller than the radius of the semicircle of the electrodes 410A, 410B. In one example of the second electrode configuration 400B, the gap between the closest portions of the first and second electrodes 410A, 410B spans approximately 10.158 mm, the height (along the straight edge) of each of the electrodes 410A, 410B is approximately 25.399 mm, and the radius of the semicircle of each of the electrodes 410A, 410B is approximately 12.703 mm.

Figure 4C:
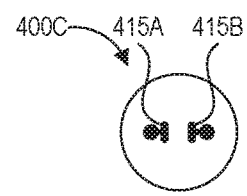

FIG. 4C depicts a third electrode configuration 400C having first and second linear electrodes 415A, 415B separated by a gap along the width of the configuration 400C, where the gap is approximately equal to the height of the electrodes 415A, 415B. The width of the electrodes 415A, 415B is approximately one half to one third of the height of the electrodes. In one example of the third electrode configuration 400C, the gap between the closest portions of the first and second electrodes 415A, 415B spans approximately 25.399 mm, the height of each of the electrodes 415A, 415B is also approximately 25.399 mm, and the width of each of the electrodes 415A, 415B is approximately 10.158 mm. The ends of the first and second electrodes 415A, 415B can be radiused, for example having a radius of around 5.078 mm.

Figure 4D:
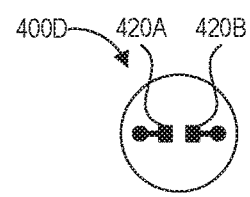

FIG. 4D depicts a fourth electrode configuration 400D having first and second rectangular electrodes 420A, 420B separated by a gap along the width of the configuration 400D, where the gap is approximately equal to the width of the electrodes 420A, 420B. In one example of the fourth electrode configuration 400D, the gap between the closest portions of the first and second electrodes 420A, 420B spans approximately 20.325 mm, the height of each of the electrodes 420A, 420B is also approximately 23.496 mm, and the width of each of the electrodes 420A, 420B is approximately 17.777 mm.

Figure 4E:
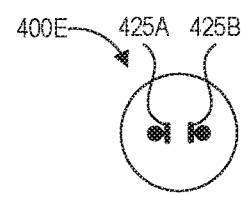

FIG. 4E depicts a fifth electrode configuration 400E having first and second linear electrodes 425A, 425B separated by a gap along the width of the configuration 400E, where the gap is approximately equal to the height of the electrodes 425A, 425B. The fifth electrode configuration 400E is similar to the third electrode configuration 400C, with the width of the electrodes 425A, 425B reduced to around one half to two thirds of the width of the electrodes 415A, 415B while having the same height. In one example of the fifth electrode configuration 400E, the gap between the closest portions of the first and second electrodes 425A, 425B spans approximately 25.399 mm, the height of each of the electrodes 425A, 425B is also approximately 25.399 mm, and the width of each of the electrodes 425A, 425B is approximately 5.078 mm. The ends of the first and second electrodes 425A, 425B can be radiused, for example having a radius of around 2.542 mm.

Figure 4F:
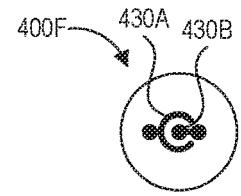

FIG. 4F depicts a sixth electrode configuration 400F having concentric annular electrodes 430A, 430B. The sixth electrode configuration 400F is the configuration shown in the test wells 175 of FIG. 1D. The inner electrode 430B can be a disc or circular-shaped electrode and can be positioned in the center of the test well. The outer electrode 430A can be a semicircular electrode formed concentrically around the inner electrode 430B and separated from the inner electrode 430B by a gap. In the sixth electrode configuration 400F, the gap is approximately equal to the radius of the inner electrode 430B. A break in the semicircle of the outer electrode 430A occurs where a conductive lead connects the inner electrode 430B to the current providing conductor. In one example of the sixth electrode configuration 400F, the gap between the inner edge of the annular first electrode 430A and the outer perimeter of the circular second electrode 430B spans approximately 11.430 mm, the radius of the circular second electrode 430B is approximately 17.777 mm, and the thickness of the annulus of the annular first electrode 430A is approximately 5.080 mm. The ends of the first electrode 430A can be radiused, for example having a radius of around 2.555 mm, and the gap between the open ends of the annulus of the first electrode 435A can be around 28.886 mm from vertex to vertex.

Figure 4G:
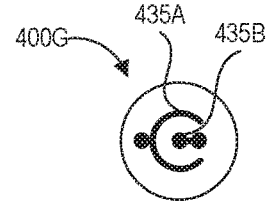

FIG. 4G depicts a seventh electrode configuration 400G having concentric annular electrodes 435A, 435B. Similar to the embodiment of FIG. 4F, the inner electrode 435B can be a disc or circular-shaped electrode having the same radius as inner electrode 430B and can be positioned in the center of the test well. The outer electrode 435A can be a semicircular electrode formed concentrically around the inner electrode 435A and separated from the inner electrode 435A by a gap. In the seventh electrode configuration 400G, the gap is greater than the radius of the inner electrode 435B, for example two to three times greater. Correspondingly, the outer electrode 435B has a larger radius than the outer electrode 430B. In one example of the seventh electrode configuration 400G, the gap between the inner edge of the annular first electrode 435A and the outer perimeter of the circular second electrode 435B spans approximately 24.131 mm, the radius of the circular second electrode 435B is approximately 17.777 mm, and the thickness of the annulus of the annular first electrode 435A is approximately 5.080 mm. The ends of the first electrode 435A can be radiused, for example having a radius of around 2.555 mm, and the gap between the open ends of the annulus of the first electrode 435A can be around 46.846 mm from vertex to vertex.

In the embodiments of FIGS. 4A-4E, either electrode can be used as the excitation electrode and the other electrode can be used as the signal electrode. In the embodiments of FIGS. 4F and 4G, the inner electrode 430B, 435B is configured to be used as the excitation electrode (e.g., coupled to a current source) and the outer electrode 430A, 435A is configured to be used as the signal electrode (e.g., provides its signal to a memory or processor). In some example tests, the sixth electrode configuration 400F exhibited the best performance of the configurations shown in FIGS. 4A-4G.

Figure 5A:
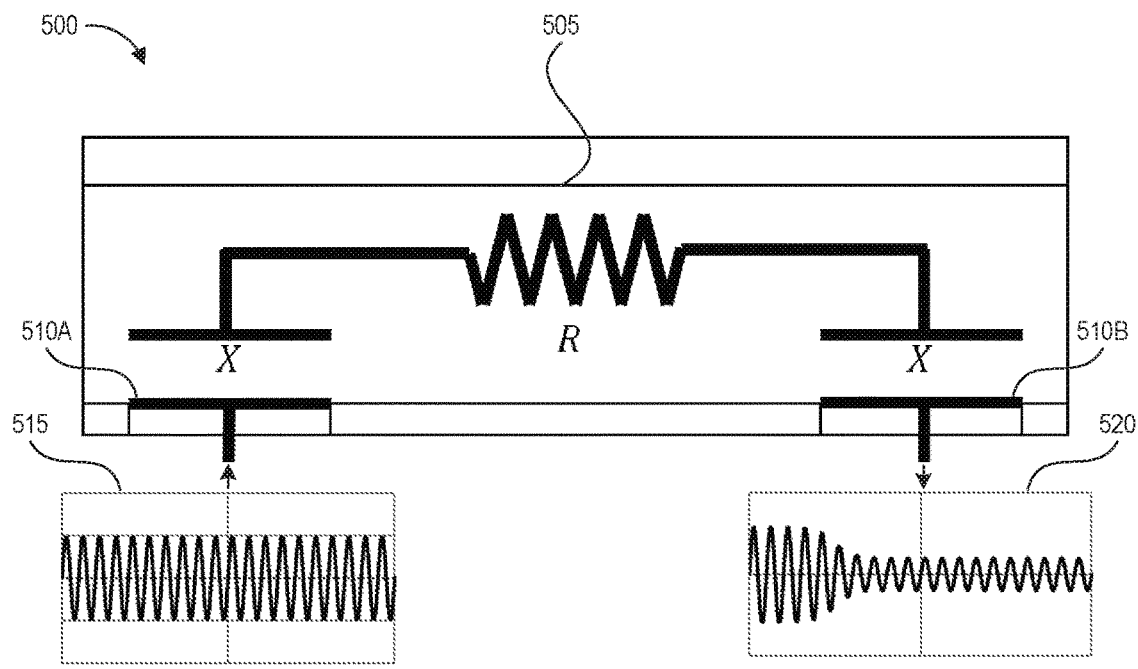
FIG. 5A depicts a first electrode or excitation electrode and a second electrode or signal electrode that may be spaced apart from one another within a test well of the cartridges of FIGS. 1A-3B or in the test well or channel of another suitable target detection cartridge as described herein.

FIG. 5A depicts a first electrode or excitation electrode and a second electrode or signal electrode that may be spaced apart from one another within a test well of the cartridges of FIGS. 1A-3B or in the test well or channel of another suitable target detection cartridge as described herein.

The formation of an aggregate, nucleic acid complex, or polymer, for example during an amplification process in the test wells of cartridges of FIGS. 1A-3B, can affect waveform characteristics of one or more electrical signals that are sent through a channel. As shown in FIG. 5A, a first electrode or excitation electrode 510A is spaced apart from a second electrode or sensing electrode 510B within test well 505. The test well 505 can contain a test solution undergoing an amplification process. During some of all of that process, an excitation voltage 515 can be provided to the excitation electrode 510A, from which the excitation voltage 515 is transmitted into the fluid (preferably all or substantially all liquid) within the well 505.

After passage through and attenuation by the liquid sample (represented schematically by the resistance R and reactance X), the attenuated excitation voltage is sensed or detected at the sensing electrode 510B. The fluid acts as a resistor R in series with the excitation electrode 510A and the sensing electrode 510B. The fluid also acts as in series capacitor(s), shown by the reactance X. The raw sensed signal during some or all of the duration of a test can be represented over time as a sinusoidal curve with varying amplitudes, similar to that shown in plot 520.

The excitation voltage 515 can be an alternating current at a predetermined drive frequency. The particular frequency selected can depend for example upon the particular target sought to be detected, the medium of the test sample, the chemical makeup of the amplification process constituents, the temperature of the amplification process, and/or the excitation voltage. In some embodiments of the cartridges of FIGS. 1A-3B, the excitation drive frequency can be between 1 kHz and 10 kHz at as low an excitation voltage as possible. As one example, in tests performed to identify a target of H. Influienza ($10^6$ copies/reaction) spiked into 5% whole blood, excitation sensor drive frequency was varied from 100 Hz to 100,000 Hz at 0.15 Volts. These tests revealed that the desired "signal cliff," an artifact in a portion of the signal indicative of a positive test sample described in more detail below, becomes more easily detectable below 100 Hz and is most easily detectable between 1 kHz and 10 kHz. Further, with frequencies in the range between 1 kHz and 10 kHz, the signal cliff advantageously could be identified before 12 minutes of test time had elapsed. Beneficially, faster identification of the signal cliff can result in shorter test times, in turn resulting in quicker provision of test results and the ability to perform more tests per day. At frequencies lower than 1 kHz, the reactance component of the signal (in which the signal cliff may be found in a positive sample) decreased monotonically. The sensor drive frequency can be similarly fine-tuned for other tests to optimize performance, that is, to optimize the detectability of a signal cliff. Detectability of a signal cliff refers to the ability to consistently differentiate between a positive sample and a negative sample.

Figure 5B:
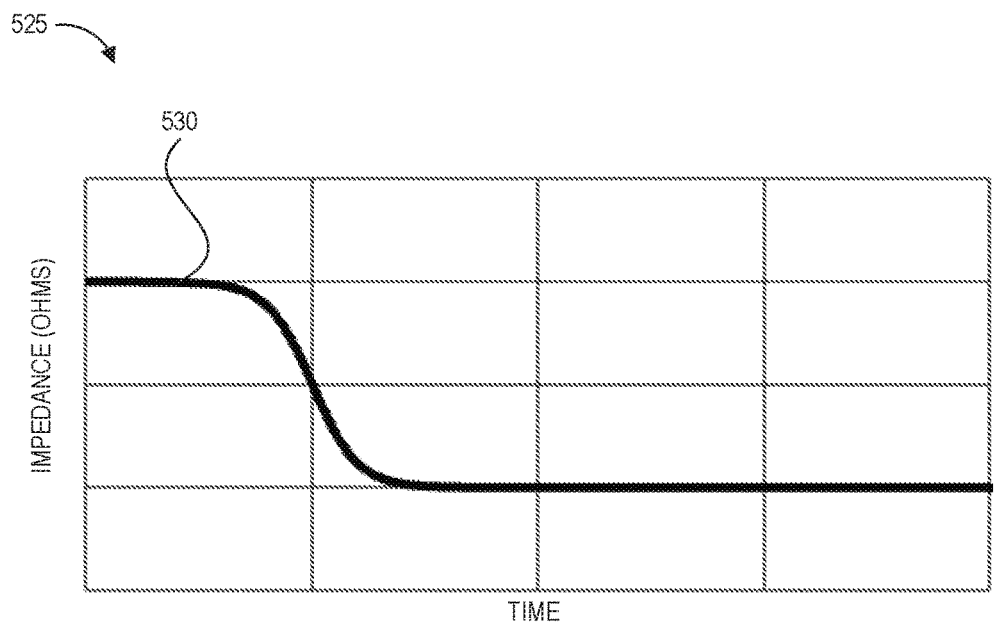
FIG. 5B depicts an example signal that can be extracted from the signal electrode of FIG. 5A.

FIG. 5B depicts an example plot 525 showing an impedance signal 530 that can be extracted from the raw signal 520 provided by the sensing electrode 510B. The impedance signal 530 represents the electrical impedance Z of the test well over time. The impedance Z can be represented by a Cartesian complex number equation as follows:

$$Z=R+jX$$

where R represents the resistance of the test well and is the real part of the above equation and the X represents the reactance of the test well and is the imaginary part of the above equation (denoted by j). Thus, the impedance of the test well can be parsed into two components, the resistance R and the reactance X.

Initially, the value of the resistance R can be determined by taking a baseline measurement of the test well prior to or at the outset of the amplification process. Although the resistance of the test fluid can drift away from this baseline value throughout the duration of the test, the current sensed by the sensing electrode 510B due to the resistance of the test fluid can be in phase with the signal provided through the excitation electrode 510A. Thus, changes or drift in the resistance can be identified by values of the in phase component of the signal 520 over time. The reactance can arise from the effect of inductance in the test fluid, capacitance in the test fluid, or both; this effect can cause the fluid to retain current (e.g., electrons provided by excitation electrode 510A) temporarily. After some time this retained current flows out of the test fluid into the sensing electrode 510B. Due to this delay, the current sensed by the sensing electrode 510B due to the reactance of the test fluid can be out of phase with the current sensed from the resistance of the test fluid. Thus, values of the reactance of the test fluid can be identified by values of the out of phase component of the signal 520 over time. The reactance can fluctuate throughout the duration of the test based on changes to the chemical constituents of the test fluid due to the amplification process. The signal cliff (e.g., a rise or drop in the reactance at or greater than a threshold rate or magnitude and/or during a predetermined window of time) indicative of a positive sample can be found in the reactance X.

During a test, the excitation electrode 510A can be sinusoidally excited with some amplitude and voltage. The excitation electrode 510A is in series with the test liquid in the well, which can be considered as a resistor R. The resistor (e.g., the test fluid) and electrode form a voltage divider, which has a voltage determined by the ratio of the resistor and electrode chemistry/impedances. The resulting voltage waveform sensed at the sensing electrode 510B represents the complex impedance signal 530. In some embodiments, a curve such as the impedance signal 530 may not be generated, but rather the raw sensed signal 520 can be parsed into its resistance and reactance components as described herein. The impedance signal 530 is provided as an example representation of a combined curve representing both the resistance of the test fluid and the reactance of the test fluid over time. The complex impedance signal 530 can be interpreted as a quadrature-modulated waveform (e.g., a combination of an in-phase waveform resulting from the resistance of the test fluid and an out-of-phase waveform resulting from the reactance of the test fluid), where the in-phase and out-of-phase components change on a timescale much greater than the modulation frequency. The in-phase waveform is in-phase with the composite waveform of the complex impedance. Some implementations can use a synchronous detector, for example having multipliers and low pass filters implemented in a field programmable gate array (FPGA), to extract the in-phase and out-of-phase components from the raw signal 520 and compute their amplitude and phase.

In order to parse the impedance signal 530 (or the raw sensed signal 520) into its constituent resistance and reactance components, the voltage waveform 520 at the sensing electrode 510B is sampled faster than its Nyquist frequency (e.g., two times the highest frequency of the excitation voltage) and then decomposed into an in-phase component (resistance) and an out-of-phase component (reactance). The in-phase and out-of-phase voltage components can be computed using the known series resistance (e.g., the value of R) to calculate the real component of the impedance (the resistance) and the imaginary component of the impedance (the reactance).

Figure 5C:
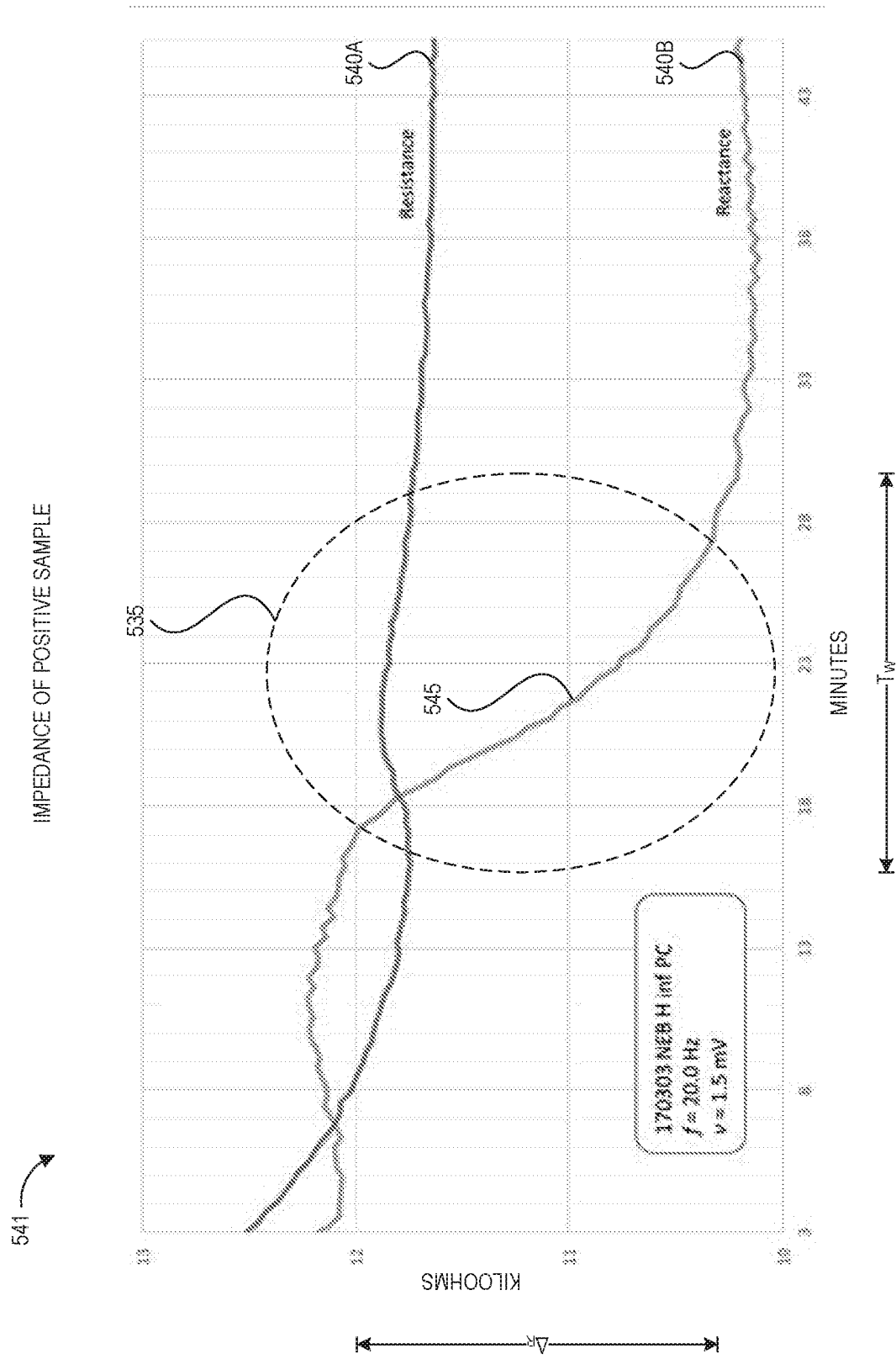
FIG. 5C depicts the resistance and reactance components extracted from a signal as shown in FIG. 5B generated based on an example positive test.

FIG. 5C depicts a plot 541 of the resistance 540A and reactance components 540B over time (t=3 minutes to t=45 minutes) extracted from a raw signal 520 generated based on an example positive test. As illustrated, the signal cliff 545 represents a change $\Delta_R$ in the reactance 540B during a particular window of time $T_W$. The signal cliff 545 indicates a positive sample. At times occurring prior to the signal cliff 545, the reactance curve 540B is relatively flat or stable, and again after the signal cliff 545 the reactance curve 540B is relatively flat or stable. Thus, in this embodiment the signal cliff 545 for the particular test parameters represented by the plot 541 occurs as a drop of $\Delta_R$ in the expected region 535.

The magnitude of the change $\Delta_R$ in the reactance that corresponds to a positive sample signal cliff 545, as well as the position and/or duration of the particular window of time $T_W$ at which the signal cliff 545 is expected to occur, can vary depending on a number of parameters of the test. These parameters include the particular target of the test (e.g., the rate at which that target amplifies), the frequency of the excitation voltage, the configuration of the excitation and sensor electrodes (e.g., their individual shapes and dimensions, the gap separating the electrodes, and the material of the electrodes), the sampling rate, the quantity of amplification agents provided at the start of the test, the temperature of the amplification process, and the amount of target present in the sample. In some embodiments, the expected characteristics of a signal cliff of a positive sample, predetermined for example through experimentation, can be used for differentiating between positive samples and negative samples. In some embodiments, the expected characteristics of a signal cliff can be used for determining the severity or progress of a medical condition, for example via correlations between particular signal cliff characteristics and particular initial quantities of the target in the sample. The predetermined expected characteristics can be provided to, stored by, and then accessed during test result determination by a reader device configured to receive signals from the sensing electrode(s) of a test cartridge.

For a given test, the expected magnitude of the change $\Delta_R$ in the reactance and the expected window of time $T_W$ of a signal cliff 545 for a positive sample can be determined experimentally based on monitoring and analyzing the reactance curves generated by positive control samples (and optionally negative control samples). In some embodiments, the test parameters influencing the signal cliff can be varied and fine-tuned to identify the parameters that correspond to an accurately distinguishable signal cliff. A reader and cartridge as described herein can be configured to match the tested configuration and provided with expected signal cliff characteristics for that test.

For example, in a set of experimental tests for *H. influenza*, the test fluid initially included amplification primers and 1,000,000 added target copies, the excitation voltage was 200 mV P2P, the test parameters included a 10 kHz sweep start and a 10 MHz sweep stop for the frequency of the excitation current, and close and far electrode gaps were configured at 2.55 mm and 5 mm respectively. The amplification temperature was set to 65.5 degrees Celcius, and the two electrode setups (one for each of the close and far gaps) included platinum electrodes. At low frequencies (10 kHz-100 kHz), detectable signal cliffs were identified beginning around 23 minutes into amplification around 10 kHz and around 30 minutes around 100 kHz using the 5 mm gap electrode configuration, with the magnitude of change in reactance being around 3.5-4 Ohms at 10 kHz and dropping to around 3.25-3.5 Ohms at 100 kHz. At low frequencies (10 kHz-100 kHz), detectable signal cliffs were identified beginning around 25 minutes into amplification around 10 kHz and around 30 minutes around 100 kHz using the 2.5 mm gap electrode configuration, with the magnitude of change in reactance being around 3.5-4 Ohms. At higher frequencies, the drop in reactance of the signal cliff decreased, and the time at which these smaller signal cliffs were identified was shifted to later in the amplification process. Accordingly, in this example a test well in a test cartridge may be configured with the 5 mm gap electrodes and a reader device may be configured to provide 10 kHz excitation current to the test cartridge during amplification. The reader device can be provided with instructions to provide this current and monitor the resulting reactance of the test well throughout amplification or for a window of time around the expected signal cliff time (here, 23 minutes), for example between 20 and 35 minutes. The reader device can also be provided with instructions to identify a positive sample based on the reactance exhibiting around a 3.5-4 Ohm change around 23 minutes into amplification, or within the window of time around the expected signal cliff time.

Once identified, the values for $\Delta_R$ and $T_W$ can be provided to reader devices for use in distinguishing between positive and negative samples for that particular test. In some examples, such devices can determine whether the reactance curve 540B has the required value and/or slope at the identified window of time $T_W$ to correspond to the signal cliff. In other embodiments, the reader device can analyze the shape of the reactance curve over time to determine whether it contains a signal cliff. In some embodiments, a reader can modify its testing procedures based on the identified window of time $T_W$ at which the signal cliff 545 is expected to occur, for example by only providing the excitation voltage and monitoring the resultant signal within this window, advantageously conserving power and processing resources compared to continuous monitoring during an entire test time.

Figure 5D:
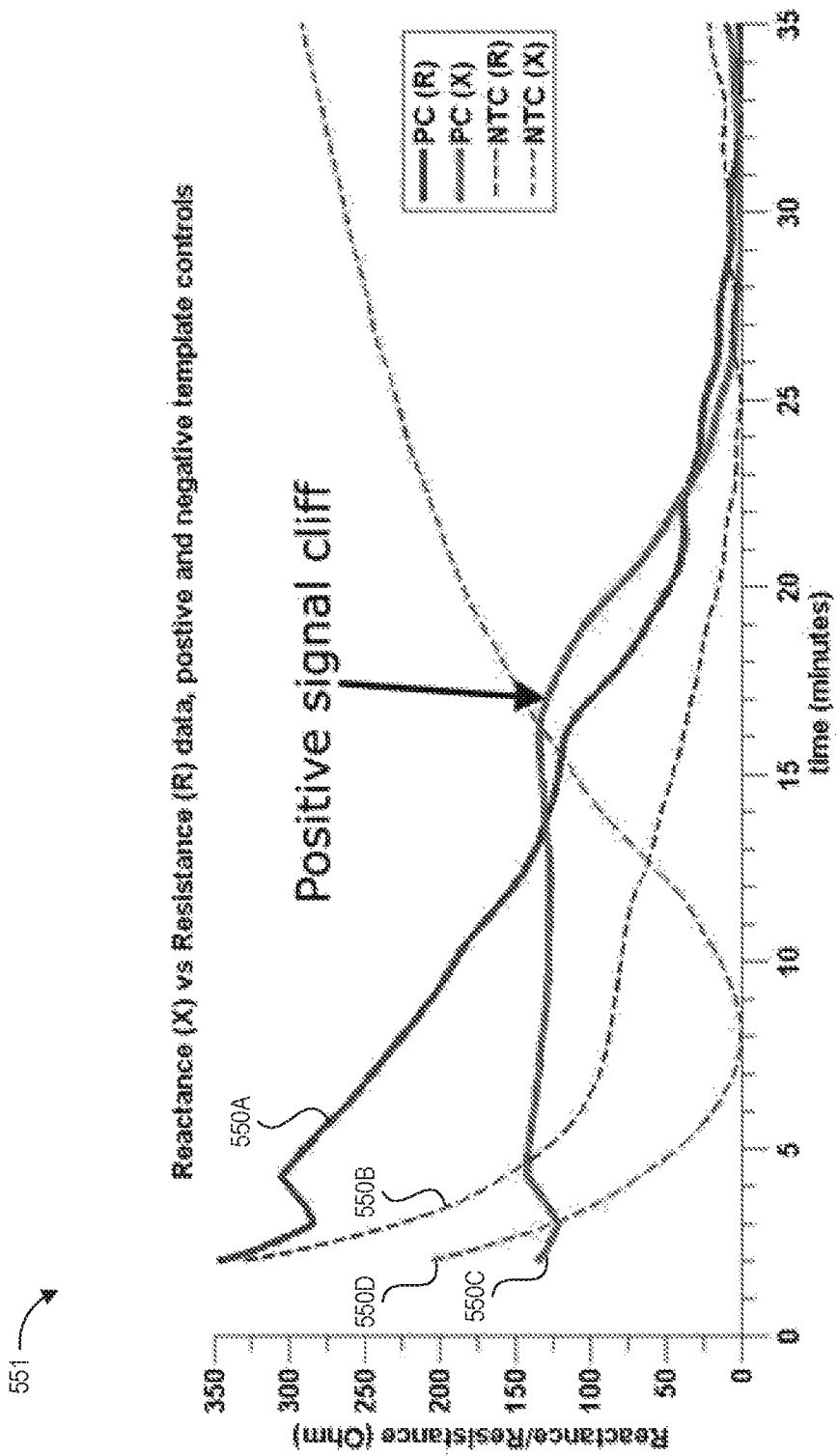
FIG. 5D depicts the resistance and reactance components extracted from signals as shown in FIG. 5B from example tests of positive and negative controls.

FIG. 5D depicts a plot 551 of the resistance and reactance components extracted from the raw sensor data of a sensing electrode 510B during example tests of positive and negative controls. Specifically, the plot 551 shows a curve 550A of the resistance of the positive sample, a curve 550B of the reactance of the positive sample, a curve 550C of the resistance of the positive sample, and a curve 550D of the reactance of the positive sample over the 35 minute duration of the test. As shown by FIG. 5D, the positive sample signal cliff occurs around 17 minutes into the test, with a relatively flat and stable reactance curve 550B leading up to the signal cliff. In contrast, at this same time the negative sample reactance curve 550D exhibits no signal cliff, but rather maintains a quadratic curvature from around t=8 minutes through the end of the test.

Figure 5E:
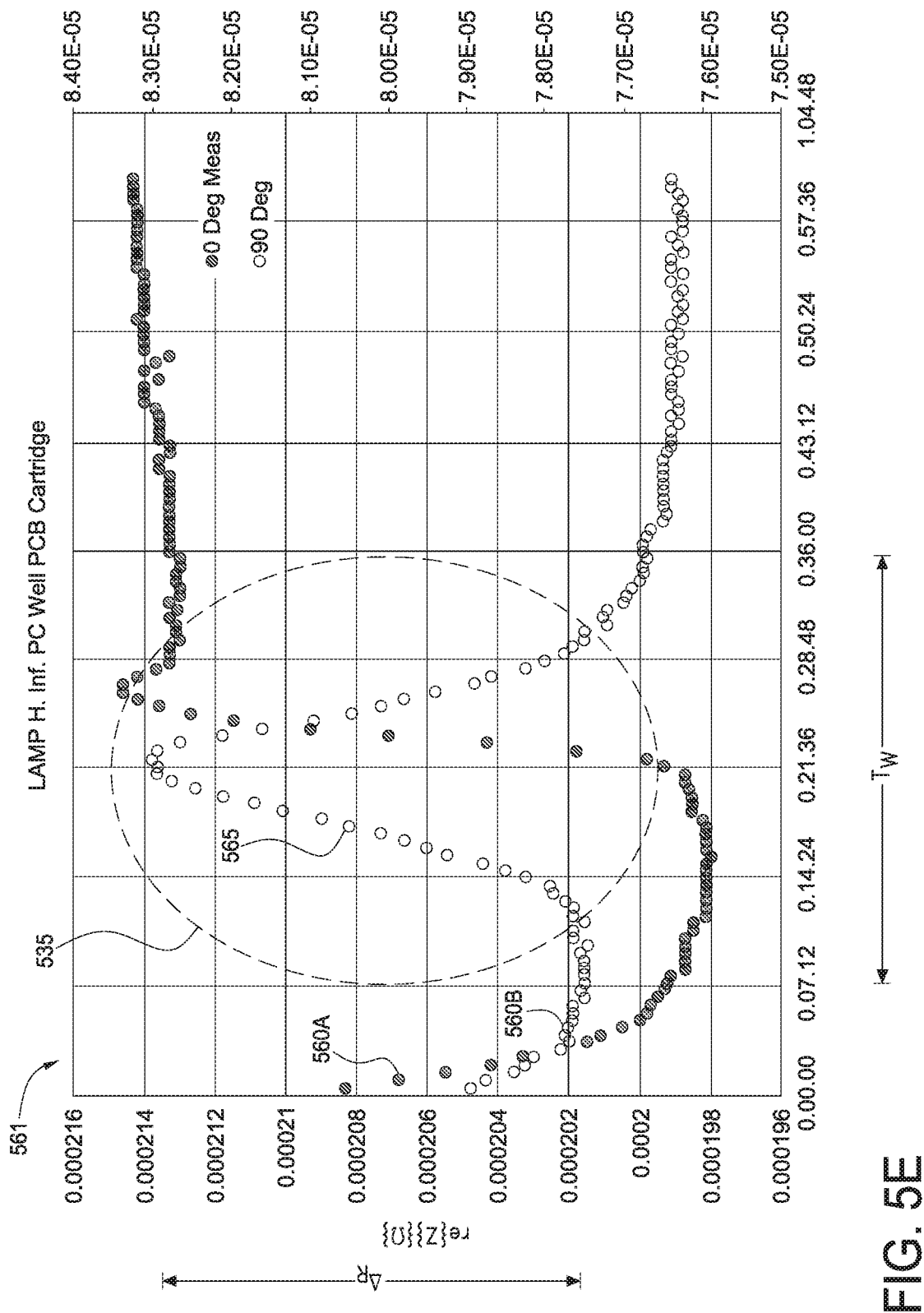
FIG. 5E depicts the resistance and reactance components extracted from a signal as shown in FIG. 5B generated based on another example positive test.

FIG. 5E depicts a plot 561 of the resistance 560A and reactance components 560B over time (t=0 minutes to t=60 minutes since the start of amplification) extracted from a raw signal 520 generated based on an example positive test. As illustrated, the signal cliff 565 represents a change $\Delta_R$ in the reactance 560B during a particular window of time $T_W$. The signal cliff 565 indicates a positive sample. At times occurring prior to the signal cliff 565, the reactance curve 560B is relatively flat or stable, and again after the signal cliff 565 the reactance curve 560B is relatively flat or stable with slight concavity. The signal cliff 565 for the particular test parameters represented by the plot 561 occurs as a peak, spike, or bell curve in the expected region 535, during which the reactance values rise and fall by the $\Delta_R$ value in an approximately parabolic curve. As described herein, varying of certain test parameters (e.g., test well configuration, chemistry and initial quantity of amplification constituents, target, and excitation current characteristics) can vary the geometry of the signal cliff yielded from a positive sample.

Thus, in some embodiments the geometry of a "signal cliff" in the reactance values vs time curve can vary from test to test, though for a particular test the curve geometry and/or timing signal cliff remains consistent within reactance change and/or timing parameters across positive samples for that test.

Figure 6:
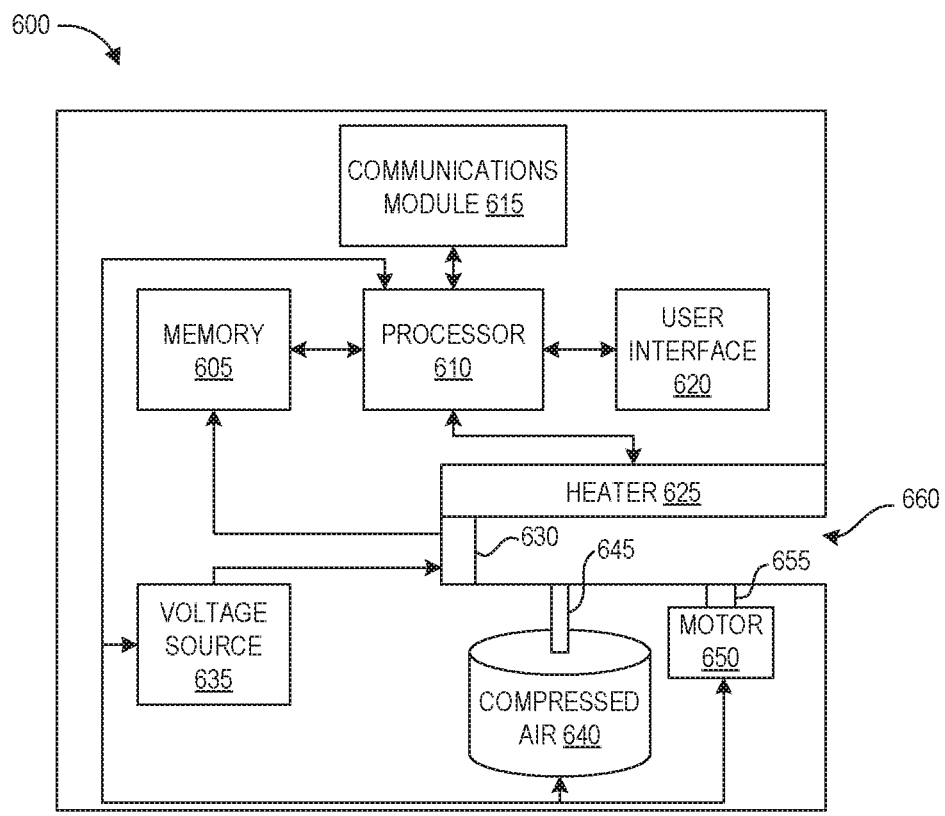
FIG. 6 depicts a schematic block diagram of an example reader device that can be used with the cartridges described herein.

FIG. 6 depicts a schematic block diagram of an example reader device 600 that can be used with the cartridges described herein, for example the cartridges 100 or 300. The reader device 600 includes a memory 605, processor 610, communications module 615, user interface 620, heater 625, electrode interface 630, voltage source 635, compressed air storage 640, motor 650, and a cavity 660 into which a cartridge can be inserted.

When test cartridge 100 is inserted into the reader device, the electrode interface 135 of the cartridge couples with the electrode interface 630 of the reader device 600. This can allow the reader device 600 to detect that a cartridge is inserted, for example by testing whether a communication path is established. Further, such communications can enable the reader device 600 to identify a particular inserted test cartridge 100 and access corresponding testing protocols. Testing protocols can include the duration of the test, the temperature of the test, the characteristics of a positive sample impedance curve, and the information to output to the user based on various determined test results. In other embodiments, the reader device 600 can receive an indication via user interface 620 that a cartridge is inserted (e.g., by a user inputting a "begin testing" command and optionally a test cartridge identifier).

The memory 605 includes one or more physical electronic storage devices configured for storing computer-executable instructions for controlling operations of the reader device 600 and data generated during use of the reader device 600. For example, the memory 605 can receive and store data from sensing electrodes coupled to the electrode interface 630.

The processor 610 includes one or more hardware processors that execute the computer-executable instructions to control operations of the reader device 600 during a test, for example by managing the user interface 620, controlling the heater 625, controlling the communications module 615, and activating the voltage source 635, compressed air 640, and motor 650. One example of testing operations is described with respect to FIG. 7A below. The processor 610 can be also be configured by the instructions to determine test results based on data received from the excitation electrodes of an inserted test cartridge, for example by performing the process of FIG. 7B described below. The processor 610 can be configured to identify different targets in the same test sample based on signals received from different test wells of a single cartridge, or can identify a single target based on individual or aggregate analysis of the signals from the different test wells.

The communications module 615 can optionally be provided in the reader device 600 and includes network-enabled hardware components, for example wired or wireless networking components, for providing networked communications between the reader device 600 and remote computing devices. Suitable networking components include WiFi, Bluetooth, cellular modems, Ethernet ports, USB ports, and the like. Beneficially, networking capabilities can enable the reader device 600 to send test results and other test data over a network to identified remote computing devices such as hospital information systems and/or laboratory information systems that store electronic medical records, national health agency databases, and the computing devices of clinicians or other designated personnel. For example, a doctor may receive the test results for a particular patient on their mobile device, laptop, or office desktop as the test results are determined by the reader device, enabling them to provide faster turnaround times for diagnosis and treatment plans. In addition, the networking capabilities can enable the reader device 600 to receive information over the network from remote computing devices, for example updated signal cliff parameters for existing test, new signal cliff parameters for new tests, and updated or new testing protocols.

The user interface 620 can include a display for presenting test results and other test information to users, as well as user input devices (e.g., buttons, a touch sensitive display) that allow the user to input commands or test data into the reader device 600.

The heater 625 can be positioned adjacent to the cavity 660 for heating an inserted cartridge to the desired temperature for an amplification process. Though depicted on a single side of the cavity 660, in some embodiments the heater 625 can surround the cavity.

As described herein, the voltage source 635 can provide an excitation signal at a predetermined voltage and frequency to each excitation electrode of an inserted test cartridge. The compressed air storage 640 can be used to provide pneumatic pressure via channel 645 to the pneumatic interface 160 of the test cartridge 100 to promote flow of the liquid within the test cartridge. Compressed air storage 640 can store previously compressed air or generate compressed air as needed by the reader device 600. Other suitable pneumatic pumps and pressure-providing mechanisms may be used in place of stored or generated compressed air in other embodiments. The motor 650 can be operated to move actuator 655 towards and away from the blister pack 140 of an inserted cartridge in order to rupture the blister pack as described above.

Figure 7A:
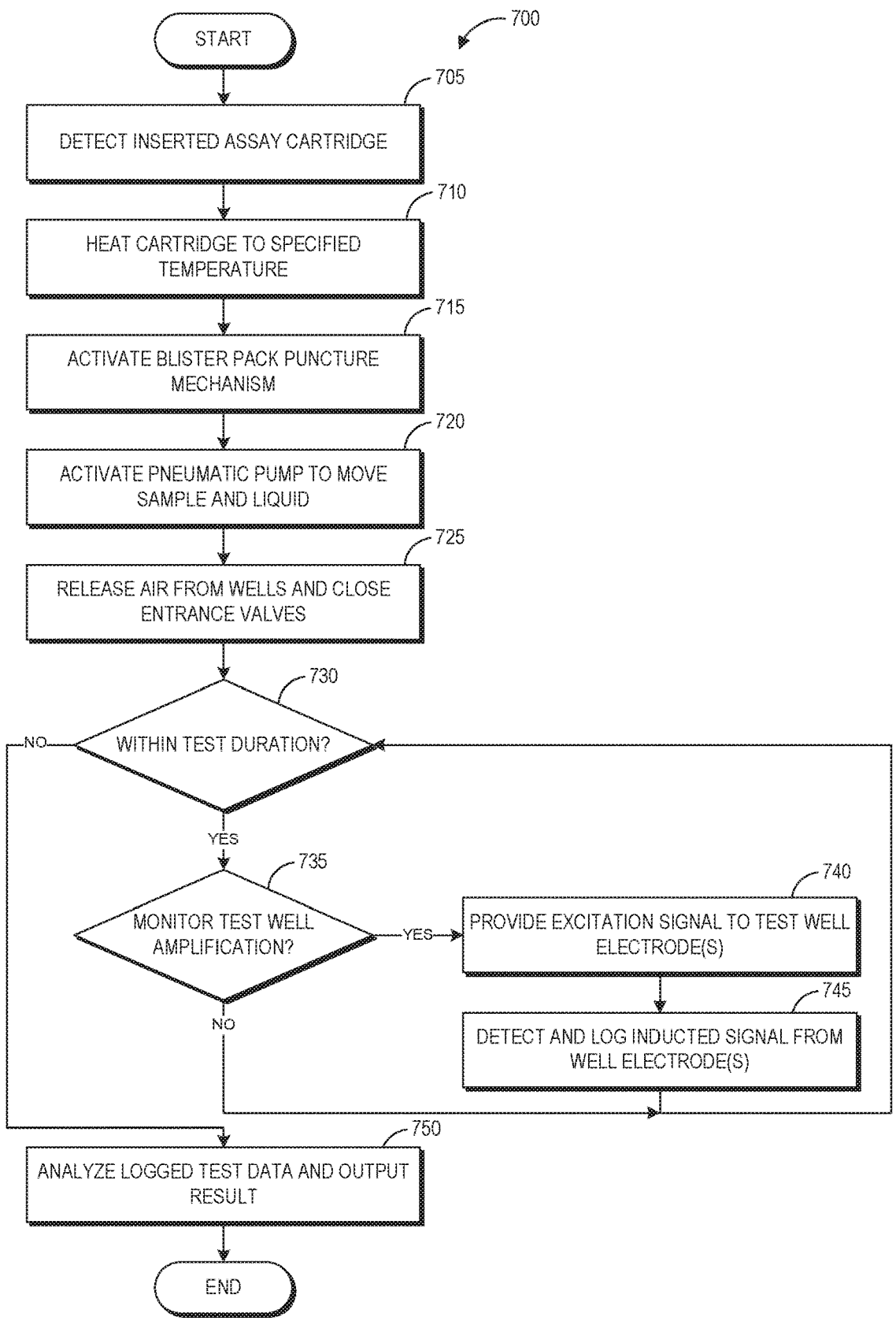
FIG. 7A depicts a flowchart of an example process for operating a reader device during a test as described herein.

FIG. 7A depicts a flowchart of an example process 700 for operating a reader device during a test as described herein. The process 700 can be performed by the reader device 600 described above.

At block 705, the reader device 600 can detect that an assay cartridge 100, 200, 300 has been inserted, for example in response to user input or in response to establishing a signal path with the inserted cartridge. In some embodiments, the cartridge 100, 200, 300 can include an information element that identifies the particular test(s) to be performed to the reader device 600 and optionally includes test protocol information.

At block 710, the reader device 600 can heat the cartridge 100, 200, 300 to a specified temperature for amplification. For example, the temperature can be provided by information stored on the cartridge 100, 200, 300 or accessed in the internal memory of the reader device 600 in response to identification of the cartridge 100, 200, 300.

At block 715, the reader device 600 can active a blister pack puncture mechanism, for example motor 650 and actuator 655. Puncturing the blister pack can cause its liquid contents, including chemical constituents for facilitating amplification, to be released from its previously sealed chamber.

At block 720, the reader device 600 can activate a pneumatic pump to move the sample and liquid from the blister pack through a fluid path of the cartridge towards the test well. As described above, the test wells can include vents that enable the pushing of liquid through the fluid path of the cartridge and also allow any trapped air to escape. The pneumatic pump can include compressed air 640 or another suitable source of pressure, and can fluidically communicate with the pneumatic interface 160.

At block 725, the reader device 600 can release any trapped air from the test wells, for example by pushing the fluid through the fluid path of the cartridge until a certain resistance is sensed (e.g., the liquid of the fluid path is pushed against the liquid impermeable, gas permeable filter of a vent). Block 725 may optionally include agitating the inserted cartridge to promote movement of any trapped air or gas bubbles up through the liquid and out through the vents. Further, at block 725 the reader device 600 optionally can provide signals to the cartridge that cause closure of valves positioned between test wells in order to avoid mixing of the amplification processes.

At decision block 730, the reader device 600 can determine whether the test is still within its specified test duration. For example, where the expected window of time in which a signal cliff should appear in a positive sample is known, the duration of the test may end at or some predetermined period of time after the end of the window. If so, the process 700 transitions to optional decision block 735 or, in embodiments omitting block 735, to block 740.

At optional decision block 735, the reader device 600 determines whether to monitor the test well amplification by logging data from the test well sensing electrode. For example, the reader 600 may be provided with instructions to only monitor the impedance of the test well during a particular window or windows of a test. If the reader device 600 determines not to monitor the test well amplification, the process 700 loops back to decision block 730.

If the reader device 600 determines to monitor the test well amplification, the process 700 transitions to block 740. At block 740, the reader device 600 provides an excitation signal to the excitation electrode of the test well(s) of the inserted cartridge. As described above, this can be an alternating current at a particular frequency and voltage.

At block 745, the reader device 600 detects and logs data from the sensing electrode of the test well(s) of the inserted cartridge. In some embodiments, this data can be stored for later analysis, for example after completion of the test. In some embodiments, the reader device 600 can analyze this data in real time (e.g., as the test is still occurring) and may stop the test once a positive sample signal cliff is identified.

When the reader device 600 determines at block 730 that the test is not still within its specified duration, the process 700 moves to block 750 to analyze the test data and output the test result. The test result can include an indication that the sample tested positive or negative for the target, or can more specifically indicate an estimated quantity of the target in the tested sample.

Figure 7B:
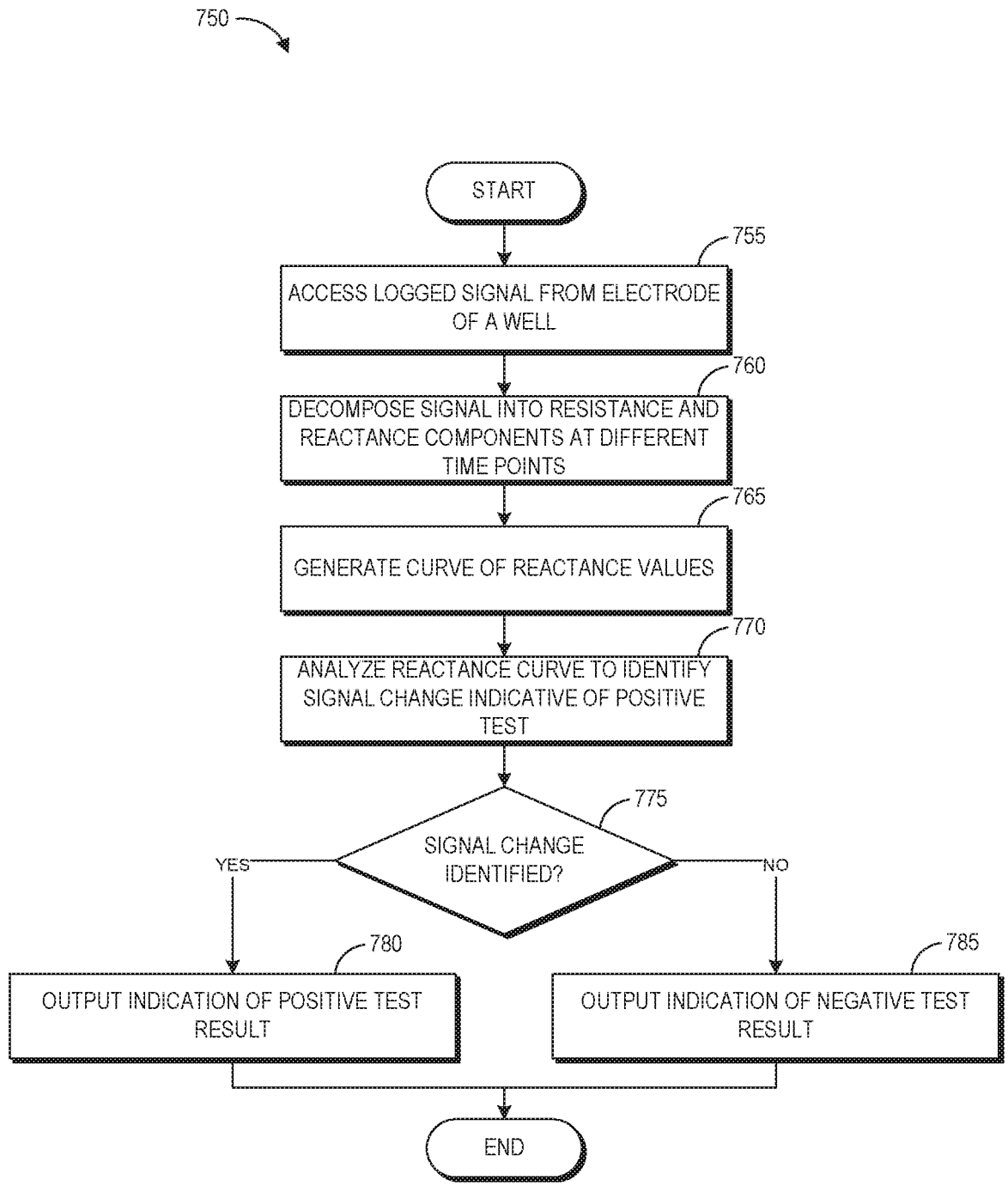
FIG. 7B depicts a flowchart of an example process for analyzing test data to detect a target as described herein.

FIG. 7B depicts a flowchart of an example process for analyzing test data to detect a target as described herein that can be performed by the reader device 600 as block 750 of FIG. 7A.

At block 755, the reader device 600 can access logged signal data received from the electrode of a well. Even if a cartridge has multiple wells, the data from each well can be analyzed individually. The test results from the wells may later be analyzed in aggregate to determine a single test result for a single target based on all tests performed within the cartridge, or to determine multiple test results for multiple targets.

At block 760, the reader device 600 can decompose the signal into resistance and reactance components across some or all of the different time points of the test. For example, as described above, at each time point the reader device 600 can determine in phase and out of phase components of the raw sampled voltage waveform and can then deconvolute these components using known series resistance of the electrode circuit to calculate the in-phase (resistance) and out-of-phase (reactance) portions of the impedance of the test well.

At block 765, the reader device 600 can generate a curve of the reactance values over time. Also at block 765, the reader device 600 can optionally generate a curve of the resistance values over time.

At block 770, the reader device 600 can analyze the reactance curve to identify a signal change indicative of a positive test. As described above with respect to the signal cliff of FIG. 5C, the reader device 600 can look for greater than a threshold change in reactance, can look for such a change within a predetermined window of time, can analyze the slope of the reactance curve at a predetermined time, or can analyze the overall shape of the reactance curve in order to determine whether a signal cliff (e.g., a rise or drop in the signal preceded and followed by relatively more stable values) is present.

At decision block 775, based on the analysis performed at block 770, the reader device 600 can determine whether the sought-after signal change was identified in the reactance curve. If so, the process 750 transitions to block 780 to output an indication of a positive test result to the user. If not, the process 750 transitions to block 785 to output an indication of a negative test result to the user. The result can be output locally, for example on the display of the device, or output over a network to a designated remote computing device.

Overview of Example Devices

Some embodiments of the methods, systems and compositions provided herein include devices comprising an excitation electrode and a sensor electrode. In some embodiments, the excitation electrode and the sensor electrode measure electrical properties of a sample. In some embodiments, the electrical properties comprise complex admittance, impedance, conductivity, resistivity, resistance, and/or a dielectric constant.

In some embodiments, the electrical properties are measured on a sample having electrical properties that do not change during the measurement. In some embodiments, the electrical properties are measured on a sample having dynamic electrical properties. In some such embodiments, the dynamic electrical properties are measured in real-time.

In some embodiments, an excitation signal is applied to the excitation electrode. The excitation signal can include direct current or voltage, and/or alternating current or voltage. In some embodiments, the excitation signal is capacitively coupled to/through a sample. In some embodiments, the excitation electrode and/or the sensor electrode is passivated to prevent direct contact between the sample and the electrode.

In some embodiments, parameters is optimized for the electric properties of a sample. In some such embodiments, parameters can include the applied voltage, applied frequency, and/or electrode configuration with respect to the sample volume size and/or geometry.

In some embodiments, the voltage and the frequency of the excitation voltage may be fixed or varied during the measurement. For example, measurement may involve sweeping voltages and frequencies during detection, or selecting a specific voltage and frequency which may be optimized for each sample. In some embodiments, the excitation voltage induces a current on the signal electrode that is can vary with the admittance of the device and/or sample characteristics.

In some embodiments, the detection parameters is optimized by modeling the admittance, device and sample by the lumped-parameter equivalent circuit consisting of electrode-sample coupling impedances, sample impedance, and inter-electrode parasitic impedance. Parameters of the lumped-parameter equivalent circuit is determined by measuring the admittance of the electrode-sample system at one or many excitation frequencies for a device. In some embodiments, the complex (number having both real and imaginary components) admittance of the electrode-sample system is measured using both magnitude- and phase-sensitive detection techniques. In some embodiments, the detection parameters are optimized by determining the frequencies corresponding to the transitions between the frequency regions by measuring the admittance across a wide range of frequencies. In some embodiments, the detection parameters are optimized by determining the frequencies corresponding to the transitions between the frequency regions by computing from the values given lumped-parameter model.

In some embodiments, the admittance of a capacitively-coupled electrode-sample system comprises three frequency regions: a low frequency region dominated by the electrode-sample coupling impedance, a mid-frequency region dominated by the sample impedance, and a high frequency region dominated by parasitic inter-electrode impedance. The admittance in the electrode-sample coupling region is capacitive in nature and is characterized by a magnitude that increases linearly with frequency, whose phase is ninety degrees. The admittance in the sample region is conductive in nature and is characterized by an admittance that does not vary significantly with respect to frequency, whose phase is approximately zero degrees. The admittance inter-electrode region is capacitive in nature and is characterized by a magnitude that increases linearly with frequency and a phase of ninety degrees.

In some embodiments, an induced current at the pick-up electrode is related to the excitation voltage and complex admittance by the relation:

$$\text{current} = (\text{complex admittance}) \times (\text{voltage})$$

In some embodiments, the device measures both the excitation voltage magnitude and induced current magnitude to determine the magnitude of the complex admittance. In some embodiments, the device is calibrated to known excitation voltages and measure the magnitude of the induced current. In order to determine the phase of complex admittance, the device may measure the relative phase difference between the excitation voltage and the induced current.

In some embodiments, the magnitude and phase is measured directly.

In some embodiments, the magnitude and phase is measured indirectly e.g., by using both synchronous and asynchronous detection. The synchronous detector gives the in-phase component of the induced current. The asynchronous detector gives the quadrature component of the induced current. Both components can be combined to determine the complex admittance.

In some embodiments, the electrodes are not passivated.

In some embodiments, the excitation and/or detection electrodes are passivated. The excitation and/or detection electrodes may be passivated to prevent e.g., undesirable adhesion, fouling, adsorption or other detrimental physical interactions between the electrode with the sample or components therein. In some embodiments, the passivation layer comprises a dielectric material. In some embodiments, passivation enables efficient capacitive coupling from the electrodes to the sample. The efficiency of the coupling is determined by measuring the characteristics of the electrode/sample system, for example, which may include: the dielectric properties of the passivation layer, the thickness of the passivation layer, the area of the passivation/sample interface, the passivation surface roughness, the electric double layer at the sample/passivation interface, temperature, applied voltage and applied frequency, the electrical properties of the sample, the electric and/or chemical properties of the electrode materials.

In some embodiments, the electrode configuration and fabrication is optimized to mitigate undesirable parasitic coupling between electrodes. This may be accomplished through electric field shielding, the use of a varying dielectric constant electrode substrate, layout optimization, and/or grounding layers.

Overview of Example Devices for Detection of Biomolecules

Some embodiments of the methods, systems and compositions provided herein include devices for the detection of a target, such as a biomolecule. In some such embodiments, measurement of the electrical properties of a sample is used as a detection strategy for biomolecular assays.

In some embodiments, the target is a nucleic acid, protein, small molecule, drug, metabolite, toxin, parasite, intact virus, bacteria, spore or any other antigen, which may be recognized and/or bound by a capture and/or detection probe moiety.

In some embodiments, the target is a nucleic acid. In some embodiments, methods comprise nucleic acid amplification. In some embodiments, amplification comprises isothermal amplification. In some embodiments, a nucleic acid amplification reaction is quantified by measuring the electric properties, or change therein, of the reaction solution. In some embodiments, the electrical properties of the amplification reaction is measured in real-time over the course of the reaction, or comparison measurements is made using before and after reaction electrical property measurements.

In some embodiments, a target antigen is detected via the specific binding of a detection probe such as e.g., an antibody, aptamer or other molecular recognition and/or binding moiety to the antigen. In an example embodiment, a detection antibody is linked to a nucleic acid sequence to form an antibody-nucleic acid chimeric complex. The chimeric complex is synthesized prior to the assay for the purpose of detecting the antigen. Many different nucleic acids may be conjugated to a single antibody thereby increasing the sensitivity for detection of binding of the chimeric complex to the antigen. After removing any excess chimeric complex not bound to antigen, the nucleic acids portion of the chimeric complex is amplified and the amplification reaction is quantified via the measurement of the electric properties (or changes therein) of the reaction solution as described herein. In this way, the degree of amplification of the nucleic acids, which are bound to the antigen through the chimeric complex signifies the presence of the target antigen and permits quantitation of antigen. The use of secondary amplification representative of antigen recognition, in combination with electrical detection, allows for greater ease, sensitivity and dynamic range than other antigen detection methods.

Figure 8:
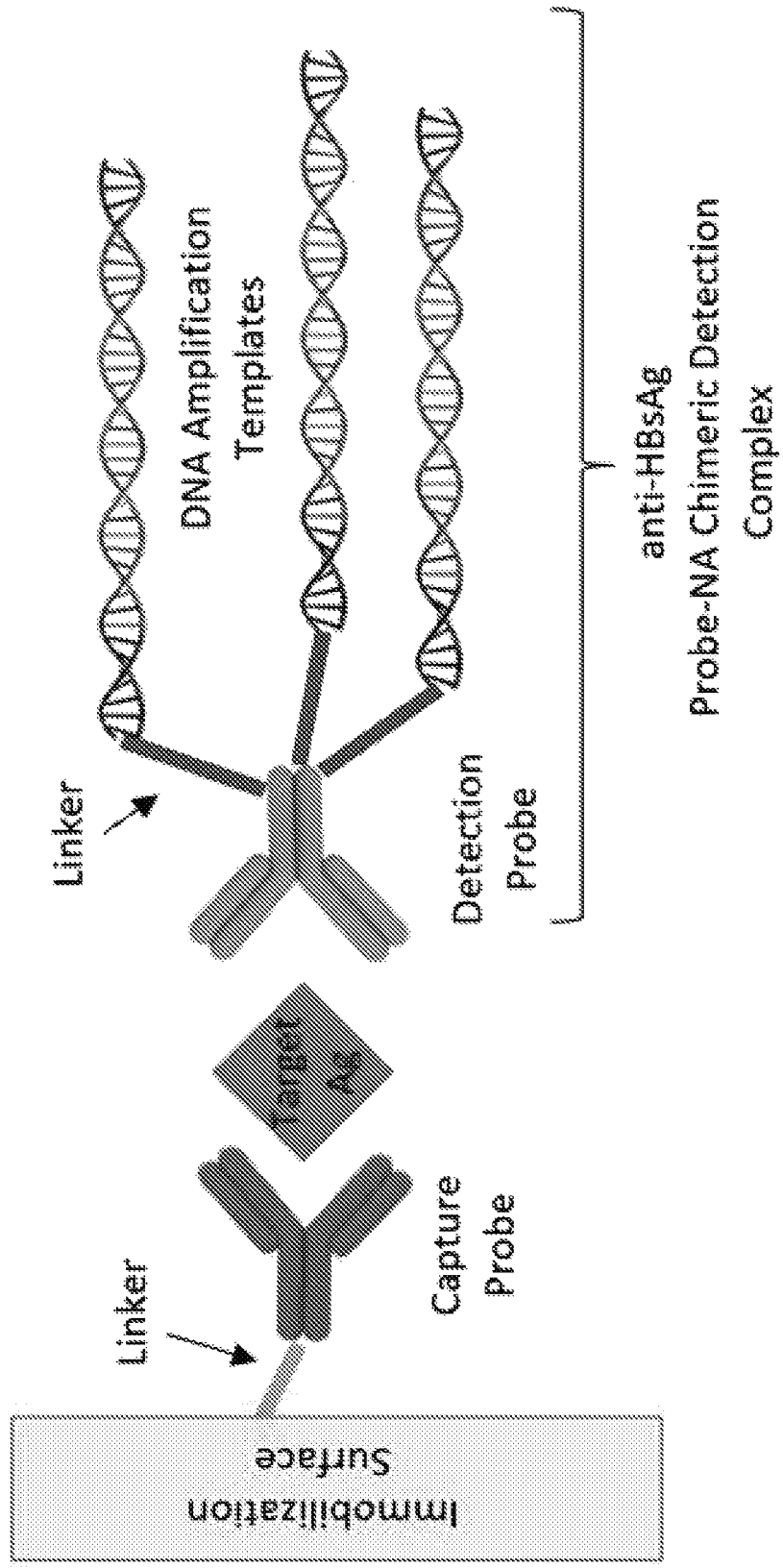
FIG. 8 depicts an amplification immunoassay scheme.

In some embodiments, a capture probe such as an antibody, aptamer or other molecular recognition and/or binding moiety to an antigen is bound to a surface by a conjugation or linkage. The immobilization of the capture probe onto a surface allows for the removal of excess, unbound reagents and/or antigen through washing. The chimeric complex is bound to the surface captured antigen enabling unbound chimera complex to be removed by washing. In this way, only captured antigen is retained for detection by the chimera complex. An example embodiment is depicted in FIG. 8. In some embodiments, the capture probe and the detection antibody are the same.

Figure 9:
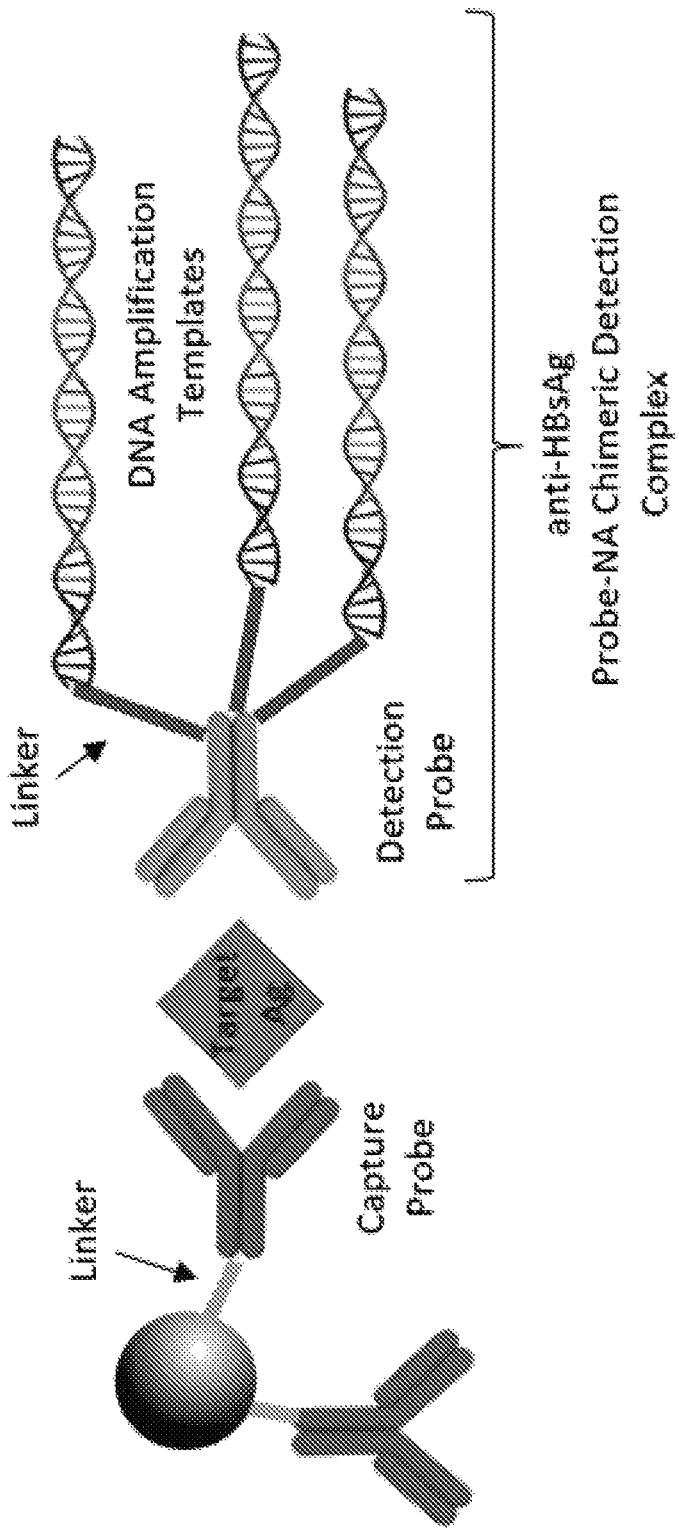
FIG. 9 depicts a bead-based amplification immunoassay scheme.

In some embodiments, the capture probe is immobilized onto a surface by covalent conjugation, the use of streptavidin-biotin linkages, or other bioconjugation and molecular immobilization methodologies as are commonly employed and familiar to those in the field. In some embodiments, the surface is a planar surface, a scaffold, a filter, a microsphere, a particle of any shape, a nanoparticle, or a bead or the like. An example embodiment is depicted in FIG. 9.

Overview of Example Magnetic Beads

Figure 10:
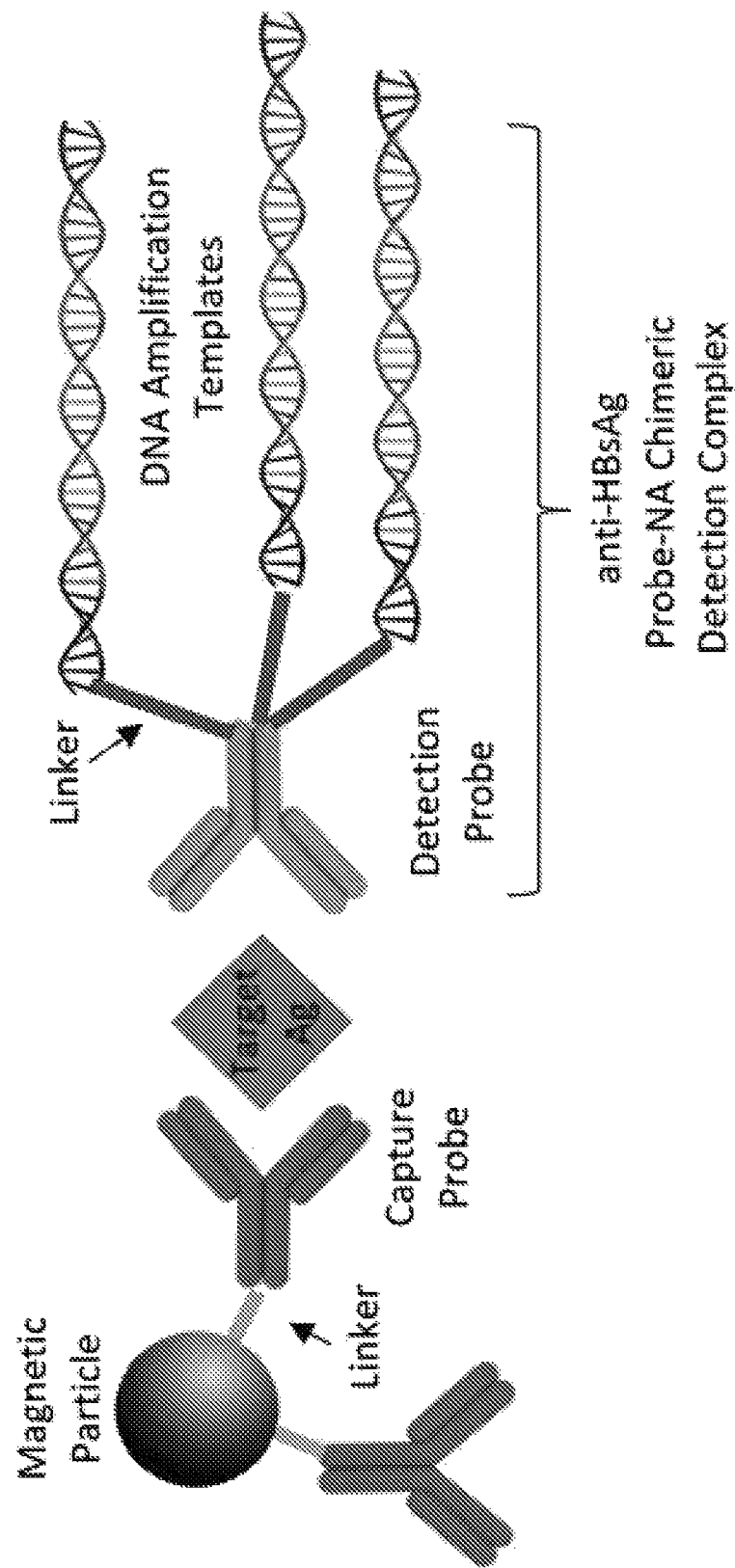
FIG. 10 depicts a magnetic bead-based amplification immunoassay scheme.

Some embodiments of the methods, systems and compositions provided herein include magnetic beads or the use thereof. In some embodiments, the microsphere, particle or bead is magnetic and/or magnetizable. The use of a magnetic support in such embodiments can facilitate the washing of the beads to remove excess, antigen and/or non-specifically adsorbed chimeric complex from the surfaces. A method, which includes the use of a magnetic particle support, may comprise a magnetic amplification immunoassay (MAIA). An example embodiment is depicted in FIG. 10.

In some embodiments, magnetic beads are useful to capture targets, and are used for magnetophoretic manipulation within the context of a purely electrical (MEMS) sample processing and/or amplification/detection cartridge and reduce or eliminate reliance on flow/pressure driven mobility within the fluidics. In some embodiments, magnetic beads are used to extract, and/or concentrate target genomic material from a sample. See e.g., Tekin, H C., et al., Lab Chip DOI: 10.1039/c31c50477h, which is incorporated by reference in its entirety. An automated microfluidic processing platform useful for embodiments provided herein is described in Sasso, L A., et al., Microfluid Nanofluidics. 13:603-612, which is incorporated by reference in its entirety. Examples of beads useful with embodiments provided herein include Dynabeads® for Nucleic Acid IVD (ThermoFisher Scientific), or Dynabeads® SILANE Viral NA Kit (ThermoFisher Scientific).

Overview of Example fC$^4$D Excitation and Detection

In some implementations, the disclosed devices, systems, and/or methods utilize a fC$^4$D based approach to monitor nucleic acid amplification in real-time. Thus, one or more phase-sensitive electrical conductivity measurements may be indicative of one or more targets within a sample.

In some aspects, a method includes rapidly sweeping frequencies at specific drive voltage values to determine an optimal excitation frequency ($f_{opt}$) where the sample conductivity linked to amplification is maximal. At $f_{opt}$ the sensor output corresponds to a minimum in the relative phase difference between the excitation voltage and the induced current, thereby enabling high-sensitivity biomolecule quantification through conductivity measurements.

In some implementations, a fC$^4$D detection system employs at least two electrodes. The two electrodes are placed in relatively close proximity to a microchannel where nucleic acid amplification is performed. An AC signal is applied to one of the two electrodes. The electrode to which the signal is applied to may be capacitively coupled through the microchannel to the second of the two electrodes. Thus, in some aspects, the first electrode is a signal electrode and the second electrode is a signal electrode.

In general, the detected signal at the signal electrode is of an identical frequency as the AC signal that is applied to the signal electrode but is smaller in magnitude and has a negative phase shift. The pickup current may subsequently be amplified. In some aspects, the pickup current is converted to a voltage. In some aspects, the voltage is rectified. In some aspects, the rectified voltage is converted to a DC signal using a low-pass filter. The signal may be biased to zero before it is sent to a DAQ system for further processing.

The above-described system may be represented by a series of capacitors and resistors. Changes in electrical conductivity that occurs during nucleic acid amplification within the channel may cause the total impedance of the system to decrease and thus cause an increase in the level of the pickup signal that is produced. Such changes in the level of the resultant output signal may appear as one or more peaks on the DAQ system.

The signal generation and demodulation electronics is implemented with circuitry. For example a printed circuit board ("PCB"), ASIC device, or other integrated circuity ("IC") is made using traditional manufacturing and fabrication techniques. In some aspects, such electronics is fully or partially designed to be single-use and/or disposable components. The physical geometry and electrical characteristics (passivation layer thickness, electrode pad area, channel cross sectional area and length, and dielectric strength) of such circuits is varied to achieve the desired results.

An example nucleic acid detection system includes at least one channel, and detects one or more physical properties, such as pH, optical properties, electrical properties and/or characteristics, along at least a portion of the length of the channel to determine whether the channel contains a particular nucleic acid of interest and/or a particular nucleotide of interest.

An example detection system is configured to include one or more channels for accommodating a sample and one or more sensor compounds (e.g., one or more nucleic acid probes), one or more input ports for introduction of the sample and the sensor compounds into the channel and, in some embodiments, one or more output ports through which the contents of the channel may be removed.

One or more sensor compounds (e.g., one or more nucleic acid probes) may be selected such that direct or indirect interaction among the nucleic acid and/or nucleotide of interest (if present in the sample) and particles of the sensor compounds results in formation of an aggregate that alters one or more physical properties, such as pH, optical properties, or electrical properties and/or characteristics, of at least a portion of the length of the channel.

In certain cases, formation of an aggregate, nucleic acid complex, or polymer inhibits or blocks fluid flow in the channel, and therefore causes a measurable drop in the electrical conductivity and electrical current measured along the length of the channel. Similarly, in these cases, formation of the aggregate, nucleic acid complex, or polymer causes a measurable increase in the resistivity along the length of the channel. In certain other cases, the aggregate, nucleic acid complex, or polymer is electrically conductive, and formation of aggregate, nucleic acid complex, or polymer enhances an electrical pathway along at least a portion of the length of the channel, thereby causing a measurable increase in the electrical conductivity and electrical current measured along the length of the channel. In these cases, formation of an aggregate, nucleic acid complex, or polymer causes a measurable decrease in the resistivity along the length of the channel.

Figure 11:
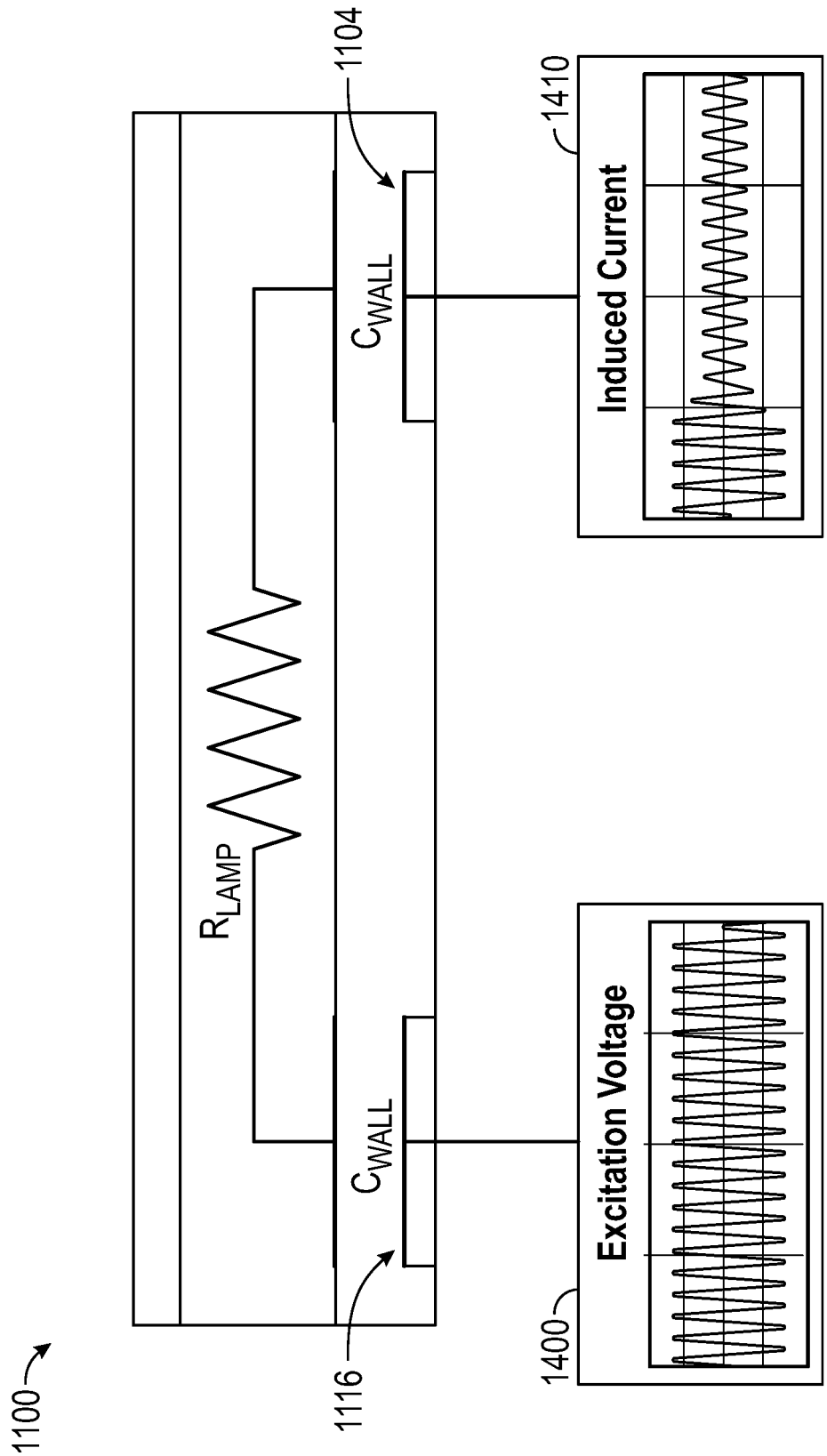
FIG. 11 depicts a first electrode or excitation electrode and a second electrode or signal electrode that may be spaced apart from one another along a channel.

In certain cases, formation of an aggregate, nucleic acid complex, or polymer affects waveform characteristics of one or more electrical signals that are sent through a channel. As shown, for example in FIG. 11, a first electrode or excitation electrode 1116 and a second electrode (a 'pickup' or 'sensor' electrode) 118 are spaced apart from one another along a channel 1104. FIG. 11 represents an alternate or complementary approach to that described above with respect to FIGS. 5A-5D. The first and second electrodes 1116, 1118 may not be in contact with the measured solution that is contained within the channel 1104. In this sense the first and second electrodes 1116, 1118 are capacitively-coupled to the solution within the channel 1104. The strength of the capacitive coupling depends on the electrode geometry, passivation layer thickness, and the passivation layer material (specifically its relative dielectric strength).

In some aspects, the solution is confined to the channel 1104. The channel may have a micron-scale cross-sectional area. As such, the solution behaves as a resistor whose resistance depends on the solution's conductivity and the channel 1104 geometry.

In some implementations, an alternating current/voltage is applied to the excitation electrode 1116 and the induced current is measured at the signal electrode 1118. The induced current is proportional to the inter-electrode impedance, which may change with the solution's conductivity. As shown, an excitation voltage 1400 is applied to the excitation electrode 1116 and an induced current 1410 is detected by the signal electrode 1118.

In some implementations, detector sensitivity is at least partially dependent on excitation frequency. Thus, in some aspects, a maximal sensitivity occurs when the absolute value of the phase of the induced current is at a minimum. In this region, chip impedance is dominated by fluid impedance. Fluid impedance is a function of fluid conductivity and chip geometry. Complex impedance information is important for ensuring maximal detector sensitivity and correct detector operation An analysis of lumped parameter model for the equivalent circuit has shown that detector sensitivity is intimately related to the strength of coupling capacitance, $C_{WALL}$, the solution resistance, $R_{LAMP}$, and the parasitic capacitance, $C_X$. Specifically, the change in inter-electrode impedance with respect to conductivity change is maximal when the excitation frequency, f, satisfies the following:

$$1/(\pi R_{LAMP} C_{WALL}) \ll f \ll 1/(\pi R_{LAMP} C_X)$$

Figure 12:
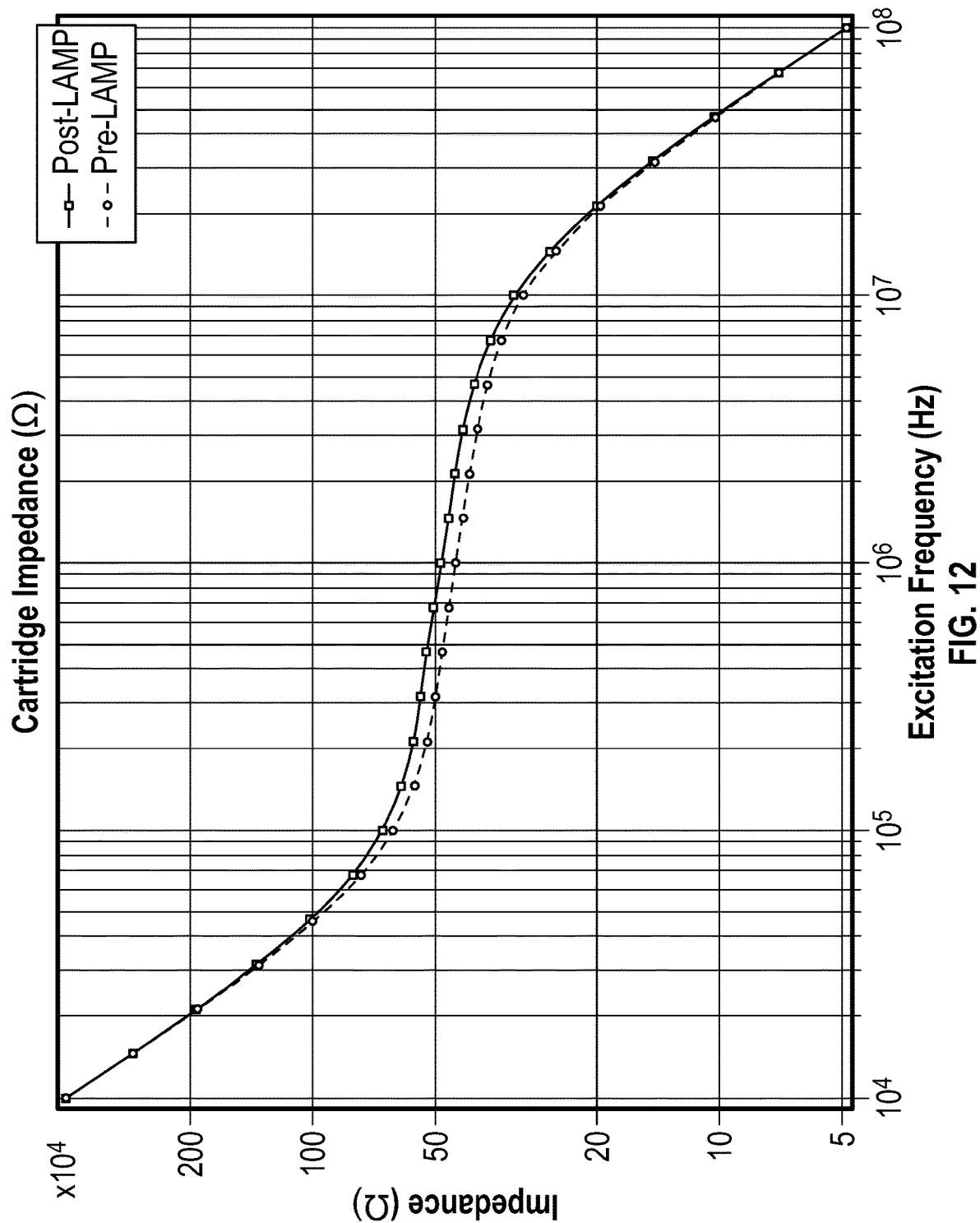
FIG. 12 is a graph showing the impedance of a signal is dependent on the excitation frequency and changes after a LAMP reaction occurs in a channel in which the left inequality may define a frequency region.

As shown in FIG. 12, the impedance of the signal is dependent on the excitation frequency and changes after a LAMP reaction occurs in the channel 1104. As also seen in FIG. 12, the left inequality may defines a frequency region below which the coupling impedance dominates and changes in the solution's impedance become practically invisible. The right inequality may define a frequency region above which parasitic effects dominate, and the electrodes 1116, 1118 are in effect shunted together.

Figure 13:
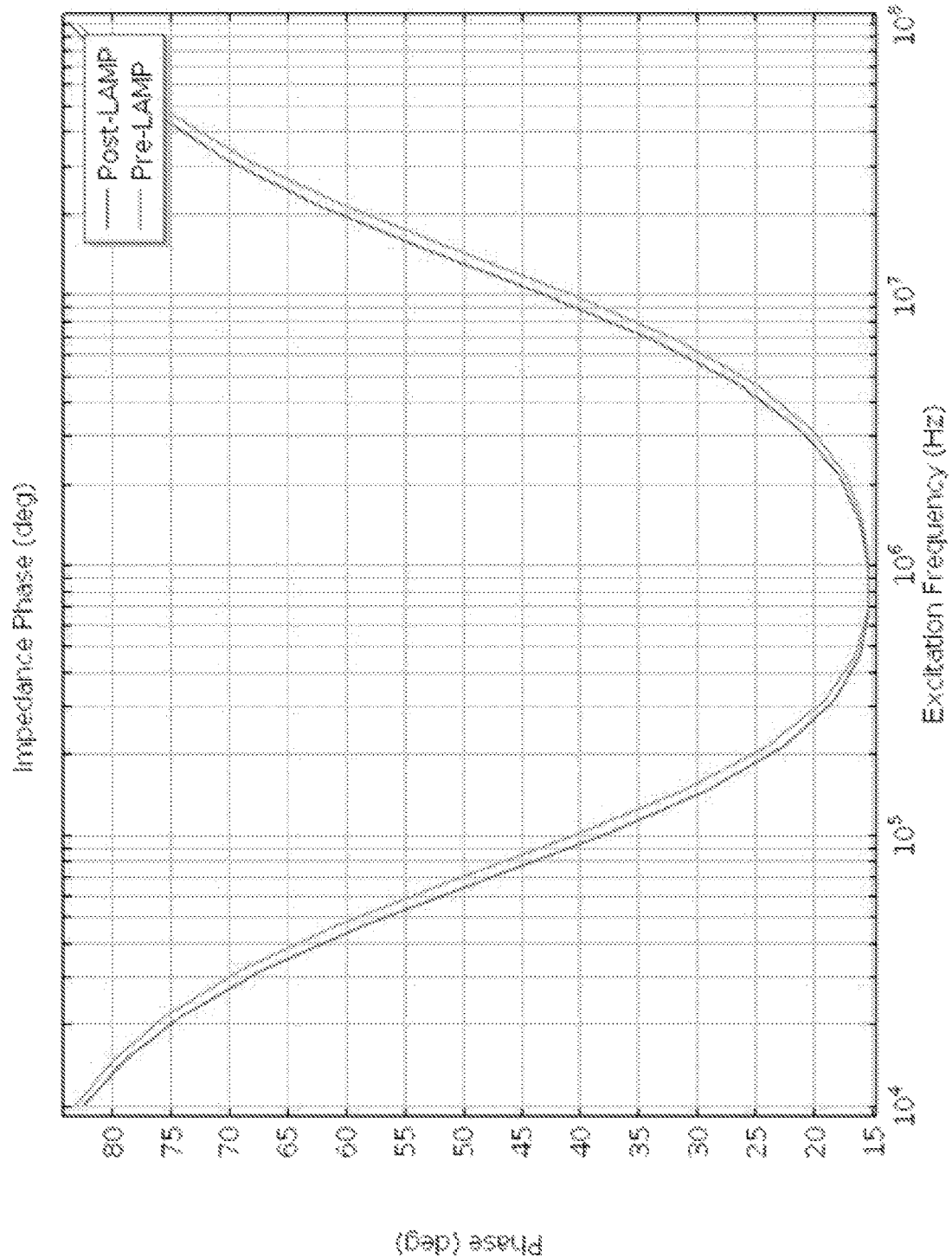
FIG. 13 is a graph showing that in both extremal regions the impedance is capacitor-like, and is out of phase (approaching 90°) with the excitation voltage.

As shown in FIG. 13, in both extremal regions, the impedance is capacitor-like, and is out of phase (approaching 90°) with the excitation voltage. Between the two regions, the impedance begins to approach the limit of a simple resistor, and the impedance versus frequency response flattens out. In fact, maximal detector sensitivity corresponds to the phase minimum of the impedance.

Figure 14:
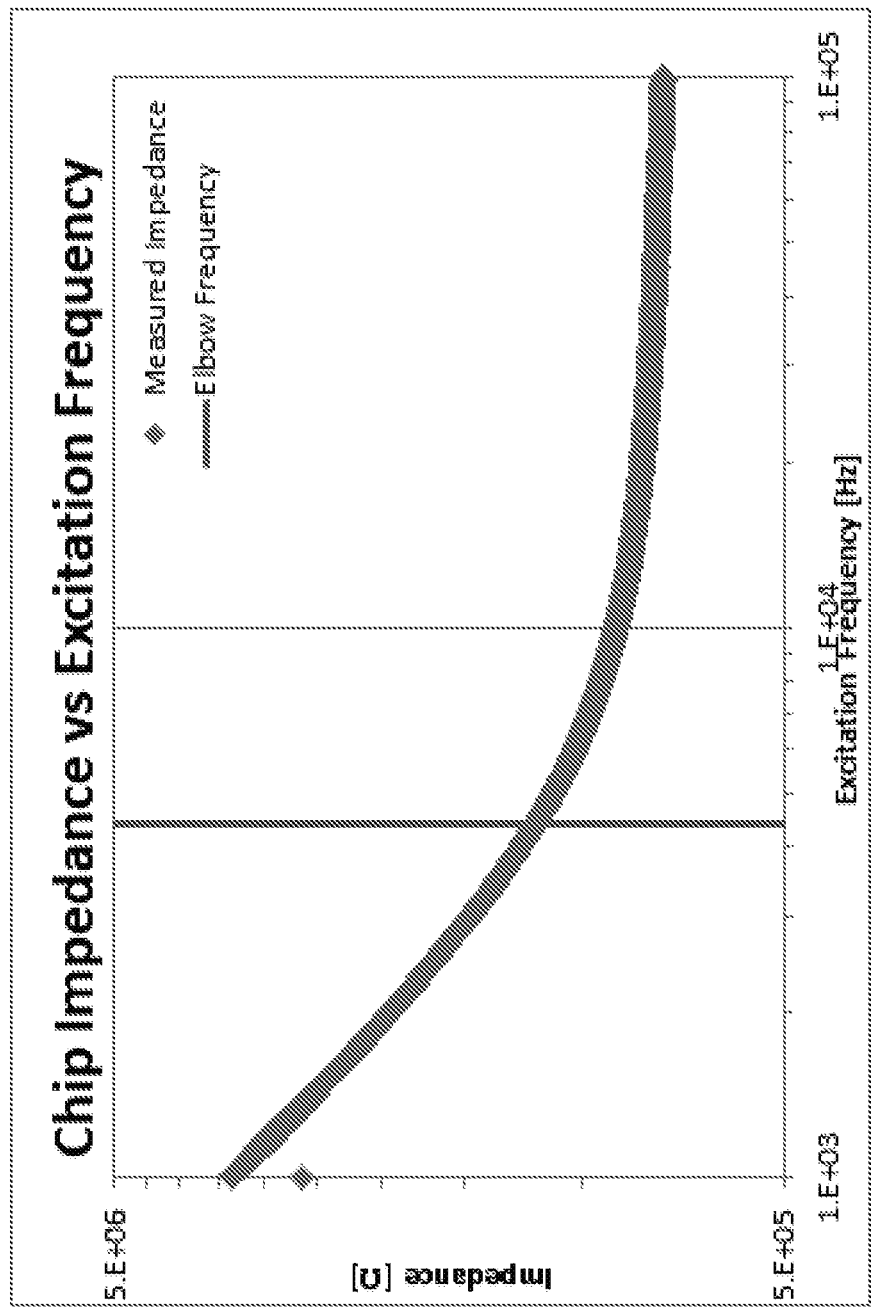
FIG. 14 is a graph depicting the measured impedance of a sample chip with respect to excitation frequency.

To elucidate the need for synchronous detection, one may consider two parallel paths for current in a simplified model: current through the chip via the fluidic channel and parasitic or geometric capacitance. Given an excitation signal, V, at a given frequency, f, the induced current, I, will be:

$$I(t) = (Y + 2\pi f C_x j) V(t)$$

where Y is the admittance of the chip due to coupling to the fluidic path, $C_x$ is the parasitic capacitance, and j is the imaginary unit. Multiplication by j means the current through the parasitic path is 90° out of phase with the excitation voltage. The measured impedance of a sample chip with respect to excitation frequency is shown in FIG. 14.

In a synchronous detector, the pickup current is multiplied by an in-phase square wave, m, then low-pass filtered.

$$m(t) = \mathrm{sgn}(\sin(2\pi f t)) = \frac{4}{\pi} \sum_{k=1}^{\infty} \frac{\sin(2\pi(2k-1)ft)}{2k-1}$$

It is straightforward to show that the contribution of signals 90° out of phase with the modulating signal will be zero, so we may ignore the parasitic capacitance in this analysis. To see the effect synchronous detection on the current through the fluidic path, one can multiply the induced current (minus the parasitic contribution), with the modulating wave $$mI = mYV = \frac{4}{\pi}|V||Y|\sin(2\pi f t + \varphi)\sin(2\pi f t) + H.F.T. =$$
$$\frac{2}{\pi}|V||Y|\cos(\varphi) - \frac{2}{\pi}|V||Y|\cos(2\pi(2f)t + \varphi) + H.F.T.$$

where $|Y|$ is the magnitude of the admittance, and $\varphi = \arg(Y)$, and H.F.T. means high frequency terms (e.g., greater than f). After low pass filtering, one may be left with the DC term of the synchronous output:

$$s = \frac{2}{\pi}|V||Y|\cos(\varphi)$$

This expression can be simplified this by noting that:

$$\cos(\varphi) = \frac{\mathrm{Re}\{Y\}}{|Y|}$$

resulting in:

$$s = \frac{2}{\pi}|V|\mathrm{Re}\{Y\}$$

Alternatively, one can express this in terms of impedance by Z, by noting that $$Y = \frac{1}{Z} = \frac{\overline{Z}}{|Z|^2}$$

where the bar denotes complex conjugation. The synchronous detector output thus becomes $$s = \frac{2}{\pi}|V|\frac{\mathrm{Re}\{Z\}}{|Z|^2}$$

Given the simple circuit models for the chip, the impedance is computed explicitly, and the output of the synchronous detector is predicted.

A simple equivalent circuit model comprises two capacitors, C, in series with a resistor, R. As discussed above, the resistance R is primarily a function of the microfluidic geometry and solution conductance. The capacitance is primarily a function of the electrode area, the dielectric used for the passivation layer and the passivation layer thickness. The impedance, Z, of the simplified circuit is given by:

$$Z = R - \left(\frac{1}{\pi f C}\right)j$$

The square of the magnitude of the impedance is:

$$|Z|^2 = R^2 + (\pi f C)^{-2}$$

and the output of the synchronous detector is:

$$s = \frac{2}{\pi}|V|\frac{R}{R^2 + (\pi f C)^{-2}} = \frac{2}{\pi}|V|\frac{G}{1 + \left(\frac{G}{\pi f C}\right)^2} =$$

where the numerator and denominator is multiplied by the square of the conductance, $G = 1/R$.

For conductivity meters, a cell constant, k, may be defined to be:

$$R = \frac{k}{\sigma}$$

where k has units of inverse length. The cell constant k, primarily depends on electrode placement, area, and fluidic path, and may not be a simple linear relationship. The synchronous detector output is then:

$$s = \frac{2}{\pi}|V|\frac{\sigma/k}{1 + \left(\frac{\sigma}{\pi k f C}\right)^2}$$

To aid in the analysis, one may introduce a dimensionless conductivity parameter, $\tilde{\sigma}$, where:

$$\tilde{\sigma} = \frac{\sigma}{\pi k f C}$$

So that:

$$s = 2|V|fC\frac{\tilde{\sigma}}{1 + \tilde{\sigma}^2}$$

The dependence of the detector output on the non-dimensional conductivity, $\tilde{\sigma}$, is of note.
1) The detector response is asymptotically proportional to $\tilde{\sigma}$ for $\tilde{\sigma} \ll 1$
2) The detector response reaches a local maximum of $s_{max} = |V|fc$ at $\tilde{\sigma} = 1$ 3) The detector response is asymptotically proportional to $1/\sigma$ for $\sigma \gg 1$.

Given the dependence of the detector response on the non-dimensional conductance, it is important to tightly couple the design the chip and detector. Translating the previously-stated points in terms of the actual conductance result in the following:

1) The detector response is asymptotically proportional to $\sigma$ for $$f \gg \frac{\sigma}{\pi k C}$$

2) The detector response is asymptotically proportional to $$\frac{1}{\sigma} \text{ for } f \ll \frac{\sigma}{\pi k C}$$

3) The detector response becomes non-monotonic at $\sigma = \pi k f c$

Figure 15:
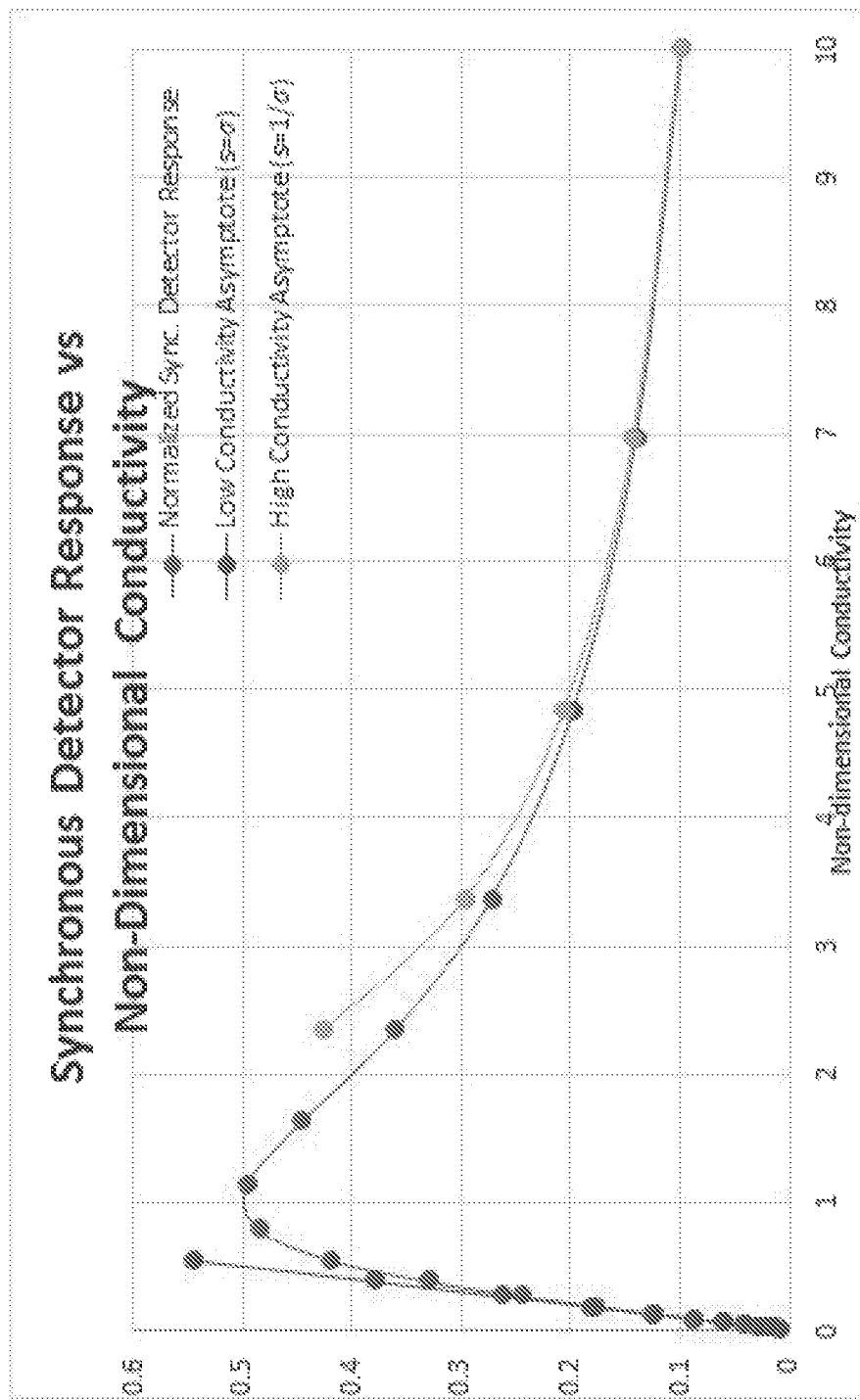
FIG. 15 is a graph depicting a synchronous detector response plotted with respect to non-dimensional conductivity.

In other words, increasing the excitation frequency expands the range of conductivities for which the synchronous detector output is linear. A synchronous detector response is plotted with respect to non-dimensional conductivity in FIG. 15.

To evaluate the lumped parameter model's validity, the detector response for known conductivity solutions of KCl was measured. The chip's channel was 2 mm with 0.01 mm² cross-sectional area. The two electrodes were each 9 mm², passivated with a 10 um layer of SU8 photoresist. The cell constant and capacitance were estimated and an excitation frequency was chosen so that the conductivity corresponding to the non-linearity in the detector output would be approximately 5 mS/cm. The experiment was repeated at excitation frequencies of 10, 15, and 20 kHz.

The conductivity of pre-LAMP chemistries has been measured to be approximately 10 mS/cm. TABLE 1 below, presents the estimates for the minimal detector frequency governed by the constraint found earlier, namely:

$$f \gg \frac{G}{\pi C}$$

frequency. The model overestimates the divergence of the frequency-dependent behavior for conductivities past the critical conductivity.

As a tool to quickly estimate the conductance and wall capacitance, one may ignore surface conductivity and capacitance effects in addition to fringe fields effects. A geometry-specific finite element model can be used to further refine this crude estimate.

The electrode is modeled as a parallel plate capacitor of area $A_\varepsilon$, separated by a dielectric of relative dielectric strength $\varepsilon_r$, and thickness $\tau$. The capacitance is then approximated as:

$$C = \frac{\varepsilon_0 \varepsilon_r A_E}{t}$$

where $\varepsilon_0$ is the dielectric constant.

The fluid may be modeled as a simple resistor of cross-sectional area $A_F$, length l, and conductivity $\sigma$. Thus, the conductance of the fluidic path may be approximated as $$G = \frac{\sigma A_F}{l}$$

From this, the cell constant is also approximated.

In some aspects, the device is configured to determine "impedance spectrum" after the chip is introduced. The device may include a digitally controlled excitation frequency. The device may have quick frequency sweeping ability. The device may include in-phase and quadrature components of the induced signal, from which complex impedance can be determined. The fitness of impedance spectrum is determined, at least in part, based on curve fit or other heuristic to determine proper chip insertion and/or proper sample introduction. In some aspects, the device is first tested by exciting at a frequency determined by initial sweep. In some implementations, the device includes a detector that utilizes synchronous detection. In this way, measured induced currents attributable to the fluidic path (at phase minimum) may be detected in real time.

Overview of Example Channels

In some embodiments, a channel has the following dimensions: a length measured along its longest dimension (y-axis) and extending along a plane parallel to the substrate

TABLE 1

| Geometry | $A_E$ [mm²] | t [μm] | $\varepsilon_r$ | C [pF] | $A_F$ [mm²] | l [mm] | G [mS] | f [MHz] |
|---|---|---|---|---|---|---|---|---|
| Restrictive Channel | 9 | 10 | 3 | 24 | 0.01 | 3 | 0.003 | 0.044 |
| Bulk Well, Planar Electrodes | 0.8 | 0.3 | 3 | 71 | 0.8 | 1 | 0.8 | 3.6 |
| Parallel Plate, Non-integrated Electrodes | 16 | 300 | 2.8 | 1.3 | 16 | 1.5 | 10.5 | 2500 |

Figure 16:
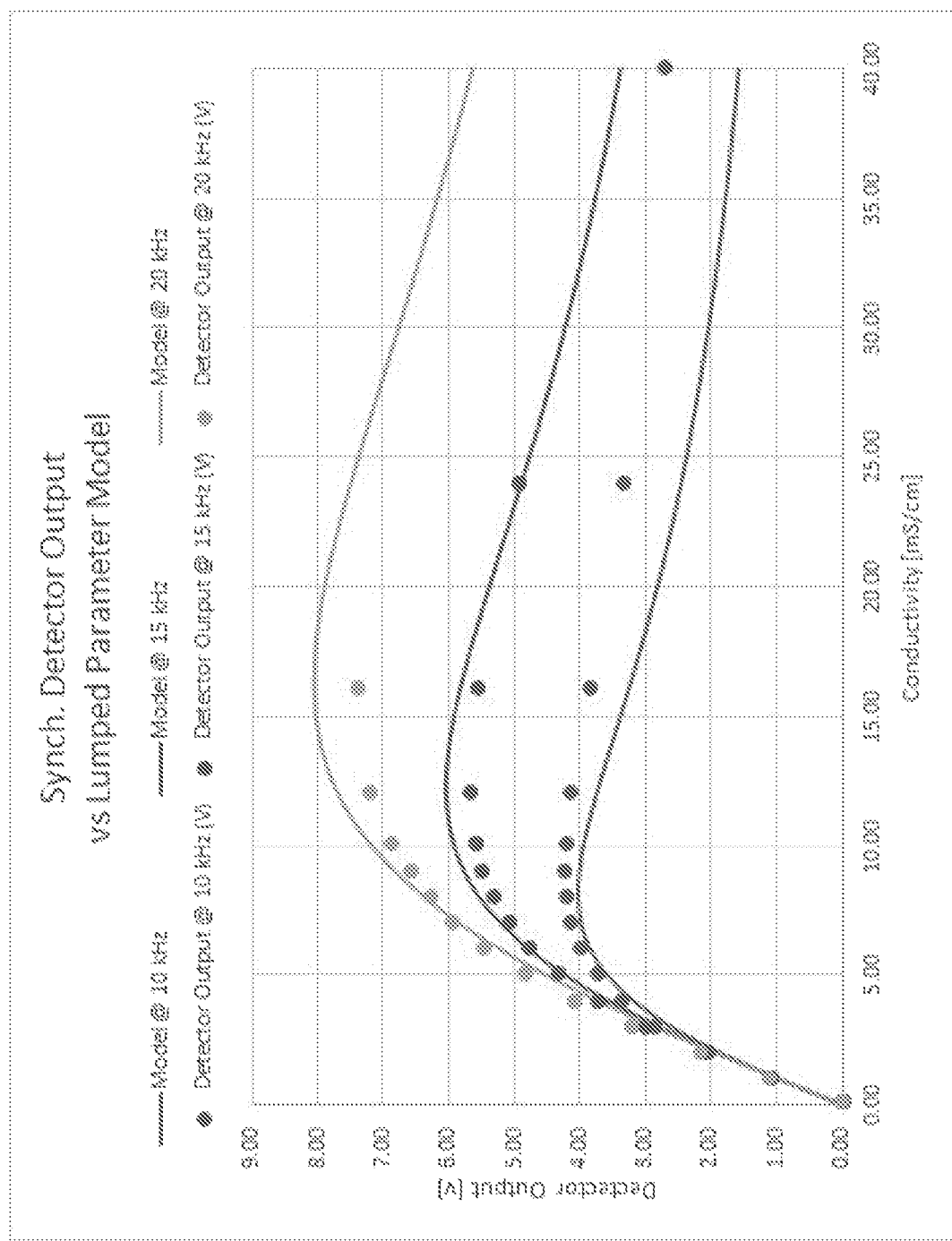
FIG. 16 is a graph depicting results of a model demonstrating agreement with a detector output for a wide range of conductivities and for a given steps in frequencies.

The results of the model, shown in FIG. 16, demonstrate good agreement with the detector output for a wide range of conductivities and for the given steps in frequencies. It is important to note that the same two parameters, k and C, are used at each frequency. The model predicts the qualitative behavior of the detector response. Namely, the functional form the response, the dependence of the critical conductivity at which the nonlinearity occurs on the excitation of the detection system; a width measured along an axis (x-axis) perpendicular to its longest dimension and extending along the plane parallel to the substrate; and a depth measured along an axis (z-axis) perpendicular to the plane parallel to the substrate. An example channel may have a length that is substantially greater than its width and its depth. In some cases, example ratios between the length: width may be: 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, or 20:1 or within a range defined by any two of the aforementioned ratios.

In some embodiments, a channel is configured to have a depth and/or a width that is substantially equal to or smaller than the diameter of an aggregate, nucleic acid complex, or polymer formed in the channel, preferably while in suspension in the channel, due to interaction between the nucleic acid of interest and particles of the sensor compounds (e.g., one or more nucleic acid probes) used to detect the nucleic acid of interest.

In some embodiments, a channel is configured to have a width taken along the x-axis ranging from about 1 nm to about 50,000 nm or a width that is within a range defined by any two numbers within the aforementioned range, but is not limited to these example ranges. An example channel has a length taken along the y-axis ranging from about 10 nm to about 2 cm, or a length that is within a range defined by any two numbers within the aforementioned range but is not limited to these example ranges. An example channel has a depth taken along the z-axis ranging from about 1 nm to about 1 micron, or a depth that is within a range defined by any two numbers within the aforementioned range but is not limited to these example ranges.

In some embodiments, a channel has any suitable transverse cross-sectional shape (e.g., a cross-section taken along the x-z plane) including, but not limited to, circular, elliptical, rectangular, square, D-shaped (due to isotropic etching), and the like.

In some embodiments, a channel has a length in a range from 10 nm to 10 cm, such as e.g., at least or equal to 10 nm, 50 nm, 100 nm, 200 nm, 400 nm, 600 nm, 800 nm, 1 µm, 10 µm, 50 µm, 100 µm, 300 µm, 600 µm, 900 µm, 1 cm, 3 cm, 5 cm, 7 cm, or 10 cm or a length that is within a range defined by any two of the aforementioned lengths. In some embodiments, a channel has a depth in a range from 1 nm to 1 µm, such as e.g., at least or equal to 1 nm, 5 nm, 7 nm, 10 nm, 50 nm, 100 nm, 200 nm, 400 nm, 600 nm, 800 nm, 1 µm, 10 µm, 20 µm, 30 µm, 40 µm, 50 µm, 100 µm, 500 µm, or 1 mm or a depth that is within a range defined by any two of the aforementioned depths. In some embodiments, a channel has a width in a range from 1 nm to 50 µm, such as e.g., 1 nm, 5 nm, 7 nm, 10 nm, 50 nm, 100 nm, 200 nm, 400 nm, 600 nm, 800 nm, 1 µm, 10 µm, 20 µm, 30 µm, 40 µm, 50 µm, 100 µm, 500 µm, or 1 mm or a width that is within a range defined by any two of the aforementioned widths.

In some implementations, the channels are formed in a cartridge that is later inserted into a device. In some aspects, the cartridge may be a disposable cartridge. In some aspects, the cartridge is made of cost-effective plastic materials. In some aspects, at least a portion of the cartridge is made from paper and laminate-based materials for fluidics.

Figure 17A:
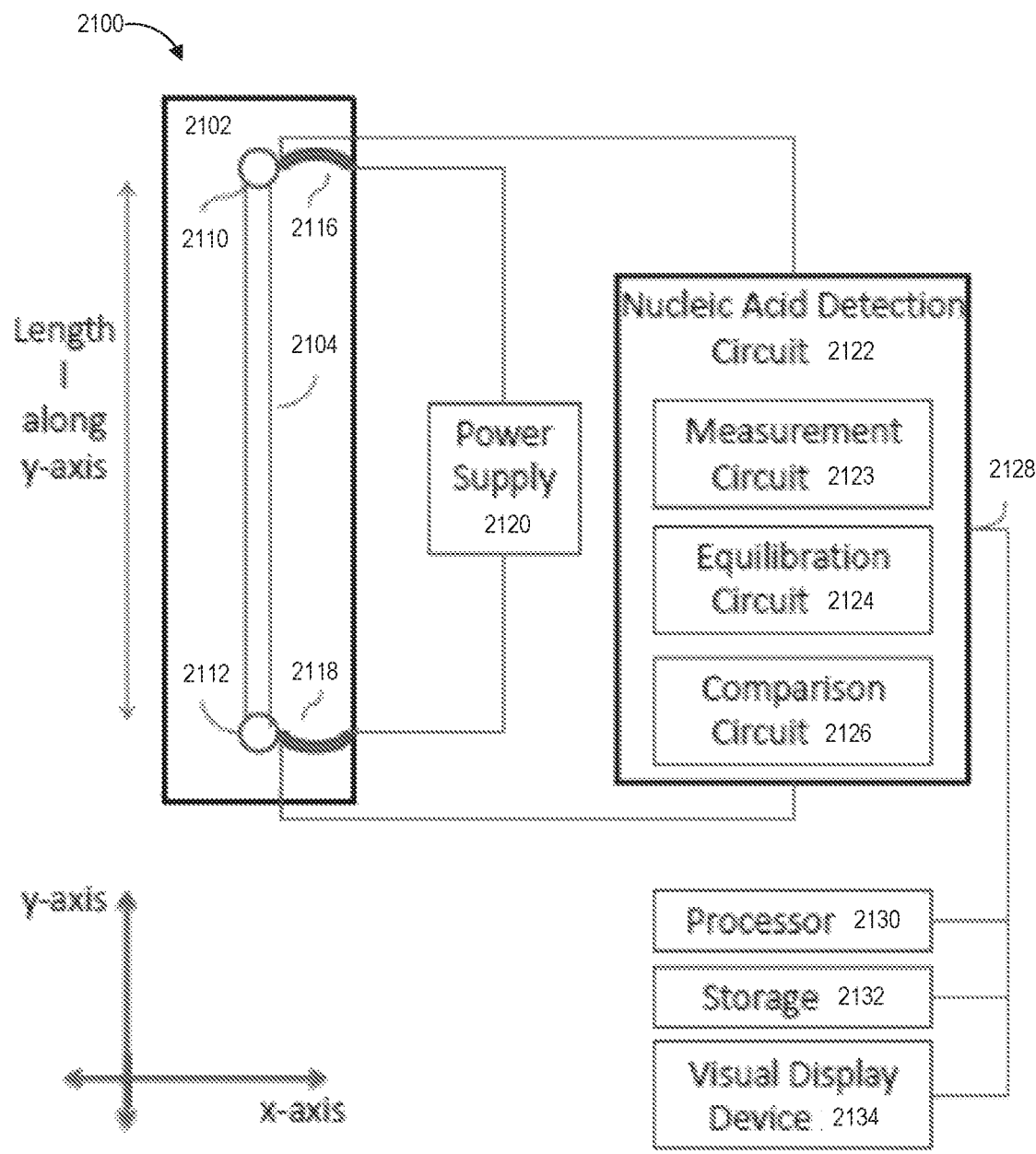
FIG. 17A and FIG. 17B depict an embodiment of a detection system that may be used to detect presence or absence of a particular nucleic acid and/or a particular nucleotide in a sample.
Figure 17B:
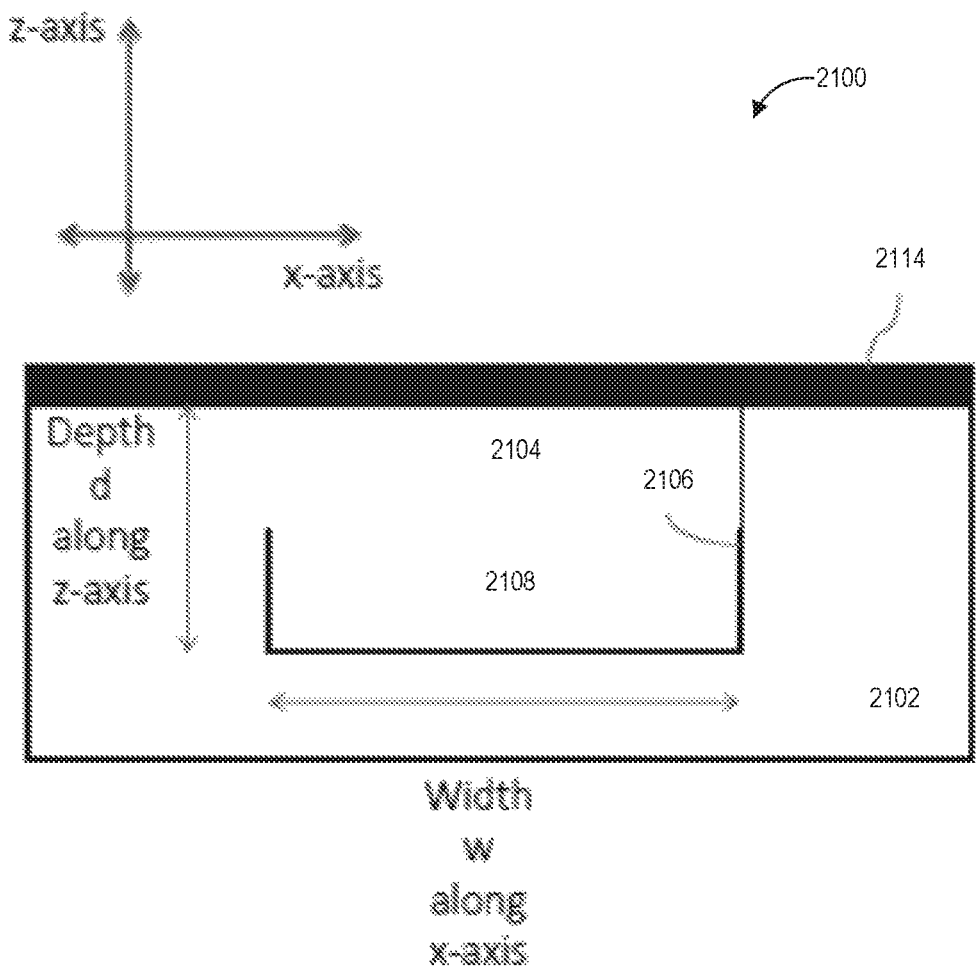

An embodiment of a detection system 2100 that is used to detect presence or absence of a particular nucleic acid and/or a particular nucleotide in a sample is illustrated in FIGS. 17A-17B. FIG. 17A is a top view of the system, while FIG. 17B is a cross-sectional side view of the system. The detection system 2100 includes a substrate 2102 that extends substantially along a horizontal x-y plane. In some embodiments, the substrate 2102 may be formed of a dielectric material, for example, silica. Other example materials for the substrate 2102 include, but are not limited to, glass, sapphire, or diamond.

The substrate 2102 supports or includes a channel 2104 having at least an inner surface 2106 and an inner space 2108 for accommodating a fluid. In some cases, the channel 2104 is etched in a top surface of the substrate 2102. Example materials for the inner surfaces 2106 of the channel 2104 include, but are not limited to, glass or silica.

The channel 2104 and the substrate 2102 are formed of glass in certain embodiments. Biological conditions represent a barrier to the use of glass-derive implantations due to the slow dissolution of glass into biological fluids and adhesion of proteins and small molecules to the glass surface. In certain non-limiting embodiments, surface modification using a self-assembled monolayer offers an approach for modifying glass surfaces for nucleic acid detection and analysis. In certain embodiments, at least a portion of the inner surface 2106 of the channel 2104 is pre-treated or covalently modified to include or be coated with a material that enables specific covalent binding of a sensor compound to the inner surface. In certain embodiments, a cover slip 2114 covering the channel may also be covalently modified with a material.

Exemplary materials that are used to modify the inner surface 2106 of the channel 2104 include, but are not limited to, a silane compound (e.g., tricholorsilane, alkylsilane, triethoxysilane, perfluoro silane), zwitterionic sultone, poly (6-9)ethylene glycol (Peg), perfluorooctyl, fluorescein, an aldehyde, or a graphene compound. The covalent modification of the inner surface of the channel decreases non-specific absorption of certain molecules. In one example, covalent modification of the inner surface may enable covalent bonding of sensor compound molecules to the inner surface while preventing nonspecific absorption of other molecules to the inner surface. For example, poly(ethylene glycol) (Peg) is used to modify the inner surface 2106 of the channel 2104 to reduce nonspecific adsorption of materials to the inner surface.

In some embodiments, the channel 2104 is nano or micro-fabricated to have a well-defined and smooth inner surface 2106. Exemplary techniques for fabricating a channel and modifying the inner surface of a channel are taught in Sumita Pennathur and Pete Crisallai (2014), "Low Temperature Fabrication and Surface Modification Methods for Fused Silica Micro- and Nanochannels," MRS Proceedings, 1659, pp 15-26. doi:10.1557/opl.2014.32, the entire contents of which are hereby expressly incorporated herein by reference.

A first end section of the channel 2104 includes or is in fluid communication with an input port 2110, and a second end section of the channel 2104 includes or is in fluid communication with an output port 2112. In certain non-limiting embodiments, the ports 2110 and 2112 are provided at terminal ends of the channel 2104.

The top surface of the substrate 2102 having the channel 2104 and the ports 2110, 2112 is covered and sealed with a cover slip 2114 in some embodiments. In some embodiments, a rigid plastic is used to define the channels, including the top, and a semipermeable membrane may also be used.

A first electrode 2116 is electrically connected at the first end section of the channel 2104, for example, at or near the input port 2110. A second electrode 2118 is electrically connected at the second end section of the channel 2104, for example, at or near the output port 2112. The first and second electrodes 2116, 2118 are electrically connected to a power supply or voltage source 2120 in order to apply a potential difference between the first and second electrodes. That is, the potential difference is applied across at least a portion of the length of the channel. When a fluid is present in the channel 2104 and is under the influence of the applied potential difference, the electrodes 2116, 2118 and the fluid create a complete electrical pathway.

The power supply or voltage source 2120 is configured to apply an electric field in a reversible manner such that a potential difference is applied in a first direction along the channel length (along the y-axis) and also in a second opposite direction (along the y-axis). In one example in which the electric field or potential difference direction is in a first direction, the positive electrode is connected at the first end section of the channel 2104, for example, at or near the input port 2110, and the negative electrode is connected at the second end section of the channel 2104, for example, at or near the output port 2112. In another example in which the electric field or potential difference direction is in a second opposite direction, the negative electrode is connected at the first end section of the channel 2104, for example, at or near the input port 2110, and the positive electrode is connected at the second end section of the channel 2104, for example, at or near the output port 2112.

The power supply or voltage source 2120 are configured to apply an AC signal in some embodiments. The frequency of the AC signal may be changed dynamically. In some aspects, the power supply or voltage source 2120 are configured to supply an electrical signal having a frequency between $10-10^9$ Hz. In some aspects, the power supply or voltage source 2120 are configured to supply an electrical signal having a frequency between $10^5-10^7$ Hz.

Figure 18:
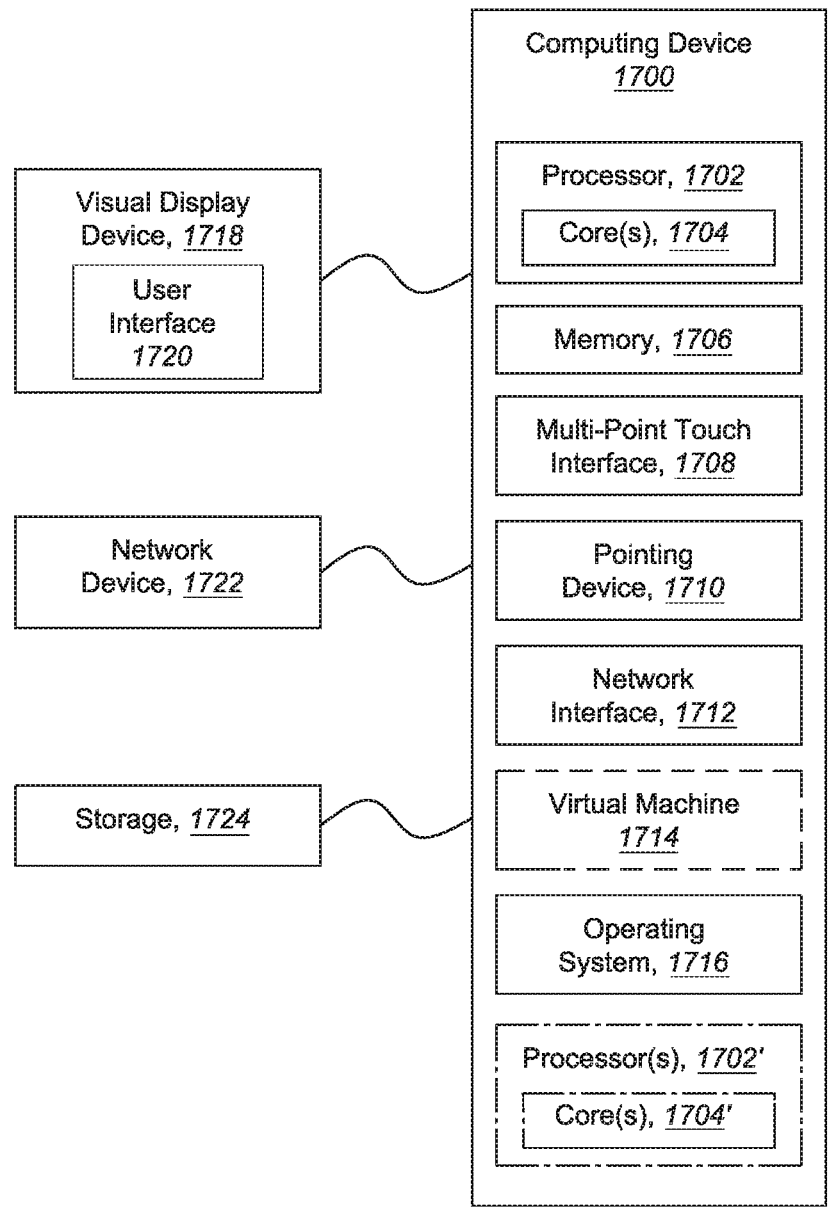
FIG. 18 is a process flow chart illustrating an implementation of device for detecting a target.

The first and second end sections of the channel 2104 (e.g., at or near the input port 2110 and the output port 2112) are electrically connected to a nucleic acid detection circuit 2122 that is programmed or configured to detect values of one or more electrical properties of the channel 2104 for determining whether the particular nucleic acid and/or nucleotide is present or absent in the channel 2104. The electrical property values are detected at a single time period (for example, a certain time period after introduction of a sample and one or more sensor compounds into the channel), or at multiple different time periods (for example, before and after introduction of both the sample and one or more sensor compound into the channel). In some aspects, the electrical property values are detected continuously for a set time period from sample introduction through LAMP amplification. Example electrical properties detected include, but are not limited to, electrical current, conductivity voltage, resistance, frequency, or waveform. Certain example nucleic acid detection circuits 2122 include or are configured as a processor or a computing device, for example as device 1700 illustrated in FIG. 18. Certain other nucleic acid detection circuits 2122 include, but are not limited to, an ammeter, a voltmeter, an ohmmeter, or an oscilloscope.

In one embodiment, the nucleic acid detection circuit 2122 comprises a measurement circuit 2123 programmed or configured to measure one or more electrical property values along at least a portion of a length of the channel 2104. The nucleic acid detection circuit 2122 also comprises an equilibration circuit 2124 that is programmed or configured to periodically or continually monitor one or more values of an electrical property of the channel over a time period, and/or to select a single one of the values after the values have reached equilibrium (e.g., have stopped varying beyond a certain threshold of variance or tolerance).

The nucleic acid detection circuit 2122 may also comprise a comparison circuit 2126 that is programmed or configured to compare two or more electrical property values of the channel, for example, a reference electrical property value (e.g., measured before a state in which both the sample and all of the sensor compounds have been introduced into the channel) and an electrical property value (e.g., measured after introduction of the sample and all of the sensor compound into the channel). The comparison circuit 2126 may use the comparison in order to determine whether the nucleic acid is present or absent in the channel. In one embodiment, the comparison circuit 2126 calculates a difference between the measured electrical property value and the reference electrical property value, and compares the difference to a predetermined value indicative of the presence or absence of the nucleic acid in the channel and this information is used to diagnose or predict a disease state or the presence or absence of an infection in the subject.

In certain embodiments, upon introduction of both the sample and the sensor compound into the channel, the comparison circuit 2126 is programmed or configured to compare a first electrical property value (e.g., magnitude of electrical current) when the electric field or potential difference is applied across the channel in a first direction along the length of the channel to a second electrical property value (e.g., magnitude of electrical current) when the electric field or potential difference is applied across the channel in a second opposite direction along the length of the channel. In one embodiment, the comparison circuit 2126 calculates a difference between the magnitudes of the first and second values, and compare the difference to a predetermined value (e.g., whether the difference is substantially zero) indicative of the presence or absence of a nucleic acid in the channel. For example, if the difference is substantially zero, this indicates absence of a nucleic acid, which may be in a dispersed, polymer form, or aggregate form, in the channel. If the difference is substantially non-zero, this indicates presence of a nucleic acid, which may be in dispersed form, a polymer form, or an aggregate form, in the channel.

In certain embodiments, the nucleic acid detection circuit 2122 is programmed or configured to determine an absolute concentration of the nucleic acid in a sample, and/or a relative concentration of the nucleic acid relative to one or more additional substances in a sample.

In some embodiments, the comparison circuit 2124 and the equilibration circuit 2126 is configured as separate circuits or modules, while in other embodiments, they are configured as a single integrated circuit or module.

The nucleic acid detection circuit 2122 has an output 2128 that may, in some embodiments, be connected to one or more external devices or modules. For example, the nucleic acid detection circuit 2122 may transmit a reference electrical property value and/or one or more measured electrical property values to one or more of: a processor 2130 for further computation, processing and analysis, a non-transitory storage device or memory 2132 for storage of the values, and/or a visual display device 2134 for display of the values to a user. In some embodiments, the nucleic acid detection circuit 2122 generates an indication of whether the sample includes the nucleic acid, and it transmits this indication to the processor 2130, the non-transitory storage device or memory 2132 and/or the visual display device 2134.

In an example method of using the system of FIG. 17A and FIG. 17B, one or more sensor compounds (e.g., one or more nucleic acid probes) and a sample are sequentially or concurrently introduced into the channel. When flow of the fluid and/or flow of the charged particles in the fluid is uninhibited (e.g., due to absence of an aggregate), the conductive particles or ions in the fluid travel along at least a portion of the length of the channel 2104 along the y-axis from the input port 2110 toward the output port 2112. The movement of the conductive particles or ions produce or generate a first or "reference" electrical property value or range of values (e.g., of an electrical current, conductivity, resistivity, or frequency) being detected by the nucleic acid detection circuit 2122 along at least a portion of the length of the channel 2104. In some embodiments, the equilibration circuit 2124 periodically or continually monitors electrical property values during a time period until the values reach equilibrium. The equilibration circuit 2124 then selects one of the values as the reference electrical property value to avoid the influence of transient changes in the electrical property.

As used herein, "reference" electrical property value refers to a value or range of values of an electrical property of a channel prior to introduction of a sample and all of the sensor compounds (e.g., one or more nucleic acid probes) into the channel. That is, the reference value is a value characterizing the channel prior to any interaction between the nucleic acid in the sample and all of the sensor compounds. In some cases, the reference value is detected at a time period after introduction of a sensor compound into the channel but before introduction of the sample and additional sensor compounds into the channel. In some cases, the reference value is detected at a time period after introduction of a sensor compound and the sample into the channel but before introduction of additional sensor compounds into the channel. In some cases, the reference value is detected at a time period before introduction of the sample or the sensor compounds into the channel. In some cases, the reference value is predetermined and stored on a non-transitory storage medium from which it may be accessed.

In some cases, formation of an electrically conductive aggregate, polymer, or nucleic acid complex in the channel (e.g., due to interactions between a nucleic acid of interest in the sample and one or more nucleic acid probes) enhances the electrical pathway along at least a portion of the length of the channel 2104. In this case, the nucleic acid detection circuit 2122 detects a second electrical property value or range of values (e.g., of an electrical current, conductivity, resistivity, or frequency) along at least a portion of the length of the channel 2104. In some embodiments, the nucleic acid detection circuit 2122 provides for a waiting or adjustment time period after introduction of the sample and all of the sensor compounds into the channel prior to detecting the second electrical property value. The waiting or adjustment time period allows an aggregate, polymer, or nucleic acid complex to form in the channel, preferably while being suspended in the channel, and for the aggregate, polymer, or nucleic acid complex formation to alter the electrical properties of the channel, preferably while being suspended in the channel.

In some embodiments, the equilibration circuit 2124 periodically or continually monitors electrical property values during a time period after the introduction of the sample and all of the sensor compounds until the values reach equilibrium. The equilibration circuit 2124 may then select one of the values as the second electrical property value to avoid the influence of transient changes in the electrical property.

The comparison circuit 2126 compares the second electrical property value to the reference electrical property value. If it is determined that the difference between the second value and the reference value corresponds to a predetermined range of increase in current or conductivity (or decrease in resistivity), the nucleic acid detection circuit 2122 determines that an aggregate, polymer, or nucleic acid complex is present in the channel and that, therefore, the nucleic acid target is present or detected in the sample. Based thereon, one can diagnose or identify the presence or absence of the target and a disease state or infection state in a subject.

In certain other embodiments, when flow of the fluid in the channel and/or flow of the charged particles in the fluid is partially or completely blocked (for example, by formation of an aggregate, polymer, or nucleic acid complex), the conductive particles or ions in the fluid are unable to freely travel along at least a portion of the length of the channel 2104 along the y-axis from the input port 2110 toward the output port 2112. The hindered or stopped movement of the conductive particles or ions produces or generates a third electrical property value or range of values (e.g., of an electrical current or signal, conductivity, resistivity, or frequency) is detected by the nucleic acid detection circuit 2122 along at least a portion of the length of the channel 2104. The third electrical property value is detected in addition to or instead of the second electrical property value. In some embodiments, the nucleic acid detection circuit 2122 may wait for a waiting or adjustment time period after introduction of both the sample and all of the sensor compounds into the channel prior to detecting the third electrical property value. The waiting or adjustment time period allows an aggregate, polymer, or nucleic acid complex to form in the channel and for the aggregate, polymer, or nucleic acid complex formation to alter the electrical properties of the channel.

In some embodiments, the equilibration circuit 2124 periodically or continually monitors electrical property values during a time period after the introduction of the sample and all of the sensor compounds until the values reach equilibrium. The equilibration circuit 2124 then selects one of the values as the third electrical property value to avoid the influence of transient changes in the electrical property.

The comparison circuit 2126 compares the third electrical property value to the reference electrical property value. If it is determined that the difference between the third value and the reference value corresponds to a predetermined range of decrease in current or conductivity (or increase in resistivity), the nucleic acid detection circuit 2122 determines that an aggregate, polymer, or nucleic acid complex is present in the channel and that, therefore, the target nucleic acid is identified as being present in the sample.

The fluid flow along the length of the channel depends on the size of the aggregate, polymer, or nucleic acid complex in relation to the dimensions of the channel, and the formation of an electrical double layer (EDL) at the inner surface of the channel.

In general terms, an EDL is a region of net charge between a charged solid (e.g., the inner surface of the channel, an analyte particle, an aggregate, polymer, or nucleic acid complex) and an electrolyte-containing solution (e.g., the fluid contents of the channel). EDLs exist around both the inner surface of the channel and around any nucleic acid particles and aggregates, polymers, or nucleic acid complexes within the channel. The counter-ions from the electrolyte are attracted towards the charge of the inner surface of the channel, and induce a region of net charge. The EDL affects ion flow within the channel and around analyte particles and aggregates, polymers, or nucleic acid complexes of interest, creating a diode-like behavior by not allowing any of the counter-ions to pass through the length of the channel.

To mathematically solve for the characteristic length of the EDL, the Poisson-Boltzmann ("PB") equation and/or Poisson-Nemst-Plank equations ("PNP") are solved. These solutions are coupled to the Navier-Stokes (NS) equations for fluid flow to create a nonlinear set of coupled equations that are analyzed to understand the operation of the example system.

In view of the dimensional interplay among the channel surface, the EDLs and the aggregates, polymers, or nucleic acid complexes, example channels are configured and constructed with carefully selected dimensional parameters that ensure that flow of conductive ions is substantially inhibited along the length of the channel when an aggregate, polymer, or nucleic acid complex of a certain predetermined size is formed in the channel. In certain cases, an example channel is configured to have a depth and/or a width that is substantially equal to or smaller than the diameter of an aggregate particle formed in the channel during nucleic acid detection. In certain embodiments, the sizes of the EDLs are also taken into account in selecting dimensional parameters for the channel. In certain cases, an example channel is configured to have a depth and/or a width that is substantially equal to or smaller than the dimension of the EDL generated around the inner surface of the channel and the aggregate, polymer, or nucleic acid complex in the channel.

In certain embodiments, prior to use of the detection system, the channel is free of the sensor compounds (e.g., one or more nucleic acid probes). That is, a manufacturer of the detection system may not pre-treat or modify the channel to include the sensor compound. In this case, during use, a user will introduce one or more sensor compounds, for example in an electrolyte buffer, into the channel and detect a reference electrical property value of the channel with the sensor compound but in the absence of a sample.

In certain other embodiments, prior to use of the detection system, the channel is pre-treated or modified so that at least a portion of an inner surface of the channel includes or is coated with a sensor compound (e.g., one or more nucleic acid capture probes). In one example, the manufacturer detects a reference electrical property value of the channel modified with the sensor compound and, during use a user may use the stored reference electrical property value. That is, a manufacturer of the detection system may pretreat or modify the channel to include a sensor compound. In this case, a user will need to introduce the sample and one or more additional sensor compounds into the channel.

Certain example detection systems include a single channel. Certain other example detection systems include multiple channels provided on a single substrate. Such detection systems may include any suitable number of channels including, but not limited to, at least or equal to 2, 3, 4, 5, 6, 7, 8, 9, or 10, or a number of channels within a range defined by any two of the aforementioned numbers.

In one embodiment, a detection system includes a plurality of channels in which at least two channels operate independent of each other. The example channel 2104 and associated components of FIGS. 17A-17B are reproduced on the same substrate to achieve such a multi-channel detection system. The multiple channels are used to detect the same nucleic acid in the same sample, different nucleic acids in the same sample, the same nucleic acid in different samples, and/or different nucleic acids in different samples. In another embodiment, a detection system includes a plurality of channels in which at least two channels operate in cooperation with each other. In some aspects, the channels are shaped differently depending on the target that is sought to be detected.

Overview of Example Devices for Point of Care Use

Figure 19:
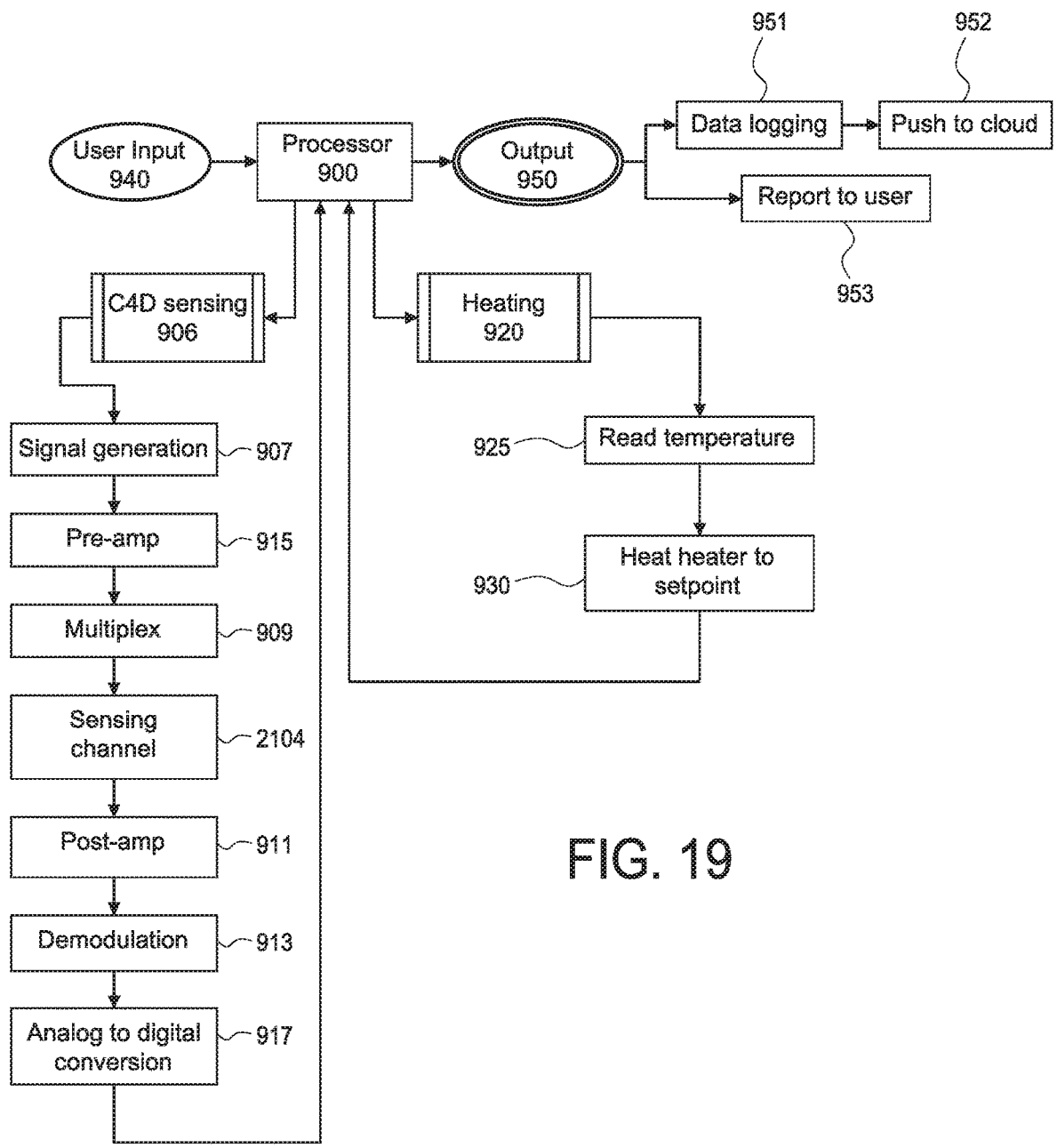
FIG. 19 is a process flow chart illustrating an implementation of a device for detecting a target.

In some implementations, the device is portable and configured to detect one or more targets in a sample. As shown in FIG. 19, the device includes a processor 900 configured to control $fC^4D$ circuitry 905. The $fC^4D$ circuitry 905 includes a signal generator 907. The signal generator 907 is configured to supply one or more signals through a channel 2104 or test well as described above. The signal generator 907 is coupled to a pre-amplifier 915 to amplify the one or more signals from the signal generator 907. The one or more signals is passed through a multiplexor 909 and through the channel 2104. From the channel 2104, the signal is amplified by a post-amplifier 911 and demodulated with a demultiplexer 913. An analog to digital 917 convertor recovers the signal and forwards the digital signal to the processor 900. The processor 900 includes circuitry configured to measure, equilibrate, compare, and the like, to determine if the desired target was detected in the sample. In some embodiments, the analog to digital conversion may happen first. In some such embodiments, the induced waves can be sampled in their entirety, and demodulated digitally in software.

The processor 900 is also coupled to one or more heating elements 920 in some embodiments. The one or more heating elements 920 may be resistive heating elements. The one or more heating elements 920 are configured to heat the sample and/or the solution in the channel 2104. In some embodiments, the sample is heated to a temperature greater than or equal to 0° C., 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 130° C., 140° C., 150° C., 160° C., 170° C., 180° C., 190° C., 200° C., 210° C., 220° C., 230° C., 240° C., 250° C., 260° C. or any temperature, or any range of temperatures between two of the foregoing numbers. In some embodiments, the sample is cooled to a temperature less than or equal to 40° C., 35° C., 30° C., 25° C., 20° C., 15° C., 10° C., 5° C., 0° C., −5° C., −10° C., −15° C., −20° C., or any temperature or any range of temperatures between two of the foregoing numbers. In view of the foregoing, the processor 900 and/or other circuitry is configured to read the temperature 925 of the sample and/or channel 2104 and control the one or more heating elements 920 until the desired heating set point 930 is reached. In some aspects the entire channel 2104 is configured to be heated by the one or more heating elements 920. In other aspects, only portions of the channel 2104 are configured to be heated by the one or more heating elements 920.

The processor 900 is configured to receive user input 940 from one or more user inputs such as keypads, touchscreens, buttons, switches, or microphones. Data is output 950 and logged 951, reported to a user 953, pushed to a cloud based storage system 952, and the like. Data is sent to another device to be processed and/or further processed in some embodiments. For example, $fC^4D$ data may be pushed to the cloud and later processed to determine the presence or absence of a target(s) in the sample.

In some aspects, the device is configured to consume relatively low power. For example, the device may only require 1-10 watts of power. In some aspects, the device requires 7 watts or less of power. The device is configured to process data, wirelessly communicate with one or more other devices, send and detect signals through the channel, heat the sample/channel, and/or detect and display input/output with a touch enabled display.

In some implementations, a sample collector, sample preparer, and fluidics cartridge are formed as separate physical devices. Thus a first sample collector device is used to collect a sample. The sample may comprise saliva, mucus, blood, plasma, stool, or cerebral spinal fluid. The sample is then transferred to a second sample preparing device. The sample preparing device includes components and reagents required for nucleic acid amplification. After the sample is prepared, it is transferred to a third device comprising a fluidics cartridge where amplification and fC$^4$D excitations and measurements take place. In some implementations, the sample collecting and sample preparation are accomplished by a single device. In some implementations, the sample preparation and fluidics cartridge are contained within a single device. In some implementations, a single device is configured to collect a sample, prepare the sample, amplify at least a portion of the sample, and analyze the sample with fC$^4$D.

Overview of Example Compact Fluidics Cartridges

In some aspects, the device includes a removable fluidics cartridge that is couplable to another companion device. The removable fluidics cartridge is configured to be a disposable single use cartridge. The cartridge includes a plurality of channels in some embodiments. The channels may be differently shaped. In some aspects, four shapes of channels are used and repeated to ensure accuracy. In some aspects, more than four shapes of channels are used and repeated to ensure accuracy. In some aspects, each channel is configured to detect one unique target. In other aspects each channel is configured to detect the same target. In some implementations, the cartridge includes one or more heating elements. In general, the fluidics cartridge may include at least one channel configured for fC$^4$D analysis.

In some aspects the cartridge includes a multi-layered laminated structure. One or more channels are stamped and/or laser cut into the substrate. The substrate includes a polypropylene film in some embodiments. One or both sides of the film are coated with an adhesive. This channel layer is secured over a polyamide heater coil in order to heat all or a portion of the channel. The channel is at least partially covered by a hydrophilic PET layer. Printed electrodes may be disposed under the PET layer. In some aspects, at least one thermistor is supplied per channel for temperature feedback.

In other aspects, the cartridge includes injected molded plastic. One or more channels are disposed within the injected molded plastic. A PET layer or PET film is coated on all or parts of the channels by laser welding the PET to the IM plastic. Injection molding may offer the benefits of rigidity and 3D structure and also allow for features such as valves, and a frame for easy handling. The cartridge may or may not include printed electronics and/or heating elements and/or thermistors depending on the particular design.

Figure 20:
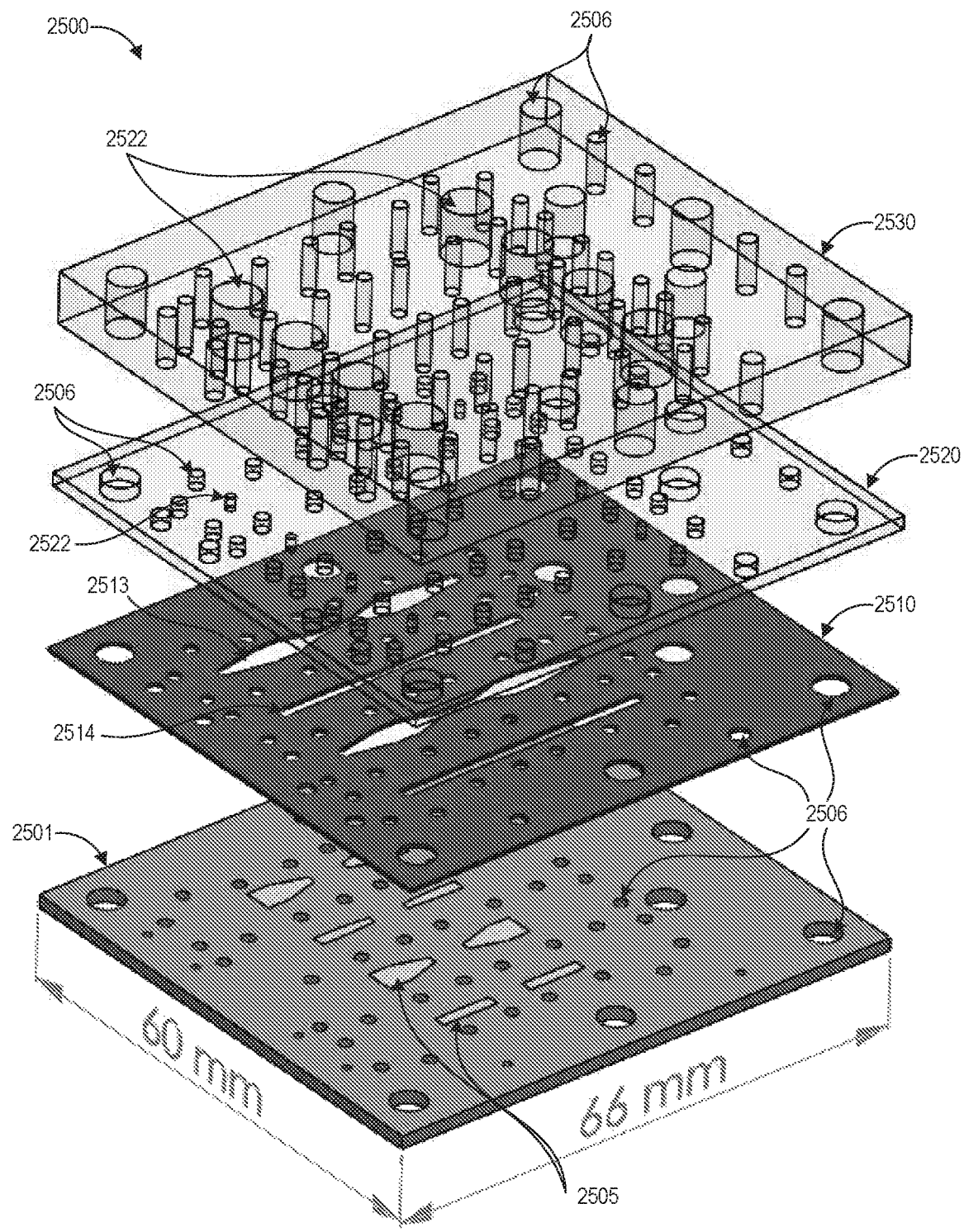
FIG. 20 depicts an example fluidics cartridge.
Figure 21:
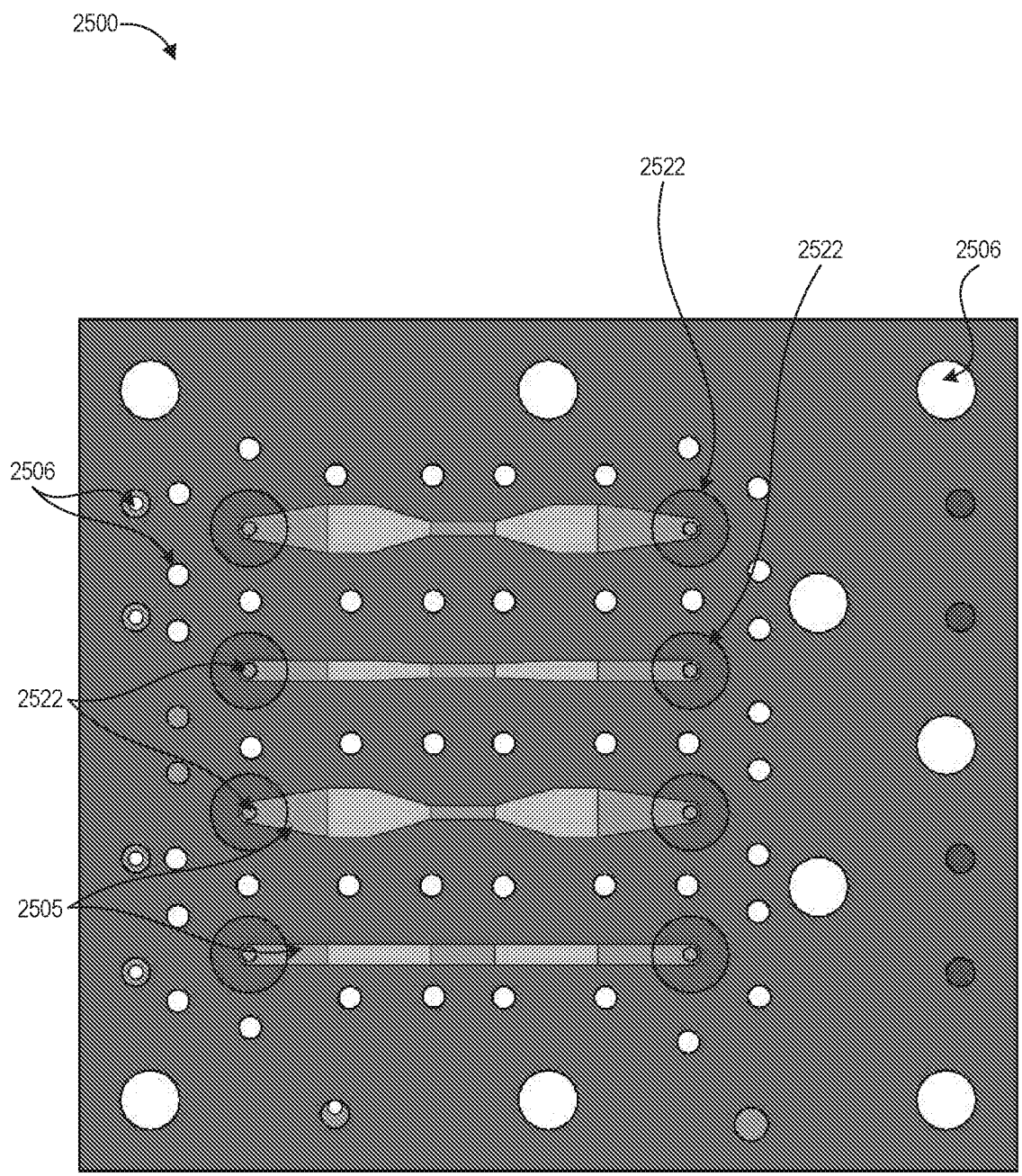
FIG. 21 is a plan view of the example fluidic cartridge of FIG. 20.
Figure 22:
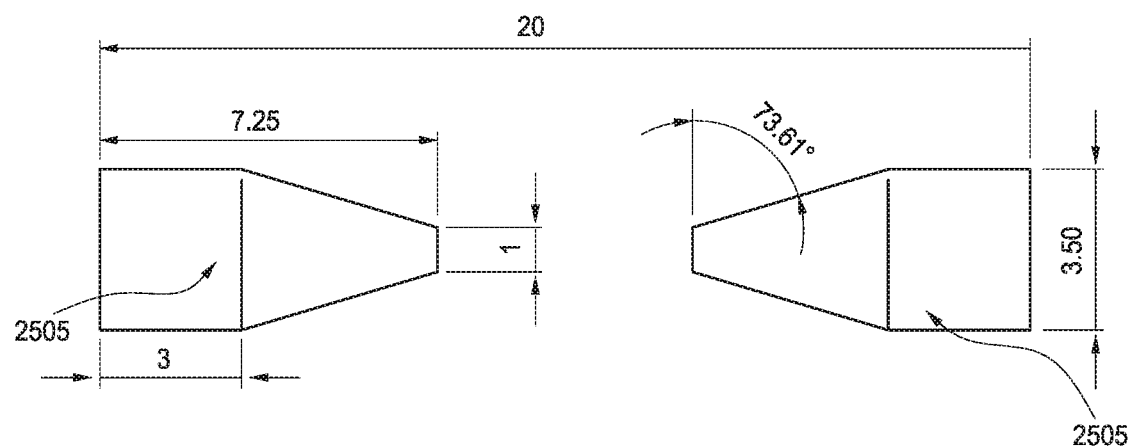
FIG. 22 depicts an example configuration for electrodes.
Figure 23:
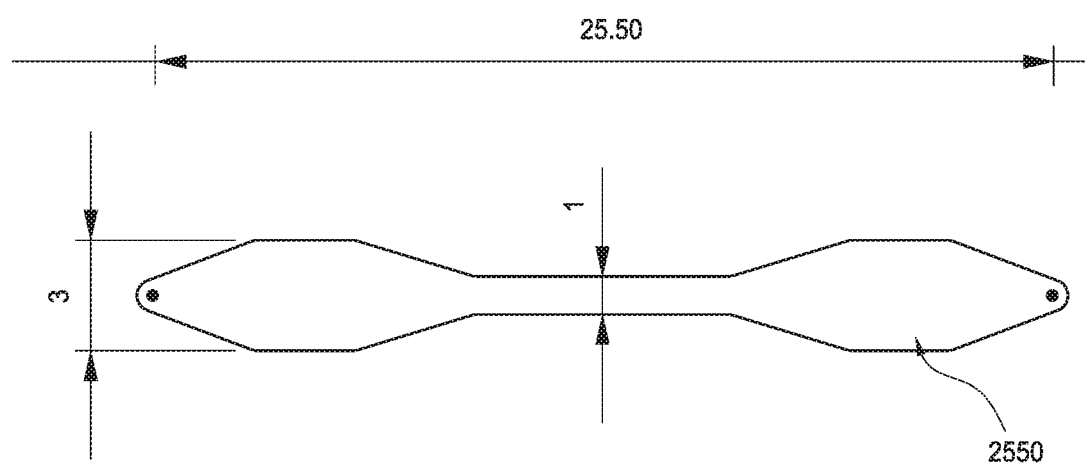
FIG. 23 depicts an example channel.

An example embodiment of a fluidics cartridge 500 is depicted in FIG. 20. As shown, the cartridge 2500 includes four layers. A PCB/PWB layer 2501 having electrodes 2505 traced thereon. The electrodes can be passivated with a 30 nm layer of titanium dioxide using methods such as atomic deposition. The PCB/PWB layer can include entry points 2506 for screws or other holding means to hold the four layers together. A power supply and detection circuitry can be in coupled to the PCB/PWB layer. A gasket layer 2510 having cutouts 2513 and 2514, and entry points 2506. The gasket layer can be manufactured from materials such as a fluorosilicone. A lower rigid substrate layer 2520 that includes entry points 2506, and inlet ports 2522. An upper rigid layer 2530 that includes entry points 2506, and inlet ports 2522. The lower and upper rigid layers can each be manufactured from materials such as acrylic. Four channels are formed when the four layers are assembled together by fixing screws or other holding means through the several entry points 2506 of the several layers. The cutouts 2513 and 2514 form the sides of the channels. The cutout 513 forms a channel having two trapezoidal ends, and the cutout 2514 forms a channel having substantially straight sides. Portions of the PCB/PWB layer 2501 including electrodes 2505 form the bottom of the channels. The lower rigid layer 2520 forms the top of the channels, and the inlet ports 2522 provide inlet and outlet ports to the channels. The inlet ports 2522 of the upper layer and inlet ports of the upper rigid layer provide a means to provide reagents to each channel. In some embodiments, a channel having two trapezoidal ends can have a volume about 30 µl to about 50 µl. In some embodiments, a channel having substantially straight sides can have a volume about 20 µl to about 30 µl. Such volumes can be adjusted by varying compression of at least the gasket layer. FIG. 21 depicts a top plan view of the fluidics cartridge 2500 of FIG. 20, and shows entry points 506 for screws or other holding means, inlet ports 2522 in communication with channels 2550, and electrodes 2505. FIG. 22 provides example dimensions for two electrodes 2505. FIG. 23 provides example dimensions for a channel 2550 having two trapezoidal ends. In some embodiments, the channel is heated to a temperature of 60° C., 61° C., 62° C., 63° C., 64° C., 65° C., 66° C., 67° C., 68° C., 69° C., 70° C., 71° C., 72° C., 73° C., 74° C., or 75° C. or within a range defined by any two of the aforementioned numbers and pressurized. In some aspects, the channel can be pressurized to 1, 2, 3, 4, 5, or 6 atmospheres or within a range defined by any two of the aforementioned pressures.

In some embodiments, a channel of a fluidics device can be adapted to or configured to hold a sample volume greater than or equal to 1 µl, 2 µl, 3 µl, 4 µl, 5 µl, 6 µl, 7 µl, 8 µl, 9 µl, 10 µl, 20 µl, 30 µl, 40 µl, 50 µl, 60 µl, 70 µl, 80 µl, 90 µl, 100 µl, 200 µl, 300 µl, 400 µl, 500 µl, 600 µl, 700 µl, 800 µl, 900 µl, or 1000 µl, or a volume or any range between any two of the foregoing volumes. In some embodiments, a channel of a fluidics device can be adapted to be pressurized. In some embodiments, the sample in a channel can be pressurized to a pressure greater than or equal to 1 atmospheres, 2 atmospheres, 3 atmospheres, 4 atmospheres, 5 atmospheres, 6 atmospheres, 7 atmospheres, 8 atmospheres, 9 atmospheres, 10 atmospheres, or any range between any two of the foregoing pressures. In some embodiments, a channel of a fluidics device can be adapted to be held at a temperature greater than or equal to −20° C., −15° C., −10° C., −5° C., 0° C., 5° C., 10° C., 15° C., 20° C., 25° C., 30° C., 35° C., 40° C., 45° C., 50° C., 55° C., 60° C., 65° C., 70° C., 85° C., 80° C., 85° C., 90° C., 95° C., 100° C., 105° C., 110° C., 115° C., 120° C., 130° C., 140° C., 150° C., 160° C., 170° C., 180° C., 190° C., 200° C., 210° C., 220° C., 230° C., 240° C., 250° C., 260° C., or any temperature or any range between any two of the foregoing temperatures.

Overview of Example Sample Collection

In some implementations, methods, systems and device disclosed herein utilize a simplified and direct sample collection process. In this way, the number of steps from sample collection to analysis is shortened. In other words, in some implementations, it is desirable to minimize the number of times the sample is transferred and/or manipulated by the user to avoid contamination of the sample. In some aspects, the devices disclosed herein are configured to be compatible with a plurality of sample collection methods to suit all types of testing environments. Thus, homogeneous vial-to-chip interfaces are utilized in some aspects. By adjusting the sample collection systems, the detection hardware remains the same regardless of the type of sample that is collected and analyzed.

Overview of Example Assays

Some embodiments of the methods, systems and compositions provided herein include a simple, lysis/amplification/detection of targets from crude samples in a single vessel. Some embodiments include immuno-based amplification for detection of non-nucleic acid targets. Some embodiments include reagents added to reaction which result in increased conductivity change. Some embodiments include isothermal amplification strategies, such as LAMP, SDA, and/or RCA. In some embodiments, targets for detection are biomarkers such as proteins, small molecules such as pharmaceuticals or narcotics, or biological weapons such as toxins. Detection of such targets can be achieved by conjugating immuno-based binding reagents, such as antibodies or aptamers, with nucleic acids which will participate in an isothermal amplification reaction. In some embodiments, additives to the amplification reaction can increase the solution conductivity change which is correlated with the quantification of the target. The use of additives can provide a greater sensitivity and dynamic range for detection.

Some embodiments of the methods provided herein allow for sample collection and processing to have one or more of the following desirable features: be centrifuge-free; be portable; be inexpensive; be disposable; may not require wall outlet electrics; may be easy and or intuitive to use; may require only a relatively low technical skill to use; may be able extract RNA and/or DNA from a small volume sample (e.g., 70 µL); may be able to stabilize the RNA and/or DNA until amplification; may use thermally stable reagents with no cold chain storage requirements; may be assay compatible for low level of detail samples (e.g., samples having 1,000 copies or less/mL), and/or have a dynamic range with the ability to detect viral load across, for example, at least 4 orders of magnitude.

Some embodiments of the methods, systems and compositions provided include the collection and processing of a sample for use in a diagnostic device, as described herein. Examples of a collected sample, also referred to as a biological sample, can include, for example, plant, blood, serum, plasma, urine, saliva, ascites fluid, spinal fluid, semen, lung lavage, sputum, phlegm, mucous, feces, a liquid medium comprising cells or nucleic acids, a solid medium comprising cells or nucleic acids, tissue, and the like. Methods to obtain samples can include the use of a finger stick, a heel stick, a venipuncture, an adult nasal aspirate, a child nasal aspirate, a nasopharyngeal wash, a nasopharyngeal aspirate, a swab, a bulk collection in cup, a tissue biopsy or a lavage sample. More examples include environmental samples, such as soil sample, and a water sample.

Overview of Example Amplification

Some embodiments of the methods, systems and compositions provided herein include amplification of nucleic acid targets. Methods of nucleic amplification are well known and include methods in which temperature is varied during the reaction, such as the PCR.

More examples include isothermal amplification in which the reaction can occur at a substantially constant temperature. In some embodiments, isothermal amplification of nucleic acid targets results in changes in conductivity of a solution. There are several types of isothermal nucleic acid amplification methods such as nucleic acid sequence-based amplification (NASBA), strand displacement amplification (SDA), loop-mediated amplification (LAMP), Invader assay, rolling circle amplification (RCA), signal mediated amplification of RNA technology (SMART), helicase-dependent amplification (HDA), recombinase polymerase amplification (RPA), nicking endonuclease signal amplification (NESA) and nicking endonuclease assisted nanoparticle activation (NENNA), exonuclease-aided target recycling, Junction or Y-probes, split DNAZyme and deoxyribozyme amplification strategies, template-directed chemical reactions that lead to amplified signals, non-covalent DNA catalytic reactions, hybridization chain reactions (HCR) and detection via the self-assembly of DNA probes to give supramolecular structures. See e.g., Yan L., et al., Mol. BioSyst., (2014) 10: 970-1003, which is hereby expressly incorporated by reference in its entirety.

In an example of LAMP, two primers in a forward primer set are named inner (F1c-F2, c strands for "complementary") and outer (F3) primers. At 60° C., the F2 region of the inner primer first hybridizes to the target, and is extended by a DNA polymerase. The outer primer F3 then binds to the same target strand at F3c, and the polymerase extends F3 to displace the newly synthesized strand. The displaced strand forms a stem-loop structure at the 5' end due to the hybridization of F1c and F1 region. At the 3' end, the reverse primer set can hybridize to this strand and a new strand with stem-loop structure at both ends is generated by the polymerase. The dumbbell structured DNA enters the exponential amplification cycle and strands with several inverted repeats of the target DNA can be made by repeated extension and strand displacement. In some embodiments of the methods provided herein components for LAMP include 4 primers, DNA polymerase, and dNTPs. Examples of the application of LAMP include Viral pathogens, including dengue (M. Parida, et al., J. Clin. Microbiol., 2005, 43, 2895-2903) Japanese encephalitis (M. M. Parida, et al., J. Clin. Microbiol., 2006, 44, 4172-4178), Chikungunya (M. M. Parida, et al., J. Clin. Microbiol., 2007, 45, 351-357), West Nile (M. Parida, et al., J. Clin. Microbiol., 2004, 42, 257-263), Severe acute respiratory syndrome (SARS) (T. C. T. Hong, Q. L. Mai, D. V. Cuong, M. Parida, H. Minekawa, T. Notomi, F. Hasebe and K. Morita, J. Clin. Microbiol., 2004, 42, 1956-1961), and highly pathogenic avian *influenza* (HPAI) H5N1 (M. Imai, et al., J. Virol. Methods, 2007, 141, 173-180), each of the foregoing references is hereby expressly incorporated by reference herein in its entirety.

In an example of SDA, a probe includes two parts: a Hinc II recognition site at the 5' end and another segment that includes sequences that are complementary to the target. DNA polymerase can extend the primer and incorporate deoxyadenosine 5'-[α-thio]triphosphate (dATP[αS]). The restriction endonuclease Hinc II then nicks the probe strand at the Hinc II recognition site because the endonuclease cannot cleave the other strand that includes the thiophosphate modification. The endonuclease cleavage reveals a 3'-OH, which is then extended by DNA polymerase. The newly generated strand still contains a nicking site for Hinc II. Subsequent nicking of the newly synthesized duplex, followed by DNA polymerase-mediated extension is repeated several times and this leads to an isothermal amplification cascade. In some embodiments of the methods provided herein components for SDA include 4 primers, DNA polymerase, REase HincII, dGTP, dCTP, dTTP, and dATPαS. An example of the application of SDA include *Mycobacterium tuberculosis* genomic DNA (M. Vincent, et al., EMBO Rep., 2004, 5, 795-800 which is hereby expressly incorporated by reference herein in its entirety).

In an example of NASBA, a forward primer 1 (P1) is composed of two parts, one of which is complementary to a 3'-end of a RNA target and the other to a T7 promoter sequence. When the P1 binds to the RNA target (RNA (+)), reverse transcriptase (RT) extends the primer into a complementary DNA (DNA (+)) of the RNA. RNase H then degrades the RNA strand of the RNA-DNA (+) hybrid. A reverse primer 2 (P2) then binds to the DNA (+), and a reverse transcriptase (RT) produces double stranded DNA (dsDNA), which contains a T7 promoter sequence. After this initial phase, the system enters the amplification phase. The T7 RNA polymerase generates many RNA strands (RNA (−)) based on the dsDNA, and the reverse primer (P2) binds to the newly formed RNA (−). RT extends the reverse primer and RNase H degrades the RNA of the RNA-cDNA duplex into ssDNA. The newly produced cDNA (DNA (+)) then becomes a template for P1 and the cycle is repeated. In some embodiments of the methods provided herein components for NASBA include 2 primers, reverse transcriptase, RNase H, RNA polymerase, dNTP, and rNTP. Examples of the application of NASBA include HIV-1 genomic RNA (D. G. Murphy, et al., J. Clin. Microbiol., 2000, 38, 4034-4041) hepatitis C virus RNA (M. Damen, et al., J. Virol. Methods, 1999, 82, 45-54), human cytomegalovirus mRNA (F. Zhang, et al., J. Clin. Microbiol., 2000, 38, 1920-1925), 16S RNA in bacterial species (S. A. Morre, et al., J. Clin. Pathol.: Clin. Mol. Pathol., 1998, 51, 149-154), and enterovirus genomic RNA (J. D. Fox, et al., J. Clin. Virol., 2002, 24, 117-130). Each of the foregoing references is hereby expressly incorporated by reference herein in its entirety.

More examples of isothermal amplification methods include: self-sustaining sequence replication reaction (3SR); 90-I; BAD Amp; cross priming amplification (CPA); isothermal exponential amplification reaction (EXPAR); isothermal chimeric primer initiated amplification of nucleic acids (ICAN); isothermal multi displacement amplification (IMDA); ligation-mediated SDA; multi displacement amplification; polymerase spiral reaction (PSR); restriction cascade exponential amplification (RCEA); smart amplification process (SMAP2); single primer isothermal amplification (SPIA); transcription-based amplification system (TAS); transcription meditated amplification (TMA); ligase chain reaction (LCR); and/or multiple cross displacement amplification (MCDA).

Overview of Example Immuno-Isothermal Amplification

Some embodiments of the methods, systems and compositions provided herein include the use of immuno-isothermal amplification to detect non-nucleic acid targets. In some such embodiments, primers useful in an isothermal amplification method are linked to an antibody or fragment thereof, or aptamer. As used herein "aptamer" can include a peptide or oligonucleotide that binds specifically to a target molecule. In some embodiments, the antibody or aptamer can be linked to primers useful in an isothermal amplification method through covalent or non-covalent bonds. In some embodiments, primers useful in an isothermal amplification method can be linked to an antibody or aptamer through biotin and streptavidin linkers. In some embodiments, primers useful in an isothermal amplification method can be linked to an antibody or aptamer using THUNDER-LINK (Innova Biosciences, UK).

In some embodiments, a target antigen binds to the antibody or aptamer, and the primers linked to the antibody or aptamer are substrates for isothermal amplification and/or initiate isothermal amplification. See e.g., Pourhassan-Moghaddam et al., Nanoscale Research letters, 8:485-496 which is hereby expressly incorporated by reference herein in its entirety. In some embodiments, a target antigen is captured in a sandwich form between two anti-bodies or aptamers (Abs), the capture antibody and the detection antibody, which are specifically bound to the target antigen. The capture Ab, which is pre-immobilized on a solid support surface, captures the target Ag, and the detection Ab, which is linked with primers useful in an isothermal amplification method, attaches to the captured Ag. After washing, isothermal amplification is performed, and the presence of amplified products indicates indirectly the presence of target Ag in the sample.

Overview of Example Enhancing Changes in Conductivity

Some embodiments of the methods, systems and compositions provided herein include enhancing changes in the conductivity of a solution that result from amplification of a nucleic acid. In some embodiments, chelation of pyrophosphate ("PPi") that results from nucleic acid amplification can be used to enhance changes in the conductivity of a solution as an amplification reaction continues. Without being bound to any one theory, conductivity changes that can occur during amplification of a nucleic may be based on precipitation of magnesium cations and PPi ions from solution. Some embodiments of the methods provided herein can include increasing the conductivity change by changing the equilibria, which otherwise results in the precipitation of magnesium cations and PPi ions. In some embodiments, this is accomplished by the addition of molecules that compete against magnesium cations for PPi. In some such embodiments, compounds are provided that have a high ionic mobility, which would result in a high contribution to net solution conductivity. Therefore, the removal of the compound from solution by precipitation of the compounds with PPi produces a dramatic change in the conductivity of the solution. In some embodiments of the methods provided herein, compounds/complexes, which may bind PPi and result in changes and/or enhanced changes in the conductivity of a solution as amplification continues, include $Cd^{2+}$-cyclen-coumarin; $Zn^{2+}$ complexes with a bis(2-pyridylmethyl)amine (DPA) unit; DPA-$2Zn^{2+}$-phenoxide; acridine-DPA-$Zn^{2+}$; DPA-$2Zn^{2+}$-pyrene; and azacrown-$Cu^{2+}$ complexes. See e.g., Kim S. K. et al., (2008) Accounts of Chemical Research 42: 23-31; and Lee D-H, et al., (2007) Bull. Korean Chem. Soc. 29: 497-498; Credo G. M. et al., (2011) Analyst 137:1351-1362; and Haldar B. C. (1950) "Pyrophosphato-Complexes of Nickel and Cobalt in Solution" Nature 4226:744-745, each of which is hereby expressly incorporated by reference herein in its entirety.

Some embodiments include compounds such as 2-amino-6-mercapto-7-methylpurine ribonucleoside (MESG). MESG is used in kits to detect pyrophosphate such as an EnzChek® Pyrophosphate Assay Kit (ThermoFischer Scientific) in which MESG is converted by the purine nucleoside phosphorylase (PNP) enzyme to ribose 1-phosphate and 2-amino-6-mercapto-7-methylpurine in the presence of inorganic phosphate. The enzymatic conversion of MESG results in a shift in absorbance maximum from 330 nm to 360 nm. PNP catalyzes conversion of pyrophosphate into two equivalents of phosphate. The phosphate is then consumed by the MESG/PNP reaction and detected by an increase in absorbance at 360 nm. Additional sensitivity is gained by the amplification of one molecule of pyrophosphate into two molecules of phosphate. Another kit includes PIPER Pyrophosphate Assay Kit (ThermoFischer Scientific)

In some embodiments, enhancing changes in the conductivity of a solution that result from amplification of a nucleic acid include compounds that bind amplified DNA. In some such embodiments, as amplification continues a charge carrying species binds to the increasing amounts of amplified DNA resulting in a net reduction in conductivity of the solution. In some embodiments, charged carrying species can include positively charged molecules commonly used as DNA/RNA stains/dyes, such as ethidium bromide, crystal violet, SYBR, which bind to nucleic acids through electrostatic attraction. The binding of these small, charged molecular species to large and less mobile amplification products can reduce the conductivity of the solution by effectively reducing the charge mobility of the dye molecules. It should be noted that while this electrostatic attraction is the mechanism by which DNA is frequently stained for gel electrophoresis, the molecules which bind to the amplicons need not be compounds traditionally used as DNA stains. Since these molecules are being utilized for their function as a charge carrier (contributor to the solution conductivity) as well as their ability to bind to the amplicon, they need not possess any DNA staining properties.

Some embodiments include the use of antibodies or aptamers linked to a nanoparticle. In some such embodiments, the presence of a target antigen results in aggregation of the antibodies and a change in conductivity of the solution. Without being bounds to any one theory, the effective electrical conductivity of colloidal nano-suspensions in a liquid can exhibit a complex dependence on the electrical double layer (EDL) characteristics, volume fraction, ionic concentrations and other physicochemical properties. See e.g., Angayarkanni S A., et al., Journal of Nanofluids, 3: 17-25 which is hereby expressly incorporated by reference herein in its entirety. Antibody-conjugated nanoparticles are well known in the art. See e.g., Arruebo M. et al., Journal of Nanomaterials 2009:Article ID 439389; and Zawrah M F., et al., HBRC Journal 2014.12.001, which are each hereby expressly incorporated by reference herein in its entirety. Examples of nanoparticles that are useful with the methods provided herein include γ-$Al_2O_3$, $SiO_2$, $TiO_2$ and α-$Al_2O_3$, and gold nanoparticles, See e.g., Abdelhalim, M A K., et al., International Journal of the Physical Sciences, 6:5487-5491 which is hereby expressly incorporated by reference herein in its entirety. The use of antibodies linked to nanoparticles may also enhance signal generated at a surface through measurements taken using electrochemical impedance spectroscopy (EIS). See e.g., Lu J., et al., Anal Chem. 84: 327-333 which is incorporated by reference herein in its entirety.

Some embodiments of the methods, systems and compositions provided herein include the use of the use of antibodies or aptamers linked to an enzyme. In some embodiments, enzyme activity produces a change in the conductivity of a solution. In some such embodiments, the change in conductivity is detected by a charge transfer to a substrate contacting the assay components.

Overview of Example Viral Targets

Some embodiments of the methods, systems and compositions provided herein include the detection of certain viruses and viral targets. A viral target can include a viral nucleic acid, a viral protein, and/or product of viral activity, such as an enzyme or its activity. Examples of viral proteins that are detected with methods and devices provided herein include viral capsid proteins, viral structural proteins, viral glycoproteins, viral membrane fusion proteins, viral proteases or viral polymerases. Viral nucleic acid sequences (RNA and/or DNA) corresponding to at least a portion of the gene encoding the aforementioned viral proteins are also detected with the methods and devices described herein. Nucleotide sequences for such targets are readily obtained from public databases. Primers useful for isothermal amplification are readily designed from the nucleic acid sequences of desired viral targets. Antibodies and aptamers to proteins of such viruses are also readily obtained through commercial avenues, and/or by techniques well known in the art. Examples of viruses that are detected with the methods, systems and compositions provided herein include DNA viruses, such as double-stranded DNA viruses and single-stranded viruses; RNA viruses such as double-stranded RNA viruses, single-stranded (+) RNA viruses, and single-stranded (−) RNA viruses; and retro-transcribing viruses, such as single-stranded retro-transcribing RNA viruses, and double-stranded retro-transcribing DNA viruses. Viruses that are detected utilizing this technology include animal viruses, such as human viruses, domestic animal viruses, livestock viruses, or plant viruses. Examples of human viruses that are detected with the methods, systems and compositions provided herein include those listed in TABLE 2 below which also provides exemplary nucleotide sequences from which primers useful for amplification are readily designed.

TABLE 2

| Example virus | Example nucleotide sequence (NCBI Accession No.) |
|---|---|
| Adeno-associated virus | NC_001401 |
| Aichi virus | NC_001918 |
| Australian bat lyssavirus | NC_003243 |
| BK polyomavirus | NC_001538 |
| Banna virus | NC_004217 |
| Barmah forest virus | NC_001786 |
| Bunyamwera virus | NC_001925 |
| Bunyavirus La Crosse | NC_004108 |
| Bunyavirus snowshoe hare | |
| Cercopithecine herpesvirus | NC_006560 |
| Chandipura virus | |
| Chikungunya virus | NC_004162 |
| Cosavirus A | NC_012800 |
| Cowpox virus | NC_003663 |
| Coxsackievirus | NC_001612 |
| Crimean-Congo hemorrhagic fever virus | NC_005301 |
| Dengue virus | NC_001477 |
| Dhori virus | |
| Dugbe virus | |
| Duvenhage virus | NC_004159 |
| Eastern equine encephalitis virus | NC_003899 |
| Ebolavirus | NC_002549 |
| Echovirus | NC_001897 |
| Encephalomyocarditis virus | NC_001479 |
| Epstein-Barr virus | NC_007605 |
| European bat lyssavirus | NC_009527 |
| GB virus C/Hepatitis G virus | NC_001710 |
| Hantaan virus | NC_005222 |
| Hendra virus | NC_001906 |
| Hepatitis A virus | NC_001489 |
| Hepatitis B virus | NC_003977 |
| Hepatitis C virus | NC_004102 |
| Hepatitis E virus | NC_001434 |
| Hepatitis delta virus | NC_001653 |
| Horsepox virus | |
| Human adenovirus | NC_001405 |
| Human astrovirus | NC_001943 |
| Human coronavirus | NC_002645 |
| Human cytomegalovirus | NC_001347 |
| Human enterovirus 68, 70 | NC_001430 |
| Human herpesvirus 1 | NC_001806 |
| Human herpesvirus 2 | NC_001798 |
| Human herpesvirus 6 | NC_001664 |
| Human herpesvirus 7 | NC_001716 |
| Human herpesvirus 8 | NC_009333 |
| Human immunodeficiency virus | NC_001802 |
| Human papillomavirus 1 | NC_001356 |
| Human papillomavirus 2 | NC_001352 |
| Human papillomavirus 16, 18 | NC_001526 |
| Human parainfluenza | NC_003461 |
| Human parvovirus B19 | NC_000883 |
| Human respiratory syncytial virus | NC_001781 |
| Human rhinovirus | NC_001617 |
| Human SARS coronavirus | NC_004718 |
| Human spumaretrovirus | |
| Human T-lymphotropic virus | NC_001436 |
| Human torovirus | |

TABLE 2-continued

| Example virus | Example nucleotide sequence (NCBI Accession No.) |
| --- | --- |
| Influenza A virus | NC_002021 |
| Influenza B virus | NC_002205 |
| Influenza C virus | NC_006308 |
| Isfahan virus | |
| JC polyomavirus | NC_001699 |
| Japanese encephalitis virus | NC_001437 |
| Junin arenavirus | NC_005080 |
| KI Polyomavirus | NC_009238 |
| Kunjin virus | |
| Lagos bat virus | |
| Lake Victoria marburgvirus | NC_001608 |
| Langat virus | NC_003690 |
| Lassa virus | NC_004296 |
| Lordsdale virus | |
| Louping ill virus | NC_001809 |
| Lymphocytic choriomeningitis virus | NC_004294 |
| Machupo virus | NC_005078 |
| Mayaro virus | NC_003417 |
| MERS coronavirus | NC_019843 |
| Measles virus | NC_001498 |
| Mengo encephalomyocarditis virus | |
| Merkel cell polyomavirus | NC_010277 |
| Mokola virus | NC_006429 |
| Molluscum contagiosum virus | NC_001731 |
| Monkeypox virus | NC_003310 |
| Mumps virus | NC_002200 |
| Murray valley encephalitis virus | NC_000943 |
| New York virus | |
| Nipah virus | NC_002728 |
| Norwalk virus | NC_001959 |
| O'nyong-nyong virus | NC_001512 |
| Orf virus | NC_005336 |
| Oropouche virus | NC_005775 |
| Pichinde virus | NC_006439 |
| Poliovirus | NC_002058 |
| Punta toro phlebovirus | |
| Puumala virus | NC_005224 |
| Rabies virus | NC_001542 |
| Rift valley fever virus | NC_002044 |
| Rosavirus A | NC_024070 |
| Ross river virus | NC_001544 |
| Rotavirus A | NC_011506 |
| Rotavirus B | NC_007549 |
| Rotavirus C | NC_007570 |
| Rubella virus | NC_001545 |
| Sagiyama virus | |
| Salivirus A | NC_012957 |
| Sandfly fever sicilian virus | |
| Sapporo virus | NC_006554 |
| Semliki forest virus | NC_003215 |
| Seoul virus | NC_005237 |
| Simian foamy virus | NC_001364 |
| Simian virus 5 | |
| Sindbis virus | NC_001547 |
| Southampton virus | |
| St. louis encephalitis virus | NC_007580 |
| Tick-borne powassan virus | NC_003687 |
| Torque teno virus | NC_002076 |
| Toscana virus | NC_006319 |
| Uukuniemi virus | NC_005220 |
| Vaccinia virus | NC_006998 |
| Varicella-zoster virus | NC_001348 |
| Variola virus | NC_001611 |
| Venezuelan equine encephalitis virus | NC_001449 |
| Vesicular stomatitis virus | NC_001560 |
| Western equine encephalitis virus | NC_003908 |
| WU polyomavirus | NC_009539 |
| West Nile virus | NC_001563 |
| Yaba monkey tumor virus | NC_005179 |
| Yaba-like disease virus | NC_002642 |
| Yellow fever virus | NC_002031; and/or |
| Zika virus | NC_012532 |

Overview of Example Bacterial Targets

Some embodiments of the methods, systems and compositions provided herein include the detection of certain bacteria and bacterial targets. A bacterial target includes a bacterial nucleic acid, a bacterial protein, and/or product of bacterial activity, such as toxins, and enzyme activities. Nucleotide sequences indicative of certain bacteria are readily obtained from public databases. Primers useful for isothermal amplification are readily designed from nucleic acid sequences of such bacterial targets. Antibodies and aptamers to proteins of certain bacteria are readily obtained through commercial avenues, and/or by techniques well known in the art. Examples of bacteria that are detected with the methods, systems and compositions provided herein include gram negative or gram positive bacteria. Examples of bacteria that are detected with the methods, systems and compositions provided herein include: *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, and/or *Staphylococcus saccharolyticus*. More example include *B. anthracis, B. globigii, Brucella, E. herbicola*, or *F. tularensis*.

Overview of Example Antigen Targets

Some embodiments of the methods, systems and compositions provided herein include the detection of certain antigen targets. Antigens are detected using antibodies, binding fragments thereof, or aptamers linked to primers that are configured for amplification, such as isothermal amplification. Antibodies and aptamers to certain antigens are readily obtained through commercial avenues, and/or by techniques well known in the art. As used herein an "antigen" includes a compound or composition that is specifically bound by an antibody, binding fragment thereof, or aptamer. Examples of antigens that are detected with the methods, systems and compositions provided herein include proteins, polypeptides, nucleic acids, and small molecules, such as pharmaceutical compounds. More examples of analytes include toxins, such as ricin, abrin, Botulinum toxin, or Staphylococcal enterotoxin B.

Overview of Example Parasite Targets

Some embodiments of the methods, systems and compositions provided herein include the detection of certain parasite targets. A parasite target includes a parasite nucleic acid, a parasite protein, and/or a product of parasite activity, such as a toxin and/or an enzyme or enzyme activity. Nucleotide sequences indicative of certain parasites are readily obtained from public databases. Primers useful for isothermal amplification are readily designed from nucleic acid sequences of such parasite targets. Antibodies and aptamers to proteins of certain parasites are readily obtained through commercial avenues, and/or techniques well known in the art. Examples of parasites that are detected with the methods, systems and compositions provided herein include certain endoparasites such as protozoan organisms such as *Acanthamoeba* spp. *Babesia* spp., *B. divergens, B. bigemina, B. equi, B. microfti, B. duncani, Balamuthia mandrillaris, Balantidium coli, Blastocystis* spp., *Cryptosporidium* spp., *Cyclospora cayetanensis, Dientamoeba fragilis, Entamoeba histolytica, Giardia lamblia, Isospora belli, Leishmania* spp., *Naegleria fowleri, Plasmodium falciparum, Plasmodium vivax, Plasmodium ovale curtisi, Plasmodium ovale wallikeri, Plasmodium malariae, Plasmodium knowlesi, Rhinosporidium seeberi, Sarcocystis bovihominis, Sarcocystis suihominis, Toxoplasma gondii, Trichomonas vaginalis, Trypanosoma brucei,* or *Trypanosoma cruzi*. Certain helminth organisms such as *Bertiella mucronata, Bertiella studeri, Cestoda, Taenia multiceps, Diphyllobothrium latum, Echinococcus granulosus, Echinococcus multilocularis, E. vogeli, E. oligarthrus, Hymenolepis nana, Hymenolepis diminuta, Spirometra erinaceieuropaei, Taenia saginata,* or *Taenia solium*. Certain fluke organism such as *Clonorchis sinensis; Clonorchis viverrini, Dicrocoelium dendriticum, Echinostoma echinatum, Fasciola hepatica, Fasciola gigantica, Fasciolopsis buski, Gnathostoma spinigerum, Gnathostoma hispidum, Metagonimus yokogawai, Metorchis conjunctus, Opisthorchis viverrini, Opisthorchis felineus, Clonorchis sinensis, Paragonimus westermani; Paragonimus africanus; Paragonimus caliensis; Paragonimus kellicotti; Paragonimus skrjabini; Paragonimus uterobilateralis, Schistosoma haematobium, Schistosoma japonicum, Schistosoma mansoni* and *Schistosoma intercalatum, Schistosoma mekongi, Schistosoma* sp, *Trichobilharzia regenti,* or *Schistosomatidae*. Certain roundworm organisms such as *Ancylostoma duodenale, Necator americanus, Angiostrongylus costaricensis, Anisakis, Ascaris* sp. *Ascaris lumbricoides, Baylisascaris procyonis, Brugia malayi, Brugia timori, Dioctophyme renale, Dracunculus medinensis, Enterobius vermicularis, Enterobius gregorii, Halicephalobus gingivalis, Loa loa filaria, Mansonella streptocerca, Onchocerca volvulus, Strongyloides stercoralis, Thelazia californiensis, Thelazia callipaeda, Toxocara canis, Toxocara cati, Trichinella spiralis, Trichinella britovi, Trichinella nelsoni, Trichinella nativa, Trichuris trichiura, Trichuris vulpis,* or *Wuchereria bancrofti*. Other parasites such as *Archiacanthocephala, Moniliformis moniliformis, Linguatula serrata, Oestroidea,* Calliphoridae, Sarcophagidae, *Cochliomyia hominivorax* (family Calliphoridae), *Tunga penetrans,* Cimicidae: *Cimex lectularius,* or *Dermatobia hominis*. More examples of parasites include ectoparasites such as *Pediculus humanus, Pediculus humanus corporis, Pthirus pubis, Demodex folliculorum/brevis/canis, Sarcoptes scabiei,* or Arachnida such as Trombiculidae, or *Pulex irritans,* or Arachnida such Ixodidae and/or Argasidae.

Overview of Example microRNA Targets

Some embodiments of the methods, systems and compositions provided herein include the detection of certain microRNA (miRNA) targets. miRNAs include small non-coding RNA molecules that function in RNA silencing or post-transcriptional regulation of gene expression. Some miRNAs are associated with deregulation in various human diseases which are caused by abnormal epigenetic patterns, including abnormal DNA methylation and histone-modification patterns. For example, the presence or absence of a certain miRNA in a sample from a subject is indicative of a disease or disease state. Primers useful to detect miRNAs and useful for isothermal amplification are readily designed from nucleotide sequences of miRNAs. Nucleotide sequences of miRNAs are readily obtained from public databases. Examples of miRNA targets that are detected with the methods, systems and compositions provided herein include: hsa-miR-1, hsa-miR-1-2, hsa-miR-100, hsa-miR-100-1, hsa-miR-100-2, hsa-miR-101, hsa-miR-101-1, hsa-miR-101a, hsa-miR-101b-2, hsa-miR-102, hsa-miR-103, hsa-miR-103-1, hsa-miR-103-2, hsa-miR-104, hsa-miR-105, hsa-miR-106a, hsa-miR-106a-1, hsa-miR-106b, hsa-miR-106b-1, hsa-miR-107, hsa-miR-10a, hsa-miR-10b, hsa-miR-122, hsa-miR-122a, hsa-miR-123, hsa-miR-124a, hsa-miR-124a-1, hsa-miR-124a-2, hsa-miR-124a-3, hsa-miR-125a, hsa-miR-125a-5p, hsa-miR-125b, hsa-miR-125b-1, hsa-miR-125b-2, hsa-miR-126, hsa-miR-126-5p, hsa-miR-127, hsa-miR-128a, hsa-miR-128b, hsa-miR-129, hsa-miR-129-1, hsa-miR-129-2, hsa-miR-130, hsa-miR-130a, hsa-miR-130a-1, hsa-miR-130b, hsa-miR-130b-1, hsa-miR-132, hsa-miR-133a, hsa-miR-133b, hsa-miR-134, hsa-miR-135a, hsa-miR-135b, hsa-miR-136, hsa-miR-137, hsa-miR-138, hsa-miR-138-1, hsa-miR-138-2, hsa-miR-139, hsa-miR-139-5p, hsa-miR-140, hsa-miR-140-3p, hsa-miR-141, hsa-miR-142-3p, hsa-miR-142-5p, hsa-miR-143, hsa-miR-144, hsa-miR-145, hsa-miR-146a, hsa-miR-146b, hsa-miR-147, hsa-miR-148a, hsa-miR-148b, hsa-miR-149, hsa-miR-15, hsa-miR-150, hsa-miR-151, hsa-miR-151-5p, hsa-miR-152, hsa-miR-153, hsa-miR-154, hsa-miR-155, hsa-miR-15a, hsa-miR-15a-2, hsa-miR-15b, hsa-miR-16, hsa-miR-16-1, hsa-miR-16-2, hsa-miR-16a, hsa-miR-164, hsa-miR-170, hsa-miR-172a-2, hsa-miR-17, hsa-miR-17-3p, hsa-miR-17-5p, hsa-miR-17-92, hsa-miR-18, hsa-miR-18a, hsa-miR-18b, hsa-miR-181a, hsa-miR-181a-1, hsa-miR-181a-2, hsa-miR-181b, hsa-miR-18 b-1, hsa-miR-181b-2, hsa-miR-181c, hsa-miR-181d, hsa-miR-182, hsa-miR-183, hsa-miR-184, hsa-miR-185, hsa-miR-186, hsa-miR-187, hsa-miR-188, hsa-miR-189, hsa-miR-190, hsa-miR-191, hsa-miR-192, hsa-miR-192-1, hsa-miR-192-2, hsa-miR-192-3, hsa-miR-193a, hsa-miR-193b, hsa-miR-194, hsa-miR-195, hsa-miR-196a, hsa-miR-196a-2, hsa-miR-196b, hsa-miR-197, hsa-miR-198, hsa-miR-199a, hsa-miR-199a-1, hsa-miR-199a-1-5p, hsa-miR-199a-2, hsa-miR-199a-2-5p, hsa-miR-199a-3p, hsa-miR-199b, hsa-miR-199b-5p, hsa-miR-19a, hsa-miR-19b, hsa-miR-19b-1, hsa-miR-19b-2, hsa-miR-200a, hsa-miR-200b, hsa-miR-200c, hsa-miR-202, hsa-miR-203, hsa-miR-204, hsa-miR-205, hsa-miR-206, hsa-miR-207, hsa-miR-208, hsa-miR-208a, hsa-miR-20a, hsa-miR-20b, hsa-miR-21, hsa-miR-22, hsa-miR-210, hsa-miR-211, hsa-miR-212, hsa-miR-213, hsa-miR-214, hsa-miR-215, hsa-miR-216, hsa-miR-217, hsa-miR-218, hsa-miR-218-2, hsa-miR-219, hsa-miR-219-1, hsa-miR-22, hsa-miR-220, hsa-miR-221, hsa-miR-222, hsa-miR-223, hsa-miR-224, hsa-miR-23a, hsa-miR-23b, hsamiR-24, hsa-miR-24-1, hsa-miR-24-2, hsa-miR-25, hsa-miR-26a, hsa-miR-26a-1, hsa-miR-26a-2, hsa-miR-26b, hsa-miR-27a, hsa-miR-27b, hsa-miR-28, hsa-miR-296, hsa-miR-298, hsa-miR-299-3p, hsa-miR-299-5p, hsa-miR-29a, hsa-miR-29a-2, hsa-miR-29b, hsa-miR-29b-1, hsa-miR-29b-2, hsa-miR-29c, hsa-miR-301, hsa-miR-302, hsa-miR-302a, hsa-miR-302b, hsa-miR-302c, hsa-miR-302c, hsa-miR-302d, hsa-miR-30a, hsa-miR-30a-3p, hsa-miR-30a-5p, hsa-miR-30b, hsa-miR-30c, hsa-miR-30c-1, hsa-miR-30d, hsa-miR-30e, hsa-miR-30e, hsa-miR-30e-5p, hsa-miR-31, hsa-miR-31a, hsa-miR-32, hsa-miR-32, hsa-miR-320, hsa-miR-320-2, hsa-miR-320a, hsa-miR-322, hsa-miR-323, hsa-miR-324-3p, hsa-miR-324-5p, hsa-miR-325, hsa-miR-326, hsa-miR-328, hsa-miR-328-1, hsa-miR-33, hsa-miR-330, hsa-miR-331, hsa-miR-335, hsa-miR-337, hsa-miR-337-3p, hsa-miR-338, hsa-miR-338-5p, hsa-miR-339, hsa-miR-339-5p, hsa-miR-34a, hsa-miR-340, hsa-miR-340, hsa-miR-341, hsa-miR-342, hsa-miR-342-3p, hsa-miR-345, hsa-miR-346, hsa-miR-347, hsa-miR-34a, hsa-miR-34b, hsa-miR-34c, hsa-miR-351, hsa-miR-352, hsa-miR-361, hsa-miR-362, hsa-miR-363, hsa-miR-355, hsa-miR-365, hsa-miR-367, hsa-miR-368, hsa-miR-369-5p, hsa-miR-370, hsa-miR-371, hsa-miR-372, hsa-miR-373, hsa-miR-374, hsa-miR-375, hsa-miR-376a, hsa-miR-376b, hsa-miR-377, hsa-miR-378, hsa-miR-378, hsa-miR-379, hsa-miR-381, hsa-miR-382, hsa-miR-383, hsa-miR-409-3p, hsa-miR-419, hsa-miR-422a, hsa-miR-422b, hsa-miR-423, hsa-miR-424, hsa-miR-429, hsa-miR-431, hsa-miR-432, hsa-miR-433, hsa-miR-449a, hsa-miR-451, hsa-miR-452, hsa-miR-451, hsa-miR-452, hsa-miR-452, hsa-miR-483, hsa-miR-483-3p, hsa-miR-484, hsa-miR-485-5p, hsa-miR-485-3p, hsa-miR-486, hsa-miR-487b, hsa-miR-489, hsa-miR-491, hsa-miR-491-5p, hsa-miR-492, hsa-miR-493-3p, hsa-miR-493-5p, hsa-miR-494, hsa-miR-495, hsa-miR-497, hsa-miR-498, hsa-miR-499, hsa-miR-5, hsa-miR-500, hsa-miR-501, hsa-miR-503, hsa-miR-508, hsa-miR-509, hsa-miR-510, hsa-miR-511, hsa-miR-512-5p, hsa-miR-513, hsa-miR-513-1, hsa-miR-513-2, hsa-miR-515-3p, hsa-miR-516-5p, hsa-miR-516-3p, hsa-miR-518b, hsa-miR-519a, hsa-miR-519d, hsa-miR-520a, hsa-miR-520c, hsa-miR-521, hsa-miR-532-5p, hsa-miR-539, hsa-miR-542-3p, hsa-miR-542-5p, hsa-miR-550, hsa-miR-551a, hsa-miR-561, hsa-miR-563, hsa-miR-565, hsa-miR-572, hsa-miR-582, hsa-miR-584, hsa-miR-594, hsa-miR-595, hsa-miR-598, hsa-miR-599, hsa-miR-600, hsa-miR-601, hsa-miR-602, hsa-miR-605, hsa-miR-608, hsa-miR-611, hsa-miR-612, hsa-miR-614, hsa-miR-615, hsa-miR-615-3p, hsa-miR-622, hsa-miR-627, hsa-miR-628, hsa-miR-635, hsa-miR-637, hsa-miR-638, hsa-miR-642, hsa-miR-648, hsa-miR-652, hsa-miR-654, hsa-miR-657, hsa-miR-658, hsa-miR-659, hsa-miR-661, hsa-miR-662, hsa-miR-663, hsa-miR-664, hsa-miR-7, hsa-miR-7-1, hsa-miR-7-2, hsa-miR-7-3, hsa-miR-708, hsa-miR-765, hsa-miR-769-3p, hsa-miR-802, hsa-miR-885-3p, hsa-miR-9, hsa-miR-9-1, hsa-miR-9-3, hsa-miR-9-3p, hsa-miR-92, hsa-miR-92-1, hsa-miR-92-2, hsa-miR-9-2, hsa-miR-92, hsa-miR-92a, hsa-miR-93, hsa-miR-95, hsa-miR-96, hsa-miR-98, hsa-miR-99a, and/or hsa-miR-99b.

Overview of Example Agricultural Analytes

Some embodiments of the methods, systems and compositions provided herein include the detection of certain agricultural analytes. Agricultural analytes include nucleic acids, proteins, or small molecules. Nucleotide sequences indicative of certain agricultural analytes are readily obtained from public databases. Primers useful for isothermal amplification are readily designed from nucleic acid sequences of such agricultural analytes. Antibodies and aptamers to proteins of certain agricultural analytes are readily obtained through commercial avenues, and/or techniques well known in the art.

Some embodiments of the methods and devices provided herein are used to identify the presence of an organism or product of the organism in a meat product, fish product, or yeast product such as beer, wine or bread. In some embodiments, species-specific antibodies or aptamers, or species-specific primers are used to identify the presence of a certain organism in a food product.

Some embodiments of the methods, systems and compositions provided herein include the detection of pesticides. In some embodiments, pesticides are detected in samples such as soils samples or food samples. Examples of pesticides that are detected with the devices and methods described herein include herbicides, insecticides, or fungicides. Examples of herbicides include 2,4-dichlorophenoxyacetic acid (2,4-D), atrazine, glyphosate, mecoprop, dicamba, paraquat, glufosinate, metam-sodium, dazomet, dithopyr, pendimethalin, EPTC, trifluralin, flazasulfuron, metsulfuron-methyl, diuron, nitrofen, nitrofluorfen, acifluorfen, mesotrione, sulcotrione, or nitisinone. Examples of insecticides that are detected with the devices and methods described herein include organochlorides, organophosphates, carbamates, pyrethroids, neonicotinoids, or ryanoids. Examples of fungicides that are detected with the devices and methods described herein include carbendazim, diethofencarb, azoxystrobin, metalaxyl, metalaxyl-m, streptomycin, oxytetracycline, chlorothalonil, tebuconazole, zineb, mancozeb, tebuconazole, myclobutanil, triadimefon, fenbuconazole, deoxynivalenol, or mancozeb.

Overview of Example Biomarkers

Some embodiments of the methods, systems and compositions provided herein include the detection of certain biomarkers for certain disorders. Biomarkers can include nucleic acids, proteins, protein fragments, and antigens. Some biomarkers can include a target provided herein. Example disorders include cancers, such as breast cancers, colorectal cancers, gastric cancers, gastrointestinal stromal tumors, leukemias and lymphomas, lung cancers, melanomas, brain cancers, and pancreatic cancers. Some embodiments can include detecting the presence or absence of a biomarker, or the level of a biomarker in a sample. The biomarker can be indicative of the presence, absence or stage of a certain disorder. Example biomarkers include estrogen receptor, progesterone receptor, HER-2/neu, EGFR, KRAS, UGT1A1, c-KIT, CD20, CD30, FIP1L1-PDGFRalpha, PDGFR, Philadelphia chromosome (BCR/ABL), PML/RAR-alpha, TPMT, UGT1A1, EML4/ALK, BRAF, and elevated levels of certain amino acids such as leucine, isoleucine, and valine.

EXAMPLES

Example 1—fC4D LAMP Pre/Post Amplification Detection in PDMS

Figure 24:
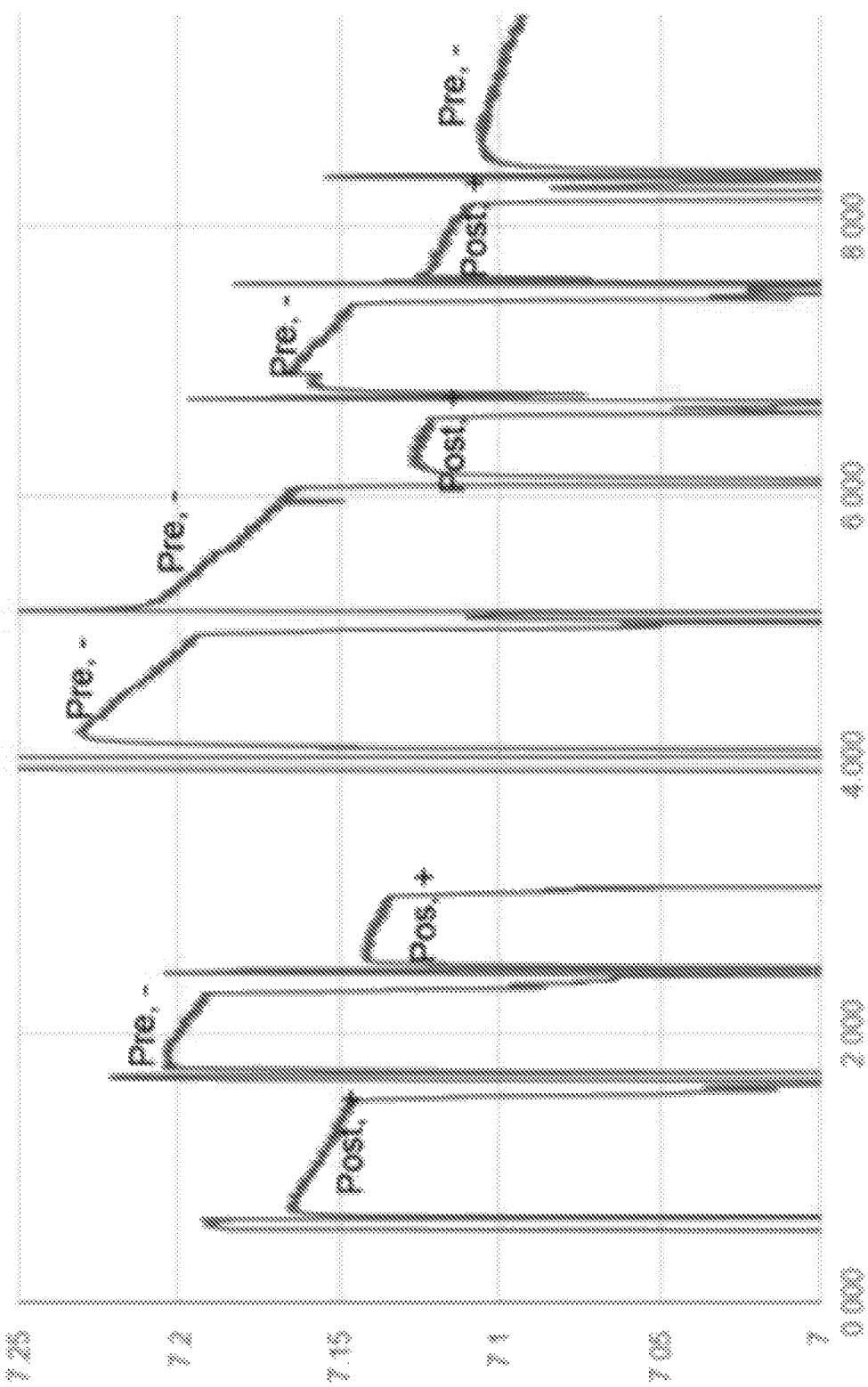
FIG. 24 is a graph depicting sensor voltage over time for pre-amplification (− control), and post-amplification (+ control).

A LAMP reaction mix was prepared according to NEB's standard protocol using the 5' untranslated region of the genome of *H. influenza* as the target. The mix was aliquoted into a pre-amplification vial (− control), and post-amplification vial (+ control). The pre-amplification vial was heat-inactivated at 85° C. for 20 minutes to prevent amplification. The post-amplification vial was amplified at 63° C. for 60 minutes. Aliquots from each vial were loaded sequentially, alternating between the two vials at room temperature on to the PDMS/Glass Chip v.1.1 while real time data collection was performed. FIG. 24 is a graph depicting sensor voltage over time.

Example 2—fC4D Pre/Post Amplification Detection with Whole Blood in PDMS

Figure 25:
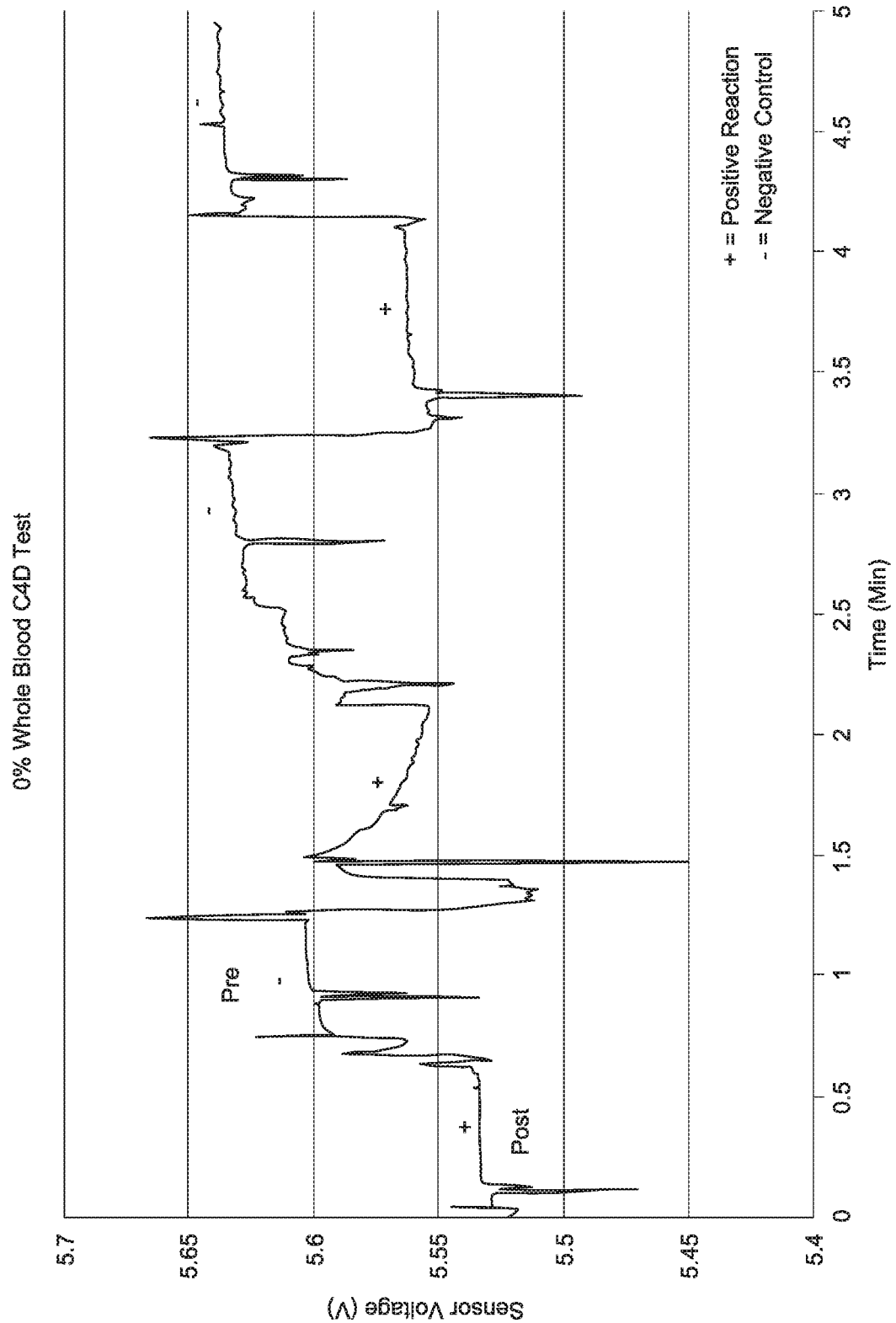
FIG. 25 is a graph depicting sensor voltage over time for pre-amplification (− control), and post-amplification (+ control) for 0% whole blood.
Figure 26:
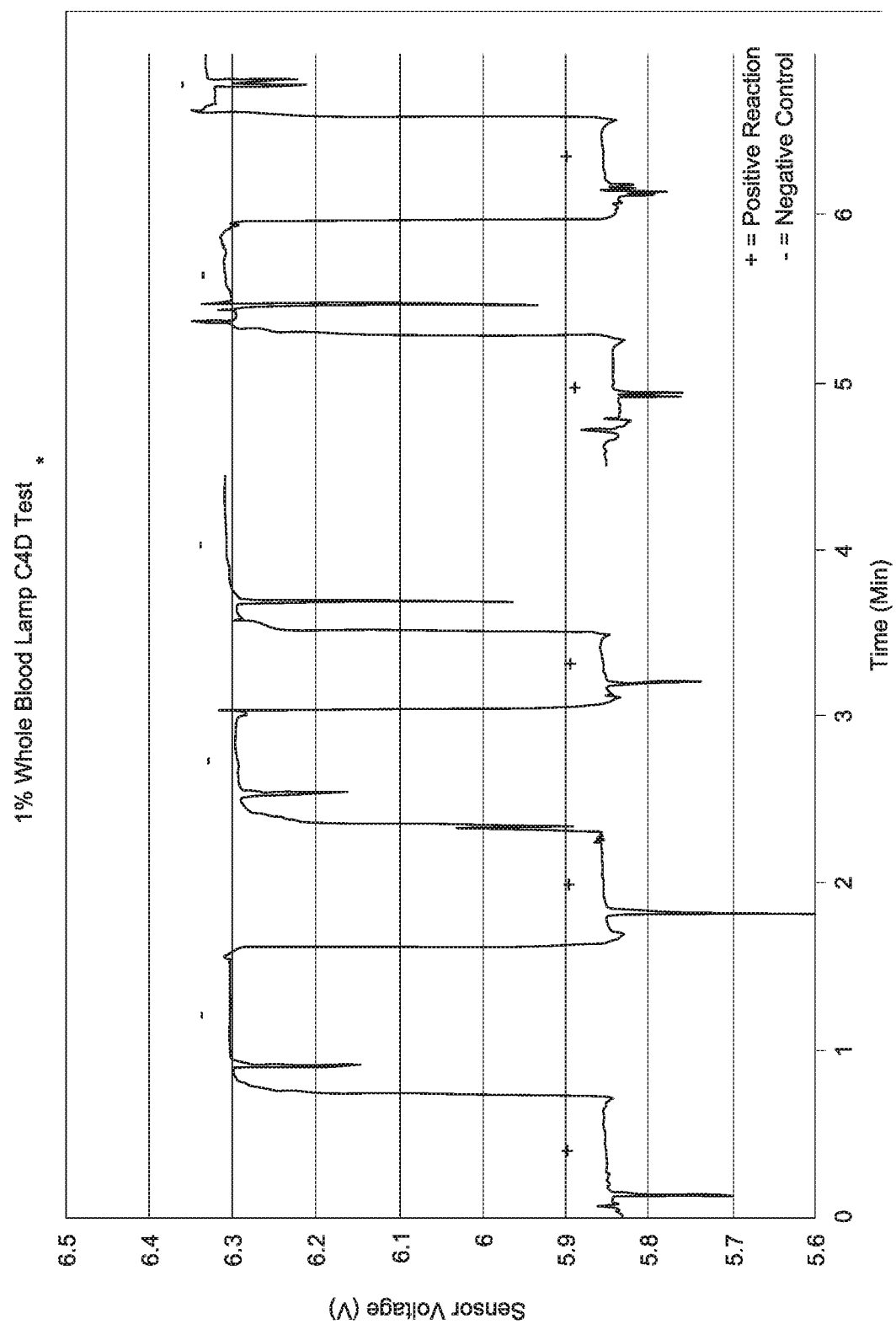
FIG. 26 is a graph depicting sensor voltage over time for pre-amplification (− control), and post-amplification (+ control) for 1% whole blood.
Figure 27:
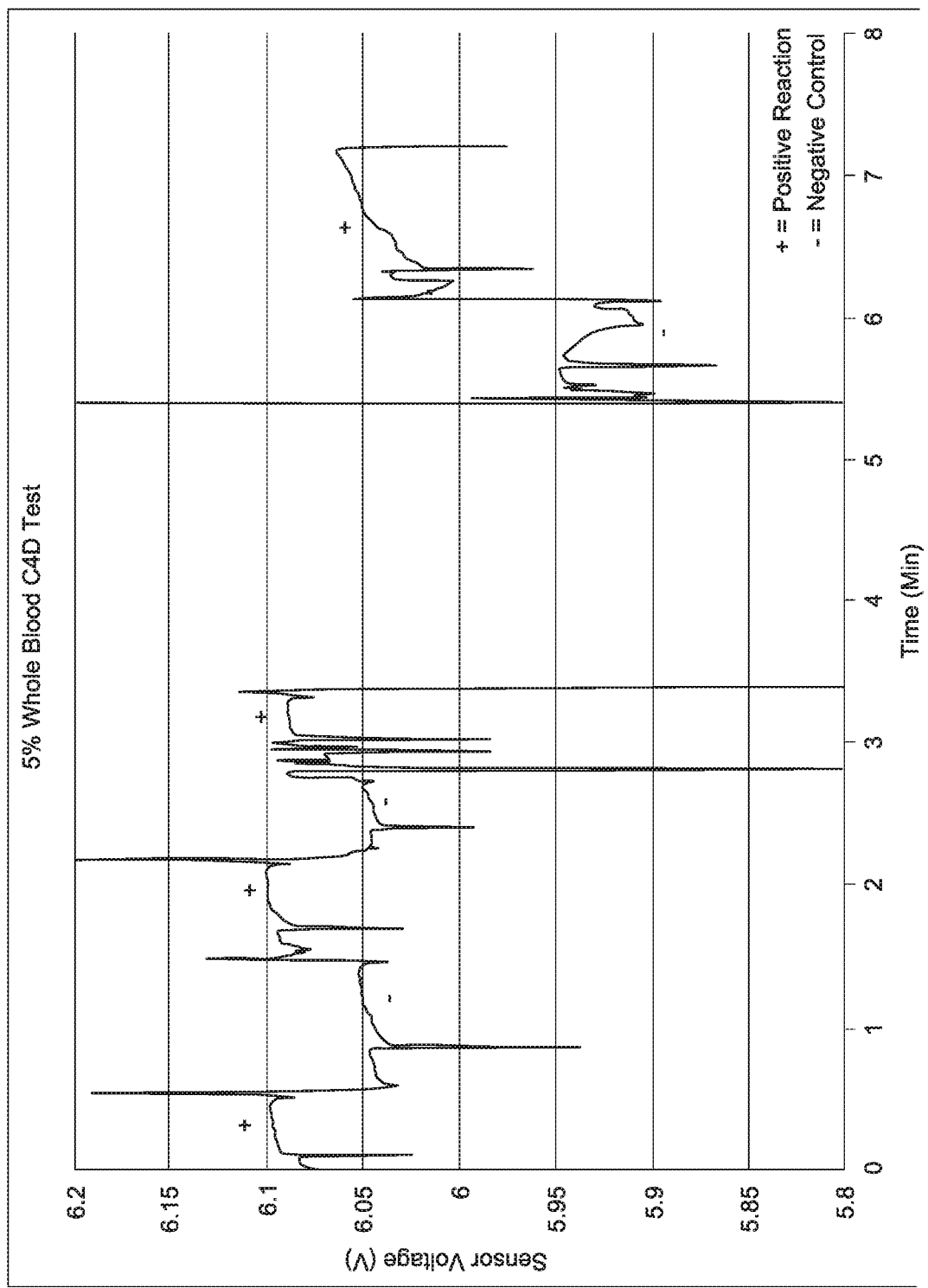
FIG. 27 is a graph depicting sensor voltage over time for pre-amplification (− control), and post-amplification (+ control) for 5% whole blood.

A reaction mix was prepared using the 5' untranslated region of the genome of *H. influenza* as the target with 0%, 1%, and 5% whole blood (v/v). The mix was aliquoted into a pre-amplification vial (− control), and post-amplification vial (+ control). The pre-amplification vial was heat-inactivated at 85° C. for 20 minutes to prevent amplification. The post-amplification vial was amplified at 63° C. for 60 minutes. Aliquots from each vial were loaded sequentially, alternating between the two vials at room temperature on to the PDMS/Glass Chip v.1.1 while real time data collection was performed. FIG. 25, FIG. 26 and FIG. 27 are graphs depicting sensor voltage over time for pre-amplification (− control), and post-amplification (+ control) for 0%, 1%, and 5% whole blood, respectively.

Example 3—Filtering LAMP Pre/Post Amplification

Figure 28:
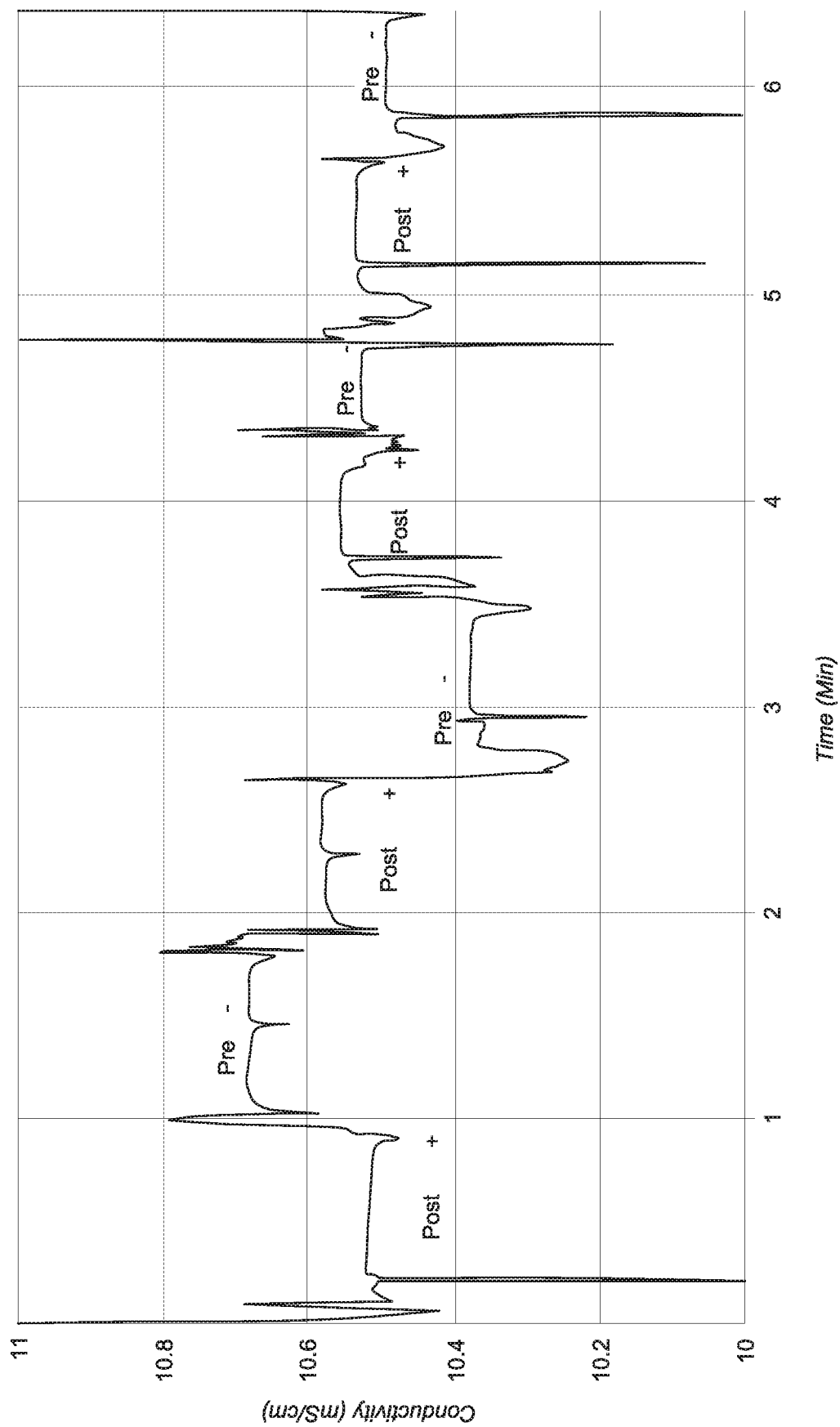
FIG. 28 is a graph depicting sensor voltage over time for pre-amplification (− control), and post-amplification (+ control) with 0% whole blood for unfiltered sample.
Figure 29:
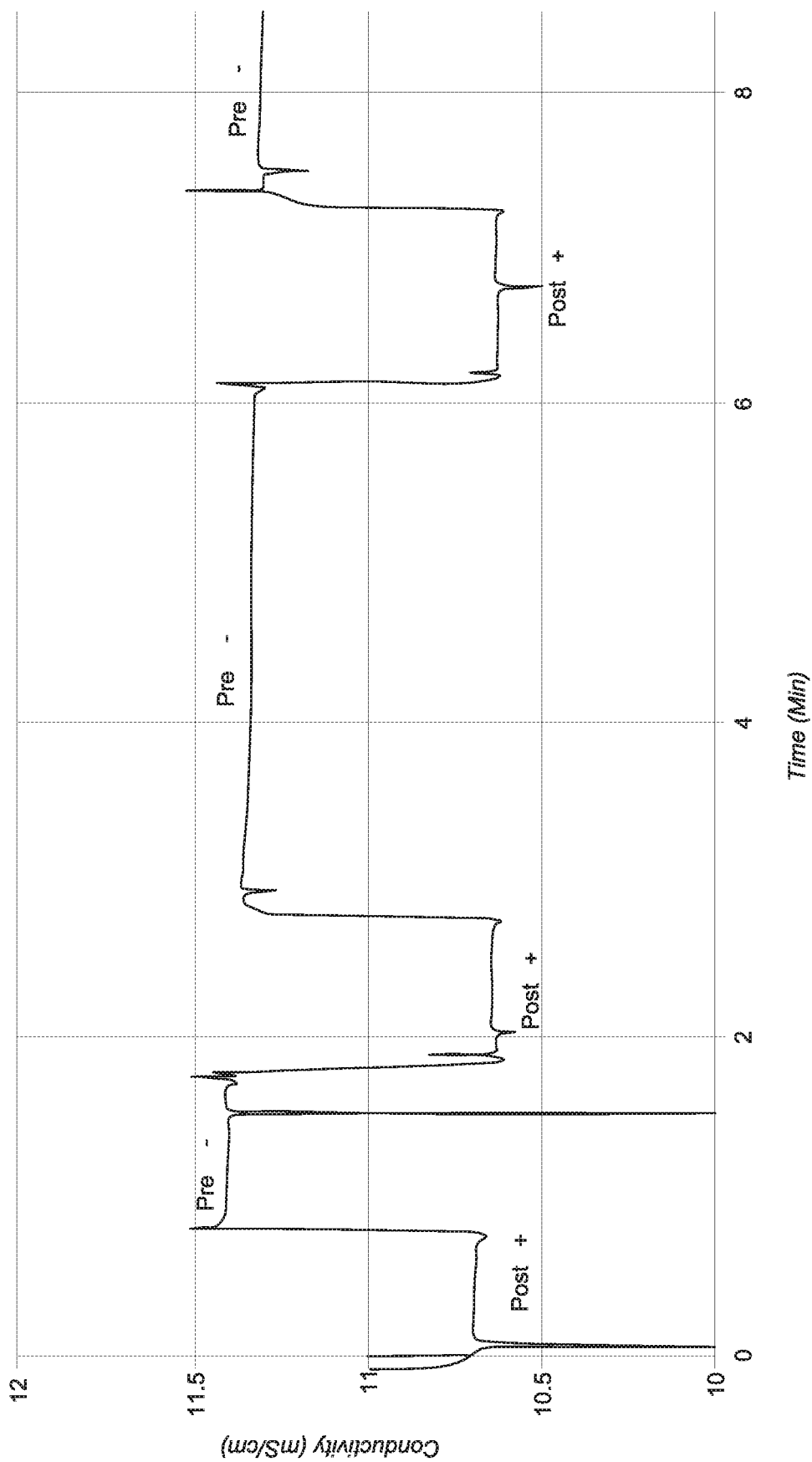
FIG. 29 is a graph depicting sensor voltage over time for pre-amplification (− control), and post-amplification (+ control) with 0% whole blood for filtered sample.

Samples were prepared as in Example 1. Prior to measurement, all samples (minus one as a control) were spin-filtered using a 50 kD filter. Aliquots from each vial were loaded sequentially, alternating between the two vials at room temperature on to the PDMS/Glass Chip v.1.1 while real time data collection was performed. Filtration improved S/N and conductivity change. FIG. 28 and FIG. 29 are graphs depicting sensor voltage over time for pre-amplification (− control), and post-amplification (+ control) with 0% whole blood, for unfiltered sample and filtered sample, respectively.

Example 4—Conductivity Detection of 1k-1M Target Copies

Figure 30:
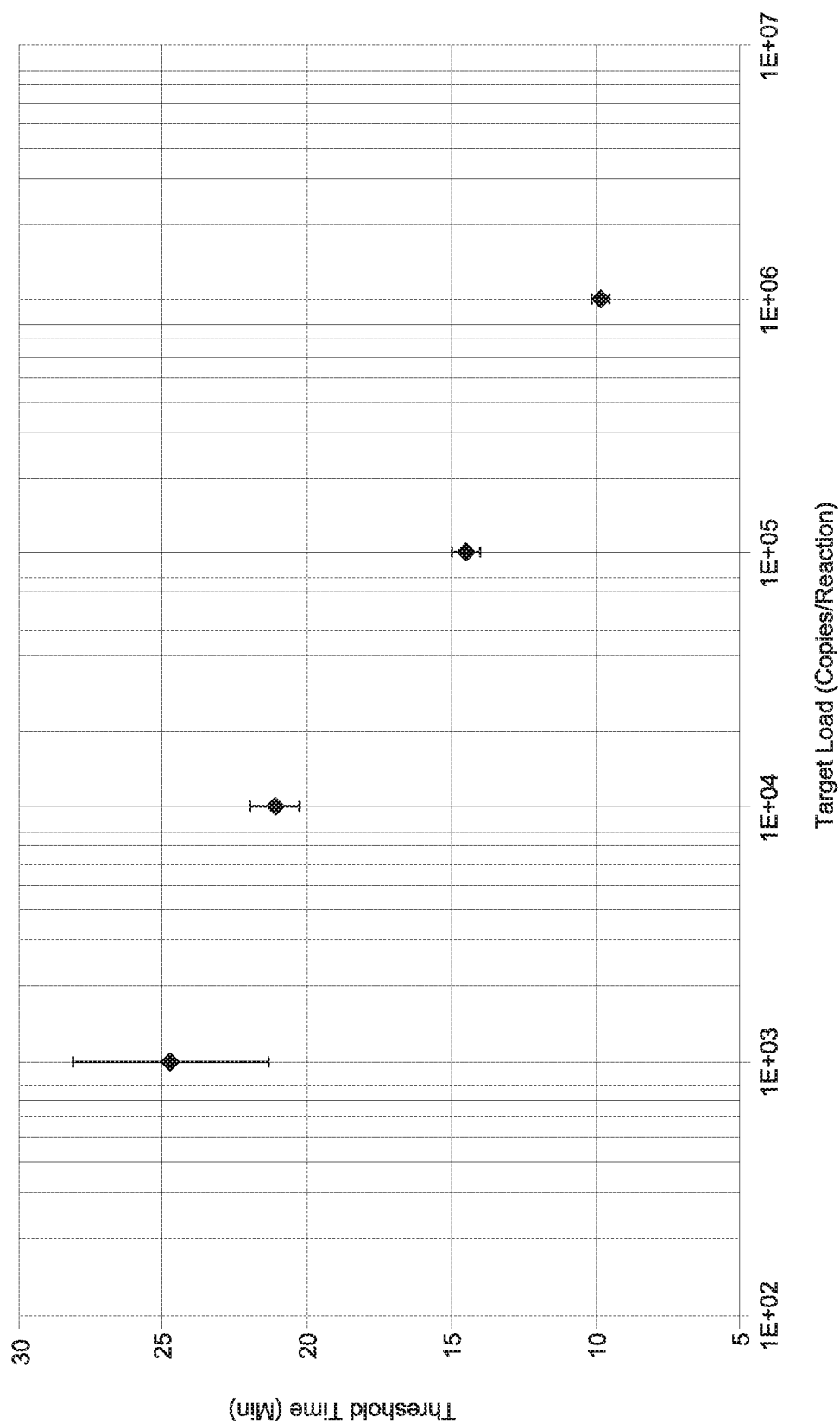
FIG. 30 depicts a graph of time over target load with error bars showing standard deviation.

A reaction mix was prepared using the 5' untranslated region of the genome of *H. influenza* as the target. Detection was performed using a $fC^4D$ instrument. Data was averaged for 3 replicates. FIG. 30 depicts a graph of time over target load with error bars showing standard deviation. No template negative controls showed no signal at 60 minutes heating.

Example 5—fC4D Pre/Post Amplification Detection with Whole Blood in PDMS

Figure 31:
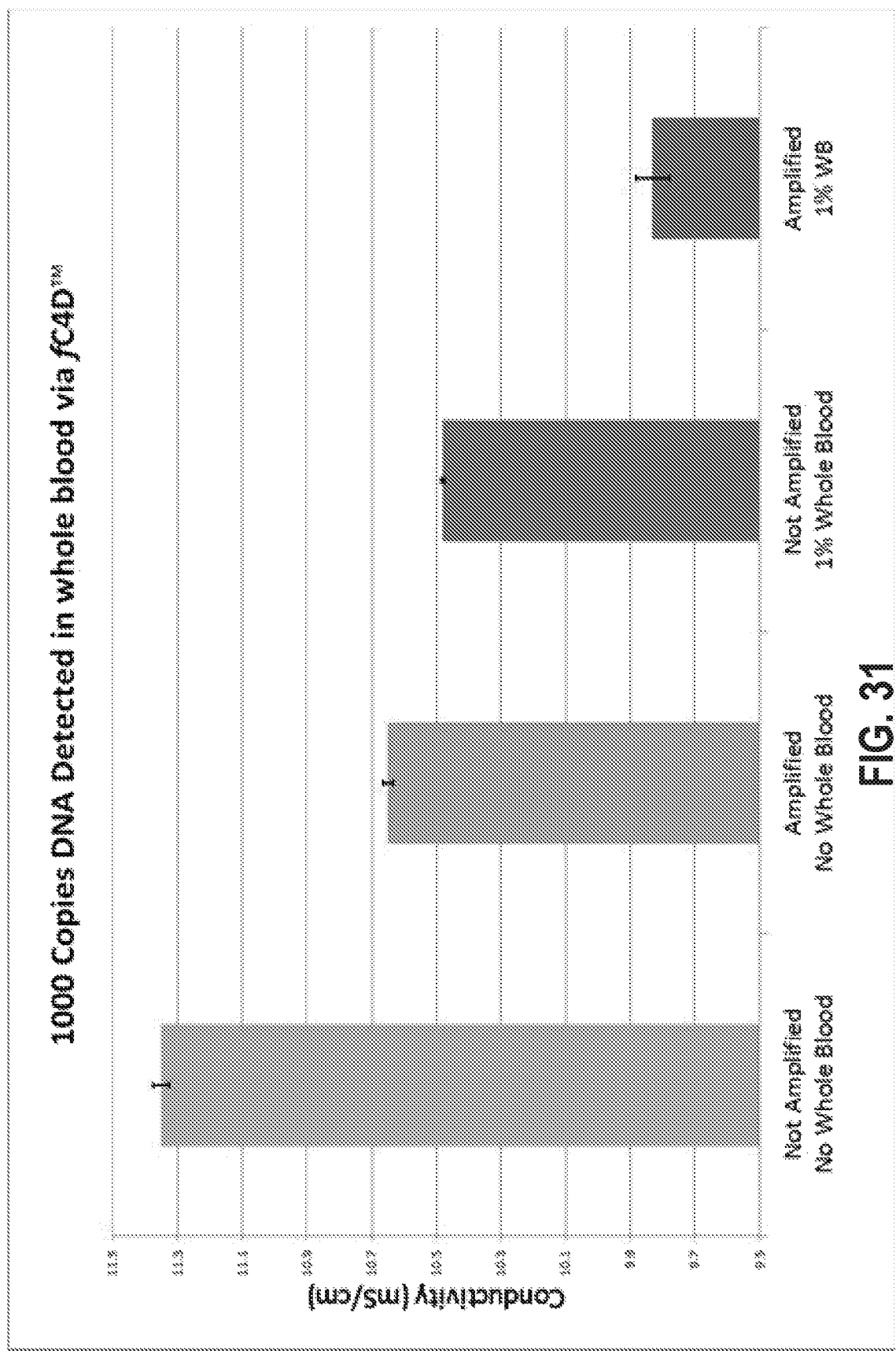
FIG. 31 depicts a graph of conductivity for various samples from pre-amplification vial (− control), and post-amplification vial (+ control).

A reaction mix was prepared using the 5' untranslated region of the genome of *H. influenza* as the target with 0% or 1% whole blood (v/v). The mix was aliquoted into a pre-amplification vial (− control), and post-amplification vial (+ control). The pre-amplification vial was heat-inactivated at 85° C. for 20 minutes to prevent amplification. The post-amplification vial was amplified at 63° C. for 60 minutes. Aliquots from each vial were loaded sequentially, alternating between the two vials at room temperature on to the PDMS/Glass Chip v.1.1 while real time data collection was performed. FIG. 31 depicts a graph of conductivity for various samples from pre-amplification vial (− control), and post-amplification vial (+ control).

Example 6—Detection of Hepatitis B Surface Antigen Using MAIA

Figure 32:
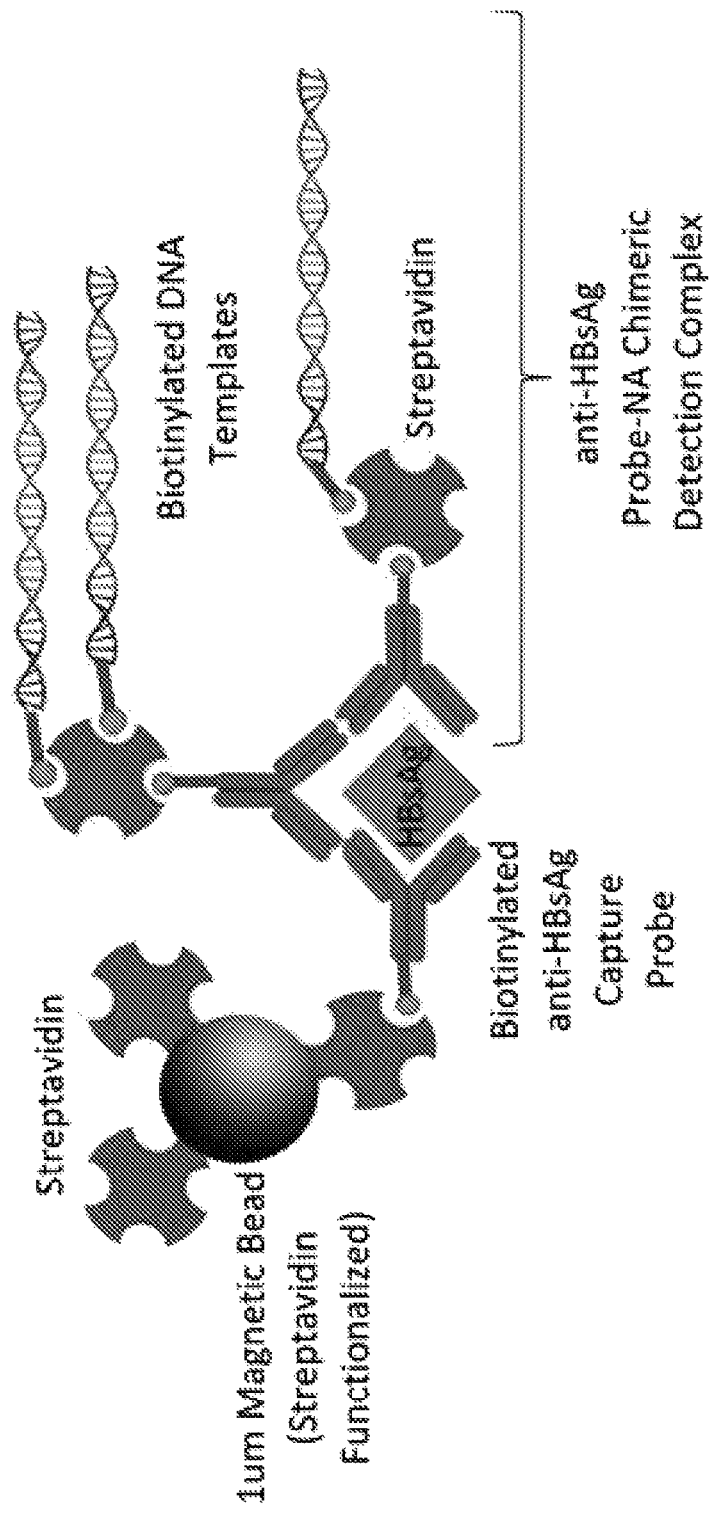
FIG. 32 depicts a magnetic bead-based amplification immunoassay scheme for the detection of HBsAg.
Figure 33:
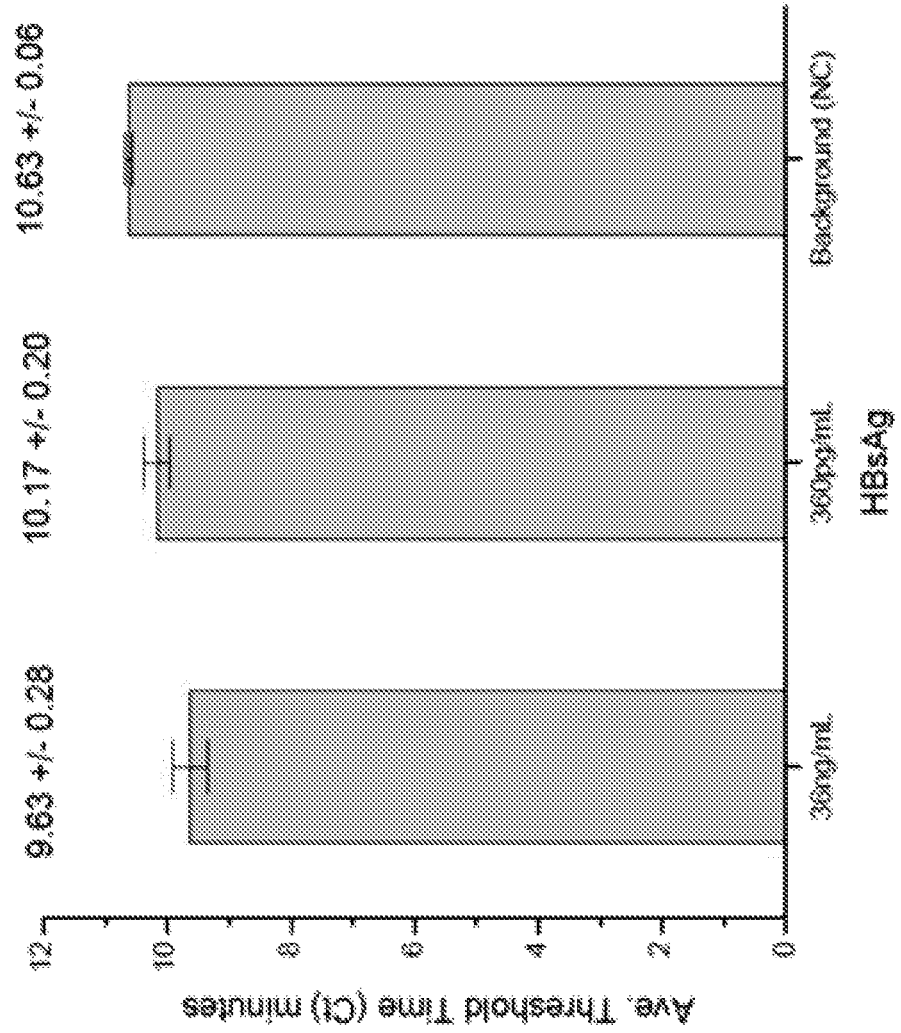
FIG. 33 depicts a graph illustrating detection of HBsAg.

Biotinylated, polyclonal antibody capture probe (anti-HBsAg) was conjugated to streptavidin functionalized 1 micron magnetic microspheres (Dynal Ti). Chimeric detection complexes were synthesized by conjugating biotinylated, polyclonal capture probe (anti-HBsAg) to streptavidin, and conjugating to the streptavidin-Antibody complex to biotinylated DNA target. The Antibody functionalized beads captured HBsAntigen from solution. The HBsAntigen was detected by the binding of the chimera Ab-DNA complex followed by amplification of the DNA template portion of the chimera complex. FIG. 32 depicts binding between antigen, antibody conjugated with nucleic acids. FIG. 33 depicts a graph showing detection of hepatitis B surface antigen.

Example 7—Detection with Low Ionic Strength Buffer

A commercial amplification solution, and a T10 amplification solution were prepared with the reagents listed in TABLE 2 and TABLE 3, respectively. The commercial amplification solution would typically be used in general amplification reactions. The T10 amplification solution had a reduced content of Tris-HCl, and ammonium sulfate was absent. 400 μL of each solution was prepared, and about 15 μL of each solution was loaded into a different channel of an experimental cartridge. The solutions were heated to 63.0° C. Data was collected using a data collection board.

Figure 34:
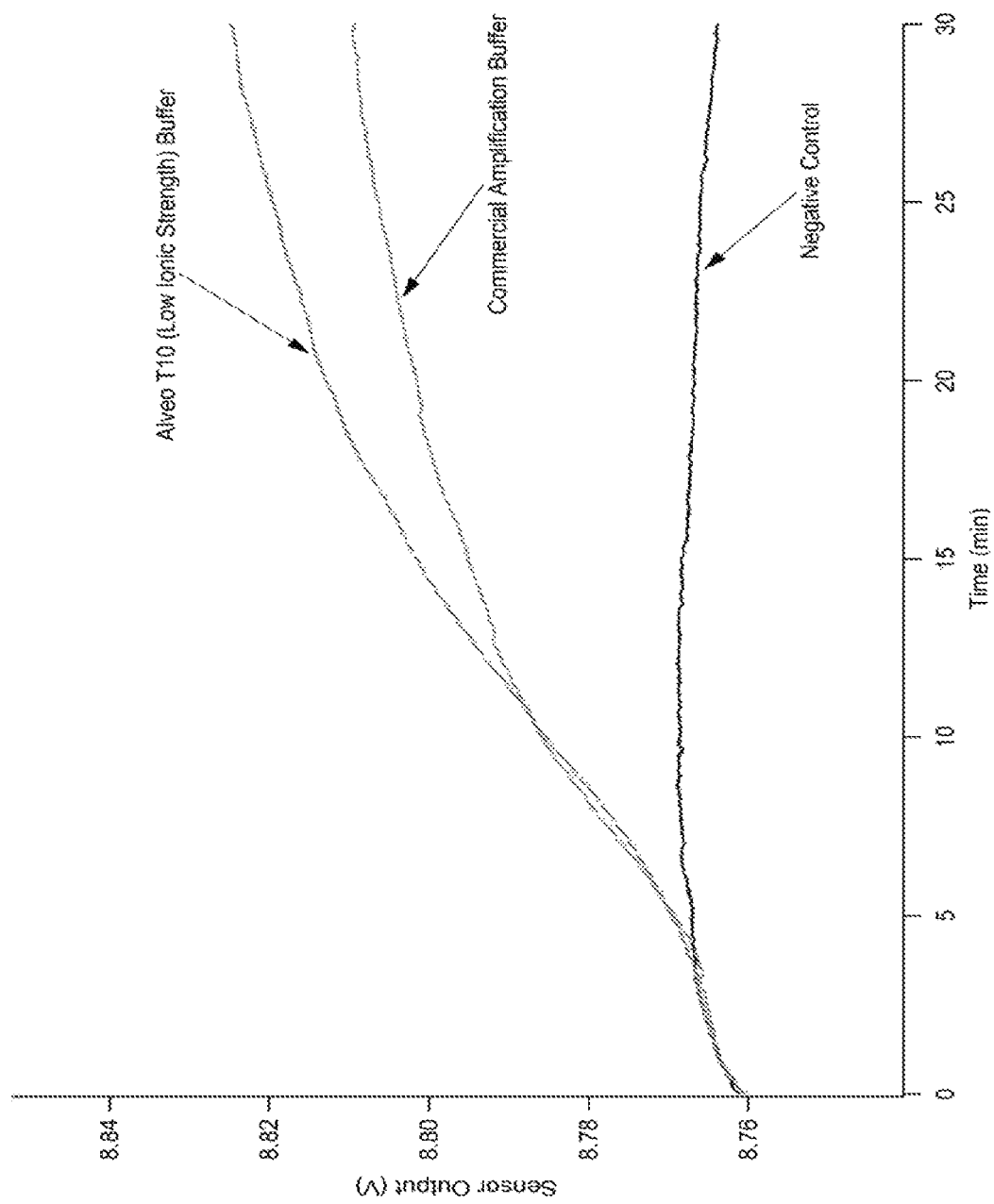
FIG. 34 depicts a graph illustrating detection of HBsAg with a low ionic buffer (T10).

The results are depicted in FIG. 34. The T10 amplification buffer provided at least 30% greater signal compared to the signal provided by the commercial amplification solution.

TABLE 2

| Reagent | Volume ratio | Final reagent concentration | Final added volume |
|---|---|---|---|
| Isothermal amplification buffer (10x; NEB) | 0.1 | 1x (contains 2 mM MgSO$_4$) | 40 |
| MgSO$_4$ (100 mM; NEB) | 0.06 | 6 mM (8 mM Total) | 24 |
| dNTP mix (10 mM each; NEB) | 0.14 | 1.4 mM each | 56 |
| 10x H. inf. primer mix | 0.1 | 1x (1.6 μM FIP/BIP, 0.2 μM F3/B3, 0.4 mM LoopF/B | 40 |
| Bst 2.0 WarmStart polymerase (8000 U/L; NEB) | 0.04 | 320 U/L | 16 |
| UDG (NEB) | 0 | | 0 |
| RTx (NEB) | 0 | | 0 |
| H. inf. DNA Sample (1 Mc/uL) | 0.04 | | 16 |
| Ultra Pure Water | 0.52 | | 208 |
| Total | | | 400 |

TABLE 3

| Reagent | 1x concentration (mM) | 10x concentration (mM) | FW | mg to add for 10 mL 10x |
|---|---|---|---|---|
| Tris-HCl | 2 | 20 | 157.6 | 31.52 |
| (NH$_4$)$_2$SO$_4$ | 0 | 0 | 132.14 | 0.00 |
| KCl | 50 | 500 | 74.55 | 372.75 |
| MgSO$_4$ | 2 | 20 | 246.48 | 49.30 |
| Tween 20 | 0.10% | 1% | 100% | 0.1 mL |
| DI Water | | | | 9.9 mL |

Example 8—Impedance Characteristics of a Fluidics Cartridge

Figure 35:
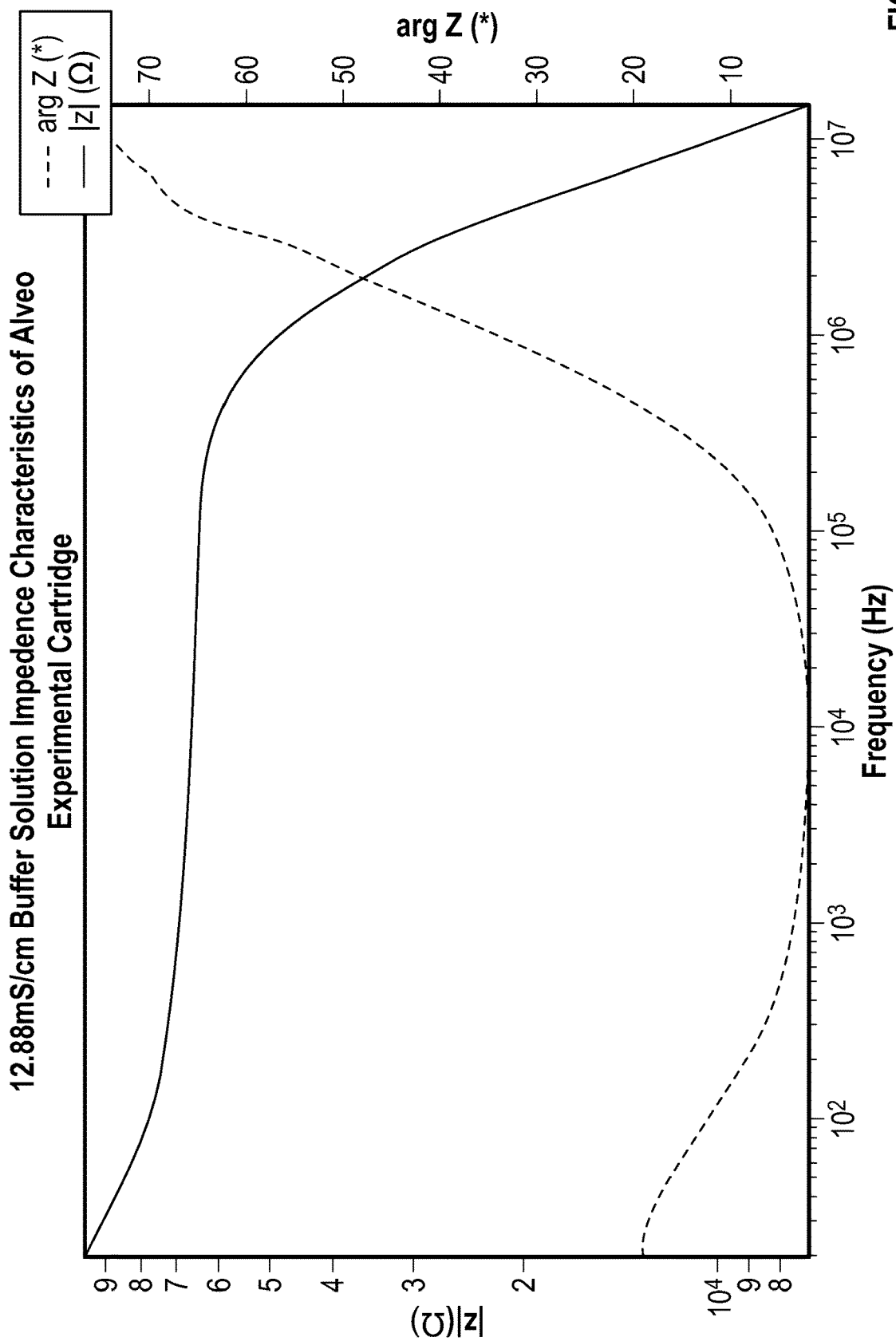
FIG. 35 depicts a graph illustrating impedance characteristics of a fluidics cartridge.

The channels of a fluidics cartridge depicted in FIG. 17A were filled with a 1288 mS/cm reference buffer, and an excitation frequency was swept from less than about 100 Hz to greater than about 1 MHz, and the impedance ("|Z|") or arg Z over frequency were measured. The results are shown in FIG. 35 which depicts either |Z| or arg Z over frequency.

Example 9—Amplification of Nucleic Acids Containing HCV Sequences

Samples containing nucleic acids comprising Hepatitis C virus (HCV) sequences were amplified in a series of experiments by LAMP under various conditions, and threshold cycle ($C_t$) values along with standard deviations (SD) and % relative standard deviations (RSD) were determined. Nucleic acids included synthetic nucleic acids comprising an HCV sequence; synthetic RNA comprising an HCV sequence. All reactions contained 5% TWeen-20. For experiments with reactions containing about a million copies of synthetic nucleic acids comprising an HCV sequence, the average Ct was 856, with a SD of 15, and a RSD of 1.72%.

Samples of plasma containing synthetic RNA comprising an HCV sequence were amplified by LAMP under various conditions including: untreated, treated by heating before addition of the synthetic RNA, by heating after addition of the synthetic RNA, and by adding 100 mM DTT. Each reaction contained about 25 k copies of the nucleic acid. TABLE 4 summarizes the results.

TABLE 4

| Parameter | Untreated | Heat-treated before addition of the synthetic RNA | Heat-treated after addition of the synthetic RNA | 100 nM DTT added |
|---|---|---|---|---|
| Average $C_t$ | 1043 | 983 | 1190 | 999 |
| SD | 53 | 26 | 145 | 19 |
| RSD (%) | 5.12 | 2.64 | 12.22 | 1.93 |
| n | 12 | 16 | 8 | 4 |

Addition of 100 mM DTT, or heat-treating plasma before addition of the synthetic RNA improved amplification as shown by RSD compared to untreated samples. Adding DTT, or heat-treating plasma before addition of the synthetic RNA also produced faster amplification (about 50 s faster) compared to untreated samples (P=0.03 and 0.002, respectively).

Samples of plasma containing HCV (SeraCare, Milford Mass.) were amplified by LAMP under various conditions including: heat-treating the plasma, adding 100 mM DTT, adding SDS and/or DTT. TABLE 5 summarizes the results.

TABLE 5

| Parameter | Untreated | Heat-treated | 100 nM DTT | 0.05% SDS | 0.1% SDS | 0.05% SDS + 100 mM DTT | 0.05% SDS + 100 mM DTT |
|---|---|---|---|---|---|---|---|
| Average $C_t$ | 2020 | 1081 | 1117 | 2032 | 2793 | 1190 | 1288 |
| SD | 1368 | 111 | 130 | 2052 | 1617 | 230 | 278 |
| RSD (%) | 67.72 | 10.23 | 11.63 | 100.96 | 57.89 | 19.36 | 21.57 |
| n | 15 | 18 | 16 | 16 | 15 | 16 | 16 |

Heat treating the plasma or adding DTT improved amplification results, compared to untreated plasma, as shown by RSD values. Adding either 0.05% or 0.1% SDS reduced the reproducibility and speed of the amplification compared to plasma that was untreated, heat-treated, or DTT was added.

Example 10—Amplification of Clinical Samples Containing HCV

Clinical plasma samples containing HCV were amplified by LAMP with various concentrations of DTT. WarmStart LAMP master mix (New England Biolabs) was used to prepare samples in quadruplicates. Samples included: 5% plasma (SeraCare, Milford Mass.) containing about −20 k copies of HCV/reaction, 50 U/reaction murine RNase inhibitor, with various concentrations of TWeen and DTT. Samples containing synthetic nucleic acids comprising an HCV sequence (IM copies/rxn) were tested with 1% and 5% TWeen. No target controls (NTCs) were also tested. The LAMP was carried out at 67° C., and results measured on a Zeus QS3 system for 60 cycles at 1 min/cycle, with data taken each cycle, and an up/down melt curve was applied after LAMP was complete. Results are summarized in TABLE 6.

TABLE 6

| Sample | Average $C_t$ | SD | RSD (%) |
|---|---|---|---|
| Synthetic nucleic acids + 1% Tween | 1214 | 15 | 1.22 |
| Synthetic nucleic acids + 5% Tween | 1123 | 54 | 4.84 |
| Plasma + 1% Tween | 1754 | 1040 | 59.32 |
| Plasma + 1% Tween + 5 mM DTT | 1728 | 1030 | 59.61 |
| Plasma + 1% Tween + 10 mM DTT | 1202 | 213 | 17.76 |
| Plasma + 1% Tween + 25 mM DTT | 1467 | 609 | 41.53 |
| Plasma + 1% Tween + 50 mM DTT | 1576 | 543 | 34.43 |
| Plasma + 1% Tween + 100 mM DTT | 1391 | 165 | 11.84 |
| Plasma + 5% Tween | 1038 | 48 | 4.64 |
| Plasma + 5% Tween + 5 mM DTT | 961 | 52 | 5.43 |
| Plasma + 5% Tween + 10 mM DTT | 979 | 68 | 6.94 |
| Plasma + 5% Tween + 25 mM DTT | 983 | 38 | 3.89 |
| Plasma + 5% Tween + 50 mM DTT | 965 | 122 | 12.66 |
| Plasma + 5% Tween + 100 mM DTT | 1111 | 102 | 9.18 |
| No template control | No amplification detected | | |

Samples containing 5% TWeen had improved amplification compared to samples containing 1% TWeen, as shown by RSD values. A similar study was carried out further varying the concentrations of TWeen in reaction tubes. The results are summarized in TABLE 7.

TABLE 7

| Sample | Average $C_t$ | SD | RSD (%) |
|---|---|---|---|
| Synthetic nucleic acids + 2% Tween | 957 | 3 | 0.27 |
| Synthetic nucleic acids + 5% Tween | 842 | 12 | 1.37 |
| Plasma + 2% Tween | 2163 | n/a | n/a |

TABLE 7-continued

| Sample | Average $C_t$ | SD | RSD (%) |
|---|---|---|---|
| Plasma + 2% Tween + 0.5 mM DTT | 1671 | 989 | 59.16 |
| Plasma + 2% Tween + 1 mM DTT | 1512 | 623 | 41.17 |
| Plasma + 2% Tween + 5 mM DTT | 1234 | 154 | 12.45 |
| Plasma + 2% Tween + 10 mM DTT | 1042 | 56 | 5.38 |
| Plasma + 3% Tween | 1995 | 1004 | 50.34 |
| Plasma + 3% Tween + 0.5 mM DTT | 1119 | 63 | 5.65 |
| Plasma + 3% Tween + 1 mM DTT | 1581 | 948 | 59.87 |
| Plasma + 3% Tween + 5 mM DTT | 1067 | 107 | 10.03 |
| Plasma + 3% Tween + 10 mM DTT | 1237 | 120 | 9.73 |
| Plasma + 4% Tween | 1182 | 71 | 6.04 |
| Plasma + 4% Tween + 0.5 mM DTT | 1112 | 117 | 10.56 |
| Plasma + 4% Tween + 1 mM DTT | 1229 | 301 | 24.50 |
| Plasma + 4% Tween + 5 mM DTT | 1076 | 114 | 10.64 |
| Plasma + 4% Tween + 10 mM DTT | 1017 | 57 | 5.61 |
| Plasma + 5% Tween | 1142 | 62 | 5.42 |
| Plasma + 5% Tween + 0.5 mM DTT | 1104 | 93 | 8.46 |
| Plasma + 5% Tween + 1 mM DTT | 1510 | 800 | 52.99 |
| Plasma + 5% Tween + 5 mM DTT | 1020 | 65 | 6.34 |
| Plasma + 5% Tween + 10 mM DTT | 1014 | 59 | 5.79 |
| No template control | No amplification detected | | |

Reaction volumes with greater concentrations of TWeen and DTT had better reproducibility of amplification results for the HCV samples, specifically, in replicated reactions there were fewer extreme outliers, fewer failed amplifications, and lower RSD values for amplified replicates. At 5 mM DTT and 10 mM DTT, there were no replicates that did not amplify for any concentration of TWeen. Likewise, at 4% and 5% TWeen, there were no failed replicates or extreme outliers, except for the low (1 mM and below) DTT concentrations.

Example 11—Amplification of Targets with Cartridges

A series of three experiments were performed using a cartridge substantially similar to the cartridge depicted in FIG. 2 having six wells, each well having an annular ring electrode. Each well was associated with a measured channel. Samples included targets nucleic acids comprising sequences from *Haemophilus influenza* (Hinf), or Hepatitis B virus (HBV). Samples were amplified by LAMP, and changes in impedance were measured.

Wells were prepared by pre-heating the cartridge to 72° C. for 20 minutes, filling each well with 25 µl 'no template and primer control' (NTPC) buffer, capping the buffer with mineral oil, heating the cartridge to 72° C. for 20 minutes, removing bubbles from the wells, cooling the cartridge at room temperate for 10 minutes. Samples were injected at the bottom of the prefilled wells, and the cartridge was placed at 67° C., or 76.5° C. to carry out the LAMP for a particular experiment. The frequency used for the Hinf studies was 60 kHz. Samples and corresponding wells/channels for each cartridge are listed in TABLE 8. Target sequences and primers are listed in TABLE 9. Reaction components are listed in TABLE 10.

TABLE 8

| Well/channel | Sample |
|---|---|
| 1 | Synthetic HBV |
| 2 | Synthetic HBV |
| 3 | Synthetic HBV |
| 4 | NTPC |
| 5 | Hinf |
| 6 | Hinf |

TABLE 9

| SEQ ID NO: | Sequence |
|---|---|
| SEQ ID NO: 01 (HBV target) | GACAAGAATCCTCACAATACCGCAGAGTCTAGA CTCGTGGTGGACTTCTCTCAATTTTCTAGGGGG ATCACCCGTGTGTCTTGGCCAAAATTCGCAGTC CCCAACCTCCAATCACTCACCAACCTCCTGTCC TCCAATTTGTCCTGGTTATCGCTGGATGTGTCT GCGGCGTTTTATCATATTCCTCTTCATCCTGCT GCTATGCC |
| SEQ ID NO: 02 (HBV F3 primer) | TCCTCACAATACCGCAGAGT |
| SEQ ID NO: 03 (HBV B3 primer) | GCATAGCAGCAGGATGAAGA |
| SEQ ID NO: 04 (HBV FIP primer) | GTTGGGGACTGCGAATTTTGGCCTCGTGGTGGA CTTCTCTCA |
| SEQ ID NO: 05 (HBV BIP primer) | TCACCAACCTCCTGTCCTCCAAATAAAACGCCG CAGACACAT |
| SEQ ID NO: 06 (HBV LF primer) | ACGGGTGATCCCCCTAGAAAA |
| SEQ ID NO: 07 (HBV LB primer) | TTTGTCCTGGTTATCGCTGG |
| SEQ ID NO: 08 (Hinf target) | TGGTACGCCAATACATTCAACAAGAAATTAATC CAAAAGAAAAATTTGCGTTTGTTGAATTCTGGG GGCGAGGCTATACACAAGATACCTTTGGTCGTC TGCTAAATGATGCCTTTGGTAAAGAAGTAAAAA ACCCATTCTATTATGTCAGAAGTTTTACTGATG ATATGGGTACATCTGTTCGCCATAACTTCATCT TAGCACCACAAAACTTCTCATTCTTCGAGCCTA TTTTTGCACAAACCCCATACGACAGTATTCCTG ATTACTACGAAGAAAAAGGCAGAATTGAACCAA TTA |
| SEQ ID NO: 09 (Hinf LF primer) | GCAGACGACCAAAGGTATCTTG |
| SEQ ID NO: 10 (Hinf B3 primer) | CGTATGGGGTTTGTGCA |
| SEQ ID NO: 11 (Hinf F3 primer) | CGCCAATACATTCAACAAGA |
| SEQ ID NO: 12 (Hinf BIP primer) | CTGATGATATGGGTACATCTGTTCGCGAAGAAT GAGAAGTTTTGTGG |
| SEQ ID NO: 13 (Hinf FIP primer sequence) | ACTTCTTTACCAAAGGCATCATTTTGCGTTTGT TGACGCCAAATTCTGG |

TABLE 10

| Mix | Component | Volume (µl) |
|---|---|---|
| Master mix 1 | LAMP master mix (2X; NEB) | 12.5 |
| | dUTP Additive (100 mM; Sigma) | 0.175 |
| NTPC mix | Master mix 1 | 12.675 |
| | Water | 12.325 |
| Hinf mix | Master mix 1 | 12.675 |
| | Hinf primers (25X) | 1 |
| | Hinf target (1 M/µl) | 1 |
| | Water | 10.325 |
| Master mix 2 | Master mix 1 | 12.675 |
| | UDG | 0.5 |
| | HBV primers (25X) | 1 |
| Synthetic HBV | Master mix 2 | 13.175 |
| | HBV target (10e10 c/µl) | 1 |
| | Water | 10.825 |

Figure 36A:
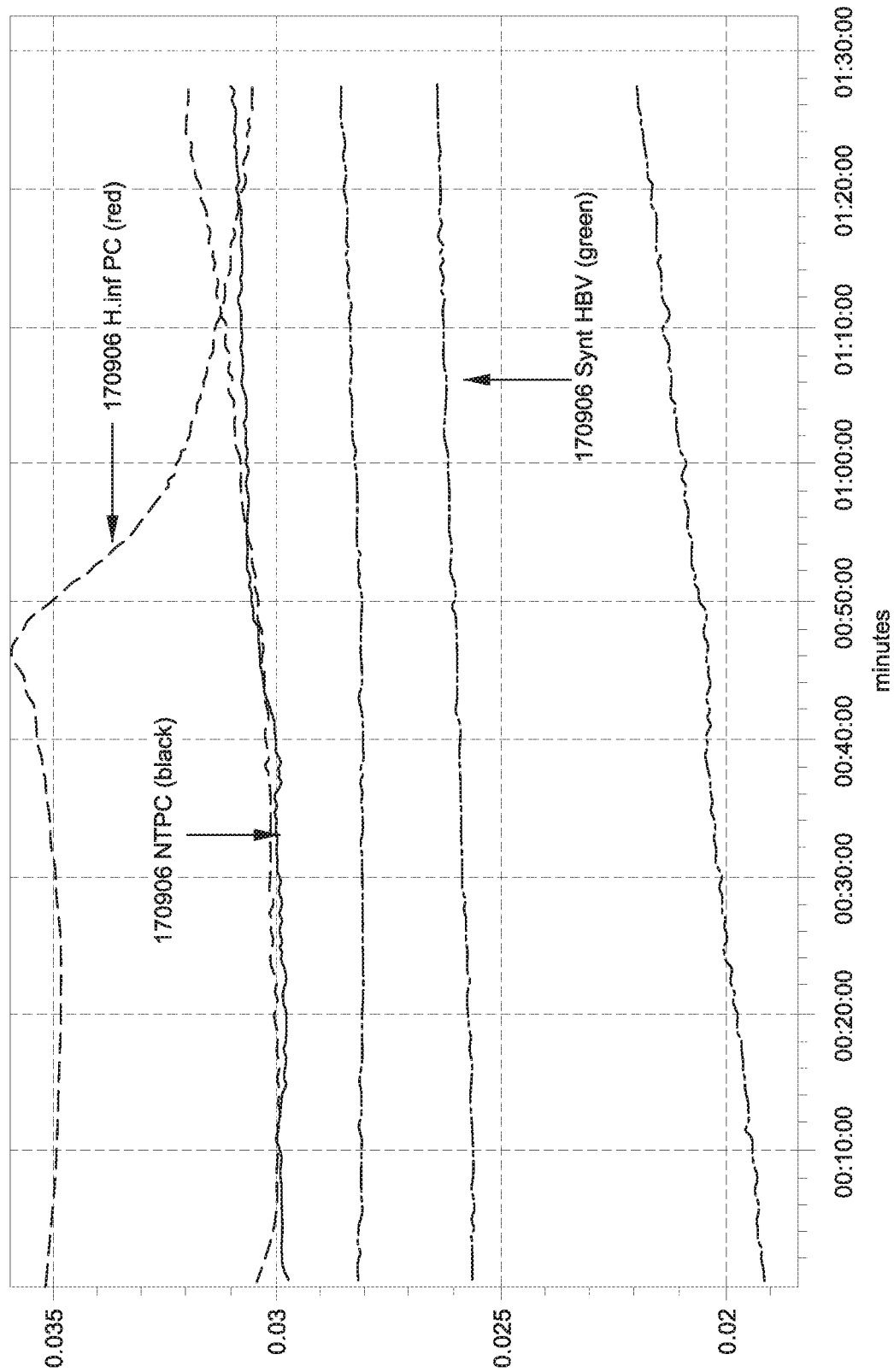
FIG. 36A depicts a graph for out of phase signals for LAMP carried on a cartridge at 65° C.
Figure 36B:
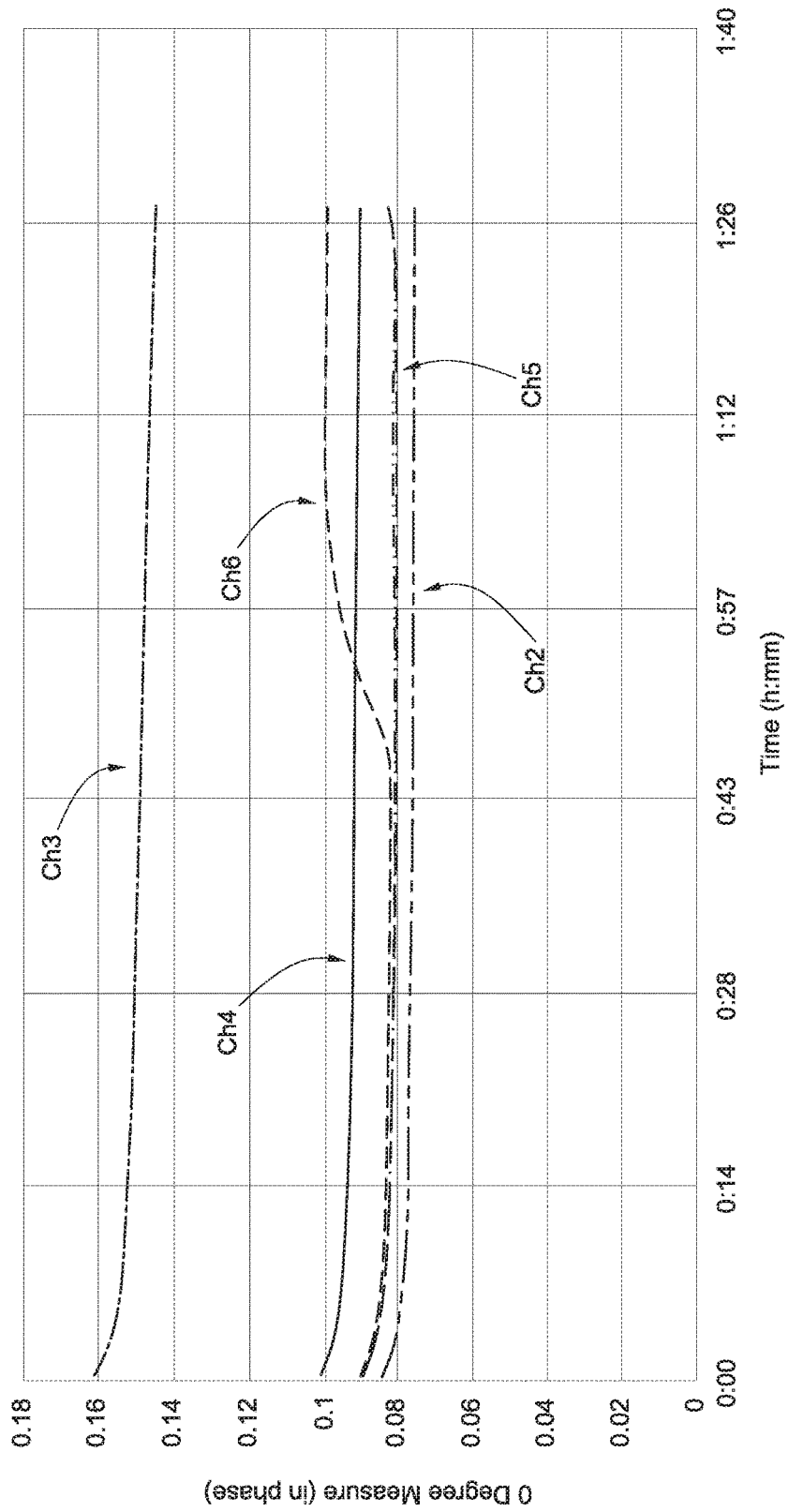
FIG. 36B depicts a graph for in phase signals for LAMP carried on a cartridge at 65° C.

Data for LAMP carried out on the cartridge at 65° C. are shown in FIGS. 36A and 36B. FIG. 36A is a graph of the out of phase portion of an attenuated excitation signal sensed in a test well of the cartridge of FIG. 2, in which the x-axis is time, and lines representing LAMP on samples for NTPC, and examples of Hinf and synthetic HBV are labelled. FIG. 36B is a graph of the in phase portion of an attenuated excitation signal sensed in a test well of the cartridge of FIG. 2, with lines representing synthetic HBV (channels 1-3), NTPC (channel 4) and Hinf (channels 5-6). Samples containing synthetic HBV were not amplified on the cartridge at 65° C. The labeled Hinf sample shows an example signal cliff indicative of a positive sample.

Figure 36C:
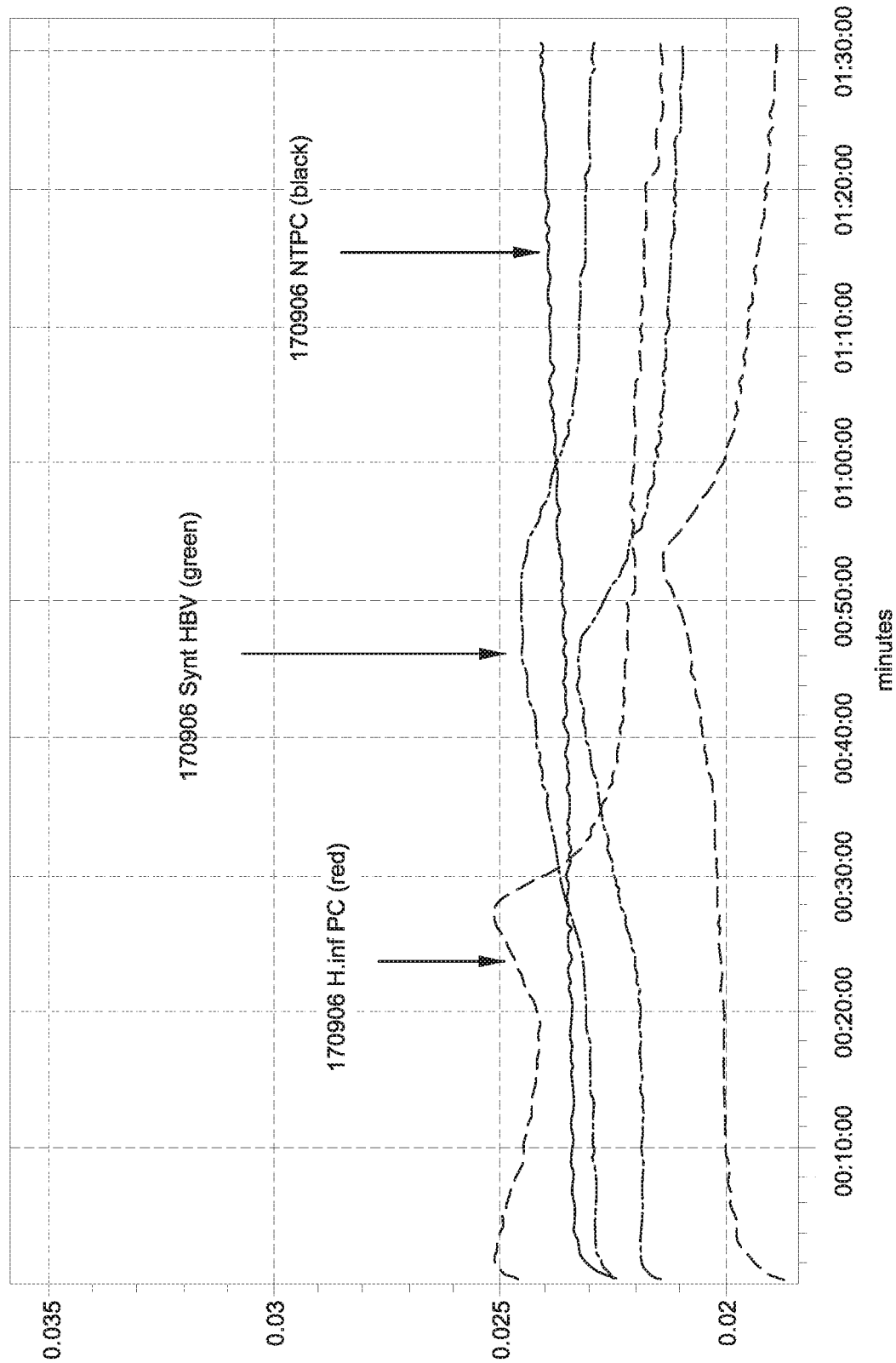
FIG. 36C depicts a graph for out of phase signals for LAMP carried on a cartridge at 67° C.
Figure 36D:
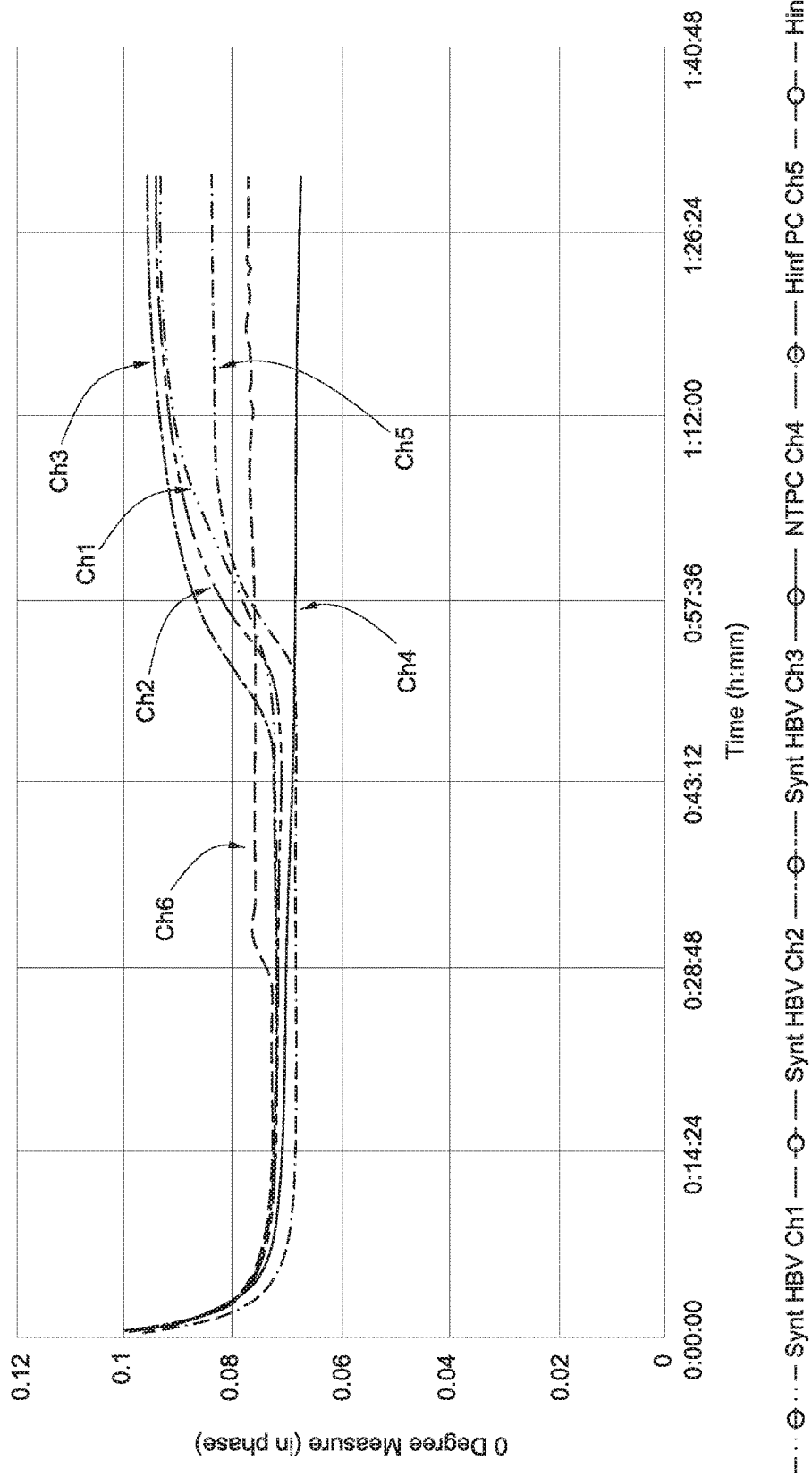
FIG. 36D depicts a graph for in phase signals for LAMP carried on a cartridge at 67° C.

Data for LAMP carried out on the cartridge at 67° C. are shown in FIGS. 36C and 36D. FIG. 36C is a graph of the out of phase portion of an attenuated excitation signal sensed in a test well of the cartridge of FIG. 2, in which the x-axis is time, and lines representing LAMP on samples for NTPC, and examples of Hinf and synthetic HBV are labelled. FIG. 36D is a graph of the in phase portion of an attenuated excitation signal sensed in a test well of the cartridge of FIG. 2 with lines representing synthetic HBV (channels 1-3), NTPC (channel 4) and Hinf (channels 5-6). Samples containing synthetic HBV amplified on the cartridge at 67° C. at about 49 minutes. The labeled Hinf sample shows an example signal cliff indicative of a positive sample.

Figure 36E:
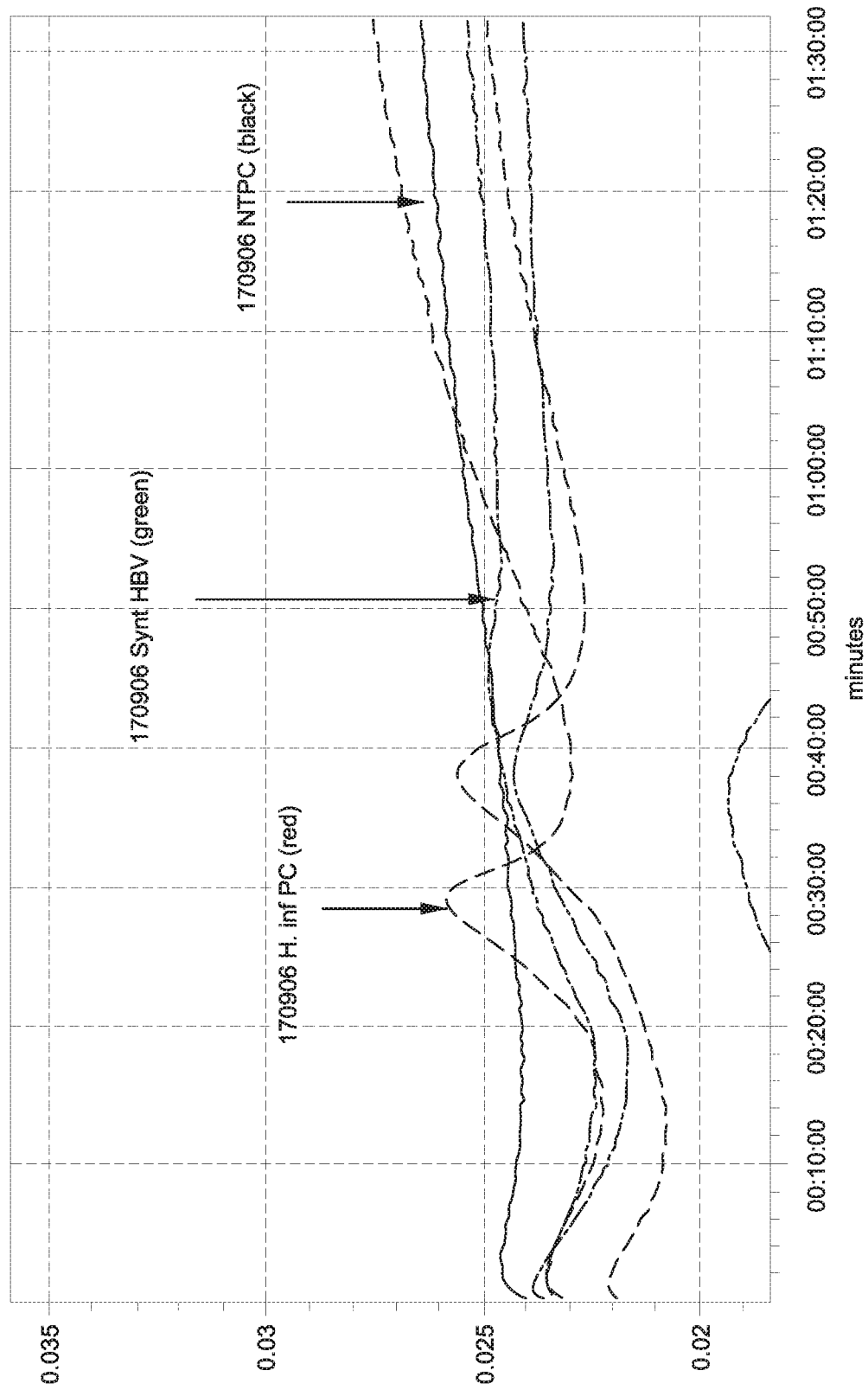
FIG. 36E depicts a graph for out of phase signals for LAMP carried on a cartridge at 67° C.
Figure 36F:
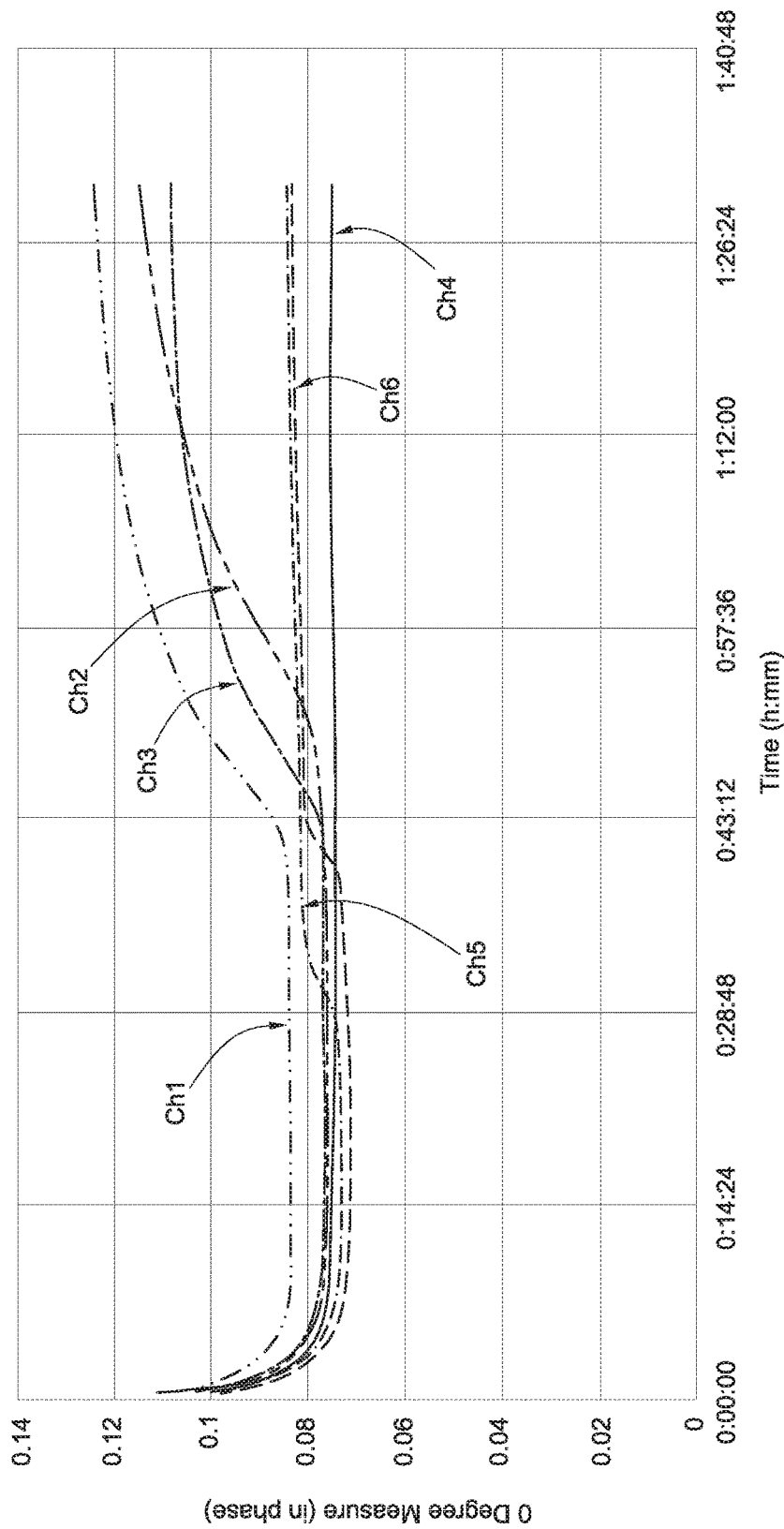
FIG. 36F depicts a graph for in phase signals for LAMP carried on a cartridge at 67° C.

Data for LAMP carried out on the cartridge at 67° C. is shown in FIGS. 36E and 36F. FIG. 36E is a graph of the out of phase portion of an attenuated excitation signal sensed in a test well of the cartridge of FIG. 2, in which the x-axis is time, and lines representing LAMP on samples for NTPC, and examples of Hinf and synthetic HBV are labelled. FIG. 36F is a graph of the in-phase portion of an attenuated excitation signal sensed in a test well of the cartridge of FIG. 2, with lines representing synthetic HBV (channels 1-3), NTPC (channel 4) and Hinf (channels 5-6). Samples containing synthetic HBV amplified on the cartridge at 67° C. at about 46 minutes.

Samples were also tested by quantative PCR using an Applied Biosystems QuantStudio™ 3 Real-Time PCR System at 67° C. Threshold cycles ($C_t$) were calculated using Thermo Fisher's QS3 software with a threshold set at 100 k and the baseline set for the same value for each set of the same reactions. TABLE 11 lists average Ct values for samples containing Hinf, or synthetic HBV.

TABLE 11

| Sample (target concentration) | Average Ct | SD | RSD (%) |
|---|---|---|---|
| Hinf PC (1M c/uL) | 1704.5 | 10.4 | 0.6 |
| HBV Synt (10B c/uL) | 380.4 | 5.5 | 1.5 |

Implementing Systems and Terminology

Implementations disclosed herein provide systems, methods and apparatus for detection of the presence and/or quantity of a target analyte. One skilled in the art will recognize that these embodiments may be implemented in hardware or a combination of hardware and software and/or firmware.

The signal processing and reader device control functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A system for detecting a target agent, the system comprising:
   an assay cartridge comprising a test well containing an excitation electrode and a sensing electrode, wherein the test well is configured to contain a sample comprising the target agent undergoing an amplification process; and
   a reader device comprising:
      a region configured to receive the assay cartridge,
      a heater positioned to heat the assay cartridge in use within the cavity,
      a memory storing at least computer-readable storing instructions, and
      a processor configured by the instructions to at least:
         cause the heater to heat the assay cartridge to a predetermined temperature for performing the amplification process within the test well;
         provide an excitation current to the excitation electrode for at least a portion of a duration of the amplification process,
         receive a signal from the sensing electrode, the signal representing the excitation current after attenuation by at least the sample within the test well,
         decompose the signal into a resistance component and a reactance component,
         analyze the reactance component to determine whether a signal cliff indicative of a positive sample including the target agent occurred during at least the portion of the duration of the amplification process, wherein the signal cliff represents a change $\Delta_R$ in the reactance during a window of time $T_W$, and
         in response to determining that the signal cliff occurred, output a positive test result or, in response to determining that the signal cliff did not occur, output a negative test result.

2. The system of claim 1, wherein the assay cartridge further comprises:
   a sample introduction area configured to receive the sample; and
   a fluid path fluidically coupling the sample introduction area to the test well.

3. The system of claim 2, wherein the assay cartridge further comprises:
   a sealed chamber containing liquid constituents of the amplification process, the sealed chamber positioned in a region of the assay cartridge having an aperture leading into the fluid path, wherein the sample introduction area is positioned between the aperture and the test well along the fluid path; and
   a pneumatic fluid path fluidically coupling a pneumatic interface to the region of the assay cartridge,
   wherein the test well is provided with dried constituents of the amplification process.

4. The system of claim 3, wherein the reader device includes a pneumatic system configured to apply pressure through the pneumatic interface, the processor further configured by the instructions to at least:
   actuate a motor coupled to an actuator positioned to rupture the sealed chamber and cause the liquid constituents to flow into the region of the assay cartridge;
   activate the pneumatic system to cause the liquid constituents to flow into the fluid path and carry the sample received at the sample introduction area to the test well.

5. The system of claim 4, wherein the assay cartridge further comprises a mixing chamber positioned between the sample introduction area and the test well along the fluid path, the mixing chamber configured to mix the liquid constituents and the sample into a substantially evenly mixed test fluid.

6. The system of claim 1, wherein the assay cartridge comprises a first electrode interface including a first contact pad leading to the excitation electrode and a second contact pad leading to the sensing electrode.

7. The system of claim 6, wherein the reader device comprises a second electrode interface configured to couple to the first electrode interface with the assay cartridge received in the region of the reader device.

8. The system of claim 7, wherein the reader device further comprises a voltage source configured to generate the excitation current, and wherein the second electrode interface includes:
   a third contact pad positioned to couple to the first contact pad, the third contact pad coupled to the voltage source; and
   a fourth contact pad positioned to couple to the second contact pad, the fourth contact pad coupled to the memory.

9. The system of claim 1, wherein, to decompose the signal into the resistance component and the reactance component, the processor is further configured by the instructions to at least:
   sample the signal faster than its Nyquist frequency, the signal representing an impedance of the sample;
   decompose the signal into an in-phase component and an out of phase component; and
   calculate the resistance component based on the in-phase component and calculate the reactance component based on the out-of-phase component.

10. The system of claim 1, wherein, to analyze the reactance component, the processor is further configured by the instructions to at least access predetermined expected characteristics of the signal cliff from the memory.

11. The system of claim 10, wherein the predetermined expected characteristics of the signal cliff stored in the memory include a window of time during the duration of the amplification process at which the signal cliff is predicted to occur.

12. The system of claim 10, wherein the predetermined expected characteristics of the signal cliff stored in the memory include a threshold change in a value of the reactance component.

13. The system of claim 10, wherein the predetermined expected characteristics of the signal cliff stored in the memory include a threshold slope of a curve of the reactance component, the curve of the reactance component representing values of the reactance component sampled throughout the least a portion of the duration of the amplification process.

14. A method of detecting a target agent, the method comprising:
providing the system of claim 1;
introducing a sample comprising the target agent into the assay cartridge;
inserting the assay cartridge into the reader device;
performing an amplification of the target agent comprised in the sample within the test well of said assay cartridge;
applying an excitation signal from the reader device to the excitation electrode;
sensing a signal from the test well using the excitation electrode, the signal representing an impedance of the sample undergoing the amplification;
transmitting the signal to the reader device; and
detecting the target agent based on the reader device analyzing a reactance portion of the impedance to determine whether a signal cliff indicative of a positive sample including the target agent occurred during at least the portion of the duration of the amplification process, wherein the signal cliff represents a change $\Delta_R$ in the reactance during a window of time $T_W$.

15. The method of claim 14, further comprising:
applying the sample at a sample introduction area of the cartridge;
rupturing a sealed chamber within the cartridge to release liquid constituents of the amplification process into a fluid path of the cartridge; and
causing the liquid constituents and the sample to flow along the fluid path to the test well, thereby mixing the liquid constituents and the sample into a test fluid.

16. The method of claim 15, further comprising hydrating dried components of the amplification process provided within the test well with test fluid.

17. The method of claim 15, further comprising pushing gas trapped in the test fluid out through a vent in fluid communication with the test well.

18. The method of claim 15, further comprising analyzing the reactance portion of the signal to identify a signal cliff indicative of a positive test result.

19. The method of claim 18, further comprising identifying the signal cliff based on a portion of a curve generated based on the reactance portion that has one or both of greater than a threshold change in value and a temporal location within predetermined window of time of the amplification process.

20. The method of claim 14, wherein the target agent is selected from the group consisting of a viral nucleic acid, a viral capsid protein, a viral structural protein, a viral glycoprotein, a viral membrane fusion protein, a viral protease, and a viral polymerase.

* * * * *